US010364462B2

(12) United States Patent
Stava et al.

(10) Patent No.: US 10,364,462 B2
(45) Date of Patent: *Jul. 30, 2019

(54) COMPOSITIONS AND METHODS FOR POLYNUCLEOTIDE SEQUENCING

(71) Applicant: Illumina, Inc., San Diego, CA (US)

(72) Inventors: Eric Stava, San Diego, CA (US); Jens H. Gundlach, Seattle, WA (US); Jeffrey G. Mandell, La Jolla, CA (US); Kevin L. Gunderson, Encinitas, CA (US); Ian M. Derrington, Seattle, WA (US); Hosein Mohimani, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,354

(22) Filed: May 26, 2017

(65) Prior Publication Data

US 2017/0268055 A1 Sep. 21, 2017

Related U.S. Application Data

(63) Continuation of application No. 14/554,741, filed on Nov. 26, 2014, now Pat. No. 9,689,033.

(60) Provisional application No. 61/909,316, filed on Nov. 26, 2013.

(51) Int. Cl.
*C12Q 1/6869* (2018.01)
*G01N 27/447* (2006.01)
*C07K 14/35* (2006.01)

(52) U.S. Cl.
CPC ............ *C12Q 1/6869* (2013.01); *C07K 14/35* (2013.01); *G01N 27/447* (2013.01)

(58) Field of Classification Search
CPC ..... C12Q 1/6869; C07K 14/35; G01N 27/447
See application file for complete search history.

(56) References Cited

U.S. PATENT DOCUMENTS

| | | | |
|---|---|---|---|
| 4,469,863 | A | 9/1984 | Ts'o |
| 5,034,506 | A | 7/1991 | Summerton |
| 5,216,141 | A | 6/1993 | Benner |
| 5,235,033 | A | 8/1993 | Summerton |
| 5,386,023 | A | 1/1995 | Sanghvi |
| 5,508,179 | A | 4/1996 | Wallace |
| 5,602,240 | A | 2/1997 | Mesmaeker |
| 5,637,684 | A | 6/1997 | Cook |
| 5,644,048 | A | 7/1997 | Yau |
| 6,015,714 | A | 1/2000 | Baldarelli |
| 6,890,741 | B2 | 5/2005 | Fan |
| 6,913,884 | B2 | 7/2005 | Stuelpnagel |
| 7,582,420 | B2 | 9/2009 | Oliphant |
| 7,955,794 | B2 | 6/2011 | Shen |
| 8,288,103 | B2 | 10/2012 | Oliphant |
| 2010/0196203 | A1 | 8/2010 | Sanghera |
| 2012/0055792 | A1 | 3/2012 | Gundlach |
| 2013/0244882 | A1 | 9/2013 | Oliphant |

FOREIGN PATENT DOCUMENTS

| | | |
|---|---|---|
| WO | WO 2000/079257 | 12/2000 |
| WO | WO 2006/100484 | 2/2006 |
| WO | WO 2010/109197 | 9/2010 |
| WO | WO 2012/033524 | 3/2012 |
| WO | WO 2013/153359 | 3/2013 |
| WO | WO 2013/057495 | 4/2013 |
| WO | WO 2013/016486 | 7/2013 |
| WO | WO 2013/098561 | 7/2013 |
| WO | WO 2013/098562 | 7/2013 |
| WO | WO 2010/04265 | 1/2014 |

OTHER PUBLICATIONS

Dillingham et al, Demonstration of Unidirectional Single-Stranded DNA Translocation by PcrA Helicase: Measurement of Step Size and Translocation Speed, 2000, Biochemistry, 39, 205-212 (Year: 2000).*
Data sheet-1: Seq ID No. 1 Search results by STIC pritnted on Oct. 24, 2018, pp. 1-13 (Year: 2018).*
Data sheet-1: Seq ID No. 4 Search results by STIC pritnted on Oct. 24, 2018, pp. 1-10 (Year: 2018).*
Axopatch 200 B brochure, 1999, pp. 1-153 (Year: 1999).*
International Search Report for PCT/US2014/067639 dated Jun. 24, 2015.
Written Opinion of the International Searching Authority for PCT/US2014/067639 dated Jun. 24, 2015.
International Search Report for dated Apr. 21, 2015 PCT/US2014/067582.
Written Opinion of the International Searching Authority dated Apr. 21, 2015 for PCT/US2014/067582.
Invitation to Pay Additional Fees dated Apr. 7, 2015 for PCT/US2014/067639.
Bayley, et al, "Stochastic Sensors Inspired by Biology," Nature 413:226-230 (2001).
Osaki, et al, "Multichannel Simultaneous Measurements of Single-Molecule Translocation in [alpha]-Hemolysin Nanopore Array," Analytical Chemistry 81(24):9866-9870 (2009).
Marsh, et al, "Pyrococcus furiousus DNA Ligase an the Ligase Chain Reaction" Strategies in Molecular Biology 5:73-76 (1992).
Rothemund. "Folding DNA to create nanoscale shapes and patterns." Nature. 440:297-302 (2006).
Sawai et al., "Synthesis and Properties of Oligoadenylic Acids Containing 2'-5' Phosphoramide Linkage," Chem. Lett., 805-808 ( 1984).

(Continued)

*Primary Examiner* — Narayan K Bhat
(74) *Attorney, Agent, or Firm* — Knobbe, Martens, Olson & Bear LLP

(57) ABSTRACT

Methods and compositions for characterizing a target polynucleotide, including, characterizing the sequence of the target polynucleotide, using the fractional translocation steps of the target polynucleotide's translocation through a pore.

19 Claims, 37 Drawing Sheets

Specification includes a Sequence Listing.

(56) References Cited

OTHER PUBLICATIONS

Seki, "POLO (Pol theta), a DNA polymerase and DNA-dependent ATPase in human cells," Nucleic Acids Res., 31 (21 ): 6117-6126 (2003).
Singleton et al., "Structure and Mechanism of Helicases and Nucleic Acid Translocases," Annu. Rev. Biochem., 76:23-50 (2007).
Soni et al., "Synchronous optical and electrical detection of biomolecules traversing through solid-slate nanopores," Rev. Sci. Instrum., 81(1):014301-1-7(2010).
Sprinzl et al., "Enzymatic Incorporation of ATP and CTP Analogues into the 3' End of tRNA," Eur. J. Biochem., 81 :579-589 (1977).
Tanaka et al., "ATPase/helicase motif mutants of *Escherichia coli* PriA protein essential for recombination-dependent DNA replication," Genes to Cells, 8:251-261 (2003).
Horn et al., "Oligonucleolides with Alternating Anionic and Cationic Phosphoramidale Linkages: Synthesis and Hybridization of Stereo-uniform Isomers," Tetrahedron Lett., 37(6):743-746 (1996).
Timp et al., "DNA Base-Calling from a Nanopore Using a Viterbi Algorithm," Biophysical Journal, 102:L37-L39 (2012).
Dela Torre et al., "Fabrication and Characterization of Solid-slate Nanopore Arrays for High Throughput DNA Sequencing," Nanotechnology, 23(38):385308, 12 pages (2012).
Tuteja et al., "Unraveling DNA Helicases: Motif, structure, mechanism and function," European Journal of Biochemistry, 271(10):1849-1863 (2004).
Venkatesan et al., "Stacked Graphene-Al2O3 Nanopore Sensors for Sensitive Detection of DNA and DNA-Protein Complexes," ACS Nano, 6(1):441-450 (2012).
Venkatesan et al., "Nanopore sensors for nucleic acid analysis," Nat. Nanotechnol., 6(10):615-624 (2011).
Wang et al., "Single-molecule DNA detection using a novel SP1 proteing nanopore," Chem. Commun., 49:1741-1743 (2013).
Wanunu, "Nanopores: A journey towards DNA sequencing," Phys. Life Rev., 9(2):125-158 (2012).
Anderson et al., "Self-assembly of a nanoscale DNA box with a controllable lid," Nature, 459:73-76 (2009).
Bagshaw, "ATP analogues at a glance," Cell Science at a Glance, 114(3):459-460, plus poster insert (1 page) (2011).
Bajaj et al., "Engineering Nocardia farcinica nanopore for biosensing," Biophysics, School of Engineering and Science, Poster Presentation, Jacobs University Bremen, Germany, 1 page (Jul. 28 to Aug. 3, 2013).
Barany, "The ligase chain reaction in a PCR world," PCR Methods and Applications, 1:5-16 (1991).
Beaucage et al., "The Functionalization of Oligonucleotides Via Phosphoramidite Derivatives," Tetrahedron, 49 (10):1925-1963 (1993).
Brill et al., "Synthesis of Oligodeoxynucleoside Phosphorodithioates via Thioamidites," J. Am. Chem. Soc., 111:2321-2322 (1989).
Butler et al., "Single-molecule DNA detection with an engineered MspA protein nanopore," Proc. Natl. Acad. Sci. USA, 105(52):20647-20652 (2008).
Carlsson et al., "Screening for genetic mutations," Nature, 380:207-208 (1996).
Carter et al., "A Comparison of Step-Detection Methods: How Well Can you Do?" Biophysical Journal, 94:306-319 (2008).
Cherf et al., "Automated forward and reverse ratcheting of DNA in a nanopore at 5-A precision," Nat. Biotechnol., 30 (4):344-348 (2012).
Deamer et al.. "Characterization of Nucleic Acids by Nanopore Analysis." Acc. Chem. Res., 35:817-825 (2002).
Deamer et al., "Nanopores and nucleic acids: prospects for ultrarapid sequencing," Trends in Biotechnology, 18:147-151 (2000).
Dempcy et al., "Synthesis of a thymidyl pentamer of deoxyribonucleic guanidine and binding studies with DNA homopolynucleolides," Proc. Nall. Acad. Sci. USA, 92:6097-6101 (1995).
Derrington et al., "Nanopore DNA sequencing with MspA," Proc. Nall. Acad. Sci. USA, 107(37):16060-16065 (2010).
Fan et al., "Highly Parallel SNP Genotyping," Cold Spring Harb Symp Quant Biol., 68:69-78 (2003).

Douglas et al., "Self-assembly of DNA into nanoscale three-dimensional shapes," Nature, 459(7245):414-418 (2009).
Egholm, "Peptide Nucleic Acids (PNA). Oligonucleolide Analogues with an Achiral Peptide Backbone," J. Am. Chem. Soc., 114:1895-1897 (1992).
Enemark et al., "On Helicases and other motor proteins," Curr. Opin. Struct. Biol., 18(2):243-257 (2008).
Engler et al., "DNA Ligases," The Enzymes, Boyer, ed., vol. XV, Part B:3-29 (1982).
Flechsig et al, "In Silica Investigation of Conformational Motions in Superfamily 2 Helicase Proteins," PLoS One, 6 (7): e21809, 11 pages (2011).
Frick et al., "Understanding Helicases as a Means of Virus Control," Current Pharmaceutical Design, 12:1315-1338 (2006).
Guy. "Archaeal Hel308 helicase targets replication forks in vivo and in vitro and unwinds lagging strands." Oxford Journals Life Sciences Nucleic Acids Research vol. 33(11 ): 3678-3690 (2005).
Hall et al., "Helicase motifs: the engine that powers DNA unwinding," Molecular Microbiology, 34(5):867-877 (1999).
Hishida et al., "Role of Walker Motif A of RuvB Protein in Promoting Branch Migration of Holliday Junctions: Walker motif a mutations affect ATP binding, ATP hydrolyzing, and DNA binding activities of RuvB," Journal of Biological Chemistry, 274(36):25335-25342 (1999).
Gao et al., "Unusual conformation of a 3'-thioformacetal linkage in a DNA duplex," J. Biomolecular NMR, 4:17-34 (1994).
Jena Bioscience, "Non-hydrolyzable ATP Test Kit: screening kit for ATP-binding proteins," data sheet from Jena Bioscience GmbH, Jena, Germany (2009).
Jenkins et al., "The Biosynthesis of Carbocyclic Nucleosides," Chem. Soc. Rev., 169-176 (1995).
Ke et al., "Scaffolded DNA Origami of a DNA Tetrahedron Molecular Container," Nano Letters, 9(6):2445-2447 (2009.
Kiedrowski et al., "Parabolic Growth of a Self-Replicating Hexadeoxynucleotide Bearing a 3'-5'-Phosphoamidate Linkage," Angew. Chem. Int. Ed. English, 30(4):423-426 (1991).
Kielbasa et al., "Adaptive seeds tame genomic sequence comparison," Genome Research, 21 :487-493 (2011).
Laszlo et al., "Decoding long nanopore sequencing reads of natural DNA," Nature Biotechnology, 32(8):829-834 (2014).
Lawyer et al., "Isolation, Characterization, and Expression in *Escherichia coli* of the DNA Polymerase Gene from Thermus aquaticus," J. Biol. Chem., 264(11):6427-6437 (1989).
Lawyer et al.. "High-level Expression. Purification, and Enzymatic Characterization of Full-length Thermus aquaticus DNA Polymerase and a Truncated Form Deficient in 5' to 3' Exonuclease Activity," PCR Meth. Appl., 2:275-287 (1993).
Lehman, "DNA Ligase: Structure, Mechanism, and Function," Science, 186:790-797 (1974).
Letsinger et al., "Cationic Oligonucleotides," J. Am. Chem. Soc., 110:4470-4471 (1988).
Jung et al., "Hybridization of Alternating Cationic/Anionic Oligonucleotides to RNA Segments," Nucelosides and Nucleotides, 13(6 &7):1597-1605 (1994).
Letsinger et al., "Effects of pendant groups at phosphorus on binding properties of d-ApA analogues," Nucl. Acids Res., 14(8):3487-3499 (1986).
Letsinger, "Phosphoramidate Analogs of Oligonucleotides," J. Org. Chem., 35(11 ):3800-3803 (1970).
Li et al., "DNA molecules and configurations in a solid-state nanopore microscope," Nat. Mater., 2(9):611-615 (2003).
Mag et al., "Synthesis and selective cleavage of an oligodeoxynucleotide containing a bridged internucleotide 5'- phosphorothioate linkage," Nucleic Acids Res., 19(7):1437-1441 (1991).
Manrao et al., "Reading DNA at single-nucleotide resolution with a mutant MspA nanopore and phi29 DNA polymerase," Nat. Biotechnol., 30(4):349-354 (2012).
Manrao et al., "Nucleotide Discrimination with DNA Immobilized in the MspA Nanopore,"PLos One, 6(10):e25723, 7 pages (2011).
Marini, "A Human DNA Helicase Homologous to the DNA Crosslink Sensitivity Protein Mus308," J. Biol. Chem, 277 (10): 8716-8723 (2002).

(56) References Cited

OTHER PUBLICATIONS

Zoller, M.J., "New recombinant DNA methodology for protein engineering," Curr. Opin. Biotechnol., 3:348-354 (1992).
Meier et al., "Peptide Nucleic Acids (PNAs)-Usual Properties of Nonionic Oligonucleotide Analogues," Angew. Chem. Int. Ed. Engl., 31(8):1008-1010 (1992).
Mesmaeker et al., "Comparison of Rigid and Flexible Backbones in Antisense Oligonucleotides," Bioorganic & Medicinal Chem. Lett., 4(3):395-398 (1994).
Mont Al et al., "Formation of Bimolecular Membranes from Lipid Monolayers and a Study of Their Electrical Properties," Proc. Natl. Acad. Sci. USA, 69(12):3561-3566 (1972).
Egholm et al., "PNA hybridizes to complementary oligonucleotides obeying the Watson-Crick hydrogen bonding rules," Nature, 365:566-568 (1993).
Oyama, "Atomic structures and functional implications of the archaeal RecQ-like helicase Hjm," BMC Structural Biology, 9:2, 12 pages (2009).
Pauwels et al., "Biological Activity of New 2-5 A Analogues," Chemica Scripta, 26(1):141-145 (1986).
Fairman-Williams, et al, SF1 and SF2 helicases: family matters, Curr Opin Struct Biol. Jun. 2010 ; 20(3): 313-324.

\* cited by examiner

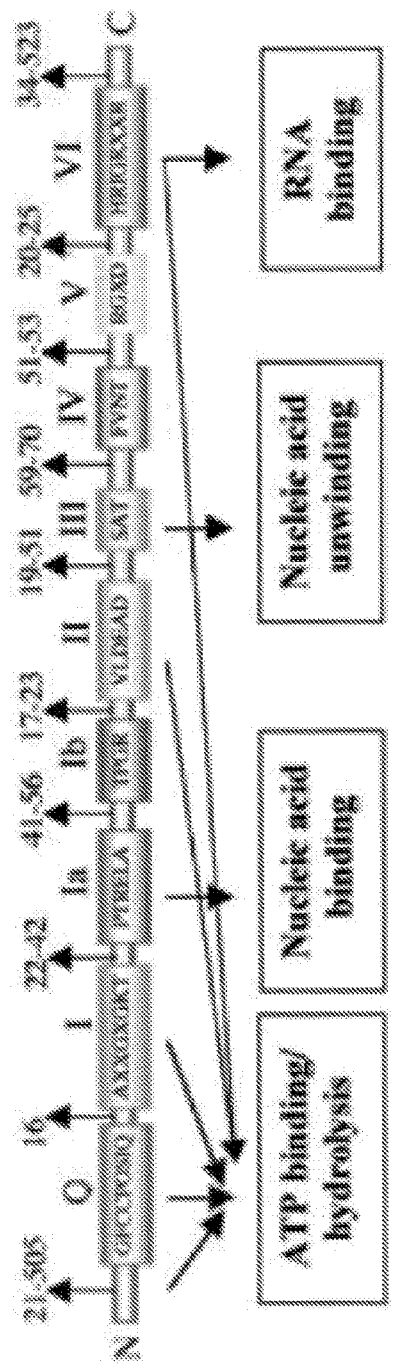
Figure 16. Adapted from Tuteja et al.

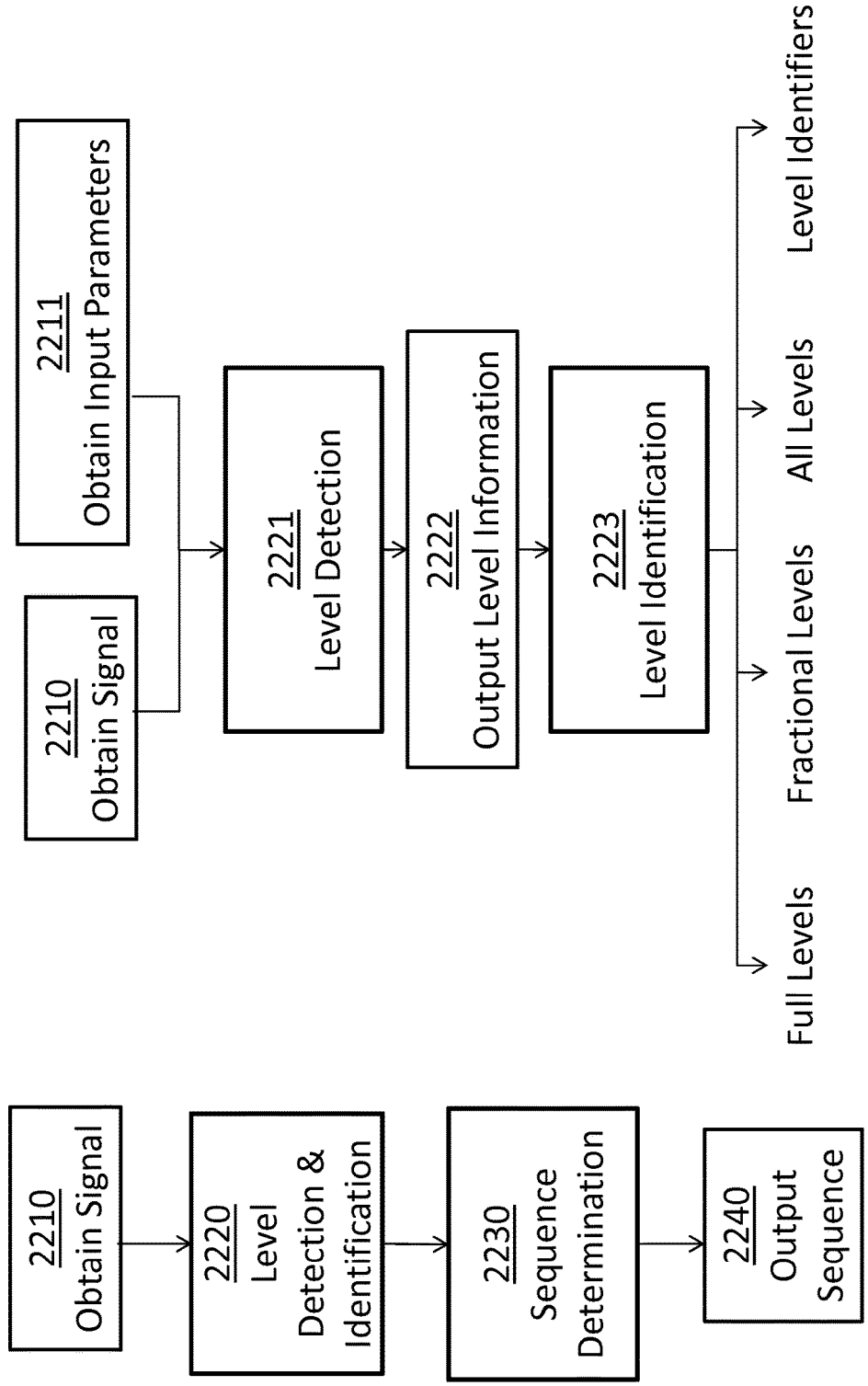

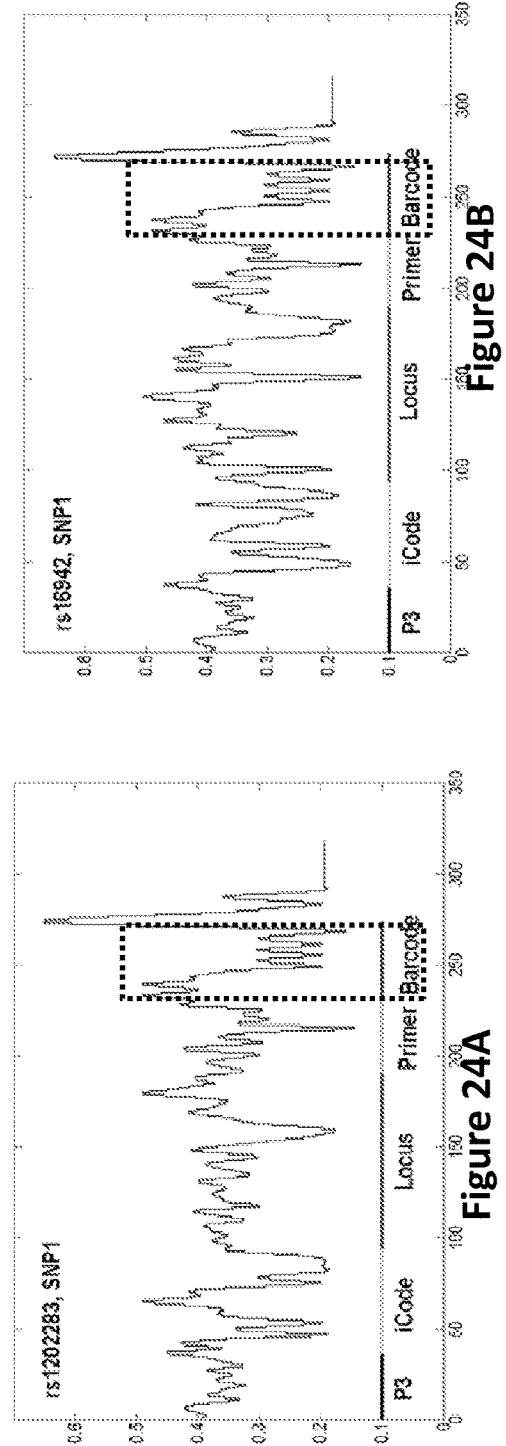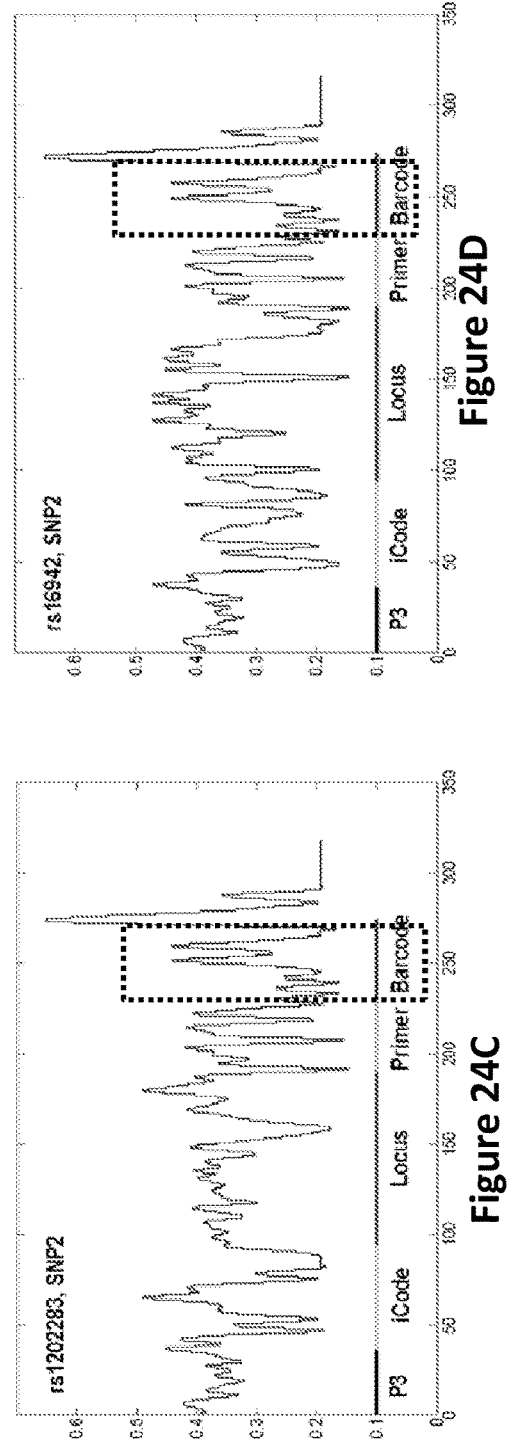
Figure 24A Figure 24B Figure 24C Figure 24D (1)

COMPOSITIONS AND METHODS FOR POLYNUCLEOTIDE SEQUENCING

CROSS-REFERENCE TO RELATED APPLICATIONS

This application is a continuation of U.S. Ser. No. 14/554,741 filed Nov. 26, 2014 which claims the benefit of U.S. Provisional Patent Application No. 61/909,316, filed on Nov. 26, 2013 and entitled "Compositions and Methods for Polynucleotide Sequencing," the entire contents of which are each incorporated by reference herein.

SEQUENCE LISTING

The present application is being filed along with a Sequence Listing in electronic format. The Sequence Listing is provided as a file entitled seqlistingILLINC383C1, created May 23, 2017, which is approximately 19 Kb in size. The information in the electronic format of the Sequence Listing is incorporated herein by reference in its entirety.

BACKGROUND

The present disclosure relates generally to methods and compositions for characterizing a target polynucleotide, including, characterizing the sequence of the target polynucleotide.

As the information encoded in a polynucleotide (e.g., DNA or RNA) is of paramount importance to medicine and life science, there exists a need to sequence a polynucleotide rapidly and inexpensively. At present, commercial sequencing techniques require sample and library preparation, both of which are laborious. Furthermore, readouts are slower than desired for many applications. Therefore, throughput is limited and cost is relatively high. Nanopore sequencing represents one new method that is being developed to rapidly and cheaply sequence a target polynucleotide.

Nanopore sequencing utilizes a nanopore, which can provide a channel for an ionic electrical current. A polynucleotide is electrophoretically driven through the nanopore, and as the polynucleotide passes through the nanopore, it reduces the electrical current through the nanopore. Each passing nucleotide, or series of nucleotides, yields a characteristic electrical current, and the record of the current levels corresponds to the sequence of the polynucleotide. Since some current levels are governed by multiple nucleotides (generally 3-4), there remains a need to improve upon the state of the art to improve accuracies. Any additional information about the current levels obtained as the polynucleotide translocates through the nanopore such as shape and duration can provide advantages.

A common challenge to nanopore sequencing is that the translocation of the polynucleotide through the nanopore is so rapid that the current levels for individual nucleotides are too short to be resolved. One approach to nanopore sequencing involves controlled translocation of a polynucleotide through the nanopore under the guidance of a polynucleotide binding protein, such as a helicase, translocase, or polymerase, against a voltage potential. In spite of this controlled translocation, a number of sequencing error modes still exist and contribute to poor sequencing accuracies.

Thus, there exists a need for methods and compositions that provide a further controlled translocation of a polynucleotide through the nanopore and better resolution of nucleotide translocation in nucleotide discrimination. The present disclosure satisfies this need and provides related advantages.

SUMMARY OF EMBODIMENTS

A method of characterizing a target polynucleotide is provided. The method includes: (a) applying a potential difference across a pore in contact with a Hel308 helicase and a target polynucleotide; (b) measuring one or more signals produced by one or more fractional translocation steps of the target polynucleotide through the pore, and (c) characterizing the target polynucleotide from the electrical signal of the fractional translocation steps. Characterization of the target polynucleotide includes identifying one or more of: (1) the sequence of the target polynucleotide; (2) the modification of the target polynucleotide; (3) the length of the target polynucleotide; (4) the identity of the target polynucleotide; (5) the source of the target polynucleotide, or (6) the secondary structure of the target polynucleotide. Also provided is a method of modulating a fractional translocation step of a target polynucleotide through a pore and a composition for characterizing a target polynucleotide, comprising a pore, a Hel308 helicase and a target polynucleotide contained in a solution of less than 1 mM ATP or a solution of a nucleotide analogue

Figure 6A:
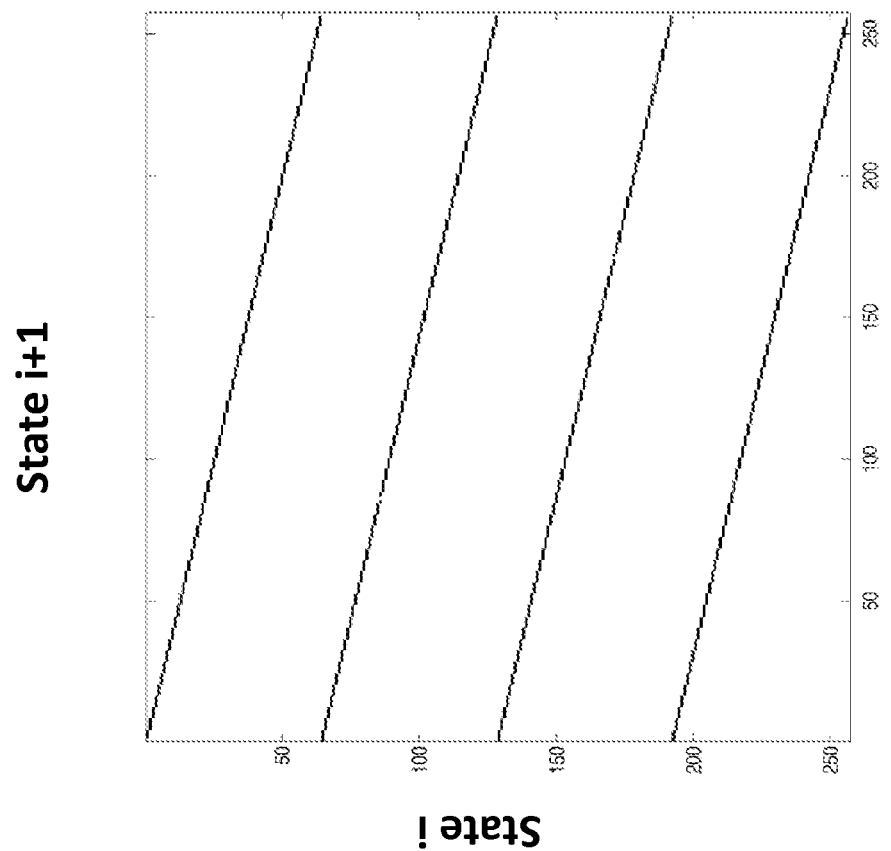

FIG. 6A depicts state transitions with non-zero probability needed for a HMM to decode sequence in a nanopore where the polynucleotide is moved by motor enzyme, according to some embodiments. The motor is phi29 DNAP or a similar enzyme moving polynucleotide in 1 nucleotide steps.

Figure 6B:
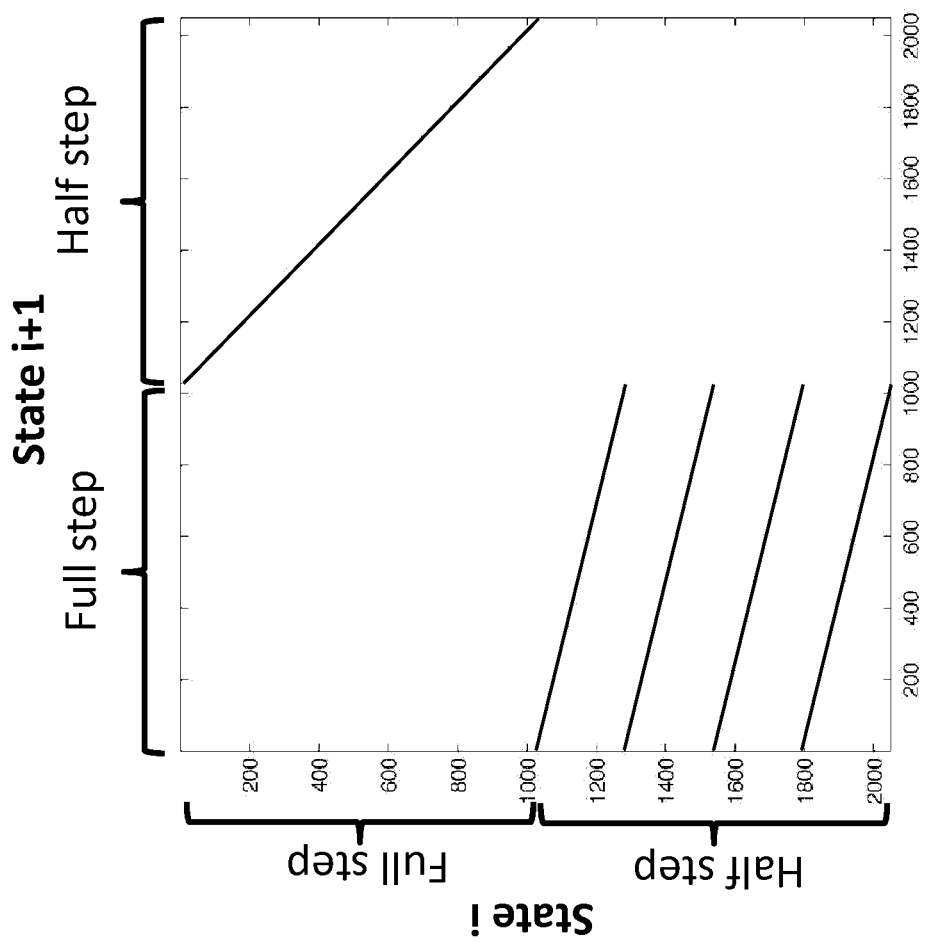

FIG. 6B depicts state transitions with non-zero probability needed for a HMM to decode sequence in a nanopore where the polynucleotide is moved by motor enzyme, according to some embodiments. The motor is Hel308 helicase or similar enzyme that enables fractional motion of the polymer.

Figure 7:
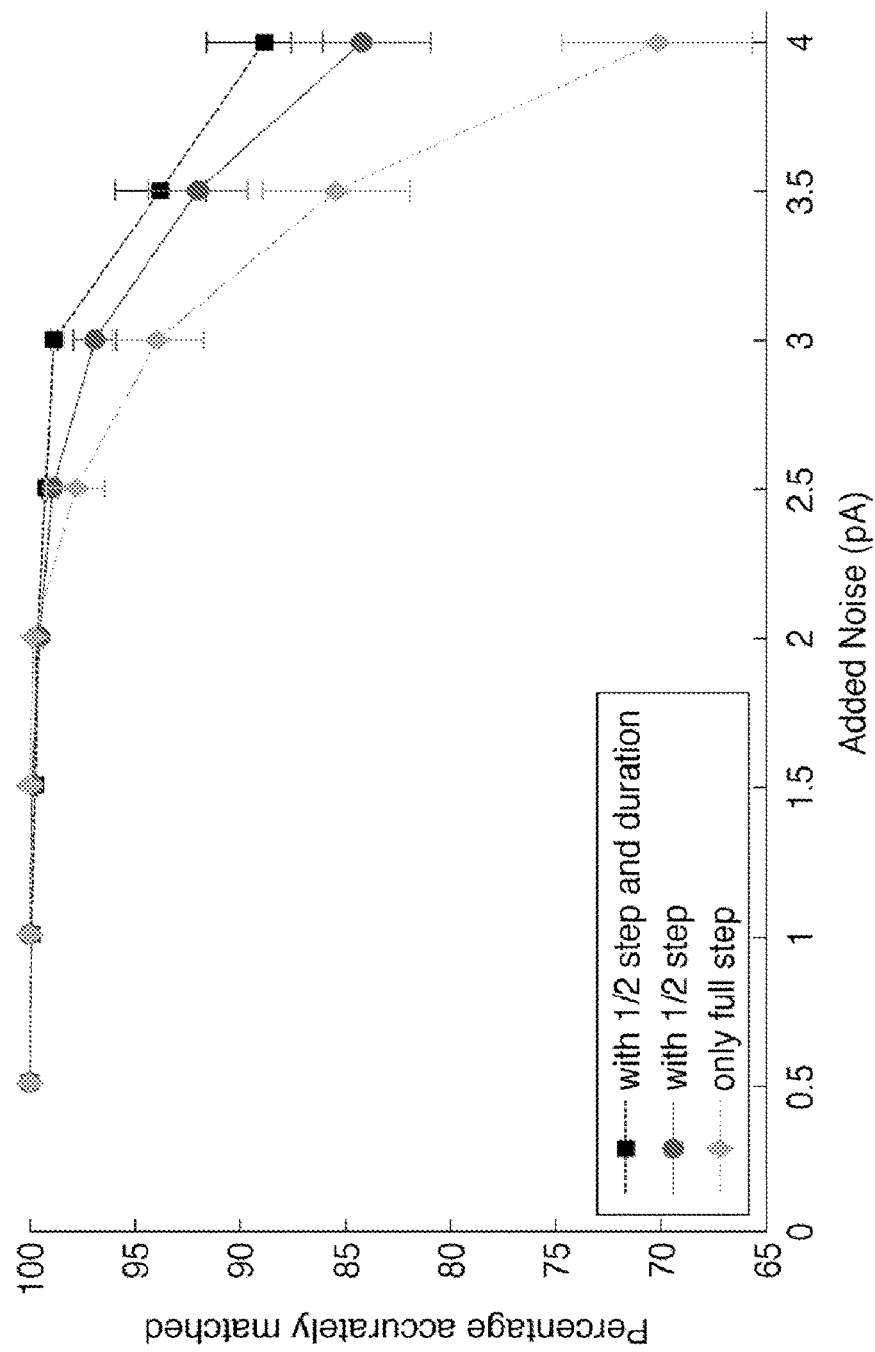

FIG. 7 depicts the expected accuracy of finding current patterns as a function of Gaussian shift, according to some embodiments. Diamonds depict a motor having a full nucleotide step. Circles depict a motor having a fractional translocation step, and squares depict a motor having a fractional translocational step combined with duration values.

Figure 8:
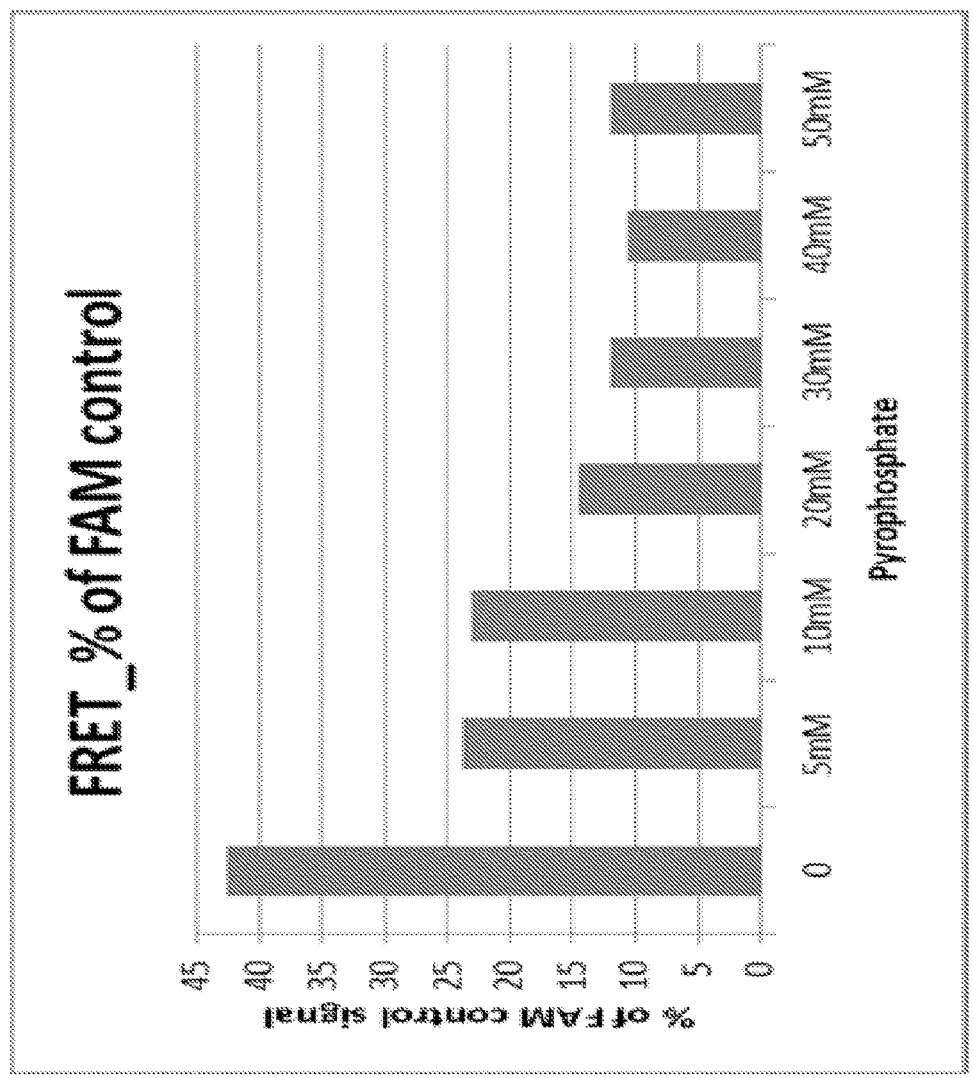

FIG. 8 shows the exemplary modulation of Hel308 helicase activity with varying concentrations of pyrophosphate, according to some embodiments.

Figure 9:
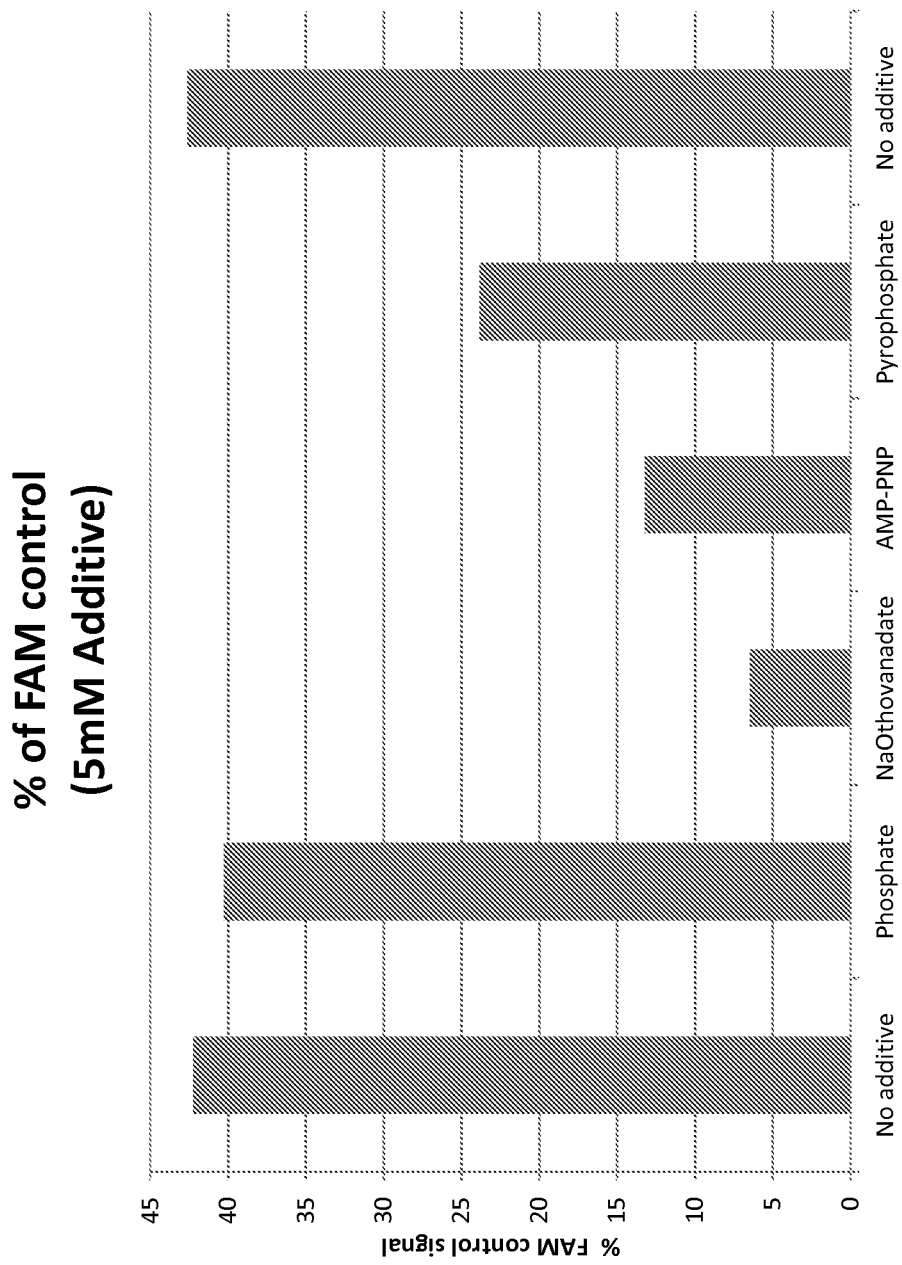

FIG. 9 shows the exemplary modulation of Hel308 helicase activity with the nucleotide inhibitor sodium orthovanadate and with the nucleotide analog adenosine 5'-(β,γ-imido)triphosphate lithium salt hydrate, according to some embodiments.

Figure 10:
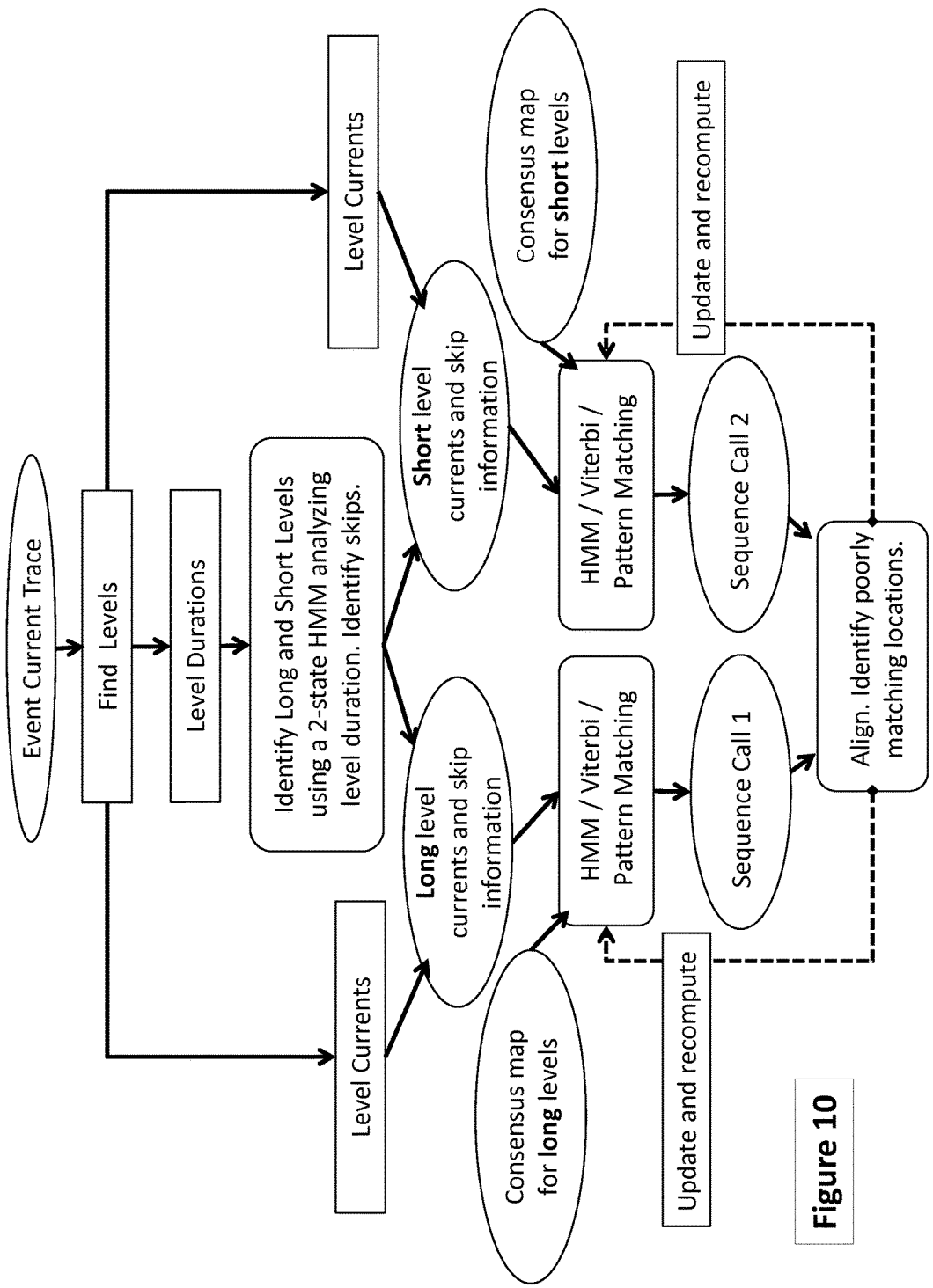

FIG. 10 depicts an example of a method to use information provided by the additional fractional translocation step that can be obtained from two independent sequence reads, using levels and level duration, according to some embodiments.

Figure 11:
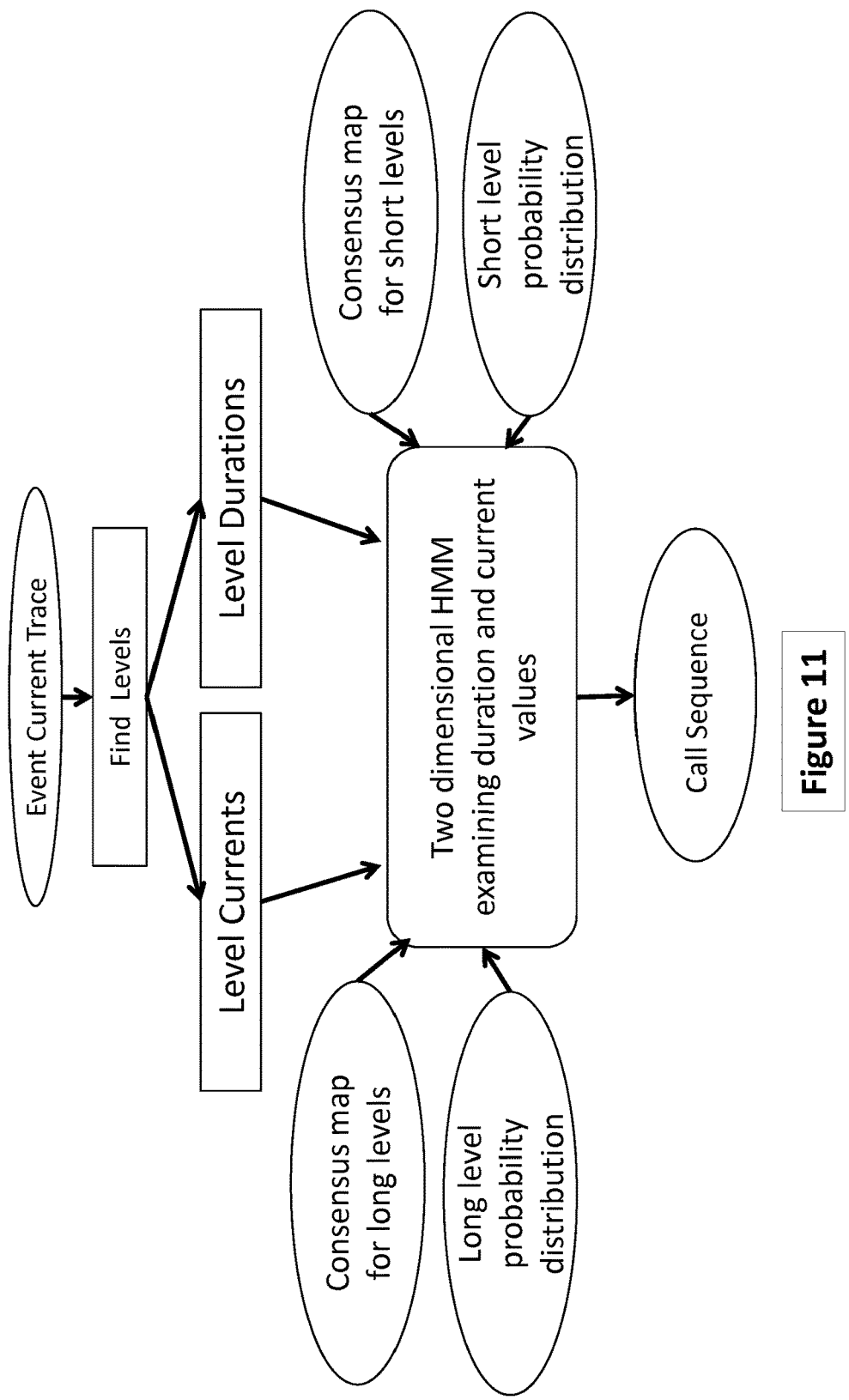

FIG. 11 depicts an example of a method to use information provided by the additional fractional translocation step that can be obtained from two concurrent sequence reads, using levels and level duration, according to some embodiments.

Figure 12:
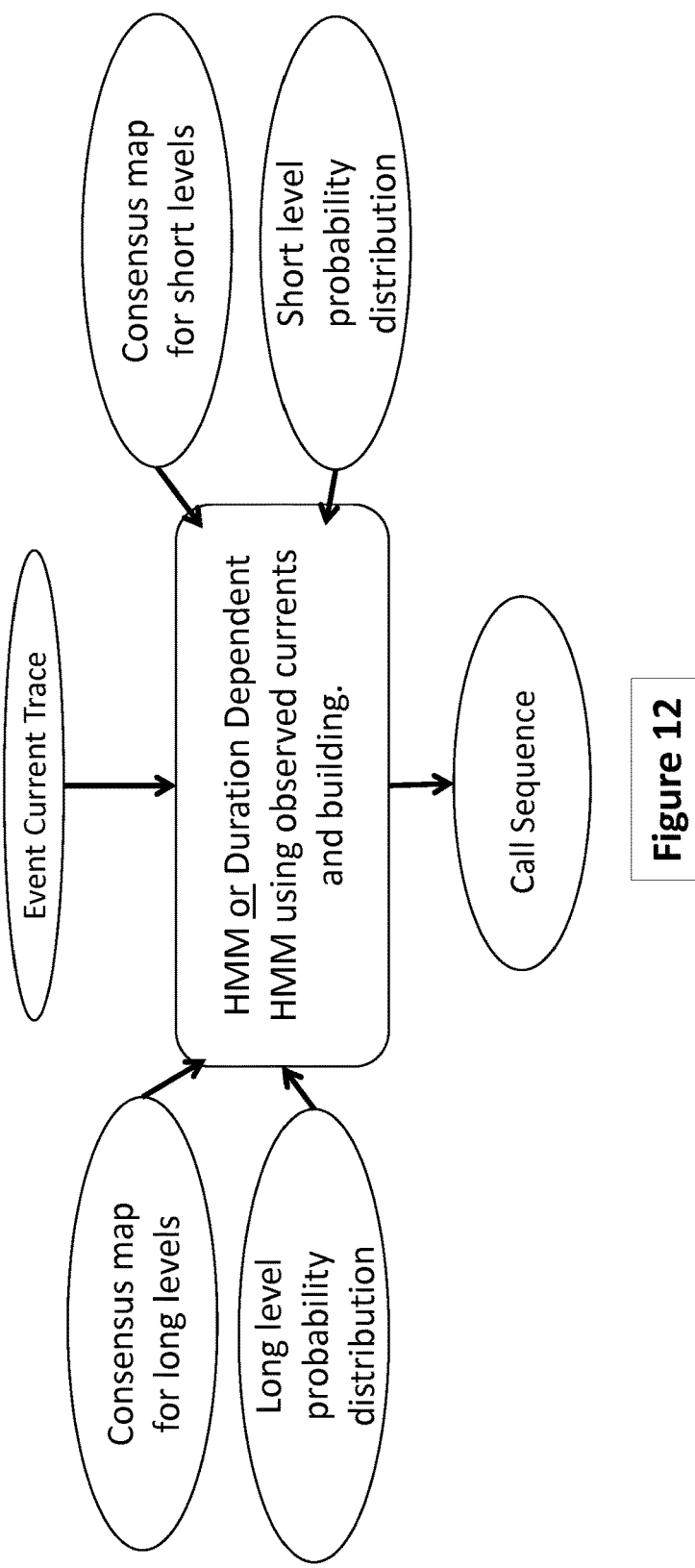

FIG. 12 depicts an example of a method to use information provided by the additional fractional translocation step using current traces, with or without duration information, according to some embodiments.

FIGS. 13A-13E show controlled polynucleotide translocation by Hel308 helicase based on a ternary polynucleotide complex with a Hel308 helicase 3' overhang binding site and cholesterol bilayer anchor, according to some embodiments. Filled circle (●) denotes a 5' phosphate. Filled diamond (♦) denotes a 3' cholesterol. Notched filled, semi-transparent circle denotes Hel308 helicase. Dotted lines indicate arbitrary length. Large grey arrows denote direction of polynucleotide motion (with or against the applied field) of the polynucleotide into or out of the pore. Large black arrows indicate direction of helicase translocation along polynucleotide, which is 3' to 5'. Pore (funnel-shaped conical object) sits in membrane (double horizontal lines).

FIGS. 14A-14D show controlled polynucleotide translocation by Hel308 helicase based on a ternary polynucleotide complex with a Hel308 helicase 3' overhang binding site and cholesterol bilayer anchor, according to some embodiments. Filled circle (●) denotes a 5' phosphate. Filled diamond (♦) denotes a 3' cholesterol. Notched filled, semi-transparent circle denotes Hel308 helicase. Dotted lines indicate arbitrary length. Large grey arrows denote direction of polynucleotide motion (with or against the applied field) of the polynucleotide into or out of the pore. Large black arrows indicate direction of helicase translocation along polynucleotide, which is 3' to 5'. Pore (funnel-shaped conical object) sits in membrane (double horizontal lines). Symbols are the same as in FIGS. 13A-13E. In this scheme, there is a single hybridization polynucleotide "i" that creates a 3' overhang on polynucleotide "ii" for Hel308 helicase to bind to, and also contains an optional cholesterol moiety.

Figure 15C:
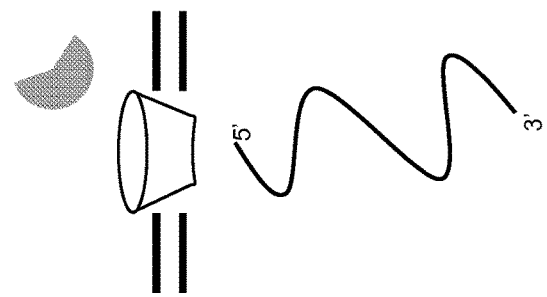
Figure 15B:
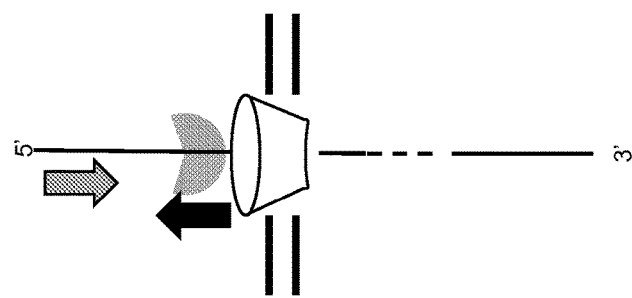
Figure 15A:
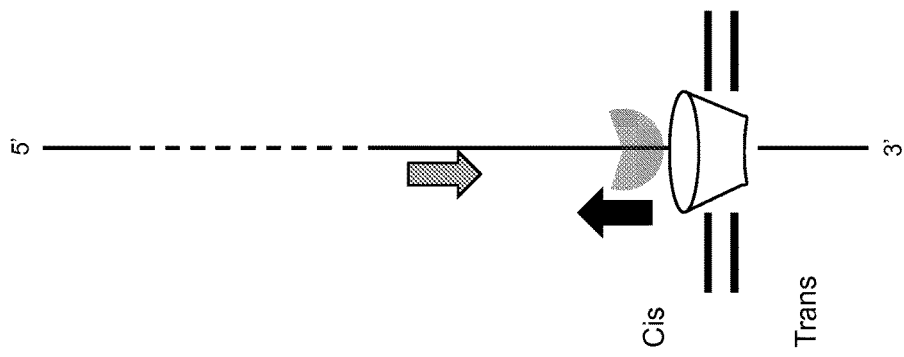

FIGS. 15A-15C show controlled translocation in the same direction as the gradient force, according to some embodiments. Notched filled, semi-transparent circle denotes Hel308 helicase. Dotted lines indicate arbitrary length. Large grey arrows denote direction of polynucleotide motion with the applied field into the pore. Large black arrows indicate direction of helicase translocation along polynucleotide, which is 3' to 5'. Pore (funnel-shaped conical object) sits in membrane (double horizontal lines).

FIG. 16 schematically illustrates various motifs (SEQ ID NOS 75-81, respectively, in order of appearance) that have been identified in the SF2 family, e.g., the DEAD-box (SEQ ID NO: 2) helicases, of which Hel308 is a member (adapted from Tuteja et al., "Unraveling DNA Helicases: Motif, structure, mechanism and function," European Journal of Biochemistry 271(10): 1849-1863 (2004)).

FIGS. 17A-17D show exemplary signals generated with Hel308 Mbu helicase, Hel308 Tga helicase, and phi29 polymerase translocation events using certain parameters, according to some embodiments.

Figure 18:
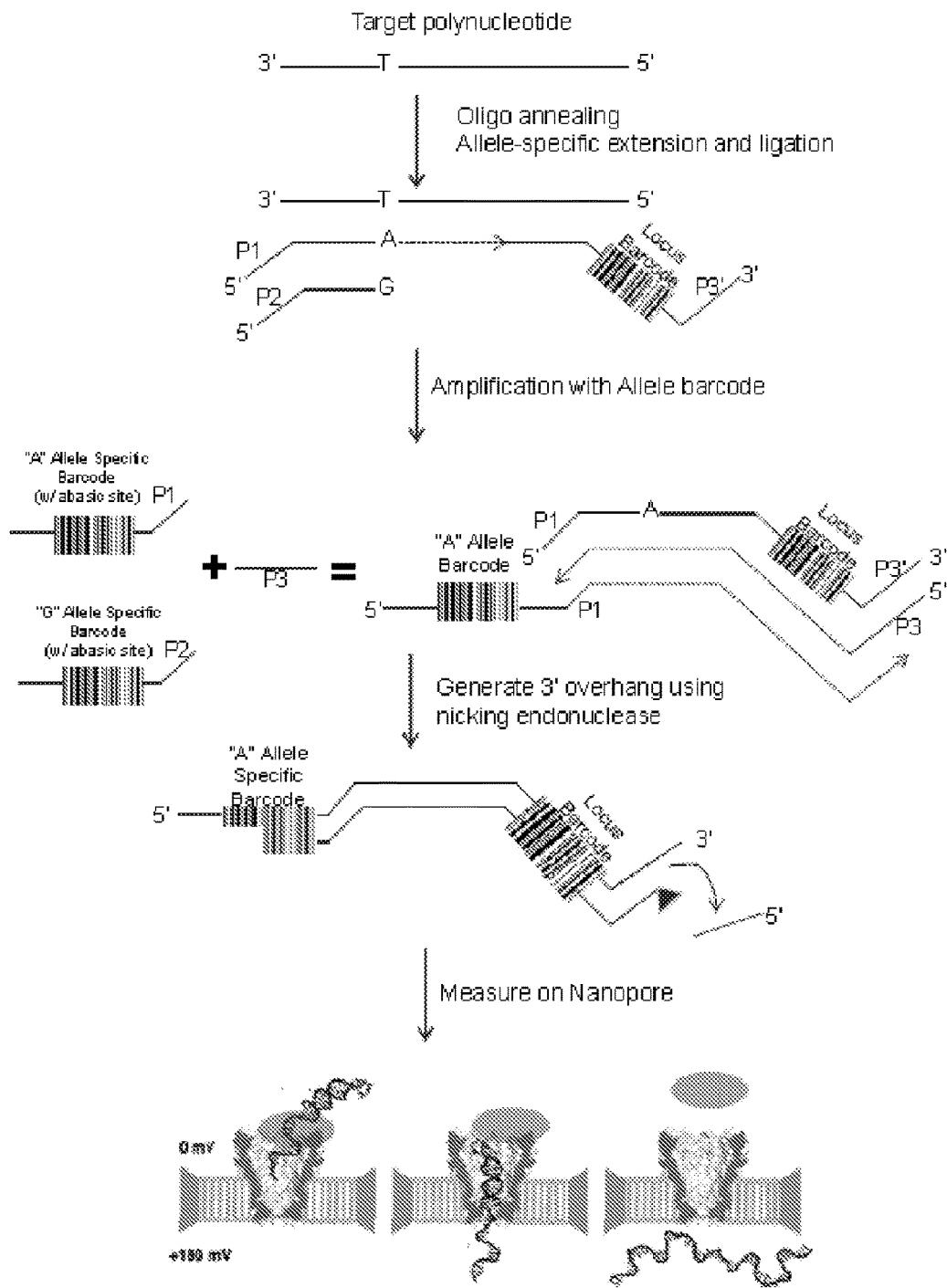

FIG. 18 schematically illustrates steps in an exemplary method for conducting assays using fractional translocation to characterize polynucleotide barcodes, according to some embodiments.

Figure 19B:
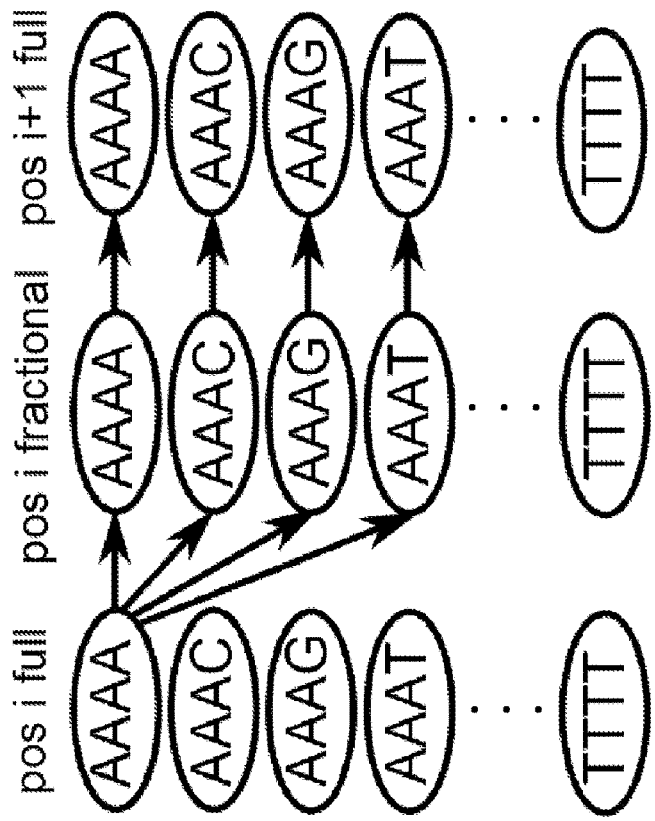
Figure 19A:
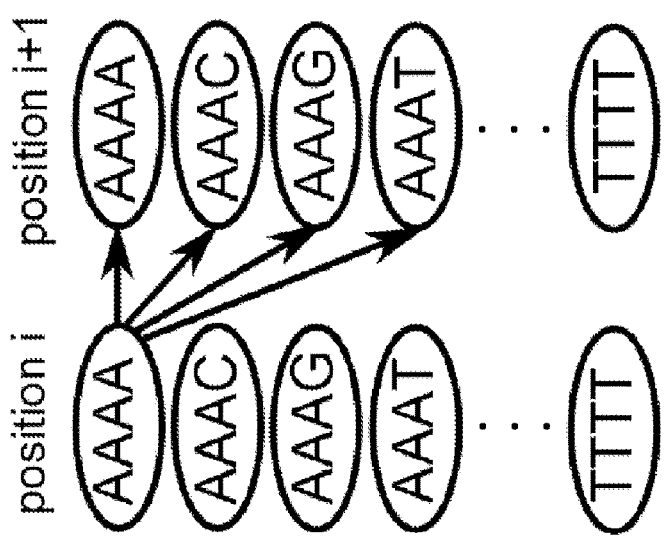

FIG. 19A schematically illustrates an aspect of an exemplary Hidden Markov Model (HMM) used to characterize a signal from single-step translocation of a polynucleotide through a pore.

FIG. 19B schematically illustrates an aspect of an exemplary HMM used to characterize signals from fractional step translocation of a polynucleotide through a pore using a Hel308 helicase, according to some embodiments.

Figure 20A:
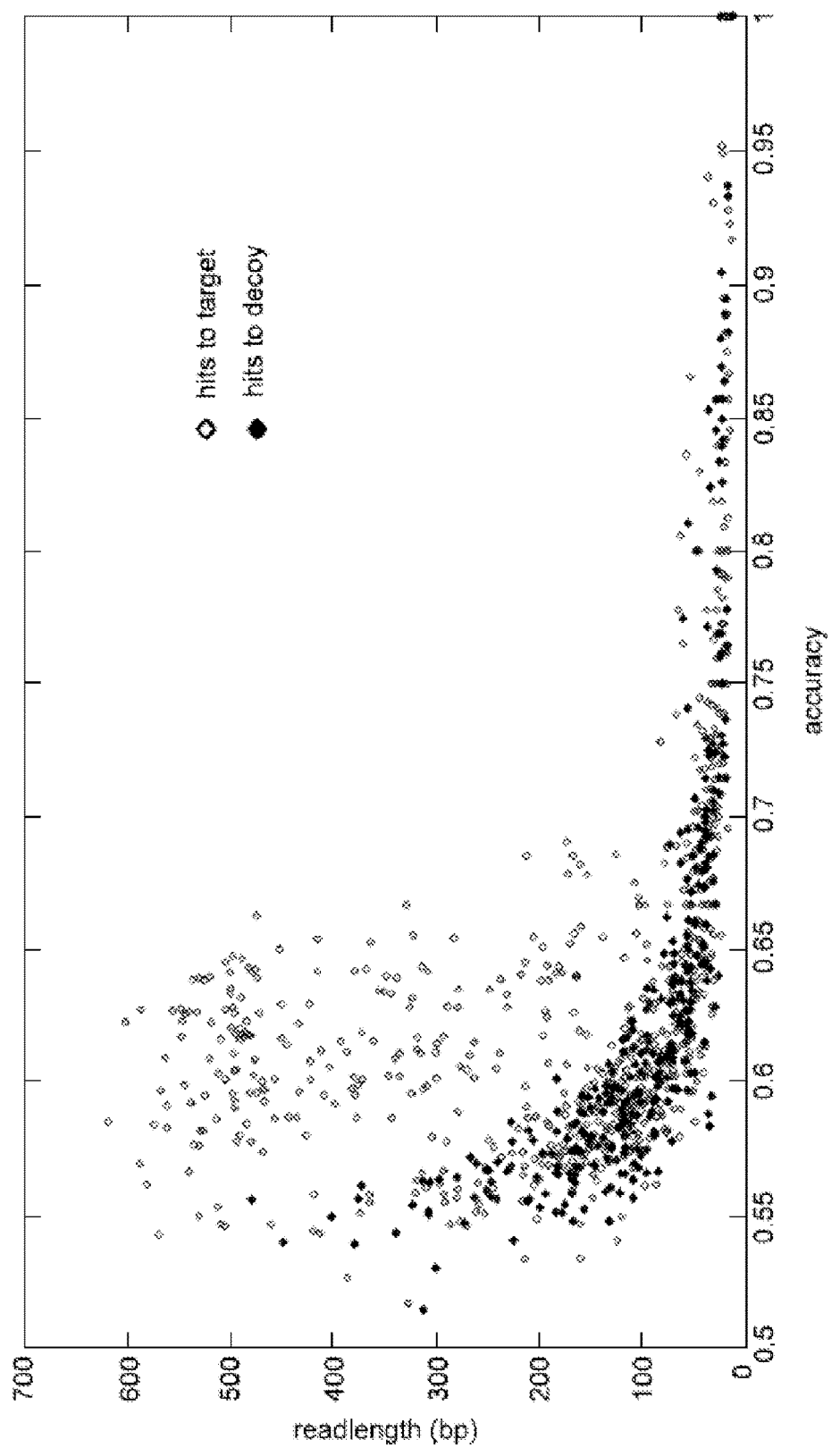

FIG. 20A illustrates exemplary results of de novo sequencing using fractional steps, according to some embodiments.

Figure 20B:
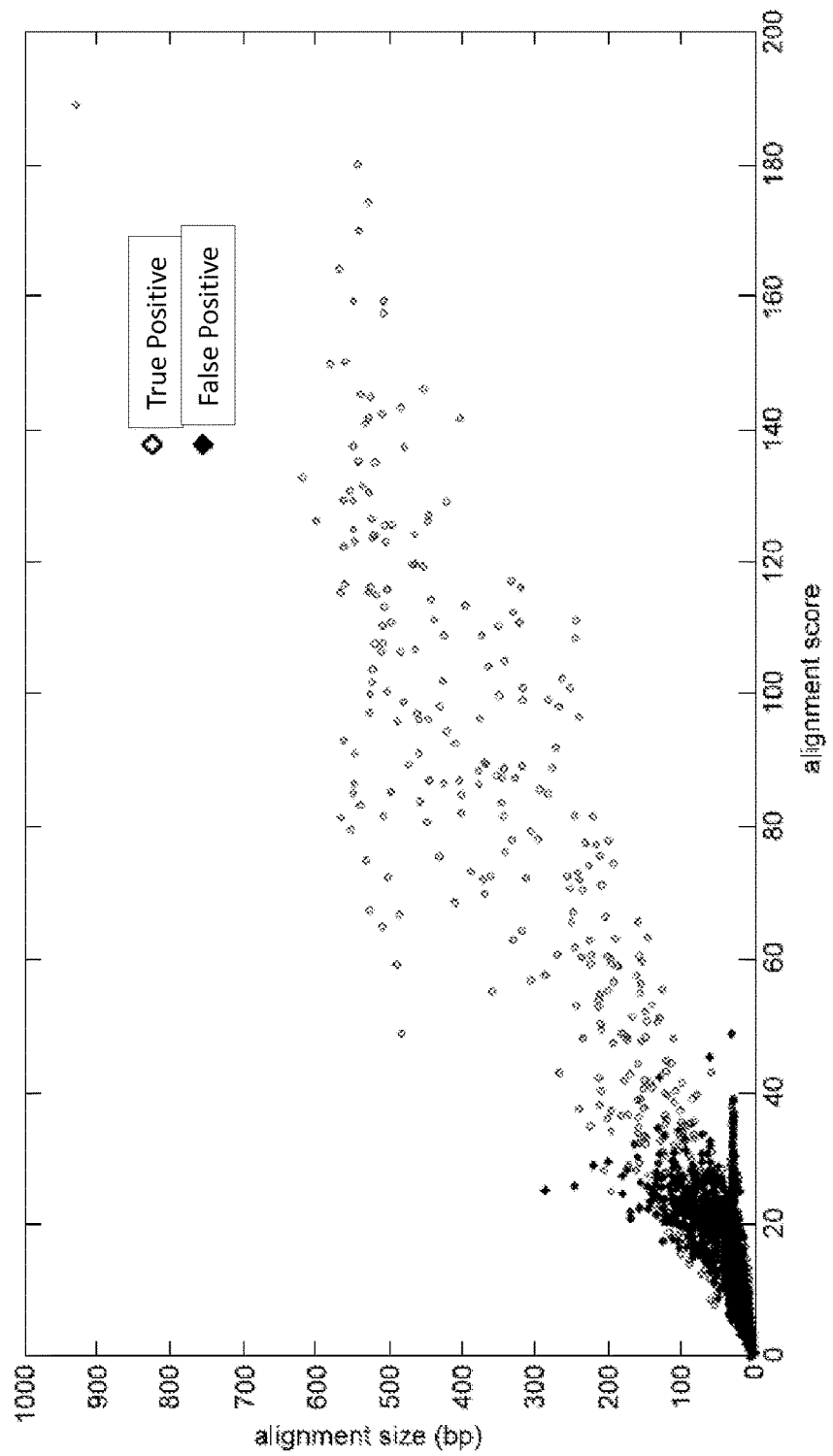
Figure 20C:
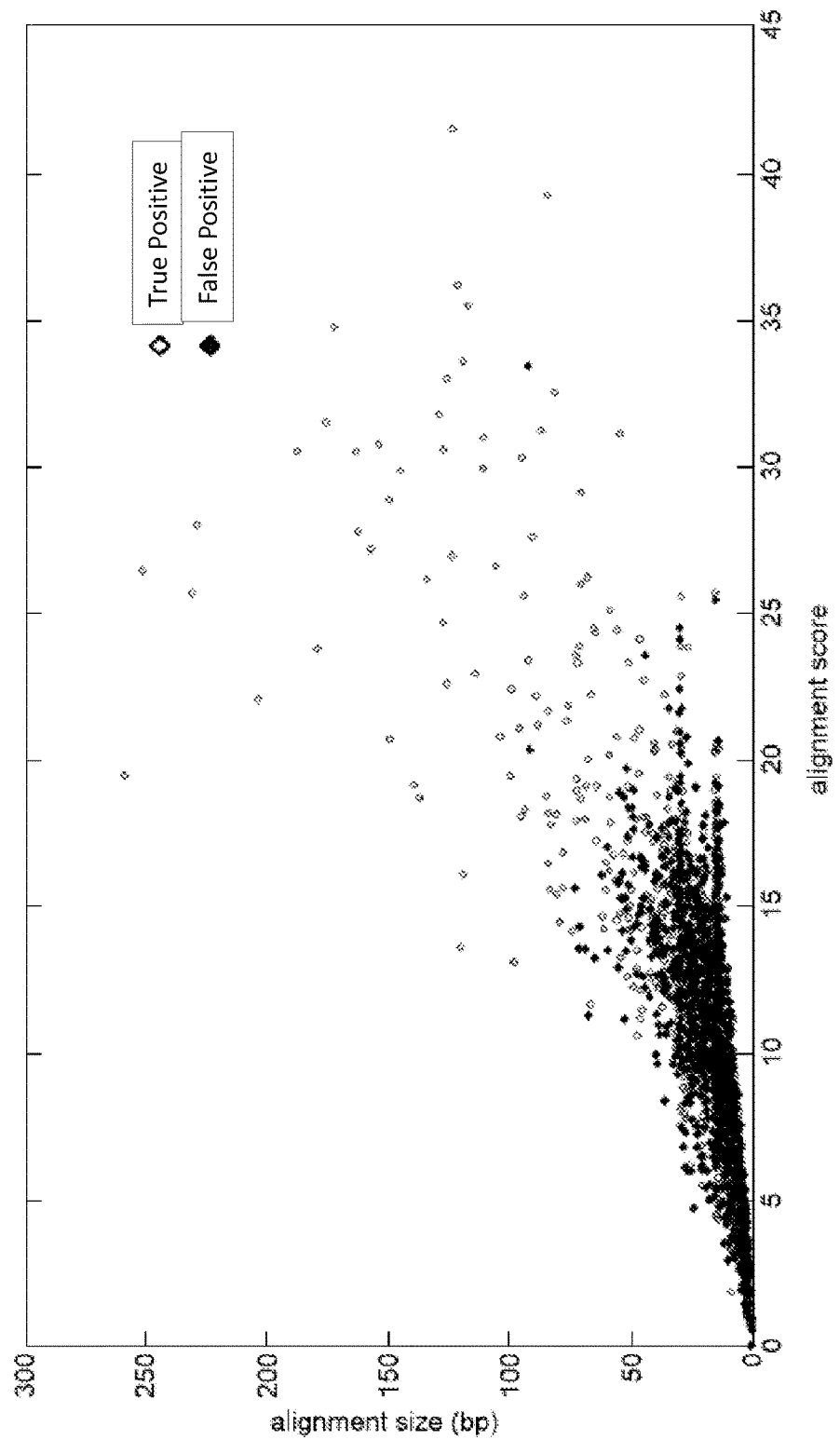

FIGS. 20B-20C illustrate exemplary results of pattern matching using fractional steps, according to some embodiments.

Figure 21A:
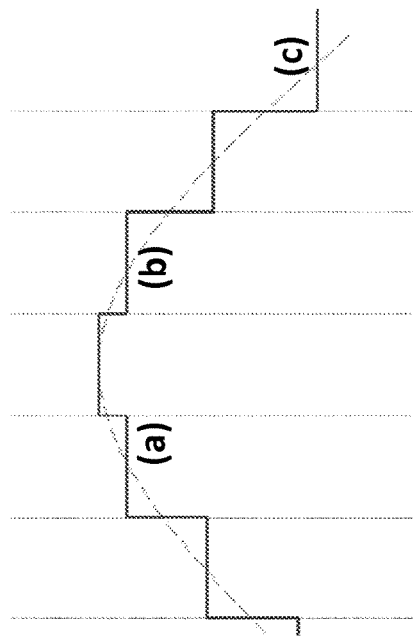
Figure 21B:
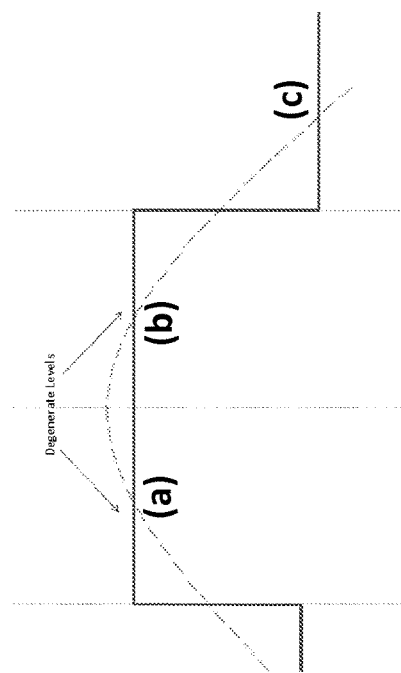
Figure 21C:
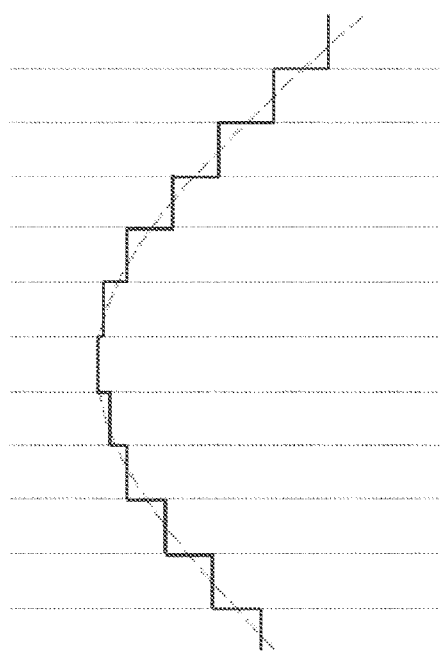

FIGS. 21A-21C schematically illustrate signals that can be generated as a function of time for different translocations of a polynucleotide through a pore, according to some embodiments.

FIGS. 22A-22D illustrate steps in illustrative methods for using information provided by fractional translocation of a polynucleotide through a pore, according to some embodiments.

Figure 23:
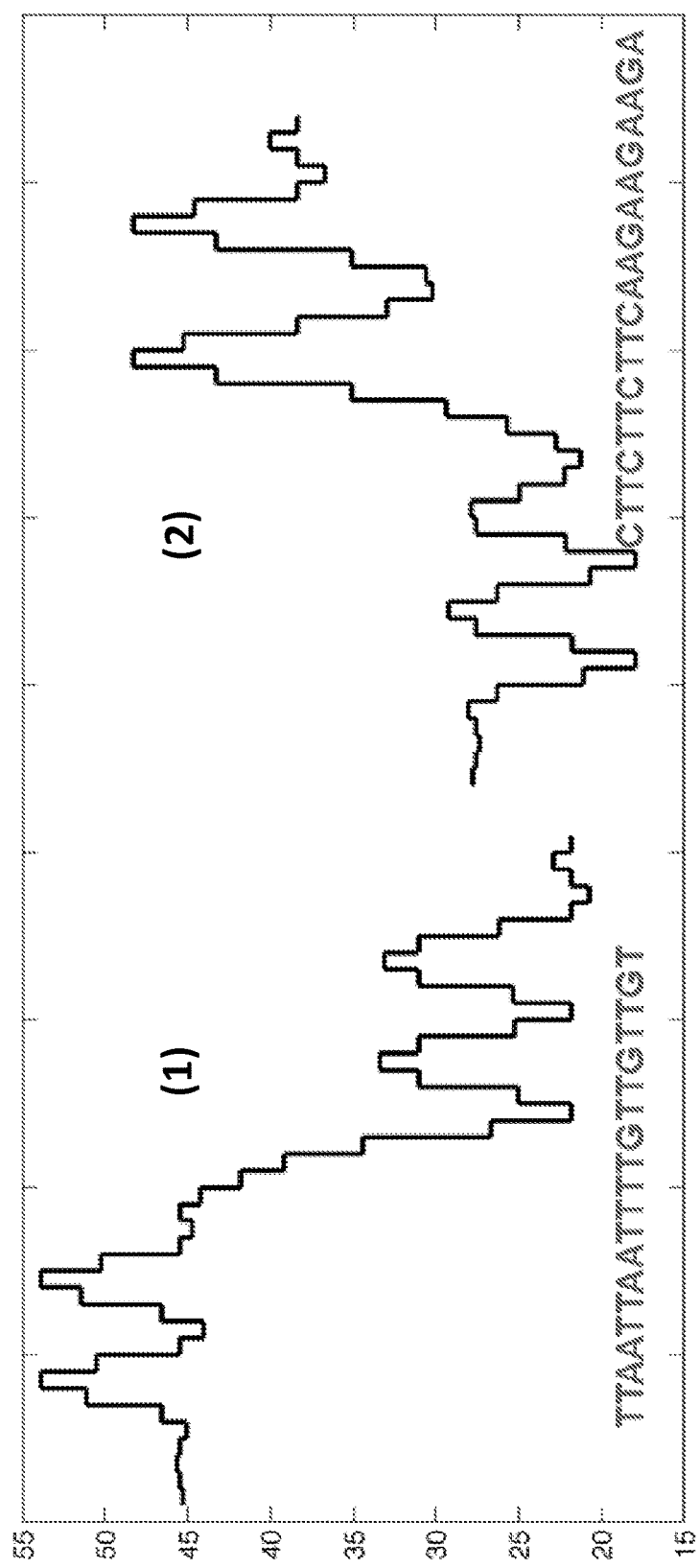

FIG. 23 illustrates exemplary simulated signals that can be generated as a function of time for a first illustrative polynucleotide sequence (SEQ ID NO: 89) and a second illustrative polynucleotide sequence (SEQ ID NO: 90) suitable for use as respective barcodes, according to some embodiments.

FIGS. 24A-24D illustrate exemplary simulated signals that can be generated as a function of time for first and second illustrative polynucleotide sequences suitable for use as respective barcodes, according to some embodiments.

Figure 25A:
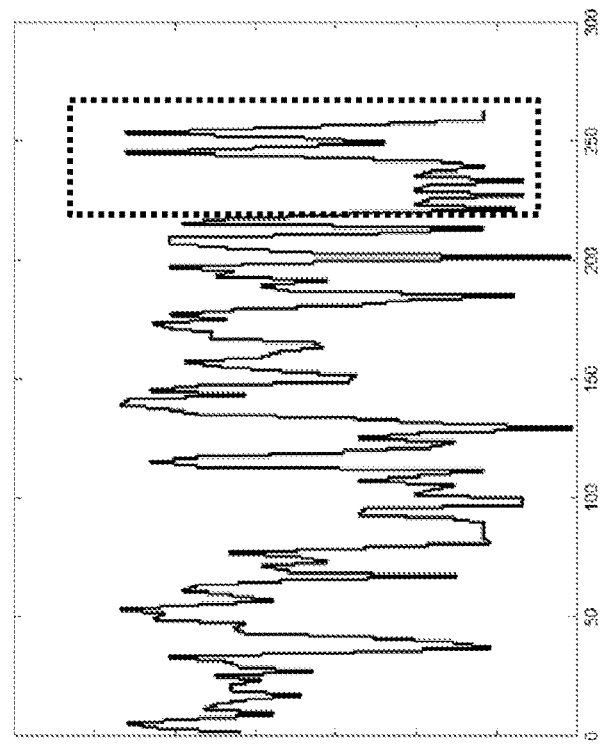
Figure 25B:
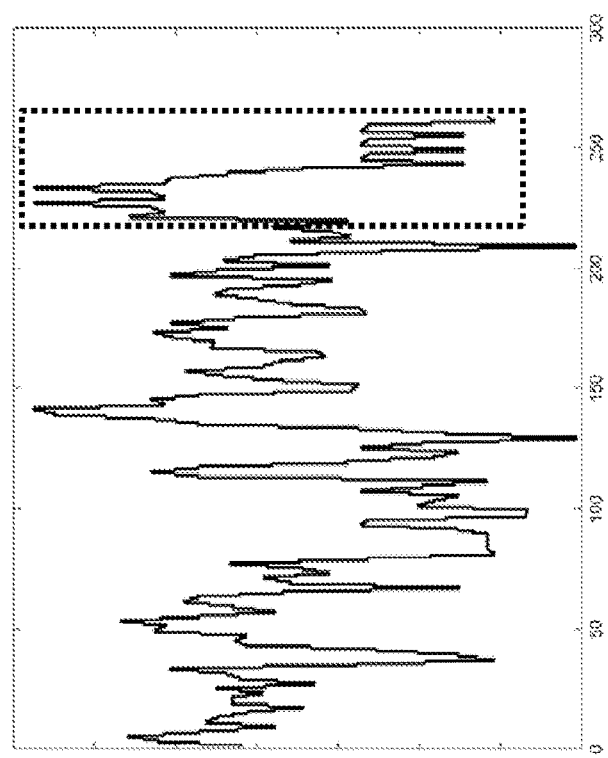
Figure 26B:
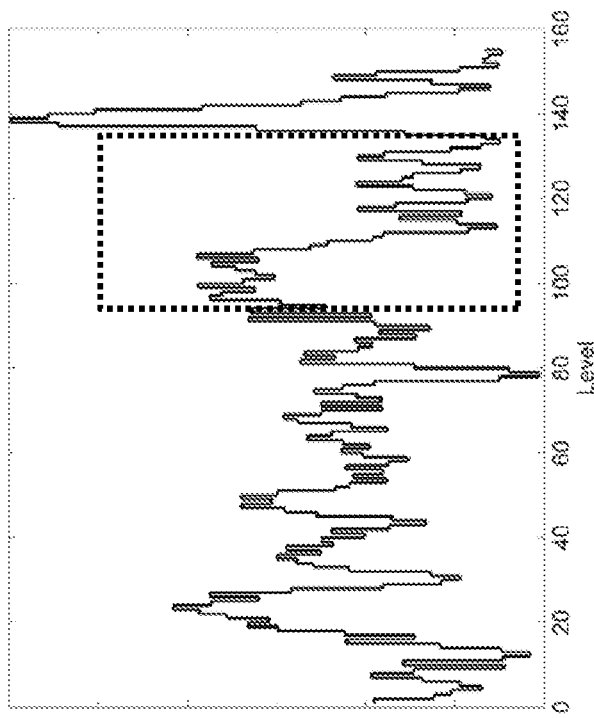
Figure 26A:
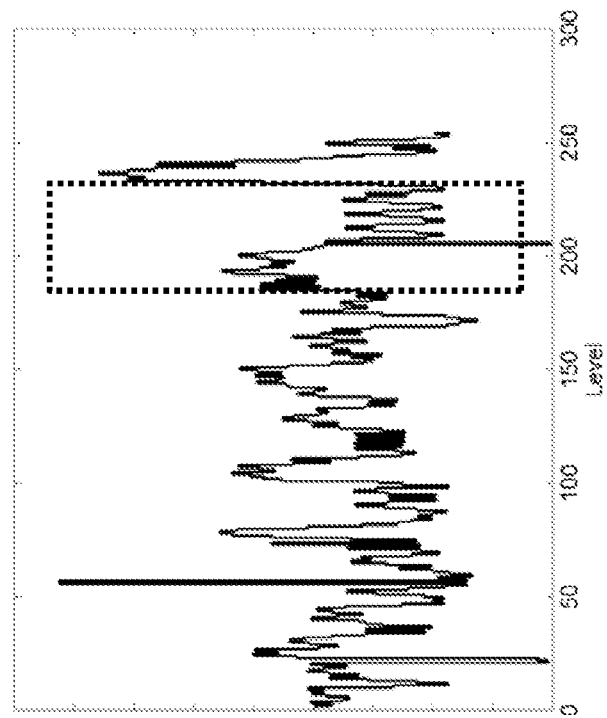
Figure 26C:
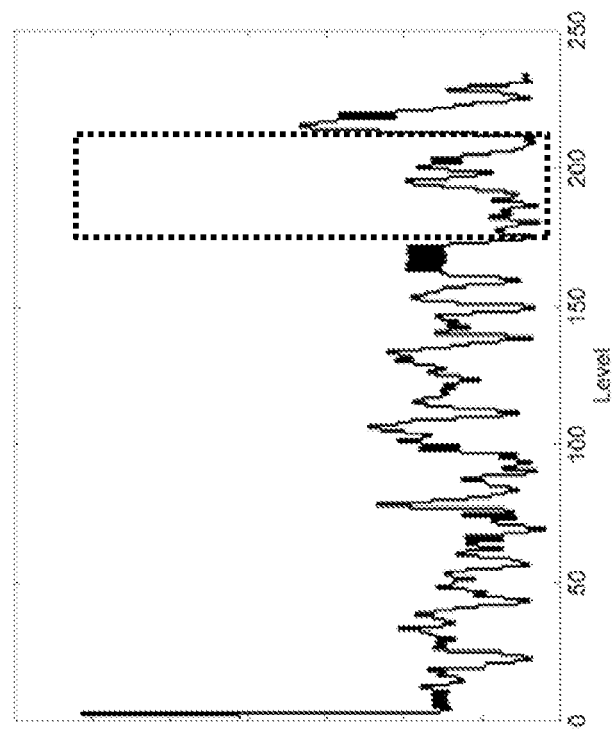
Figure 26D:
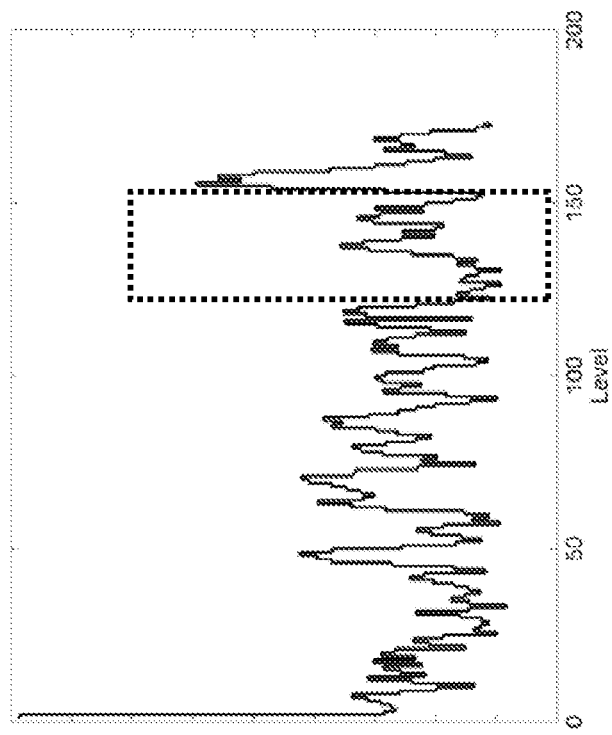

FIGS. 25A and 25B respectively illustrate exemplary simulated signals that can be generated as a function of time for first and second illustrative polynucleotide sequences suitable for use as respective barcodes, according to some embodiments.

FIGS. 26A-26D respectively illustrate exemplary measured signals that were generated as a function of time for first and second illustrative polynucleotide sequences suitable for use as respective barcodes, according to some embodiments.

DETAILED DESCRIPTION OF EMBODIMENTS

The present disclosure provides methods and compositions for characterizing a target polynucleotide, including, characterizing the sequence of a target polynucleotide, using one or more fractional translocation steps of the target polynucleotide's translocation through a pore.

In developing nanopore sequencing technology, a certain level of controlled translocation of a polynucleotide through a nanopore can be achieved under the guidance of a molecular motor, such as a helicase, translocase, or polymerase against (e.g., to resist the force generated by) an electric potential difference. Molecular motors can move the polynucleotide in a step-wise manner, normally with one or more nucleotides per step. This controlled ratcheting slows the polynucleotide translocation through the nanopore from a native rate of μsec/nucleotide to msec/nucleotide.

Figure 1A:
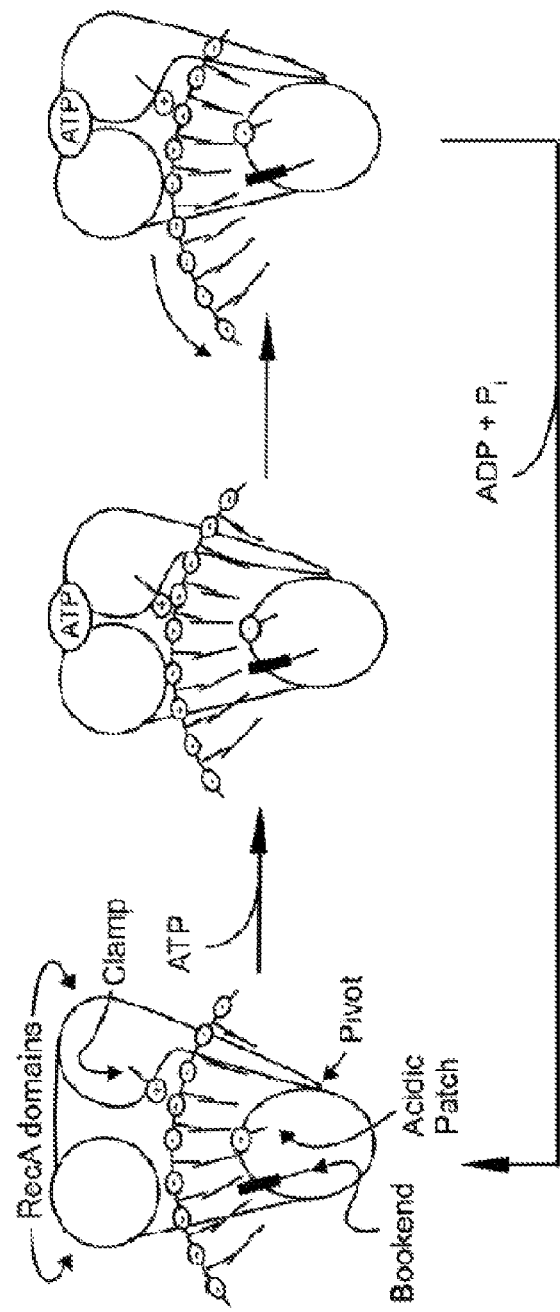
FIG. 1A shows the electrostatic inchworm model for the translocation of a polynucleotide by a helicase.

Molecular motors can use the energy of nucleotide hydrolysis to drive the translocation of the polynucleotides through the nanopore. A Helicase is an example in which ATP hydrolysis is the energy source for polynucleotide translocation. The cartoon in FIG. 1 illustrates the electrostatic inchworm model for the translocation of a polynucleotide through the helicase (see Frick et al., *Current Pharmaceutical Design*, 12:1315-1338 (2006)). In this model, a single stranded polynucleotide is held in a negatively charged cleft that separates the two RecA domains of a helicase from a third domain. In the absence of ATP, a bookend residue (e.g., Trp501 in HCV helicase) and a clamp residue (e.g., Arg393 in HCV helicase) prevent the single stranded polynucleotide from sliding through a cleft. Upon ATP binding, the RecA domains rotate, moving the positively charged Arg-clamp. The Arg-clamp attracts the negatively charged single stranded polynucleotide, which in turn clears the bookend. The single stranded polynucleotide is then repelled by the negatively charged cleft, and the single stranded polynucleotide translocates through the helicase until ATP is hydrolyzed. Therefore, in this exemplary model, the polynucleotide translocation through a helicase involves at least two steps: a first step where the helicase binds to ATP and undergoes a conformational change, and a second step where ATP is hydrolyzed and the polynucleotide translocates through the helicase.

Figure 1C:
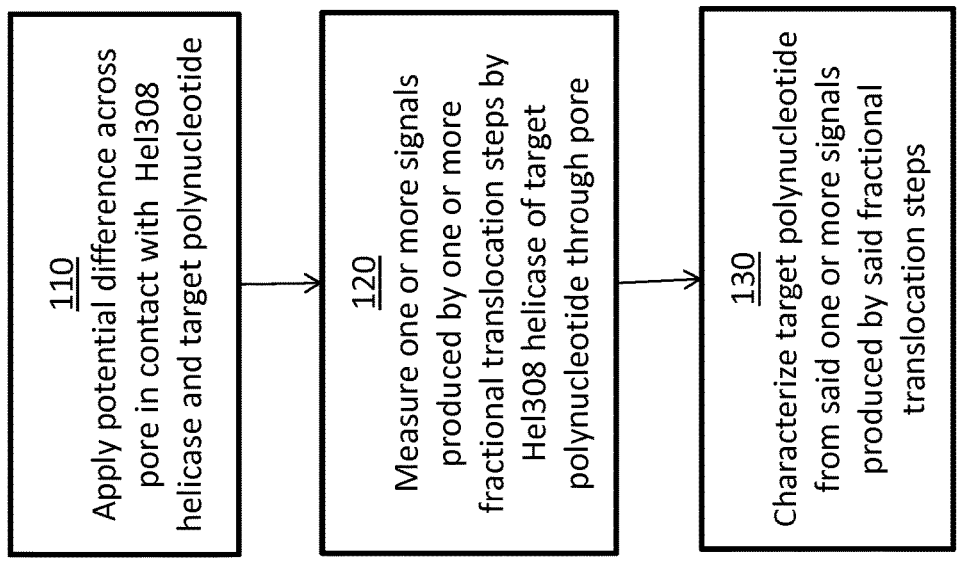
FIG. 1C schematically illustrates steps in an exemplary method for characterizing a target polynucleotide, according to some embodiments.
Figure 1B:
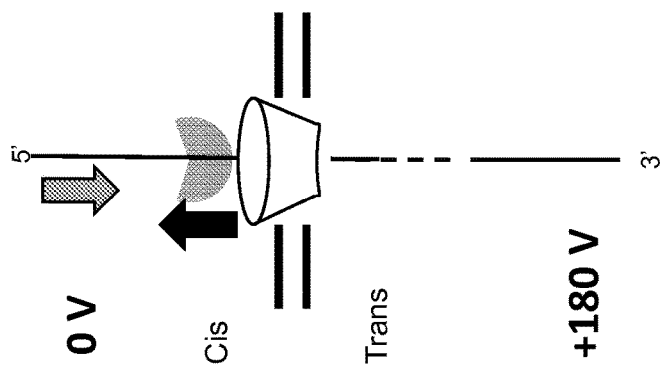
FIG. 1B schematically illustrates a first exemplary composition including a pore in contact with a Hel308 helicase, according to some embodiments.

FIG. 1B schematically illustrates a first exemplary composition including a pore in contact with a Hel308 helicase, according to some embodiments. In FIG. 1B, the notched filled, semi-transparent circle denotes a Hel308 helicase such as provided herein. The straight line denotes polynucleotide, and the dotted lines indicate an arbitrary length of the polynucleotide. The large grey arrow denotes direction of polynucleotide motion of the polynucleotide into or out of the pore, and the large black arrow indicates the direction of helicase translocation along polynucleotide, which is 3' to 5'. In the illustrated embodiment, the pore (funnel-shaped conical object) sits in a membrane (double horizontal lines), although other pore configurations suitably can be used. In the embodiment illustrated in FIG. 1B, the direction of polynucleotide motion can be with the applied field generated by a potential difference across the pore (illustratively an electrical potential difference of 180 V, although other potential differences suitably can be used). To make the direction of polynucleotide motion be agains the applied field generated by a potential difference across the pore, the orientation of the DNA can be flipped such as described in greater detail below with reference to FIGS. 15A-15C. As provided in greater detail herein, Hel308 helicases can cause fractional translocation of a polynucleotide through a pore, that can facilitate characterizing the nucleotide. For example, such fractional translocation can produce one or more signals, based upon which the polynucleotide can be characterized. The one or more signals can include an electrical signal such as described elsewhere herein, or can include an optical signal such as described elsewhere herein. Exemplary electrical signals can be a measurement selected from current, voltage, tunneling, resistance, potential, voltage, conductance, and transverse electrical measurement.

Illustratively, as the Hel308 helicase fractionally translocates the polynucleotide through the pore, the passage of different nucleotide bases within the pore can cause measurable changes in an electrical current through the pore; such an electrical current can be referred to as a "blockade" current. As described in greater detail herein, one or more characteristics of the polynucleotide, such as a sequence of the polynucleotide, a modification of the polynucleotide, a length of the polynucleotide, an identity of the polynucleotide, a source of the polynucleotide, or a secondary structure of the polynucleotide, or any suitable combination thereof, can be determined based on changes in the signal, e.g., based on changes in a current through the pore, which changes are based upon fractional translocation steps by the Hel308 helicase of the polynucleotide through the pore. In embodiments in which the pore is asymmetrical, e.g., includes a pore mouth with a greater diameter than a pore base (e.g., such as for MspA), the Hel308 helicase can be in contact with the pore mouth, such as illustrated in FIG. 1B. Such a configuration can be referred to as a "forward" configuration. More generally, a "forward configuration" can refer to the direction in which molecules can transit the pore in nature, regardless of whether the pore includes a wider pore mouth than pore base. Alternatively, "forward direction" can be arbitrarily defined.

FIG. 1C schematically illustrates steps in an exemplary method for characterizing a target polynucleotide, according to some embodiments. The method can include a step of applying a potential difference across a pore in contact with a Hel308 helicase and a target polynucleotide (step 110). In a manner analogous to that described further below with reference to FIGS. 13A-13E and 14A-14D, the translocation of the polynucleotide can be in a direction opposite of the applied force caused by the potential difference on the polynucleotide translocating through the pore, or the translocation of the polynucleotide can be in a direction with the applied force caused by the potential difference on the polynucleotide translating through the pore. Optionally, steps 110-130 can be repeated one or more times. The fractional translocation step (step 120) can include a first fractional translocation step of a full translocation cycle of the Hel308 helicase, or can include a second translocation step of a full translocation cycle of the Hel308 helicase.

As used herein, the term "polynucleotide" refers to deoxyribonucleic acid (DNA), ribonucleic acid (RNA) or an analogue thereof. A polynucleotide can be single stranded, double stranded, or contain both single stranded and double stranded sequence. The polynucleotide molecules can originate in double stranded DNA (dsDNA) form (e.g., genomic DNA, PCR and amplification products and the like), or can have originated in single stranded form as DNA (ssDNA) or RNA and can be converted to dsDNA form and vice-versa.

The precise sequence of a polynucleotide molecule can be known or unknown. The following are exemplary examples of polynucleotide: a gene or gene fragment (for example, a probe, primer, EST or SAGE tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

A polynucleotide can be composed of nucleotides or nucleotide analogues. A nucleotide typically contains a sugar, a nucleobase, and at least one phosphate group. A nucleotide can be abasic (i.e., lacking a nucleobase). Nucleotides include deoxyribonucleotides, modified deoxyribonucleotides, ribonucleotides, modified ribonucleotides, peptide nucleotides, modified peptide nucleotides, modified phosphate sugar backbone nucleotides and mixtures thereof. Examples of nucleotides include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP). Nucleotide analogues that include a modified nucleobase can also be used in the methods described herein. Exemplary modified nucleobases that can be included in a polynucleotide, whether having a native backbone or analogue structure, include, for example, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "pore" is intended to mean a structure extending across a barrier, such as a membrane, that permits ions and/or water soluble molecules to cross from one side of the barrier to the other side of the barrier. Pores can, but need not, occur in a membrane. For example, a barrier that normally inhibits passage of ions or water soluble molecules can include a pore structure that extends across the barrier to permit passage of the ions or water soluble molecules from one side of the barrier to the other side of the barrier. Pores (e.g., transmembrane pores) include, for example, biological pores, solid state pores, and biological and solid state hybrid pores.

As used herein, the term "biological pore" is intended to mean a pore, which is made from materials of biological origin, extending across a barrier, including for example a membrane that permits ions and/or water soluble molecules to cross from one side of the barrier to the other side of the barrier. Biological origin refers to material derived from or isolated from a biological environment such as an organism or cell, or a synthetically manufactured version of a biologically available structure. Biological pores include, for example, polypeptide pores and a polynucleotide pores.

As used herein, the term "polypeptide pore" is intended to mean one or more polypeptides that extends across a barrier such as a membrane for example, and permits ions and/or water soluble molecules to flow from one side of the barrier to the other side of the barrier. A polypeptide pore can be a monomer, a homopolymer or a heteropolymer. Structures of polypeptide pores include, for example, an α-helix bundle pore and a β-barrel pore as well as all others well known in the art. Exemplary polypeptide pores include α-hemolysin, *Mycobacterium smegmatis* porin A, gramicidin A, maltoporin, OmpF, OmpC, PhoE, Tsx, F-pilus, SP1 (Wang et al., *Chem. Commun.*, 49:1741-1743, 2013) and mitochondrial porin (VDAC)XX, Tom40, (U.S. Pat. No. 6,015,714 and Derrington et al., *Proc. Natl. Acad. Sci. USA,* 107:16060 (2010)). "*Mycobacterium smegmatis* porin A (MspA)" is a membrane porin produced by Mycobacteria, allowing hydrophilic molecules to enter the bacterium. MspA forms a tightly interconnected octamer and transmembrane beta-barrel that resembles a goblet and contains a central channel/pore.

As used herein, the term "polynucleotide pore" is intended to mean one or more polynucleotides that extends across a barrier such as a membrane for example, and permits ions and/or water soluble molecules to flow from one side of the barrier to the other side of the barrier. A polynucleotide pore can include, for example, a polynucleotide origami.

As used herein, the term "solid state pore" is intended to mean a pore, which is made from materials of non-biological origin, extending across a barrier such as a membrane for example, that permits ions and/or water soluble molecules to cross from one side of the barrier to the other side of the barrier. Solid-state is intended to mean materials that are not of biological origin. A solid-state pore can be of inorganic or organic materials. Solid state pores include, for example, silicon nitride pores, silicon dioxide pores, and graphene pores.

As used herein, the term "biological and solid state hybrid pore" is intended to mean a hybrid pore, which is made from materials of both biological and non-biological origins, extending across a barrier such as a membrane for example, that permits hydrated ions and/or water soluble molecules to cross from one side of the barrier to the other side of the barrier. Materials of biological origin are defined above and include, for example, polypeptide and polynucleotide. A biological and solid state hybrid pore includes, for example, a polypeptide-solid state hybrid pore and a polynucleotide-solid state pore.

As used herein, the term "helicase" is intended to mean a polynucleotide binding protein having an activity that utilizes energy derived from the hydrolysis of, for example, a nucleotide triphosphate (NTP) to unwind the double-stranded polynucleotides. Unwinding a double stranded polynucleotide results in the translocation of the polynucleotide along its active site. The term is intended to include polypeptides having activities that translocate or bind single stranded polynucleotides as well as partially double stranded polynucleotides. A "Hel308 helicase" is an ATP-dependent DNA helicase and a superfamily 2 helicase. The founding member, Mus308 from *Drosophila melanogaster*, consists of an N-terminal SF2 helicase domain fused to a C-terminal DNA polymerase domain. The Hel308 in *Homo sapiens*, functions as a SF2, 3' to 5' DNA helicase with limited processivity. Hel308 helicase is used interchangeably with ski2-like helicase. Useful homologs can consist only of a helicase domain (i.e., absent a polymerase domain). The helicase-only homologs are present in metazoans and archaea. Metozoan example are human Hel308 and Mus301. Archaea examples are Tga and Mbu.

Unless otherwise explicitly described herein, the term "Hel308 helicase substrate" as used herein is intended to mean a nucleotide or nucleotide analogue that is capable of being hydrolyzed by helicase and provides energy to unwind a double-stranded or partially double-stranded polynucleotide or translocate a single stranded polynucleotide. A common substrate for a Hel308 helicase includes ATP. However, other Hel308 helicase substrates within the meaning of the term include nucleotides other than ATP such as those described previously and nucleotide analogues that are capable of being hydrolyzed by a Hel308 helicase. Exemplary analogs include, for example, phosphate analogs such as gamma thiol analogs, alpha thiol analogs and the like, ATPγS, ATPαS, AMP, PNP, ApCpp, AppCp, and AppNHp.

As used herein, the term "translocates" or "translocation" is intended to mean the movement of a target polynucleotide along (or within) a helicase and/or a pore.

As used herein, the term "full translocation cycle" when used in reference to a helicase is intended to mean a complete interval for the movement of a unit of one or more nucleotides of a target polynucleotide along the helicase and/or pore. The complete interval can begin at any point in the cycle, and can, for example, include the interval depicted in FIG. 3 that includes the steps of ATP binding and hydrolysis of the bound ATP. Accordingly, a full translocation cycle as used herein can start at nucleotide substrate binding and end at nucleotide substrate hydrolysis. A full translocation cycle similarly can start at nucleotide substrate hydrolysis and end at nucleotide binding. Similarly, a full translocation cycle can start at any point in between the two starting points exemplified above so long as it concludes at the step just prior to the starting point.

As used herein, the term "fractional translocation step" when used in reference to a helicase is intended to mean a detectable event that characterizes a portion of a full translocation cycle. For example, a fractional translocation step can be a partial translocation of a unit of one or more nucleotides of a target polynucleotide along the helicase and/or pore. In particular embodiments, a fractional step can occur between ATP binding and hydrolysis when a conformational change occurs. The conformational change effectively divides a full translocation cycle into at least two partial or fractional translocation steps. A fractional step may or may not be concomitant with nucleic acid movement along the helicase.

As used herein, the term "signal" is intended to mean an indicator that represents information. Signals include, for example, an electrical signal and an optical signal.

As used herein, the term "electrical signal" is intended to mean an indicator of an electrical quality that represents information. The indicator can be, for example, current, voltage, tunneling, resistance, potential, voltage, conductance; and transverse electrical measurement. An "electronic current" refers to a flow of electric charge. Electric charge flows when an electric potential difference is applied across the pore.

As used herein, the term "optical signal" is intended to mean an indicator of an optical quality that represents information. Optical signals include, for example, a fluorescence signal and a Raman signal.

As used herein, the term "homology" is intended to mean a sequence similarity between two polynucleotides or between two polypeptides. Similarity can be determined by comparing a position in each sequence, which can be aligned for purposes of comparison. A degree of similarity between sequences is a function of the number of matching or homologous positions shared by the sequences. The alignment of two sequences to determine their percent sequence similarity can be done using software programs known in the art, such as, for example, those described in Ausubel et al., *Current Protocols in Molecular Biology*, John Wiley and Sons, Baltimore, Md. (1999). Preferably, default parameters are used for the alignment, examples of which are set forth below. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

The present disclosure provides a method of characterizing a target polynucleotide. The method includes: (a) applying a potential difference across a pore in contact with a Hel308 helicase and a target polynucleotide; (b) measuring one or more signals produced by one or more fractional translocation steps of the target polynucleotide through the pore, and (c) characterizing the target polynucleotide from the electrical signal of the fractional translocation steps.

As described herein, polynucleotides include deoxyribonucleic acid (DNA), ribonucleic acid (RNA) or analogues thereof. A polynucleotide will generally contain phosphodiester bonds, although in some cases, a polynucleotide can also have alternate backbones, including, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphosphoroamidite linkages (see Eckstein, *Oligonucleotides and Analogues: A Practical Approach*, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996)). Other polynucleotides include those with positive backbones (Denpcy, et al., *Proc. Natl. Acad. Sci. USA*, 92:6097 (1995)); non-ionic backbones (U.S. Pat. Nos. 5,386,023, 5,637,684, 5,602,240, 5,216,141, and 4,469,863; Kiedrowshi, et al., *Angew. Chem. Int. Ed. English*, 30:423 (1991); Letsinger, et al., *J. Am. Chem. Soc.*, 110:4470 (1988); Letsinger, et al., *Nucleosides & Nucleotides*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. The polynucleotide molecules containing one or more carbocyclic sugars are also included within the definition of polynucleotide (see Jenkins, et al., *Chem. Soc. Rev.*, (1995) pp. 169-176). Several polynucleotides are described in Rawls, C & E News, Jun. 2, 1997, page 35.

The target polynucleotide can be characterized in accordance with the methods of the present disclosure. Exemplary polynucleotide include, for example, a gene or gene fragment (for example, a probe, primer, EST or SAGE tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

A target polynucleotide used in particular embodiments herein can be of any of a variety of lengths, typically being of sufficient length to extend through a pore and be bound on one side of the pore by a helicase. In general, such a length is at least about 10 nucleotides long. However, numerous lengths longer than this minimum size are applicable for characterization using the methods of the present disclosure. Exemplary lengths of a useful polynucleotide include, for example, at least about 10, 20, 30, 40, 50, 60, 70, 80, 90, 100, 150, 200, 300, 400, 500, 1,000, 5,000, or 10,000, 100,000 nucleotides or longer. Alternatively or additionally, the length can be no longer than 1,000,000, 100,000, 10,000, 1,000, 100 nucleotides or fewer. Accordingly, a polynucleotide that can be sequenced using the methods of the present disclosure can range, for example, from short polynucleotides, fragments, cDNA, genes and genomic fragments.

The polynucleotide used in the methods of the present disclosure can be single stranded, double stranded, or contain both single stranded and double stranded sequence. The polynucleotide molecules can originate in a double stranded polynucleotide (e.g., dsDNA) and can be converted to a single stranded polynucleotide. The polynucleotide molecules can also originate in a single stranded polynucleotide (e.g., ssDNA, ssRNA), and the ssDNA can be converted into a double stranded polynucleotide. In some aspects of the present disclosure, the double stranded or the partially double stranded polynucleotide includes a blocking polynucleotide. Such polynucleotide species can include those exemplified in connection with FIGS. 13A-13E, 14A-14D, and 15A-15C herein. Exemplary modes of translocating polynucleotides through a pore are set forth in WO 2013/057495.

In some aspects, the present disclosure provides a method of characterizing a target polynucleotide. The method includes identifying: (1) the sequence of the target polynucleotide; (2) the modification of the target polynucleotide; (3) the length of the target polynucleotide; (4) the identity of the target polynucleotide; (5) the source of the target polynucleotide, or (6) the secondary structure of the target polynucleotide.

The sequence of the polynucleotide refers to the primary structure of the polynucleotide or the sequential order of the nucleotides in a polynucleotide molecule. The sequence of the polynucleotide can be determined by characterizing the nucleotides in the target polynucleotide using the signals produced by fractional translocation steps of the target polynucleotide through the pore.

A modification of the polynucleotide refers to any covalent or non-covalent modification of a nucleotide in the polynucleotide, including, for example, nucleotide methylation or hydroxymethylation. Indeed, modifications can include any number of nucleotide analogs that can be incorporated into a polynucleotide strand, including, for example, 8-oxoguanosine, 5-formylcytosine and 5-carboxylcytosine and others set forth elsewhere herein. The modification of a nucleotide provides a corresponding change in signal. Accordingly, one or modifications of a polynucleotide can be determined by characterizing the modified nucleotides in the target polynucleotide using the signals produced by the fractional translocation steps of the target polynucleotide through the pore.

The length of the polynucleotide refers to the numbers of nucleotides in the polynucleotide. The length of the polynucleotide can be determined by, for example, determining the primary sequence of the polynucleotide or by measuring its dwell time in a pore or by counting the number of nucleotides that pass through the pore. In some embodiments, dwell time corresponds to the duration of transient change of current. A transient change can be considered any deviation in the pore current, due to the presence of a polynucleotide. In some embodiments, the deviation results in a reduction of the magnitude of the current. This reduction can generally be at most 95%, 90%, 80%, 60%, 50%, 40%, 30%, 20% or 10% or less of the original unblocked pore current. Alternatively or additionally, the reduction can be at least 10%, 20%, 30%, 40%, 50%, 60%, 70%, 80%, or 90% or more. In some cases, the polynucleotide can result in the increase of current magnitude relative to the unblocked pore. The relationship between the duration and the length of the polynucleotide can be described by a reproducible mathematical function that depends on the experimental condition used. The function can be a linear or non-linear (e.g., sigmoidal or exponential) function for a given type of polynucleotide (e.g., DNA or RNA).

The identity of the polynucleotide refers to the type of polynucleotide. The identity also can refer to the name of the polynucleotide as it is known in the art. For example, the identity of a polynucleotide can be, for example, DNA, RNA, a double stranded polynucleotide, a single stranded polynucleotide and/or a partially double stranded polynucleotide. The identity of a polynucleotide also can include the determining the gene product or structural function of the polynucleotide. For example, the polynucleotide can encode a polypeptide or it can be a structural polynucleotide such as ribosomal RNA. The identity of a polynucleotide can be determined from the nucleotide sequence of all or part of the polynucleotide, the sequence of a second polynucleotide that is complementary to all or part of the polynucleotide, the sequence of an RNA that is encoded by all or part of the polynucleotide or the sequence of a protein that is encoded by all or part of the polynucleotide. In particular examples, a polynucleotide can be identified by a "tag" or "barcode" sequence that forms part of the polynucleotide. In such examples, the identity of the polynucleotide can be assigned by a signal pattern expected from the tag or barcode. The source of the polynucleotide can refer to the species of origin of the polynucleotide or to a synthetic origin. The identity and source of the polynucleotide can be determined by aligning the sequence of the polynucleotide in polynucleotide sequence database, using programs well known in the art, for example, the BLASTN.

The secondary structure of the polynucleotide refers to the intramolecular base pairing of regions of self-complementarity in a polynucleotide molecule. Exemplary secondary structures include, for example, a double helix, hairpin, loop, bulge, duplex, junction, stem, pseudoknot, triple helix, H-DNA, hammerhead, and self-splicing ribozyme. The secondary structure of the polynucleotide can be determined, for example, by measuring its corresponding change in dwell time in a pore or measuring the corresponding change in signal produced by fractional translocation steps.

A pore is a structure extending across a barrier, including for example, a membrane, that permits ions and/or water soluble molecules to cross from one side of the barrier to the other side of the barrier. Pores can, but need not, occur in a membrane. For example, a barrier that normally inhibits passage of ions or water soluble molecules can include a pore structure that extends across the barrier to permit passage of the ions or water soluble molecules from one side of the barrier to the other side of the barrier. A membrane of the present disclosure can be, for example, a non-permeable or semi-permeable barrier that separates two liquid chambers which can have the same or different compositions. Any membrane can be used in accordance with the present disclosure, so long as the membrane can be configured to include a transmembrane pore and to maintain a potential difference across the membrane. Suitable potential differences are described below.

A variety of membranes well known in the art can be used in the compositions and methods of the present disclosure. Such membranes well known in the art include a variety of different structures and compositions. For example, a membrane can be a monolayer or multilayer structure so long as a pore can be incorporated for the characterization of a polynucleotide. A layer in the membrane refers to the non-permeable or semi-permeable material that forms the barrier. Examples of monolayer and multilayer membranes are further described below.

The membrane-forming material can be of biological or non-biological origins. A material that is of biological origin refers to material derived from or isolated from a biological environment such as an organism or cell, or a synthetically manufactured version of a biologically available structure. An exemplary membrane that is made from the material that is of biological origin includes a lipid bilayer. A material that is not of biological origin is also called a solid state material and can form a solid state membrane.

Suitable lipid bilayers and methods for making or obtaining lipid bilayers are well known in the art and disclosed in, for example, U.S. patent publication US 2010/0196203 and PCT patent publication WO 2006/100484. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by the method of Montal and Mueller (*Proc. Natl. Acad. Sci. USA.*, 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Other common methods of bilayer formation include tip-dipping, painting bilayers, and patch-clamping of liposome bilayers. A variety of other methods for obtaining or generating lipid bilayers are well known in the art and are equally applicable for use in the compositions and methods of the present disclosure.

Solid state membranes are well known in the art and disclosed in, for example, PCT patent publication WO 2000/079257. As described above, the solid state membrane is made from one or more layers of materials that are not of biological origin. The solid state membrane can be a monolayer, such as a coating or film on a supporting substrate, or a free-standing element. The solid state membrane can also be a composite of multilayer of materials in a sandwich configuration. There is no specific limitation to the materials that can be used according to the present disclosure, so long as the resulting solid state membrane can be configured to include a transmembrane pore and set up with a potential difference across the membrane. The solid state membranes can be made from both organic and inorganic materials, including, for example, microelectronic materials, insulating materials such as $Si_3N_4$, $Al_2O_3$, and SiO, organic and inorganic polymers such as polyamide, triblock copolymers (for example amphiphilic PMOXA-PDMS-PMOXA ABA triblock copolymers), plastics such as Teflon® or elastomers such as two-component addition-cure silicone rubber, and glasses. In addition, the solid state membrane can be made from a monolayer of graphene, which is an atomically thin sheet of carbon atoms densely packed into a two-dimensional honeycomb lattice, a multilayer of graphene, or one or more layers of graphene mixed with one or more layers of other solid state materials (PCT patent publication WO 2013/016486). A graphene containing solid state membrane can include at least one graphene layer that is a graphene nanoribbon or graphene nanogap, which can be used as an electrical sensor to characterize the target polynucleotide (see PCT patent publication WO 2013/016486). Solid state membrane can be made by the methods well known in the art. For example, the graphene membrane can be prepared through either chemical vapor deposition (CVD) or exfoliation from graphite (PCT patent publication WO 2013/016486).

The compositions and methods of the present disclosure can employ a pore that sits in a barrier for characterization of a target polynucleotide. A pore can be made from materials that are of biological or non-biological origins. Accordingly, a pore includes, for example, a biological pore, a solid state pore, and a biological and solid state hybrid pore.

A pore can have a functionality associated with it that facilitates detection of the sequence of nucleotides in a polynucleotide. For example, a pore can include an enzyme such as helicase or other functionality attached to, associated with, or located near the pore to control the rate at which polynucleotides transit through the pore. A pore can have a detection circuit or sensor associated with it including, for example, a patch clamp circuit, a tunneling electrode circuit, or a transverse conductance measurement circuit (such as a graphene nanoribbon, or a graphene nanogap). A pore also can include an optical sensor that detects a label including, for example, a fluorescent moiety or a Raman signal generating moiety, on the polynucleotide that determines a nucleotide sequence based on interaction of a fragment with the pore (e.g., passing the fragment through the pore).

In particular embodiments, a biological pore, including a polypeptide pore and a polynucleotide pore, can be used in the compositions and methods of the present disclosure, so long as the pore has a constriction zone that allows the passage of the polynucleotide through the barrier (e.g., membrane). A constriction zone is a location in the lumen of the pore where blockage by an analyte (e.g., a polynucleotide or nucleotide) affects a detectable signal produced by the pore. Pores having a variety of constriction zone lengths can be employed in the composition and methods of the present disclosure including, for example, lengths of at least 1, 2, 3, 4, 5, 6, 7, 8, 9, or 10 nucleotides. Alternatively or additionally, lengths of at most about 10, 9, 8, 7, 6, 5, 4, 3, 2, or 1 nucleotide(s) can be used. However, the length of the constriction zone can affect the quality of the signal. For example, shorter constriction zones can result in a better resolution of nucleotide translocation or reconstruction accuracy. In one embodiment, the biological pore has a constriction zone of about five nucleotides or less, the five or less than five nucleotides located in the constriction zone modulate the electrical signal, which has a better resolution of nucleotide translocation than the electrical signal obtained from more than five nucleotides. In some cases, signal-to-noise enhancement does not result in a sequencing accuracy improvement for constriction that is smaller than 2 nt. This can result if homopolymers greater than the smaller constriction can no longer be detected and the lack of re-reading reduces accuracy when nucleotides are skipped due to the stochastic motion of the enzyme. Accordingly, suitable polypeptide pores and polynucleotide pores having a constriction zone of five nucleotides or less can be used in accordance with the present disclosure. Given the teachings and guidance provided herein, those skilled in the art will understand what length constriction zone is applicable for a particular need. For example, those skilled in the art can employ pores having shorter constriction zones in applications requiring higher quality results.

A biological pore is a pore that is made from materials of biological origin, extending across a barrier (e.g., membrane) that permits ions and/or water soluble molecules to cross from one side of the barrier to the other side of the barrier. As with the membranes used as set forth herein, when referring to pores, biological origin refers to a structure derived from or isolated from a biological environment such as an organism or cell, or a synthetically manufactured version of a biologically available structure. Materials of biological origin include, for example, polypeptide and polynucleotide. Accordingly, biological pores include, for example, polypeptide pores and polynucleotide pores.

A polypeptide pore reconstituted into a barrier (e.g., membrane), such as a lipid bilayer, can be used for nanopore sequencing. There are a variety of polypeptide pores that can be used in accordance to the present disclosure, so long as the polypeptide(s) can form a constriction zone that allows the passage of the target polynucleotide across the barrier (e.g., membrane). Depending on the polypeptide(s) involved, the polypeptide pore can be a monomer, a homopolymer or a heteropolymer. The polypeptide pore can include several repeating subunits, such as 7 or 8 subunits. Accordingly, the polypeptide pore can be, for example, a hexameric, heptameric or octameric pore.

Polypeptide pores include, for example, an α-helix bundle pore and a β-barrel pore as well as all others well known in the art. The α-helix bundle pore includes a pore that is formed by α-helices. Suitable α-helix bundle pores include, for example, inner membrane proteins and α outer membrane proteins, such as WZA and ClyA toxin. The β-barrel pore includes a pore that is formed by β-strands. Suitable β-barrel pores include, for example, β-toxins, such as α-hemolysin, anthrax toxin and leukocidins, and outer membrane proteins/porins of bacteria, such as *Mycobacterium smegmatis* porin (Msp), including MspA, outer membrane porin F (OmpF), outer membrane porin G (OmpG), outer membrane phospholipase A and *Neisseria* autotransporter lipoprotein (NalP). Other pores include, for example, lysenin (see for example, WO 2013 153359, or the MspA homolog from *Norcadia farcinica*.

An α-hemolysin polypeptide is a heptameric polypeptide pore that can be used in the methods and compositions of the present disclosure. It is comprised of a 3.6 nm vestibule connected to a β-barrel of ~5 nm in length, containing a 1.4 nm constriction that permits the passage of single stranded polynucleotide but not double stranded polynucleotide. α-hemolysin's ~5 nm long cylindrical β-barrel pore can accommodate up to about 10 nucleotides at a time. Nucleotides located in this β-barrel significantly modulate the pore current and subsequently dilute the ionic signature specific to a single nucleotide in the narrowest 1.4 nm pore constriction, reducing the overall resolution of nucleotide translocation in sequencing applications.

MspA is an octameric polypeptide pore that can be used in the compositions and methods of the present disclosure. It contains a single constriction of diameter ~1.2 nm with a constriction length of ~0.5 nm; the inner pore forms a tapered funnel shape, as opposed to the cylindrical structure of α-hemolysin. Derrington et al. demonstrated the ability of genetically engineered MspA to discriminate between trinucleotide sets (AAA, GGG, TTT, CCC) with an impressive 3.5 fold enhancement in nucleotide separation efficiency over native α-hemolysin (Derrington et al., *Proc. Natl. Acad. Sci. USA,* 107:16060 (2010)). It was reported that in experiments involving immobilized single stranded polynucleotide, as few as three nucleotides within or near the constriction of MspA were seen to contribute to the pore current, a significant improvement over the ~10 nucleotides known to modulate ionic current in native α-hemolysin. The authors hypothesize that this could be further improved to perhaps a single nucleotide through site-specific mutagenesis, a goal of future MspA mutants.

In some aspects, the polypeptide pore is a *Mycobacterium smegmatis* porin A (MspA). In some aspects, the MspA has an amino acid sequence of SEQ ID NO: 1 or having at least 15%, at least 20%, at least 25%, at least 30%, at least 35%, at least 40%, at least 45%, at least 50%, at least 55%, at least 60%, at least 65%, or at least 70%, at least 75%, at least 80%, at least 85%, at least 90%, at least 95%, or at least 99% homology to SEQ ID NO: 1.

MspA is a suitable polypeptide pore. In addition, MspA mutants can be used in the compositions and methods of the present disclosure to regulate the polynucleotide translocation through the pore. The MspA pore used in embodiments herein can have the amino acid sequence of SEQ ID NO: 1, corresponding to GLDNELSLVDGQDRTLTVQQWDT-FLNGVFPLDRNRLTREWFHSGRAKYIVAGPGADEF EGTLELGYQIGFPWSLGVGINFSYTTPNILINNGNI-TAPPFGLNSVITPNLFPGVSISARLGN GPGIQE-VATFSVRVSGAKGGVAVSNAHGTVTGAAGGVLLRP-FARLIASTGDSVTTYGEP WNMN, which is the sequence of MspA with the following mutations: D90N, D91N, D93N, D118R, D134R & E139K. The MspA pore mutant of SEQ ID NO: 1 is named "M2 NNN". Other MspA mutants can be used in the compositions and methods of the present disclosure, which have at least 15%, at least 20%, at least 25%, at least 30%, at least 35%, at least 40%, at least 45%, at least 50%, at least 55%, at least 60%, at least 65%, or at least 70%, at least 75%, at least 80%, at least 85%, at least 90%, at least 95%, or at least 99% homology to SEQ ID NO: 1. A polypeptide or polypeptide region (or a polynucleotide or polynucleotide region) has a certain percentage (e.g., 50%) of homology to another sequence means that, when aligned, that percentage of amino acids (or nucleotide bases) are the same in comparing the two sequences. The alignment of two sequences to determine their percent sequence identity can be done using software programs known in the art, as described herein. Mutations to the native MspA polypeptide, including insertions, deletions, substitutions, or other selected modifications of particular regions or specific amino acids residues, can be made according to methods that are well-known in the art, including site-specific mutagenesis of the nucleic acid encoding the MspA polypeptide (Zoller, M. J., Curr. Opin. Biotechnol., 3:348-354, (1992)). Useful, MspA mutants are also set forth in US 2012/0055792A1.

A native or mutant MspA polypeptide used in the compositions and methods of the present disclosure can be isolated by a variety of methods well-known in the art, for example, recombinant expression systems, precipitation, gel filtration, ion-exchange, reverse-phase and affinity chromatography, and the like. Other well-known methods are described in Deutscher et al., Guide to Protein Purification: Methods in Enzymology, Vol. 182, (Academic Press, (1990)). Alternatively, the isolated native or mutant MspA polypeptide of the present disclosure can be obtained using well-known recombinant methods. The methods and conditions for biochemical purification of the native or mutant MspA polypeptide of the present disclosure can be chosen by those skilled in the art, and purification can be monitored, for example, by a functional assay.

One exemplary method for preparing a native or mutant MspA polypeptide is to express the polynucleotide encoding the polypeptide in a suitable host cell, such as a bacterial cell, a yeast cell, or other suitable cell, using methods well known in the art, and recovering the expressed native or mutant MspA polypeptide, again using well-known purification methods, such as those described herein. A native or mutant MspA polypeptide can be isolated directly from cells that have been transformed with expression vectors as described herein. Recombinantly expressed native or mutant MspA polypeptide can also be expressed as fusion polypeptides with appropriate affinity tags, such as glutathione S transferase (GST) or poly His, and affinity purified. A native or mutant MspA polypeptide can also be produced by chemical synthesis using a method of polypeptide synthesis well known to one of skill in the art.

A polynucleotide pore reconstituted into a barrier (e.g., membrane), such as a lipid bilayer, can also be used for nanopore sequencing. The polynucleotide pore is one or more polynucleotides that extends across a barrier (e.g., membrane) and permits ions and/or water soluble molecules to flow from one side of the barrier to the other side of the barrier. Any polynucleotide pores can be used in accordance with particular embodiments of the present disclosure, so long as the polynucleotide(s) can form a constriction zone that allows the passage of the target polypeptide across the barrier (e.g., membrane). Exemplary polynucleotide pores include, for example, a polynucleotide origami pore. The polynucleotide origami pore whose patterns extend in two or three dimensions can be made using "origami" as described in Rothemund, Nature, 440:297-302 (2006). Origami is a generic technique that makes use of a long strand of genomic polynucleotide and many shorter synthetic "staple" polynucleotide strands to create an extended structure. The original origami structures were substantially two-dimensional structures. The origami technique has since been extended to three-dimensional structures (Douglas et al., Nature 459:414-418 (2009); Ke et al., Nano Letters, 6:2445-2447 (2009); Andersen et al., Nature 459:73-76 (2009)).

A solid state pore can also be used in the compositions and methods of the present disclosure. The solid state pore is a pore, which is made from materials of non-biological origin, extending across a barrier (e.g., membrane) that permits ions and/or water soluble molecules to cross from one side of the barrier to the other side of the barrier.

A solid state pore can be formed by creating a pore in the solid state barrier (e.g., membrane). Accordingly, similarly to the solid state membrane and as described herein, the solid state pore can be formed by a variety of materials, encompassing both inorganic and organic materials.

Suitable solid state pores include, for example, Aluminum Oxide, Tantalum Oxide, Titanium Oxide, Silicon Dioxide, Hafnium Oxide, Zirconium Oxide, Boron Nitride, Silicon Nitride, graphene or nanolaminates thereof (e.g., graphene-$Al_2O_3$), or any combination thereof (PCT patent publication WO 2013016486A1). The solid state pore can be made by using a custom built feedback controlled ion beam sculpting tool, or using focused convergent electron beam from a field emission gun (FEG) TEM to decompositionally sputter a nanopore in the membrane, or any other methods well known in the art (PCT patent publication WO 2013016486A1). For example, a graphene nanolaminate pore, such as a graphene-$Al_2O_3$ pore, can be made by drilling through a graphene-$Al_2O_3$ membrane using a focused convergent electron beam from a FEG TEM (Venkatesan et al., ACS Nano., 6:441-450 (2012)).

A biological and solid state hybrid pore can be used in the compositions and methods of the present disclosure. The biological and solid state hybrid pore is a hybrid pore, which is made from materials of both biological and non-biological origins, extending across a barrier (e.g., membrane) that permits ions and/or water soluble molecules to cross from one side of the barrier to the other side of the barrier. Materials of biological origin are defined above and include, for example, polypeptide and polynucleotide. Materials of non-biological origins are called solid state materials, as described herein.

Accordingly, the biological and solid state hybrid pores include, for example, a polypeptide-solid state hybrid pore and a polynucleotide-solid state hybrid pore. The polypeptide-solid state hybrid pore includes one or more polypeptides and solid state material. The polynucleotide-solid state hybrid pore includes one or more polynucleotides and solid state material. The biological and solid state hybrid pores are made by engineering the polypeptide or polynucleotide pore with the solid state pore (see PCT patent publication WO 2013/016486). Examples of suitable polypeptide pores, polynucleotide pores, and solid state pores are described above.

A nanopore sequencing apparatus can have singular or multiple pores. Multiple pores can be used as a nanopore array to characterize more than one target nucleotides, which have same or different compositions. Exemplary numbers of the multiple pores used herein include, for example, at least 1, 4, 16, 64, 256, 512, 1028, 4096, 16384, 32768, 100000, 1 million, 10 million pores or more. In preferred embodiments, the number of multiple pores will be greater than 4096. Nanopore arrays are known in the art and disclosed in, for example, PCT patent publication WO 2013/016486. For example, high density arrays of ~15 nm diameter solid state pores can be fabricated using electron beam lithography and reactive ion etch steps in SiN/Al$_2$O$_3$ membranes, facilitating high throughput analysis of polynucleotide molecules.

A method of the present disclosure can utilize a potential difference across a barrier (e.g., a membrane). The potential difference can be an electric potential difference, chemical potential difference, or an electrochemical potential difference. An electric potential difference can be imposed across the barrier (e.g., membrane) via a voltage source that injects or administers current to at least one of the liquid pools. A chemical potential can be imposed across the barrier via a difference in ionic composition of the two pools. An electrochemical potential difference can be established by a difference in ionic composition of the two pools in combination with an electrical potential. The different ionic composition can be, for example, different ions in each pool or different concentrations of the same ions in each pool.

The application of an electrical potential across a pore to force the translocation of a polynucleotide through the pore is well known in the art and can be used in accordance with the present disclosure (Deamer et al., *Trends Biotechnol.*, 18:147-151 (2000); Deamer et al., *Ace Chem Res.*, 35:817-825 (2002); and Li et al., *Nat Mater.*, 2(9):611-615 (2003)). A method of the present disclosure can be carried out with a voltage applied across a pore. The range for the voltage can be selected from 40 mV to upwards of 1 V. Typically a method of the present disclosure will run in the range of 100 to 200 mV. In specific instances, the method is run at 140 mV or 180 mV. The voltages are not required to be static during the motion of the motor. The voltage polarity is typically applied such that the negatively charged polynucleotide is electrophoretically driven into the pore. In some instances, the voltage can be reduced, or the polarity reversed, to facilitate appropriate function of the motor.

In some instances, the application of pressure differentials can be utilized to force translocation of a polynucleotide through a pore. Pressure differentials can be used in place of electrical potentials or other potential differences in methods exemplified herein.

The methods of the present disclosure produce one or more signals that correspond to the translocation of one or more nucleotides through a pore. Accordingly, as a target polynucleotide transits through a pore the current across the barrier changes due to base-dependent blockage of the constriction, for example. The signal from that change in current can be measured using any of a variety of methods as described herein or as otherwise known in the art. Each signal is unique to the species of nucleotide(s) in the pore such that the resultant signal can be used to determine a characteristic of the polynucleotide as described previously. For example, the identity of one or more species of nucleotide(s) that produces a characteristic signal can be determined. Signals useful in the methods of the present disclosure include, for example, electrical signals and optical signals, which are further described below. In some aspects, the electrical signal can be a measurement of current, voltage, tunneling, resistance, voltage, conductance; or transverse electrical measurement (PCT patent publication WO 2013/016486. In some aspects, the electrical signal is an electrical current passing through a pore.

An electrical signal detected in a method set forth herein can be an electrical current, which is a flow of electric charge, passing through a pore (Deamer et al., *Trends Biotechnol.*, 18:147-151 (2000); Deamer et al., *Ace Chem Res.*, 35:817-825 (2002); and Li et al., *Nat Mater.*, 2(9):611-615 (2003)). As described herein, the electrical signals can be measured using the detection circuit coupled to a pore, for example, a patch clamp circuit or a tunneling electrode circuit. Examples of voltage, tunneling, resistance and conductance signals that can be detected, and apparatus for their detection are know in the art as described, for example, in Wanunu, *Phys Life Rev.*, 9(2):125-58 (2012); and Venkatesan et al., *Nat Nanotechnol.*, 6(10):615-24 (2011).

Optical signals useful in the methods of the present disclosure include, for example, fluorescence and Raman signal. The optical signals can be generated by coupling the target nucleotide with an optical signal generating label, for example, a fluorescent moiety or a Raman signal generating moiety. For example, in dela Torre et al., *Nanotechnology*, 23(38):385308 (2012), the optical scheme of Total Internal Reflection Fluorescence (TIRF) microscopy was employed to illuminate a wide area of the TiO$_2$-coated membrane. In Soni et al., *Rev Sci Instrum.*, 81(1):014301 (2010), a method was used for integrating two single-molecule measurement modalities, namely, total internal reflection microscopy and electrical detection of biomolecules using nanopores.

As described herein, the pores can be coupled with a detection circuit, including, for example, a patch clamp circuit, a tunneling electrode circuit, or a transverse conductance measurement circuit (such as a graphene nanoribbon, or a graphene nanogap), to record the electrical signals in the present embodiments. In addition, the pore can also be coupled with an optical sensor that detects labels, for example, a fluorescent moiety or a Raman signal generating moiety, on the polynucleotides.

Nanopore sequencing methods can employ a mechanism to slow down translocation of a target polynucleotide through a pore. For example, a polynucleotide binding protein, such as a helicase, translocase, or polymerase, can be attached or incorporated to regulate the translocation rate. The attachment can be, for example, transient or persistent and can be mediated by the target polynucleotide as it is drawn through the pore or by a variety of polypeptide, chemical linkers or capture moieties well known in the art. Exemplary techniques are described in Manrao et al., *Nat Biotechnol.*, 30(4):349-353 (2012) and Cherf et al., *Nat Biotechnol.*, 30(4):344-348 (2102). In particular embodiments, a helicase or other molecular motor can be used to slow down or stop translocation of a target polynucleotide through a pore. For example, when using a motor that hydrolyzes nucleotides to effect translocation, the nucleotide can be omitted from the motor and/or the motor can be subjected to an inhibitor (e.g. a nonhydrolyzable nucleotide analog) such that the target polynucleotide remains bound to the motor and does not appreciably translocate through the pore. In some embodiments translocation can subsequently be allowed to occur by delivering nucleotide to the motor and/or removing the inhibitor. A method of the present disclosure can include a step of contacting a pore with a target polynucleotide and a Hel308 helicase to control the translocation rate of the polynucleotide through the pore. As described further below, a Hel308 helicase can be characterized as an ATP-dependent DNA helicase and a superfamily 2 helicase. Given the teachings and guidance provided herein, one skilled in the art could suitably select or adapt any Hel308 helicase for use in accordance with the present embodiments. Suitable Hel308 helicases are further described below.

In some aspects of a method set forth herein, translocation of the target polynucleotide is in a direction opposite of the direction of a current through the pore. In other aspects, a translocation of the target polynucleotide is in the same direction as the direction of a current passing through the pore.

Accordingly, a method of the present disclosure can be carried out in at least two modes, where a translocation of the target polynucleotide is either opposite to or with, for example, the direction of a current or other potential through a pore. This result can be achieved by binding a Hel308 helicase of the present disclosure to either the 5' or 3' end of the target polynucleotide. When referring to a double stranded polynucleotide the 5' or 3' orientation refers to a single strand within the double stranded polynucleotide. Therefore, a Hel308 helicase can either pull or feed the polynucleotide out of or into the pore, that is, in the direction against the force on the polynucleotide generated by the voltage gradient (see FIGS. 13A-13E and 14A-14D), or using the helicase to regulate the translocation speed as the polynucleotide moves in the same direction as the force generated by the voltage gradient or other potential (see FIGS. 15A-15C).

FIGS. 13A-13E exemplify controlled polynucleotide translocation by Hel308 helicase against the force generated by a potential such as a voltage gradient, e.g., based on a ternary polynucleotide complex with a Hel308 helicase 3' overhang binding site and cholesterol bilayer anchor, according to some embodiments. Filled circle (●) denotes a 5' phosphate. Filled diamond (♦) denotes a 3' cholesterol. Notched filled, semi-transparent circle denotes Hel308 helicase. Dotted lines indicate arbitrary length. Large grey arrows denote direction of polynucleotide motion (with or against the applied field) of the polynucleotide into or out of the pore. Large black arrows indicate direction of helicase translocation along polynucleotide, which is 3' to 5'. Pore (funnel-shaped conical object) sits in membrane (double horizontal lines).

Figure 13B:
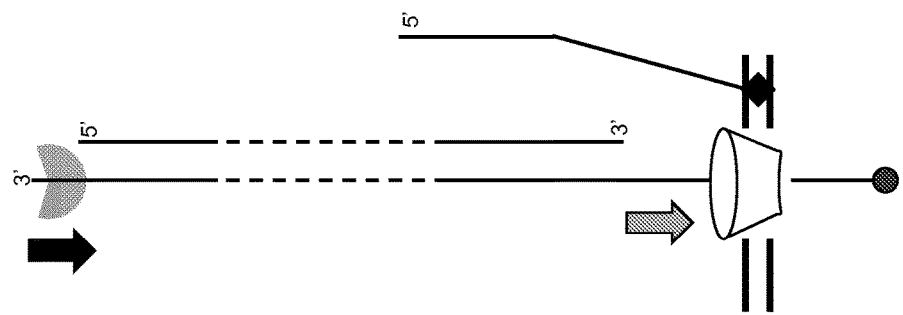
Figure 13A:
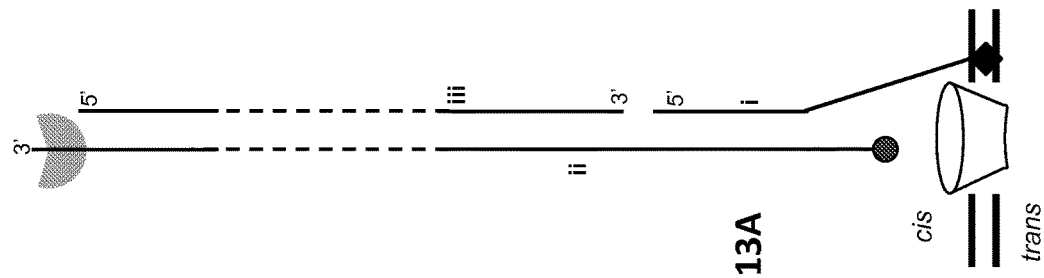
Figure 13E:
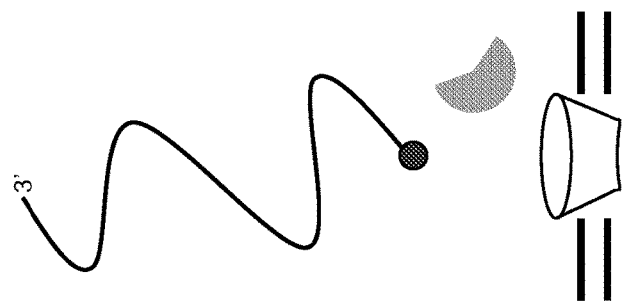
Figure 13D:
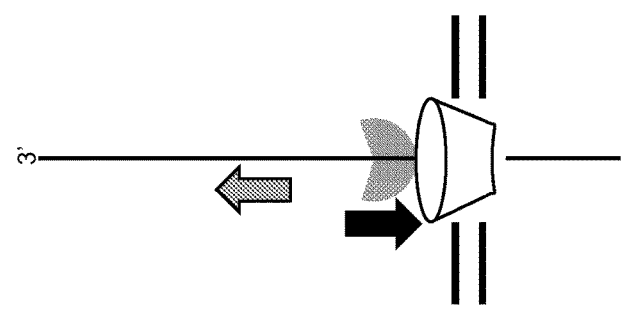
Figure 13C:
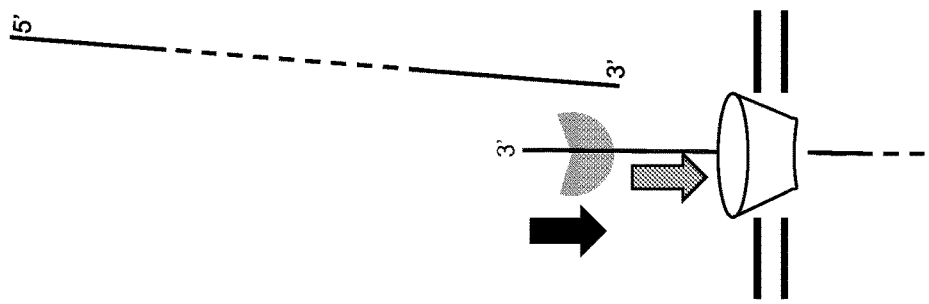
Figure 14D:
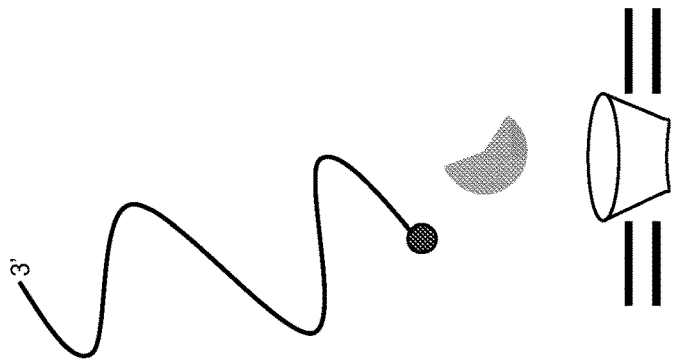
Figure 14C:
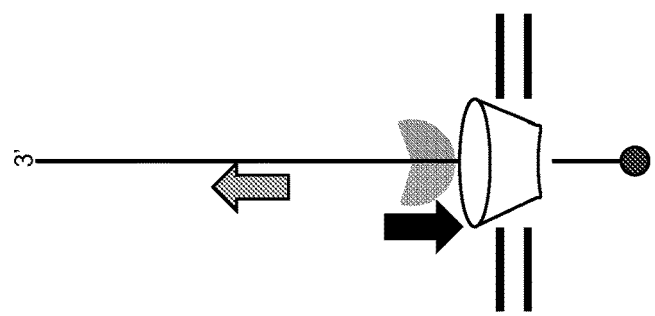
Figure 14B:
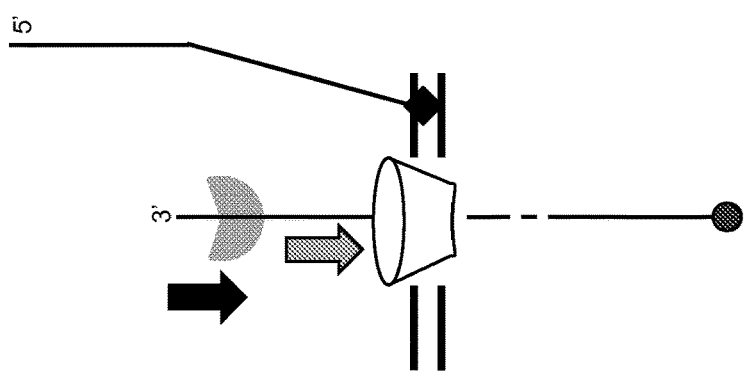
Figure 14A:
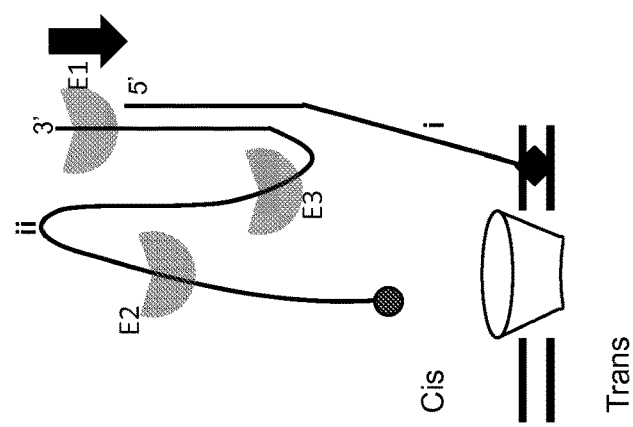

FIGS. 13A-13E illustrate the use of a ternarypolynucleotide complex with a Hel308 helicase 3' overhang binding site and cholesterol bilayer anchor for polynucleotide sequencing. The cholesterol-labeled polynucleotide "i" is optional and is used to hybridize to the target polynucleotide "ii" that will translocate through the pore and facilitates recruitment of the entire complex to the lipid bilayer (FIG. 13A). The 5' phosphate is pulled through the pore by, for example, a voltage gradient, resulting in the 5' end of target polynucleotide "ii" to enter the pore first, and causing the cholesterol-labeled polynucleotide to be stripped off (FIG. 13B). As the phosphate-containing polynucleotide is pulled through the pore to the trans side, the second hybridized polynucleotide "iii" is stripped off because the pore is too narrow to permit double-stranded polynucleotide to translocate (FIG. 13C). One purpose of polynucleotide iii is to create a Hel308 helicase binding site, generally a 3' single-stranded polynucleotide overhang of about 8 nucleotides, that a Hel308 helicase can preferentially bind. Furthermore, by forcing the Hel308 helicase molecule to bind at the 3' end of the translocating polynucleotide the length of polynucleotide translocating through the pore is maximized. The polynucleotide "iii" of the complex can be of any length, including an arbitrary length, and the 3' end need not be adjacent to the 5' end of polynucleotide "i." Upon reaching the pore mouth the Hel308 helicase pulls the polynucleotide against the voltage gradient via its 3' to 5' translocase activity back into the cis chamber (FIGS. 13D and 13E).

FIGS. 14A-14D also illustrate controlled polynucleotide translocation by Hel308 helicase against the force generated by a potential such as a voltage gradient, e.g., based on a ternary polynucleotide complex with a Hel308 helicase 3' overhang binding site and cholesterol bilayer anchor, according to some embodiments. Filled circle (●) denotes a 5' phosphate. Filled diamond (♦) denotes a 3' cholesterol. Notched filled, semi-transparent circle denotes Hel308 helicase. Dotted lines indicate arbitrary length. Large grey arrows denote direction of polynucleotide motion (with or against the applied field) of the polynucleotide into or out of the pore. Large black arrows indicate direction of helicase translocation along polynucleotide, which is 3' to 5'. Pore (funnel-shaped conical object) sits in membrane (double horizontal lines). However, this scheme exemplifies use of a single hybridization polynucleotide "i" to create a 3' overhang on target polynucleotide "ii" for a Hel308 helicase to bind to, and also contains an optional cholesterol moiety. It is possible that Hel308 helicase can bind anywhere on the single-stranded regions of polynucleotide "ii". Multiple Hel308 helicase molecules are shown and are denoted by "E1", "E2" and "E3." The Helicase that reaches the pore mouth first will initiate the controlled translocation process back to the cis side. Should it fall off, uncontrolled translocation would ensue until the next bound Hel308 helicase molecule reaches the pore mouth and commences controlled translocation.

FIGS. 15A-15C exemplify use of a Hel308 helicase to regulate polynucleotide translocation speed as the polynucleotide moves in the same direction as the force generated by a potential such as a voltage gradient. Notched filled, semi-transparent circle denotes Hel308 helicase. Dotted lines indicate arbitrary length. Large grey arrows denote direction of polynucleotide motion with the applied field into the pore. Large black arrows indicate direction of helicase translocation along polynucleotide, which is 3' to 5'. Pore (funnel-shaped conical object) sits in membrane (double horizontal lines). In this exemplary scheme, the target polynucleotide enters the pore 3' end first. The Hel308 helicase controls the speed of translocation of the polynucleotide into the pore as it translocates from 3' to 5' along the translocating polynucleotide.

As described previously, a fractional translocation step in the context of a Hel308 helicase can refer to a partial translocation of one or more nucleotides of the target polynucleotide along the helicase and/or pore. Accordingly, a fractional translocation step refers to a portion of a nucleotide step that is less than the full translocation cycle. A fractional translocation step can occur between ATP binding and hydrolysis when a conformational change occurs. One or more fractional translocation steps can be required for a full nucleotide step. The conformational change effectively divides a full translocation cycle into at least two partial or fractional translocation steps.

The partial or fractional translocation steps can be employed in the same manner to generate a unique signal to characterize one or more nucleotides that transits through a pore. Thus, the methods of the present disclosure can produce at least two electrical signals due to a change in current corresponding to each fractional translocation step for each one or more nucleotide translocation through a pore. Accordingly, in some aspects, a fractional translocation step includes a first fractional translocation step of a full translocation cycle of the Hel308 helicase. In other aspects, the fractional translocation step includes a second fractional translocation step of a full translocation cycle of the Hel308 helicase. Each first or second fractional translocation step can be used alone or together with its partner, for example, the second or first fractional translocation step, respectively, to characterize one or more nucleotides transiting a constriction zone of a pore.

For example, as described further in Example I, a Hel308 helicase can bind to ATP and undergo a conformational change, providing a first fractional translocation step, and Hel308 helicase can translocate one or more nucleotides of the target polynucleotide along the helicase and/or the pore by ATP hydrolysis, providing a second fractional translocation step. Either or both of the first and second fractional translocation steps can be used to determine, for example, the nucleotide or nucleotide sequence of the one or more nucleotides generating the signal. When a signal is generated by more than one nucleotide, the portion of the polynucleotide generating the signal is referred to as a word. Accordingly, such nucleotide words can be at least 4, 5, 6, 7, 8, 9, 10 or more nucleotides in length and correspond to the length of the pore's constriction zone. Alternatively or additionally the nucleotide words can be at most 10, 9, 8, 7, 6, 5, or 4 or fewer nucleotides in length.

As described above and exemplified further below in Example III, one or more nucleotide residues in the polynucleotide can be identified using electrical signals obtained from two fractional steps of a full translocation cycle. Employing the signals from both fractional translocation steps provides a duplicate signal for the same one or more nucleotides and allows greater accuracy within a single determination. Accordingly, employing signals from both fractional translation steps can result in an increased characterization accuracy, with error rates reduced by between 25 and 50% compared to identification of one or more nucleotides using a single electrical or other signal obtained from a full translocation cycle. Similarly, employing signals from both fractional translation steps can result in error rates reduced by at least 5%, 10%, 20%, 30%, 40%, 45%, 55%, 60%, 65%, 70%, 75%, 80% 85%, 90% or higher. Given the teachings and guidance provided herein, those skilled in the art will know how to adjust accuracy for a given purpose, such as by, for example, decreasing the size of the constriction zone as described previously to increase the resolution of nucleotide translocation.

In other embodiments, the additional information obtained from fractional translocation steps can be used to advance nanopore sequencing in a number of ways. For example, measurements obtained from fractional translocation steps for the same nucleotide word can be used in algorithms to improve nanopore base-calling accuracy. Measurements obtained from fractional translocation steps for the same nucleotide word can be used to reduce homopolymer read error rates because the same nucleotide word is read twice within a single determination. Accordingly, measurements obtained from fractional translocation steps for the same nucleotide word doubles the resolvable resolution of the native polynucleotide translocation response, resulting in enhanced resolution of sequence-specific patterns. One utilization of the latter is sequence-specific pattern recognition algorithms for detecting sequence repeats or single-nucleotide polymorphisms (SNPs).

As set forth above a method can include (a) causing a potential difference across a pore in contact with a Hel308 helicase and a target polynucleotide; (b) measuring one or more signals produced by one or more fractional translocation steps of the target polynucleotide through the pore, and (c) characterizing the target polynucleotide from the electrical signal of the fractional translocation steps. In some aspects, the method further includes repeating steps (a)-(c) one or more times. By repeating steps (a)-(c), adjacent nucleotides or adjacent nucleotide words can be characterized. Repeating steps (a)-(c) can be repeated as desired until some or all of the target polynucleotide is characterized. For example, the sequence of a portion or all of a target polynucleotide can be determined through any desired number of iterations of steps (a)-(c). Accordingly, one or more characteristics for the whole or part of a target polynucleotide can be determined.

As described herein, any Hel308 helicase or variant thereof can be used in accordance with the present embodiments. Exemplary Hel308 helicases are presented below in Tables 1 and 2.

TABLE 1

Exemplary Hel308 helicases

| Accession | Description |
|---|---|
| NP_578406.1 | ski2-like helicase [*Pyrococcus furiosus* DSM 3638] >sp|O73946.1|HELS_PYRFU RecName: Full=Putative ski2-type helicase >pdb|2ZJ2|A Chain A, Archaeal Dna Helicase Hjm Apo State In Form 1 >pdb|2ZJ5|A Chain A, Archaeal Dna Helicase Hjm Complexed With Adp In Form 1 >pdb|2ZJ8|A Chain A, Archaeal Dna Helicase Hjm Apo State In Form 2 >pdb|2ZJA|A Chain A, Archaeal Dna Helicase Hjm Complexed With Amppcp In Form 2 >dbj|BAA32016.1| helicase [*Pyrococcus furiosus*] >gb|AAL80801.1| helicase [*Pyrococcus furiosus* DSM 3638] |
| NP_126564.1 | ski2-like helicase [*Pyrococcus abyssi* GE5] >sp|Q9V0A9.1|HELS_PYRAB RecName: Full=Putative ski2-type helicase >emb|CAB49795.1| DNA helicase [*Pyrococcus abyssi* GE5] |
| NP_143168.1 | ski2-like helicase [*Pyrococcus horikoshii* OT3] >sp|O59025.1|HELS_PYRHO RecName: Full=Putative ski2-type helicase >dbj|BAA30383.1| 715aa long hypothetical protein [*Pyrococcus horikoshii* OT3] |
| YP_004424773.1 | ski2-like helicase [*Pyrococcus* sp. NA2] >gb|AEC52769.1| ski2-like helicase [*Pyrococcus* sp. NA2] |
| YP_004623750.1 | ski2-like helicase [*Pyrococcus yayanosii* CH1] >gb|AEH24478.1| ski2-like helicase [*Pyrococcus yayanosii* CH1] |
| YP_002307730.1 | ski2-like helicase [*Thermococcus onnurineus* NA1] >•gb|ACJ16833.1| DNA helicase [*Thermococcus onnurineus* NA1] |
| YP_004763427.1 | ski2-like helicase [*Thermococcus* sp. 4557] >gb|AEK73750.1| ski2-like helicase [*Thermococcus* sp. 4557] |
| YP_002959236.1 | ski2-1ike helicase [*Thermococcus gammatolerans* EJ3] >gb|ACS33372.1| ski2-type helicase, putative [*Thermococcus gammatolerans* EJ3] |
| YP_004071709.1 | ski2-type helicase [*Thermococcus barophilus* MP] >gb|ADT84486.1| putative ski2-type helicase [*Thermococcus barophilus* MP] |
| YP_002994328.1 | Putative ski2-type helicase [*Thermococcus sibiricus* MM 739] >gb|ACS89979.1| Putative ski2-type helicase [*Thermococcus sibiricus* MM 739] |

TABLE 1-continued

Exemplary Hel308 helicases

| Accession | Description |
|---|---|
| ZP_04875329.1 | Type III restriction enzyme, res subunit family [*Aciduliprofundum boonei* T469] >gb|EDY35111.1| Type III restriction enzyme, res subunit family [*Aciduliprofundum boonei* T469] |
| YP_003436565.1 | DEAD (SEQ ID NO: 2)/DEAH (SEQ ID NO: 3) box helicase [*Ferroglobus placidus* DSM 10642] >gb|ADC66290.1| DEAD (SEQ ID NO: 2)/DEAH (SEQ ID NO: 3) box helicase domain protein [*Ferroglobus placidus* DSM 10642] |
| YP_004485304.1 | ski2-type helicase [*Methanotorris igneus* Kol5] >gb|AEF97239.1| ski2-type helicase [*Methanotorris igneus* Kol 5] |
| YP_004616424.1 | DEAD (SEQ ID NO: 2)/DEAH (SEQ ID NO: 3) box helicase domain-containing protein [*Methanosalsum zhilinae* DSM 4017] >gb|AEH61205.1 | DEAD (SEQ ID NO: 2)/DEAH (SEQ ID NO: 3) box helicase domain protein [*Methanosalsum zhilinae* DSM 4017] |
| ZP_04873370.1 | Type III restriction enzyme, res subunit family [*Aciduliprofundum boonei* T469] >ref|YP_003482774.1| DEAD (SEQ ID NO: 2)/DEAH (SEQ ID NO: 3) box helicase domain protein [*Aciduliprofundum boonei* T469] >gb|EDY36687.1 Type III restriction enzyme, res subunit family [*Aciduliprofundum boonei* T469] >gb|ADD08212.1| DEAD (SEQ ID NO: 2)/DEAH (SEQ ID NO: 3) box helicase domain protein [*Aciduliprofundum boonei* T469] |
| YP_004342552.1 | ski2-type helicase [*Archaeoglobus veneficus* SNP6] >gb|AEA47837.1| ski2-type helicase [*Archaeoglobus veneficus* SNP6] |
| NP_071282.1 | SKI2-family helicase [*Archaeoglobus fulgidus* DSM 4304] |
| 2P6R_A | Chain A, Crystal Structure Of Superfamily 2 Helicase Hel308 In Complex With Unwound Dna >pdb|2P6U|A Chain A, Apo Structure Of The Hel308 Superfamily 2 Helicase |
| YP_685308.1 | ski2-like helicase [uncultured methanogenic archaeon RC-1] >sp|Q0W6L1.1|HELS_UNCMA RecName: Full=Putative ski2-type helicase >emb|CAJ35982.1| putative ski2-type helicase [uncultured methanogenic archaeon RC-1] |
| YP_001048404.1 | ski2-like helicase [*Methanoculleus marisnigri* JR1 >gb|ABN58422.1| DEAD (SEQ ID NO: 2)/DEAH (SEQ ID NO: 3) box helicase domain protein [*Methanoculleus marisnigri* JR1] |
| YP_919908.1 | DEAD (SEQ ID NO: 2)/DEAH (SEQ ID NO: 3) box helicase domain-containing protein [*Thermofilum pendens* Hrk 5] >gb|ABL77905.1|DEAD (SEQ ID NO: 2)/DEAH (SEQ ID NO: 3) box helicase domain protein [*Thermofilum pendens* Hrk 5] |
| YP_843229.1 | ski2-like helicase [*Methanosaeta thermophila* PT] >gb|ABK14589.1| DEAD (SEQ ID NO: 2)/DEAH (SEQ ID NO: 3) box helicase domain protein [*Methanosaeta thermophila* PT] |
| ZP_08045937.1 | ski2-like helicase [*Haladaptatus paucihalophilus* DX253] >gb|EFW90585.1| ski2-like helicase [*Haladaptatus paucihalophilus* DX253] |
| NP_280985.1 | ski2-like helicase [*Halobacterium* sp. NRC-1] >ref|YP_001690117.1| ski2-like helicase [*Halobacterium salinarum* R1]•sp|Q9HMV6.1|HELS_HALSA RecName: Full=Putative ski2-type helicase>sp|B0R7Q2.1|HELS_HALS3 RecName: Full=Putative ski2-type helicase >gb |AAG20465.1| DNA repair protein [*Halobacterium* sp. NRC-1] >emb|CAP14771.1| putative DNA helicase [*Halobacterium salinarum* R1] |
| YP_003357840.1 | Holliday junction migration helicase [*Methanocella paludicola* SANAE] dbj|BAI62857.1| Holliday junction migration helicase [*Methanocella paludicola* SANAE] |
| YP_003457479.1 | DEAD (SEQ ID NO: 2)/DEAH (SEQ ID NO: 3) box helicase domain protein [*Methanocaldococcus* sp. FS406-22] >gb|ADC68743.1 DEAD (SEQ ID NO: 2)/DEAH (SEQ ID NO: 3) box helicase domain protein [*Methanocaldococcus* sp. FS406-22] |
| YP_003127632.1 | DEAD (SEQ ID NO: 2)/DEAH (SEQ ID NO: 3) box helicase domain protein [*Methanocaldococcus fervens* AG86] >gb|ACV24132.1| DEAD (SEQ ID NO: 2)/DEAH (SEQ ID NO: 3) box helicase domain protein [*Methanocaldococcus fervens* AG86] |
| YP_003735335.1 | ski2-like helicase [*Halalkalicoccus jeotgali* B3] >gb|ADJ13543.1| ski2-like helicase [*Halalkalicoccus jeotgali* B3] |
| YP_503885.1 | ski2-1ike helicase [*Methanospirillum hungatei* JF-1] >gb|ABD42166.1| DEAD (SEQ ID NO: 2)/DEAH (SEQ ID NO: 3) box helicase-like protein [*Methanospirillum hungatei* JF-1] |
| BAJ48115.1 | helicase [*Candidatus Caldiarchaeum subterraneum*] >dbj|BAJ48144.1| helicase [*Candidatus Caldiarchaeum subterraneum*] >dbj|BAJ50919.1| helicase [*Candidatus Caldiarchaeum subterraneum*] |
| YP_001405615.1 | ski2-like helicase [*Candidatus Methanoregula boonei* 6A8] >sp|A71B61.1|HELS_METB6 RecName: Full=Putative ski2-type helicase >gb|ABS56972.1| DEAD (SEQ ID NO: 2)/DEAH (SEQ ID NO: 3) box helicase domain protein [*Methanoregula boonei* 6A8] |
| YP_306959.1 | ski2-like helicase [*Methanosarcina barkeri* str. *Fusaro*] >sp|Q465R3.1|HELS_METBF RecName: Full=Putative ski2-type helicase >gb|AAZ72379.1| helicase [*Methanosarcina barkeri* str. *Fusaro*] |
| YP_001031179.1 | ski2-like helicase [*Methanocorpusculum labreanum* Z] >gb|ABN07912.1| DEAD (SEQ ID NO: 2)/DEAH (SEQ ID NO: 3) box helicase domain protein [*Methanocorpusculum labreanum* Z] |
| YP_003541733.1 | DEAD (SEQ ID NO: 2)/DEAH (SEQ ID NO: 3) box helicase [*Methanohalophilus mahii* DSM 5219] >gb|ADE36088.1| DEAD(SEQ ID NO: 2)/DEAH (SEQ ID NO: 3) box helicase domain protein [*Methanohalophilus mahii* DSM 5219] |
| YP_004384692.1 | putative Ski2-type helicase [*Methanosaeta concilii* GP6] >gb|AEB68874.1| putative Ski2-type helicase [*Methanosaeta concilii* GP6] |
| YP_003725904.1 | DEAD (SEQ ID NO: 2)/DEAH (SEQ ID NO: 3) box helicase domain-containing protein [*Methanohalobium evestigatum* Z-7303] >gb|AD173108.1|DEAD (SEQ ID NO: 2)/DEAH (SEQ ID NO: 3) box helicase domain protein [*Methanohalobium evestigatum* Z-7303] |
| YP_003405271.1 | DEAD (SEQ ID NO: 2)/DEAH (SEQ ID NO: 3) box helicase [*Haloterrigena tarkmenica* DSM 5511] >gb|ADB62598.1| DEAD (SEQ ID NO: 2)/DEAH (SEQ ID NO: 3) box helicase domain protein [*Haloterrigena turkmenica* DSM 5511] |

TABLE 1-continued

Exemplary Hel308 helicases

| Accession | Description |
|---|---|
| YP_004244914.1 | DEAD (SEQ ID NO: 2)/DEAH (SEQ ID NO: 3) box helicase [*Vulcanisaeta moutnovskia* 768-28] >gb|ADY01412.1| DEAD (SEQ ID NO: 2)/DEAH (SEQ ID NO: 3) box helicase domain protein [*Vulcanisaeta moutnovskia* 768-28] |
| YP_001540156.1 | DEAD (SEQ ID NO: 2)/DEAH (SEQ ID NO: 3) box helicase domain-containing protein [*Caldivirga maquilingensis* IC-167] >sp|A8MB76.1|HELS_CALMQ RecName: Full=Putative ski2-type helicase >gb |ABW01166.1| DEAD (SEQ ID NO: 2)/DEAH (SEQ ID NO: 3) box helicase domain protein [*Caldivirga maquilingensis* IC-167] |
| NP_618094.1 | ski2-like helicase [*Methanosarcina acetivorans* C2A] >sp|Q8TL39.1|HELS_METAC RecName: Full=Putative ski2-type helicase >gb|AAM06574.1| helicase [*Methanosarcina acetivorans* C2A] |
| YP_003900980.1 | DEAD (SEQ ID NO: 2)/DEAH (SEQ ID NO: 3) box helicase domain-containing protein [*Vulcanisaeta distributa* DSM 14429] >gb|ADN49929.1| DEAD (SEQ ID NO: 2)/DEAH (SEQ ID NO: 3) box helicase domain protein [*Vulcanisaeta distributa* DSM 14429] |
| YP_003896003.1 | DEAD (SEQ ID NO: 2)/DEAH (SEQ ID NO: 3) box helicase domain-containing protein [*Methanoplanus petrolearius* DSM 11571] >gb|ADN37565.1| DEAD (SEQ ID NO: 2)/DEAH (SEQ ID NO: 3) box helicase domain protein [*Methanoplanus petrolearius* DSM 11571] |
| YP_003615773.1 | DEAD (SEQ ID NO: 2)/DEAH (SEQ ID NO: 3) box helicase domain protein [*Methanocaldococcus infernus* ME] >gb|ADG12809.1| DEAD (SEQ ID NO: 2)/DEAH (SEQ ID NO: 3) box helicase domain protein [*Methanocaldococcus infernus* ME] |
| YP_183745.1 | RNA helicase Ski2-like protein [*Thermococcus kodakarensis* KOD1] >sp|Q5JGV6.1|HELS_PYRKO RecName: Full=Putative ski2-type helicase; Contains: RecName: Full=Endonuclease P1-PkoHel; AltName: Full=Pko Hel intein >dbj|BAD85521.1|RNA helicase Ski2 homolog [*Thermococcus kodakarensis* KOD1] |
| YP_001322557.1 | DEAD (SEQ ID NO: 2)/DEAH (SEQ ID NO: 3) box helicase domain-containing protein [*Methanococcus vannielii* SB] >sp|A6UN73.1|HELS_METVS RecName: Full=Putative ski2-type helicase >gb|ABR53945.1| DEAD (SEQ ID NO: 2)/DEAH (SEQ ID NO: 3) box helicase domain protein [*Methanococcus vannielii* SB] |
| YP_002467772.1 | ski2-like helicase [*Methanosphaerula palustris* E1-9c] >gb|ACL18049.1| DEAD (SEQ ID NO: 2)/DEAH (SEQ ID NO: 3) box helicase domain protein [*Methanosphaerula palustris* E1-9c] |
| YP_003480097.1 | DEAD (SEQ ID NO: 2)/DEAH (SEQ ID NO: 3) box helicase [*Natrialba magadii* ATCC 43099] >gb|ADD05535.1| DEAD (SEQ ID NO: 2)/DEAH (SEQ ID NO: 3) box helicase domain protein [*Natrialba magadii* ATCC 43099] |
| YP_004577043.1 | ski2-type helicase [*Methanothermococcus okinawensis* IH1] >gb|AEH07265.1| ski2-type helicase [*Methanothermococcus okinawensis* IH1] |
| YP_004742641.1 | superfamily II helicase [*Methanococcus maripaludis* XI] >gb|AEK19898.1| superfamily II helicase [*Methanococcus maripaludis* XI] |
| NP_632449.1 | ski2-like helicase [*Methanosarcina mazei* Go1] >sp|Q8PZR7.1|HELS_METMA RecName: Full=Putative ski2-type helicase >gb|AAM30121.1| helicase [*Methanosarcina mazei* Go1] |
| YP_001097223.1 | DEAD (SEQ ID NO: 2)/DEAH (SEQ ID NO: 3) box helicase domain-containing protein [*Methanococcus maripaludis* C5 >gb| ABO35008.1| DEAD (SEQ ID NO: 2)/DEAH (SEQ ID NO: 3) box helicase domain protein [*Methanococcus maripaludis* C5] |
| YP_004742247.1 | DEAD (SEQ ID NO: 2)/DEAH (SEQ ID NO: 3) box helicase domain-containing protein [*Methanococcus maripaludis* XI] >gb|AEK19504.1| DEAD (SEQ ID NO: 2)/DEAH (SEQ ID NO: 3) box helicase domain-containing protein [*Methanococcus maripaludis* XI] |
| YP_004794766.1 | ski2-like helicase [*Haloarcula hispanica* ATCC 33960] >gb|AEM55778.1| ski2-like helicase [*Haloarcula hispanica* ATCC 33960] |
| NP_988010.1 | superfamily II helicase [*Methanococcus maripaludis* S2] >emb|CAF30446.1| superfamily II helicase [*Methanococcus maripaludis* S2] |
| YP_565780.1 | ski2-like helicase [*Methanococcoides burtonii* DSM 6242] >sp|Q12WZ6.1|HELS_METBU RecName: Full=Putative ski2-type helicase >gb|ABE52030.1| DEAD (SEQ ID NO: 2)/DEAH (SEQ ID NO: 3) box helicase-like protein [*Methanococcoides burtonii* DSM 6242] |
| YP_001549808.1 | DEAD (SEQ ID NO: 2)/DEAH (SEQ ID NO: 3) box helicase domain-containing protein [*Methanococcus maripaludis* C6] >gb|ABX02576.1| DEAD (SEQ ID NO: 2)/DEAH (SEQ ID NO: 3) box helicase domain protein [*Methanococcus maripaludis* C6] |
| YP_001548609.1 | DEAD (SEQ ID NO: 2)/DEAH (SEQ ID NO: 3) box helicase domain-containing protein [*Methanococcus maripaludis* C6] >gb|ABX01377.1| DEAD (SEQ ID NO: 2)/DEAH (SEQ ID NO: 3) box helicase domain protein [*Methanococcus maripaludis* C6] |
| YP_001329359.1 | DEAD (SEQ ID NO: 2)/DEAH (SEQ ID NO: 3) box helicase domain-containing protein [*Methanococcus maripaludis* C7] >gb|ABR65208.1| DEAD (SEQ ID NO: 2)/DEAH (SEQ ID NO: 3) box helicase domain protein [*Methanococcus maripaludis* C7] |
| YP_004595982.1 | ski2-type helicase [*Halopiger xanaduensis* SH-6] >gb|AEH36103.1| ski2-type helicase [*Halopiger xanaduensis* SH-6] |
| YP_656795.1 | ski2-like helicase [*Haloquadratum walsbyi* DSM 16790] >emb|CAJ51138.1| ATP-dependent DNA helicase [*Haloquadratum walsbyi* DSM 16790] |
| CCC38992.1 | ATP-dependent DNA helicase Hel308 [*Haloquadratum walsbyi* C23] |
| YP_004035272.1 | superfamily ii helicase [*Halogeometricum borinquense* DSM 11551] |
| YP_137330.1 | ski2-like helicase [*Haloarcula marismortui* ATCC 43049] >sp | Q5UYM9, 1|HELS_HALMA RecName: Full=Putative ski2-type helicase >gb | AAV47624.1 | putative ski2-type helicase [*Haloarcula marismortui* ATCC 43049] |

TABLE 1-continued

Exemplary Hel308 helicases

| Accession | Description |
|---|---|
| YP_001581577.1 | DEAD (SEQ ID NO: 2)/DEAH (SEQ ID NO: 3) box helicase domain-containing protein [*Nitrosopumilus maritimus* SCM] >gb \| ABX12139.1 \| DEAD (SEQ ID NO: 2)/DEAH (SEQ ID NO: 3) box helicase domain protein [*Nitrosopumilus maritimus* SCM1] |
| EET90255.1 | DEAD (SEQ ID NO: 2)/DEAH (SEQ ID NO: 3) box helicase domain protein [*Candidatus Micrarchaeum acidiphilum* ARMAN-2] |
| NP_376477.1 | Helicase [*Sulfolobus tokodaii* str. 7 \| >sp \| Q974S1.1 \| HELS_SULTO RecName: Full=Putative ski2-type helicase >dbj \| BAK54341.1 \| Holliday junction migration helicase [*Sulfolobus tokodaii* str. 7] |
| YP_001097792.1 | DEAD (SEQ ID NO: 2)/DEAH (SEQ ID NO: 3) box helices domain-containing protein [*Methanococcus maripaludis* C5] >gb \| ABO35578.1 \| DEAD (SEQ ID NO: 2)/DEAH (SEQ ID NO: 3) box helicase domain protein [*Methanococcus maripaludis* C5] |
| ZP_08667240.1 | DEAD (SEQ ID NO: 2)/DEAH (SEQ ID NO: 3) box helicase domain protein [*Nitrosopumilus* sp. MYI] >gb \| EGP92972.1 \| DEAD (SEQ ID NO: 2)/DEAH (SEQ ID NO: 3) box helicase domain protein [*Nitrosopumilus* sp. MYI] |
| YP_254972.1 | DNA helicase [*Sulfolobus acidocaldarius* DSM 639] >sp \| Q4JC00.1 \| HELS_SULAC RecName: Full=Putative ski2-type helicase >gb \| AAY79679.1 \| DNA helicase [*Sulfolobus acidocaldarius* DSM 639] |
| EFD92533.1 | DEAD (SEQ ID NO: 2)/DEAH (SEQ ID NO: 3) box helicase domain protein [*Candidatus Parvarchaeum acidophilus* ARMAN-5] |
| YP_003176527.1 | ski2-like helicase [*Halomicrobium mukohataei* DSM 12286] >gb \| ACV46820.1 \| DEAD (SEQ ID NO: 2)/DEAH (SEQ ID NO: 3)box helicase domain protein [*Halomicrobium mukohataei* DSM 12286] |
| EGD71904.1 | DEAD (SEQ ID NO: 2)/DEAH (SEQ ID NO: 3) box helicase dmain protein [*Candidatus Parvarchaeum acidophilus* ARMAN-5_'5-way FS'] |
| YP_001040230.1 | DEAD (SEQ ID NO: 2)/DEAH (SEQ ID NO: 3) box helicase domain-containing protein [*Staphylothermus marinus* F1] >gb \| ABN69322.1 \| DEAD (SEQ ID NO: 2)/DEAH (SEQ ID NO: 3) box helicase domain protein [*Staphylothermus marinus* F1] |
| ABZ07376.1 | putative DEAD (SEQ ID NO: 2)/DEAH (SEQ ID NO: 3) box helicase [uncultured marine crenarchaeote HF4000_AN1W133M9] |
| YP_001097458.1 | DEAD (SEQ ID NO: 2)/DEAH (SEQ ID NO: 3) box helicase daomain-containing protein [*Methanococcus maripaludis* C5] >gb \| AB035243.1 \| DEAD (SEQ ID NO: 2)/DEAH (SEQ ID NO: 3) box helicase domain protein [*Methanococcus maripaludis* C5] |
| ABZ08606.1 | putative DEAD (SEQ ID NO: 2)/DEAH (SEQ ID NO: 3) box helicase [uncultured marine crenarchaeote HF4000_APKG3H9] |
| YP_325906.1 | ski2-like helicase [*Natronomonas pharaonis* DSM 2160] >sp \| Q31U46.1 \| HELS_NATPD RecName: Full=Putative ski2-type helicase >emb \| CA148337.1 \| ATP-dependent DNA helicase \| [*Natronomonas pharaonis* DSM 2160] |
| YP_930665.1 | DEAD (SEQ ID NO: 2)/DEAH (SEQ ID NO: 3) box helicase domain-containing protein [*Pyrobaculum islandicum* DSM 4184] >gb \| ABL88322.1 \| DEAD (SEQ ID NO: 2)/DEAH (SEQ ID NO: 3) box helicase domain protein [*Pyrobaculum islandicum* DSM 4184] |
| YP_001435870.1 | DEAD (SEQ ID NO: 2)/DEAH (SEQ ID NO: 3) box helicase [*Ignicoccus hospitalis* KIN4/I] >gb \| ABU82463.1 \| DEAD (SEQ ID NO: 2)/DEAH (SEQ ID NO: 3) box helicase domain protein [*Ignicoccus hospitalis* KIN4/I] |
| YP_003668634.1 | DEAD (SEQ ID NO: 2)/DEAH (SEQ ID NO: 3) box helicase domain-containing protein [*Staphylothermus hellenicus* DSM 12710] >gb \| AD131735. \| DEAD (SEQ ID NO: 2)/DEAH (SEQ ID NO: 3) box helicase domain protein [*Staphylothermus hellenicus* DSM 12710] |
| ZP_08558598.1 | ski2-like helicase [*Halorhabdus tiamatea* SARL4B] >gb \| EGM36528.1 \| ski2-like helicase [*Halorhabdus tiamatea* SARL4B] |
| YP_002428409.1 | DEAD (SEQ ID NO: 2)/DEAH (SEQ ID NO: 3) box helicase domain-containing protein [*Desulfurococcus kamchatkensis* 1221n] >gb\|ACL11042.1\|DEAD (SEQ ID NO: 2)/DEAH (SEQ ID NO: 3) box helicase domain protein [*Desulfurococcus kamchatkensis* 122ln] |
| YP_004336918.1 | ATP-dependent, DNA binding helicase [*Thermoproteus uzoniensis* 768-20] >gb\|AEA11606.1\|ATP-dependent, DNA binding helicase [*Thermoproteus uzoniensis* 768-20] |
| ZP_08257442.1 | DEAD (SEQ ID NO: 2)/DEAH (SEQ ID NO: 3) box helicase domain-containing protein [*Candidatus Nitrosoarchaeum limnia* SFB1] >gb\|EGG41989.1\|DEAD (SEQ ID NO: 2)/DEAH (SEQ ID NO: 3) box helicase domain-containing protein [*Candidatus Nitrosoarchaeum limnia* SFB1] |
| YP_004459284.1 | DEAD (SEQ ID NO: 2)/DEAH (SEQ ID NO: 3) box helicase domain-containing protein [*Acidianus hospitalis* W1] >gb\|AEE94986.1\| DEAD (SEQ ID NO: 2)/DEAH (SEQ ID NO: 3) box helicase domain protein [*Acidianus hospitalis* W1] |
| NP_558924.1 | ATP-dependent, DNA binding helicase [*Pyrobaculum aerophilum* str. IM2] > gb\|AAL63106.1\|ATP-dependent, DNA binding helicase [*Pyrobaculum aerophilum* str. IM2] |
| YP_004409449.1 | DEAD (SEQ ID NO: 2)/DEAH (SEQ ID NO: 3) box helicase domain-containing protein [*Metallosphaera cuprina* Ar-4] >gb\|AEB94965.1\|DEAD (SEQ ID NO: 2)/DEAH (SEQ ID NO: 3) box helicase domain-containing protein [*Metallosphaera cuprina* Ar-4] |
| YP_003649556.1 | DEAD (SEQ ID NO: 2)/DEAH (SEQ ID NO: 3) box helicase domain-containing protein [*Thermosphaera aggregans* DSM 11486] >gb\|ADG90604.1\|DEAD (SEQ ID NO: 2)/DEAH (SEQ ID NO: 3) box helicase domain protein [*Thermosphaera aggregans* DSM 11486] |
| ZP_06387115.1 | DEAD (SEQ ID NO: 2)/DEAH (SEQ ID NO: 3) box helicase domain protein [*Sulfolobus solfataricus* 98/2] >gb\|ACX90562.1\|DEAD (SEQ ID NO: 2)/DEAH (SEQ ID NO: 3) box helicase domain protein [*Sulfolobus solfataricus* 98/2] |
| 2VA8_A | Chain A, Dna Repair Helicase Hel308>pdb\|2VA8\|B Chain B, Dna Repair Helicase Hel308>emb\|CAO85626.1\|DNA helicase [*Sulfolobus solfataricus*] |

TABLE 1-continued

Exemplary Hel308 helicases

| Accession | Description |
| --- | --- |
| YP_004809267.1 | ski2-type helicase [halophilic archaeon DL31]>gb|AEN06894.1|ski2-type helicase [halophilic archaeon DL31] |
| ADX84345.1 | DEAD (SEQ ID NO: 2)/DEAH (SEQ ID NO: 3) box helicase domain protein [Sulfolobus islandicus REY15A]>gb|ADX81629.1|DEAD (SEQ ID NO: 2)/DEAH (SEQ ID NO: 3) box helicase domain protein [Sulfolobus islandicus HVE10/4] |
| YP_002828439.1 | DEAD (SEQ ID NO: 2)/DEAH (SEQ ID NO: 3) box helicase [Sulfolobus islandicus M.14.25]> ref|YP_002842325.1|DEAD (SEQ ID NO: 2)/DEAH (SEQ ID NO: 3) box helicase domain protein [Sulfolobus islandicus M.16.27]>gb|ACP37141.1|DEAD (SEQ ID NO: 2)/DEAH (SEQ ID NO: 3) box helicase domain protein [Sulfolobus islandicus M.14.25]>gb|ACP54280.1|DEAD (SEQ ID NO: 2)/DEAH (SEQ ID NO: 3) box helicase domain protein [Sulfolobus islandicus M.16.27] |
| YP_002913571.1 | DEAD (SEQ ID NO: 2)/DEAH (SEQ ID NO: 3) box helicase domain protein [Sulfolobus islandicus M.16.41]>gb|ACR40903.1|DEAD (SEQ ID NO: 2)/DEAH (SEQ ID NO: 3) box helicase domain protein [Sulfolobus islandicus M.16.4] |
| Q97VY9.1 | RecName: Full=Putative ski2-type helicase |
| YP_002841682.1 | DEAD (SEQ ID NO: 2)/DEAH (SEQ ID NO: 3) box helicase domain protein [Sulfolobus islandicus Y.N.15.51]>gb|ACP49760.1|DEAD (SEQ ID NO: 2)/DEAH (SEQ ID NO: 3) box helicase domain protein [Sulfolobus islandicus Y.N.15.51] |
| YP_002831080.1 | DEAD (SEQ ID NO: 2)/DEAH (SEQ ID NO: 3) box helicase domain protein [Sulfolobus islandicus L.S.2.15]>ref|YP_003418425.1|DEAD (SEQ ID NO: 2)/DEAH (SEQ ID NO: 3) box helicase domain protein [Sulfolobus islandicus L.D.8.5]>gb|ACP34435.1|DEAD (SEQ ID NO: 2)/DEAH (SEQ ID NO: 3) box helicase domain protein [Sulfolobus islandicus L.S.2.15]> gb|ADB86055.1|DEAD (SEQ ID NO: 2)/DEAH (SEQ ID NO: 3) box helicase domain protein [Sulfolobus islandicus L.D.8.5] |
| YP_001054984.1 | DEAD (SEQ ID NO: 2)/DEAH (SEQ ID NO: 3) box helicase domain-containing protein [Pyrobaculum calidifontis JCM 11548]>sp|A3MSA.1.1|HELS_PYRCJ RecName: Full=Putative ski2-type helicase>gb|ABO07518.1|DEAD (SEQ ID NO: 2)/DEAH (SEQ ID NO: 3) box helicase domain protein [Pyrobaculum calidifontis JCM 11548] |
| NP_343811.1 | DNA helicase related protein [Sulfolobus solfataricus P2]>ref|YP_002836469.1|DEAD (SEQ ID NO: 2)/DEAH (SEQ ID NO: 3) box helicase [Sulfolobus islandicus Y.G.57.14]>gb|AAK42601.1|DNA helicase related protein [Sulfolobus solfataricus P2]>gb|ACP44547.1 DEAD (SEQ ID NO: 2)/DEAH (SEQ ID NO: 3) box helicase domain protein [Sulfolobus islandicus Y.G.57.14] |
| YP_001152379.1 | DEAD (SEQ ID NO: 2)/DEAH (SEQ ID NO: 3) box helicase domain-containing protein [Pyrobaculum arsenaticum DSM 13514] > gb|ABP49727.1| DEAD (SEQ ID NO: 2)/DEAH (SEQ ID NO: 3) box helicase domain protein [Pyrobaculum arsenaticum DSM 13514] |
| YP_001191456.1 | DEAD (SEQ ID NO: 2)/DEAH (SEQ ID NO: 3) box helicase domain-containing protein [Metallosphaera sedula DSM 5348] > gb|ABP95532.1| DEAD (SEQ ID NO: 2)/DEAH (SEQ ID NO: 3) box helicase domain protein [Metallosphaera sedula DSM 5348] |
| NP_147034.2 | holliday junction migration helicase [Aeropyrum pernix K1] >sp|Q9YFQ8.2|HELS_AERPE RecName: Full=Putative ski2-type helicase >dbj|BAA79103.2| holliday junction migration helicase [Aeropyrum pernix K1] |
| YP_024158.1 | ski2-like helicase [Picrophilus torridus DSM 9790] >gb|AAT43965.1| helicase involved in UV-protection [Picrophilus torridus DSM 9790] |
| YP_003816358.1 | Putative ski2-type helicase [Acidilobus saccharovorans 345-15] >gb|ADL19327.1| Putative ski2-type helicase [Acidilobus saccharovorans 345-15] |
| YP_003860265.1 | DEAD (SEQ ID NO: 2)/DEAH (SEQ ID NO: 3) box helicase domain protein [Ignisphaera aggregans DSM 17230] >gb|ADM28385.1| DEAD (SEQ ID NO: 2)/DEAH (SEQ ID NO: 3) box helicase domain protein [Ignisphaera aggregans DSM 17230] |
| NP_394295.1 | ski2-like helicase [Thermoplasma acidophilum DSM 1728] >sp|Q9HJX7.1|HELS_THEAC RecName: Full=Putative ski2-type helicase >emb|CAC11964.1| DNA helicase related protein [Thermoplasma acidophilum] |
| YP_876638.1 | superfamily II helicase [Cenarchaeum symbiosum A] >gb|ABK78334.1| superfamily II helicase [Cenarchaeum symbiosum A] |
| ZP_05571398.1 | ski2-like helicase [Ferroplasma acidarmanus fer1] |
| YP_004176252.1 | DEAD (SEQ ID NO: 2)/DEAH (SEQ ID NO: 3) box helicase domain-containing protein [Desulfurococcus mucosus DSM 2162] >gb|ADV64770.1| DEAD (SEQ ID NO: 2)/DEAH (SEQ ID NO: 3) box helicase domain protein [Desulfurococcus mucosus DSM 2162] |
| YP_001737782.1 | DEAD (SEQ ID NO: 2)/DEAH (SEQ ID NO: 3) box helicase domain-containing protein [Candidatus Korarchaeum cryptofilum OPF8] >gb|ACB08099.1| DEAD (SEQ ID NO: 2)/DEAH (SEQ ID NO: 3) box helicase domain protein [Candidatus Korarchaeum cryptofilum OPF8] |
| EGQ40435.1 | superfamily II helicase [Candidatus Nanosalinarum sp. J07AB56] |
| YP_002567343.1 | ski2-like helicase [Halorubrum lacusprofundi ATCC 49239] >gb|ACM58273.1] DEAD (SEQ ID NO: 2)/DEAH (SEQ ID NO: 3) box helicase domain protein [Halorubrum lacusprofundi ATCC 49239] |
| YP_001793507.1 | DEAD (SEQ ID NO: 2)/DEAH (SEQ ID NO: 3) box helicase domain-containing protein [Thermoproteus neutrophilus V24Sta] >gb|ACB39061.1| DEAD (SEQ ID NO: 2)/DEAH (SEQ ID NO: 3) box helicase domain protein [Thermoproteus neutrophilus V24Sta] |
| YP_003534088.1 | ATP-dependent DNA helicase Hel308 [Haloferax volcanii DS2] >gb|ADE04048.1| ATP-dependent DNA helicase Hel308a [Haloferax volcanii DS2] |
| YP_004037165.1 | superfamily ii helicase [Halogeometricum borinquense DSM 11551] >gb|ADQ67720.1| superfamily II helicase [Halogeometricum borinquense DSM 11551] |
| NP_111333.1 | ski2-like helicase [Thermoplasma volcanium GSS1] >sp|Q97AI2.1|HELS_THEVO RecName: Full=Putative ski2-type helicase >dbj|BAB59970.1| DNA helicase [Thermoplasma volcanium GSS1] |
| YP_002565871.1 | DEAD (SEQ ID NO: 2)/DEAH (SEQ ID NO: 3) box helicase [Halorubrum lacusprofundi ATCC 49239] >gb|ACM56801.1| DEAD (SEQ ID NO: 2)/DEAH (SEQ ID NO: 3) box helicase domain protein [Halorubrum lacusprofundi ATCC 49239] |

TABLE 1-continued

Exemplary Hel308 helicases

| Accession | Description |
| --- | --- |
| CCC39675.1 | ATP-dependent DNA helicase Hel308 [*Haloquadratum walsbyi* C23] |
| YP_657401.1 | ATP-dependent DNA helicase [*Haloquadratum walsbyi* DSM 16790] >emb|CAJ51759.1| ATP-dependent DNA helicase [*Haloquadratum walsbyi* DSM 16790] |
| YP_003535028.1 | ATP-dependent DNA helicase Hel308b [*Haloferax volcanii* DS2]>gb | ADE02398.1 | ATP-dependent DNA helicase HEL308b [*Haloferax volcanii* DS2] |
| YP_003706863.1 | DEAD (SEQ ID NO: 2)/DEAH (SEQ ID NO: 3) box helicase domain-containing protein [*Methanococcus voltae* A3]>gb | ADI35890.1 | DEAD (SEQ ID NO: 2)/DEAH (SEQ ID NO: 3) box helicase domain protein [*Methanococcus voltae* A3] |
| ABD17736.1 | helicase [*Methanococcus voltae* PS] |
| NP_613398.1 | superfamily II helicase [*Methanopyrus kandleri* AV19]>gb | AAM01328.1 | Predicted Superfamily 11 helicase [*Methanopyrus kandleri* AV19] |
| CBH38575.1 | putative ski2-type helicase [uncultured archaeon] |
| EEZ93258.1 | DEAD (SEQ ID NO: 2)/DEAH (SEQ ID NO: 3) box helicase domain protein [*Candidatus Parvarchaeum acidiphilum* ARMAN-4] |
| YP_004004246.1 | DEAD (SEQ ID NO: 2)/DEAH (SEQ ID NO: 3) box helicase domain protein [*Methanothermus fervidus* DSM 2088]>gb|ADP77484.1|DEAD (SEQ ID NO: 2)/DEAH (SEQ ID NO: 3) box helicase domain protein [*Methanothermus fervidus* DSM 2088] |
| YP_003850109.1 | helicase [*Methanothermobacter marburgensis* str. Marburg]>gb | ADL58796.1 | predicted helicase [*Methanothermobacter marburgensis* str. Marburg] |
| YP_003424423.1 | DEAD (SEQ ID NO: 2)/DEAH (SEQ ID NO: 3) box helicase domain-containing protein [*Methanobrevibacter ruminantium* M1]>gb | ADC47531.1 | DEAD (SEQ ID NO: 2)/DEAH (SEQ ID NO: 3) box helicae domain-containing protein [*Methanobrevibacter ruminantium* M1] |
| YP_004291107.1 | DEAD (SEQ ID NO: 2)/DEAH (SEQ ID NO: 3) box helicase domain-containing protein [*Methanobacterium* sp. AL-21]>gb | ADZ10135.1 | DEAD (SEQ ID NO: 2)/DEAH (SEQ ID NO: 3) box helicase domain protein [*Methanobacterium* sp. AL-21] |
| YP_447162.1 | helicase [*Methanosphaera stadtmanae* DSM 3091] >gb | ABC56519.1 | predicted helicase [*Methanosphaera stadtmanae* DSM 3091] |
| YP_004519549.1 | DEAD (SEQ ID NO: 2)/DEAH (SEQ ID NO: 3) box helicase domain-containing protein [*Methanobacterium* sp. SWAN-1]>gb | AEG17748.1 | DEAD (SEQ ID NO: 2)/DEAH (SEQ ID NO: 3) box helicase domain protein [*Methanobacterium* sp. SWAN-1] |
| NP_275949.1 | DNA helicase related protein [*Methanothermobacter thermautotrophicus* str. Delta H]>sp | O26901.1 | HELS . . . METTH RecName: Full=Putative ski2-type helicase>gb | AAB85310.1 | DNA helicase related protein [*Methanothermobacter thermautotrophicus* str. Delta H] |
| ZP_05975717.2 | putative Ski2-type helicase [*Methanobrevibacter smithii* DSM 2374]>gb | EFC93382.1 | putative Ski2-type helicase [*Methanobrevibacter smithii* DSM 2374] |
| ZP_03607647.1 | hypothetical protein METSMIALI . . . 00751 [*Methanobrevibacter smithii* DSM 2375]>gb | EEE41862.1 | hypothetical protein METSMIALI_00751 [*Methanobrevibacter smithii* DSM 2375] |
| YP_001273412.1 | ATP-dependent helicase [*Methanobrevibacter smithii* ATCC 35061]>gb | ABQ87044.1 | ATP-dependent helicase [*Methanobrevibacter smithii* ATCC 35061] |
| YP_003247505.1 | DEAD (SEQ ID NO: 2)/DEAH (SEQ ID NO: 3) box helicase domain protein [*Methanocaldococcus vulcanius* M7] >gb | ACX73023.1 | DEAD (SEQ ID NO: 2)/DEAH (SEQ ID NO: 3) box helicase domain protein [*Methanocaldococcus vulcanius* M7] |
| NP_248116.1 | SKI2 family helicase [*Methanocaldococcus jannaschii* DSM 2661] >sp | Q58524.1 | HELS . . . METJA RecName: Full=Putative ski2-type helicase; Contains: RecName: Full=Endonuclease PI-MjaHel; AltName: Full=Mja Hel intein; AltName: Full=Mja Pep3 intein>gb | AAB99126.1 | putative SKI2-family helicase [*Methanocaldococcus jannaschii* DSM 26621] |
| YP_001324295.1 | DEAD (SEQ ID NO: 2)/DEAH (SEQ ID NO: 3) box helicase domain-containing protein [*Methanococcus acolicus* Nakai-3]>gb | ABR 55683.1 | DEAD (SEQ ID NO: 2)/DEAH (SEQ ID NO: 3) box helicase domain protein [*Methanococcus aeolicus* Nankai-3] |
| YP_003536960.1 | Pre-mRNA splicing helicase [*Haloferax volcanii* DS2]>gb | ADE02332.1 | Pre-mRNA splicing helicase [*Haloferax volcanii* DS2] |
| YP_003131029.1 | DEAD (SEQ ID NO: 2)/DEAH (SEQ ID NO: 3) box helicase domain protein [*Halorhabdus utahensis* DSM 12940]>gb | ACV12296.1 | DEAD (SEQ ID NO: 2)/DEAH (SEQ ID NO: 3) box helicase domain protein [*Halorhabdus utahensis* DSM 12940] |
| YP_002567151.1 | DEAD (SEQ ID NO: 2)/DEAH (SEQ ID NO: 3) box helicase [*Halorubrum lacusprofundi* ATCC 49239] >gb | ACM58081.1 | DEAD (SEQ ID NO: 2)/DEAH (SEQ ID NO: 3) box helicase domain protein [*Halorubrum lacusprofundi* ATCC 49239] |
| YP_004035351.1 | superfamily ii helicase [*Halogeometricum borinquense* DSM 11551] >gb | ADQ65912.1 | superfamily II helicae [*Halogeometricum borinquense* DSM 11551] |
| YP_004808851.1 | DEAD (SEQ ID NO: 2)/DEAH (SEQ ID NO: 3) box helicase domain-containing protein [halophilic archaeon DL31]>gb | AEN06478.1 | DEAD (SEQ ID NO: 2)/DEAH (SEQ ID NO: 3) box helicae domain protein [halophilic archaeon DL31] |
| XP_002716686.1 | PREDICTED: DNA polymerase theta isoform 1 [*Oryctolagus cuniculus*] |
| YP_656834.1 | ATP-dependent DNA helicase [*Haloquadratum walsbyi* DSM 16790] >emb | CAJ51176.1 | ATP-dependent DNA helicase [*Haloquadratum walsbyi* DSM 16790] |
| XP_003248103.1 | PREDICTED: DNA polymerase theta-like isoform 1 [*Acyrthosiphon pisum*] |
| ABC72356.1 | ATP-dependent DNA helicase [*Haloquadratum walsbyi*] |
| CCC39031.1 | DEAD (SEQ ID NO: 2)/DEAH (SEQ ID NO: 3) box helicase [*Haloquadratum walsbyi* C23] |
| XP_001165150.2 | PREDICTED: DNA polymerase theta isoform 1 [*Pan troglodytes*] |
| XP_003225852.1 | PREDICTED: DNA polymerase theta-like [*Anolis carolinensis*] |
| XP_615375.3 | PREDICTED: DNA polymerase theta [*Bos Taurus*]>ref[XP_002684835.1] PREDICTED: polymerase (DNA directed), theta-like [*Bos Taurus*] >gb | DAA33456.1 | polymerase (DNA directed), theta-like [*Bos Taurus*] |

TABLE 1-continued

Exemplary Hel308 helicases

| Accession | Description |
|---|---|
| XP_002813286.1 | PREDICTED: LOW QUALITY PROTEIN: DNA polymerase theta-like [*Pongo abelii*] |
| AAR08421.2 | DNA polymerase theta [*Homo sapiens*] |
| EAW79510.1 | polymerase (DNA directed), theta, isoform CRA_a [*Homo sapiens*] |
| NP_955452.3 | DNA polymerase theta [*Homo sapiens*]>sp|O75417.2|DPOLQ . . . HUMAN RecName: Full = DNA polymerase theta; AltName: Full=DNA polymerase eta >gb|aa172289.1|Polymerase (DNA directed), theta [synthetic polynucleotide] |
| NP_001099348.1 | DNA polymerase theta [*Rattus norvegicus*]>gb|EDM11249.41|polymerase (DNA directed), theta (predicted), isoform CRA_a [*Rattus norvegicus*] |
| XP_003341262.1 | PREDICTED: LOW QUALITY PROTEIN: DNA polymerase theta-like [*Monodelphis domestica*] |
| XP_001502374.3 | PREDICTED: DNA polymerase theta [*Equus caballus*] |
| XP_545125.3 | PREDICTED: LOW QUALITY PROTEIN: DNA polymerase theta [*Canis lupus familiaris*] |
| XP_002928855.1 | PREDICTED: LOW QUALITY PROTEIN: DNA polymerase theta-like [*Ailuropoda melanoleuca*] |
| NP_084253.1 | DNA polymerase theta isoform 1 [*MUS musculus*]>gb|AAL77225.1|DNA polymerase theta [*Mus musculus*]>gb|EDK 97951.1|polymerase (DNA directed), theta, isoform CRA_a [*Mus musculus*]>gb|AA138361.1|Polymerase (DNA directed), theta [*Mus musculus*]>gbAA157901.1|Polymerase (DNA directed), theta [*Mus musculus*] |
| AAK39635.1 | DNA polymerase theta [*Homo sapiens*] |
| AAN39838.1 | DNA polymerase Q [*Mus musculus*] |
| XP_003412882.1 | PREDICTED: DNA polymerase theta [*Loxodona africana*] |
| YP_003735206.1 | DEAD (SEQ ID NO: 2)/DEAH (SEQ ID NO: 3) box helicase domain-containing protein [*Halalkalicoccus jeotgali* B3]>gb|ADJ13414.1|DEAD (SEQ ID NO: 2)/DEAH (SEQ ID NO: 3) box helicase domain protein [*Halalkalicoccus jeotgali* B3] |
| YP_004794841.1 | pre-mRNA splicing helicase [*Haloarcula hispanica* ATCC 33960] >gb|AEM55853.1|pre-mRNA splicing helicase [*Haloarcula hispanica* ATCC 33960] |
| XP_416549.2 | PREDICTED: similar to DNA polymerase theta [*Gallus gallus*] |
| XP_003427319.1 | PREDICTED: helicase POLQ-like isoform 2 [*Nasonia vitripennis*] |
| XP_003202748.1 | PREDICTED: DNA polymerase theta-like [*Meleagris gallopavo*] |
| XP_969311.1 | PREDICTED: similar to DNA polymerase theta [*Tribolium castaneum*]>gb|EEZ97532.1|hypothetical protein TcasGA2 . . . TC011380 [*Tribolium castaneum*] |
| ZP_08046037.1 | DEAD (SEQ ID NO: 2)/DEAH (SEQ ID NO: 3) box helicase domain protein [*Haladaptatus paucihalophilus* DX253]>gb|EFW90685.1|DEAD (SEQ ID NO: 2)/DEAH (SEQ ID NO: 3) box helicase domain protein [*Haladaptatus paucihalophilus* DX253] |
| YP_461714.1 | helicase [*Syntrophus aciditrophicus* SB]>gb|ABC77546.1|helicase [*Syntrophus aciditrophicus* SB] |
| YP_003176510.1 | DEAD (SEQ ID NO: 2)/DEAH (SEQ ID NO: 3) box helicase [*Halomicrobium mukohataei* DSM 12286]>gb|AAV47694.1|DEAD (SEQ ID NO: 2)/DEAH (SEQ ID NO: 3) box helicase domain protein [*Halomicrobium mukohataei* DSM 12286] |
| YP_137400.1 | pre-mRNA splicing helicase [*Haloarcula marismortui* ATCC43049]>gb|AAV47694.1|Pre-mRNA splicing helicase [*Haloarcula marismortui* ATCC 43049] |
| NP_001184156.1 | polymerase (DNA directed), theta [*Xenopus (Silurana) tropicalis*] |
| NP_280861.1 | Pre-mRNA splicing helicase [*Halobacterium* sp. NRC-1]>ref|YP . . . 001689987.1|ATP-dependent DNA helicase [*Halobacterium salinarum* R1]>gb|AAG20341.1| pre-mRNA splicing helicase [*Halobacterium* sp. NRC-1]>emb|CAP14641.1|ATP-dependent DNA helicase [*Halobacterium salinarum* R1] |
| YP_004595640.1 | DEAD (SEQ ID NO: 2)/DEAH (SEQ ID NO: 3) box helicase domain-containing protein [*Halopiger xanaduensis* SH 6]>gb|AEH35761.1|DEAD (SEQ ID NO: 2)/DEAH (SEQ ID NO: 3) box helicase domain protein [*Halopiger xanadueniss* SH-6] |
| XP_001521144.2 | PREDICTED: DNA polymerase theta, partial [*Ornithorhynchus anatinus*] |
| XP_003261953.1 | PREDICTED: DNA polymerase thea, partial [*Nomascus leucogenys*] |
| XP_001358456.2 | GA 19301 [*Drosophila pseudoobscura pseudoobscura*]>gb|EAI . . . 27595.2| GA 19301 [*Drosophila pseudoobscura pseudoobscura*] |
| ZP_08560003.1 | DEAD (SEQ ID NO: 2)/DEAH (SEQ ID NO: 3) box helicase domain protein [*Halorhabdus tiamatea* SARL4B]>gb|EGM34502.1|DEAD (SEQ ID NO: 2)/DEAH (SEQ ID NO: 3) box helicase domain protein [*Halorhabdus tiamatea* SARL4B] |
| XP_002187783.1 | PREDICTED: similar to polymerase (DNA directed), theta [*Taeniopygia guttata*] |
| XP_002112587.1 | hypothetical protein TRIADDRAFT . . . 25163 [*Trichoplax adhaerens*]>gb|EDV24697.1|hypothetical protein TRIADDRAFT . . . 25163 [*Trichoplaz adhaerens*] |
| YP_003405139.1 | DEATH/DEAH box helicase [*Haloterrigena turkmenica* DSM 5511] >gb|ADB62466.1|DEAD (SEQ ID NO: 2)/DEAH (SEQ ID NO: 3) box helicase domain protein [*Haloterrigena turkmenica* DSM 5511] |
| EGV92665.1 | DNA polymerase theta [*Cricetulus griseus*] |
| CBY24305.1 | unnamed protein product [*Oikopleura dioica*] |
| YP_003130565.1 | DEAD (SEQ ID NO: 2)/DEAH (SEQ ID NO: 3) box helicase domain protein [*Halorhabdus utahensis* DSM 12940]>gb|ACV11832.1|DEAD (SEQ ID NO: 2)/DEAH (SEQ ID NO: 3) box helicae domain protein [*Halorhabdus utahensis* DSM 12940] |
| YP_003479811.1 | DEAD (SEQ ID NO: 2)/DEAH (SEQ ID NO: 3) box helicase [*Natrialba magadii* ATCC 43099]>gb|ADD05249.1|DEAD (SEQ ID NO: 2)/DEAH (SEQ ID NO: 3) box helicase domain protein [*Natrialba magadii* ATCC 43099] |
| EFB22383.1 | hypothetical protein PANDA_000253 [*Ailuropoda melanoleuca*] |
| YP_003357334.1 | putative ATP-dependent helicase [*Methanocella paludicola* SANAE] > dbj|BA162351.1|putative ATP-dependent helicase [*Methanocella paludicola* SANAE] |
| YP_325942.1 | ATP-dependent DNA helicase 2 [*Natronomonas pharaonis* DSM 2160]>emb|CA148373.2|ATP-dependent DNA helicase 2 [*Natronomonas pharaonis* DSM 2160] |

TABLE 1-continued

Exemplary Hel308 helicases

| Accession | Description |
|---|---|
| XP_002912509.1 | PREDICTED: LOW QUALITY PROTEIN: helicase POLQ like [*Ailuropoda melanoleuca*] |
| XP_002704678.1 | PREDICTED: helicase, POLQ-like [*BOS taurus*] |
| CAE47762.2 | novel protein similar to human DNA-directed polymerase theta (POLQ) [*DANIO rerio*] |
| XP_003205636.1 | PREDICTED: helicase POLQ-like [*Meleagris gallopavo*] |
| XP_544959.2 | PREDICTED: helicase, POLQ-like [*Canis lupus familiaris*] |
| EFX86757.1 | hypothetical protein DAPPUDRAFT_312857 [*Daphnia pulex*] |
| YP_003389641.1 | DEAD (SEQ ID NO: 2)/DEAH (SEQ ID NO: 3) box helicase [*Spirosoma lingual* DSM 74]>gb \| ADB40842.1 \| DEAD (SEQ ID NO: 2)/DEAH (SEQ ID NO: 3) box helicase domain protein [*Spirosoma lingual* DSM 74] |
| XP_002602932.1 | hypothetical protein BRAFLDRAFT_251779 [*Branchiostoma floridae*]>gb \| EEN58944.1 \| hypothetical protein BRAFLDRAFT_251779 [*Branchiostoma floridae*] |
| YP_004144962.1 | peptidase C14 caspase catalytic subunit p20 [*Mesorhizobium ciceri biovar biserrulae* WSM1271>ref\| YP_004614892.1 \| DEAD (SEQ ID NO: 2)/DEAH (SEQ ID NO: 3) box helicase domain-containing protein [*Mesorhizobium opportunistum* WSM2075] >gb \| ADV14912.1 \| peptidase C14 caspase catalytic subunit p20 [*Mesorhizobium ciceri biovar biserrulae* WSM1271] >gb \| AEH90798.1 \| DEAD (SEQ ID NO: 2)/DEAH (SEQ ID NO: 3) box helicase domain protein [*Mesorhizobium opportunistum* WSM2075] |
| XP_002124758.1 | PREDICTED: similar to DNA polymerase theta [*Ciona intestinalis*] |
| XP_694437.5 | PREDICTED: DNA polymerase theta [*Danio rerio*] |
| XP_420565.1 | PREDICTED: similar to DNA helicase HEL308 [*Gallus gallus*] |
| XP_003129397.1 | PREDICTED: helicase POLQ-like [*Sus scrofa*] |
| EDL20278.1 | mCG128467, isoform CRA_b [*Mus musculus*] |
| XP_001517710.2 | PREDICTED: helicase POLQ, partial [*Ornithorhynchus anatinus*] |
| AAH82601.1 | Helicase, mus 308-like (*Drosophila*) [*Mus musculus*] |
| XP_003384429.1 | PREDICTED: DNA polymerase theta-like [*Amphimedon queenslandica*] |
| XP_003221282.1 | PREDICTED: helicase POLQ-like [*Anolis carolinensis*] |
| NP_524333.1 | mutagen-sensitive 308 [*Drosophila melanogaster*] >gb \| AAB67306.1 \| Mus308 [*Drosophila melanogaster*] >gb \| ACH92234.1 \| FI03732p [*Drosophila melanogaster*] |
| AAX33507.1 | LP14642p [*Drosophila melanogaster*] |
| NP_001074576.1 | helicase POLQ-like [*Mus musculus* >sp \| Q2VPA6.2 \| HELQ_MOUSE RecName: Full=Helicase POLQ-like; AltName: Full=Mus308-like helicase: AltName: Full-POLQ-like helicase>gb \| AAI09171.2 \| Helicase, mus308-like (*Drosophila*) [*Mus musculus*] |
| YP_003523727.1 | DEAD (SEQ ID NO: 2)/DEAH (SEQ ID NO: 3) box helicase domain protein [*Sideroxydans lithotrophicus* ES-1] >gb \| ADE11340.1 \| DEAD (SEQ ID NO: 2)/DEAH (SEQ ID NO: 3) box helicase domain protein [*Sideroxydans litotrophicus* ES-1] |
| XP 002120889.1 | PREDICTED: similar to DNA helicase HEL308 [*Ciona intestinalis*] |
| XP_001892566.1 | Type III restriction enzyme, res subunit family protein [*Brugia malayi*] >gb \| EDP38603.1 \| Type III restriction enzyme, res subunit family protein [*Brugia malayi*] |
| ABZ09232.1 | putative helicase conserved C-terminal domain protein [uncultured marine crenarchaeote HF4000_APKG7F11] |
| XP_002814981.1 | PREDICTED: LOW QUALITY PROTEIN: helicase POLQ-like [*Pongo abelii*] |
| XP_002717082.1 | PREDICTED: DNA helicase HEL308 [*Oryctolagus cuniculus*l |
| XP_001104832.1 | PREDICTED: helicase, POLQ-like [*Macaca mulatta*] |
| AAL85274.1 | DNA helicase HEL308 [*Homo sapiens*] |
| NP_598375.2 | helicase POLQ-like [*Homo sapiens*] >gb \| EAX05934.1 \| DNA helicase HEL308, isoform CRA_a[*Homo sapiens*] >gb \| AAI41525.1 \| Helicase, POLQ-like [synthetic polynucleotide] |
| Q8TDG4.2 | RecName: Full=Helicase POLQ-like; AltName: Full=Mus308-like helicase; AltName: Full=POLQ-like helicase |
| XP_003265889.1 | PREDICTED: helicase POLQ [*Nomascus leucogenys*] |
| XP_002745688.1 | PREDICTED: helicase POLQ-like [*Callithrix jacchus*] |
| XP_003310356.1 | PREDICTED: LOW QUALITY PROTEIN: helicase POLQ-like [*Pan troglodytes*] |
| NP_001014156.2 | helicase, POLQ-like [*Rattus norvegicus*] >ref\|XP_001060858.1\| PREDICTED: helicase, POLQ-like [*Rattus norvegicus*] >gb\|EDL99554.1\|rCG37823, isoform CRA_c [*Rattus norvegicus*] |
| XP_001850567.1 | ATP-dependent DNA helicase MER3 [*Culex quinquefasciatus*] >gb\|EDS32308.1\| ATP-dependent DNA helicase MER3 [*Culex quinquefasciatus*] |
| XP_003427318.1 | PREDICTED: helicase POLQ-like isoform 1 [*Nasonia vitripennis*] |
| XP_003143912.1 | hypothetical protein LOAG_08332 [*Loa loa*] >gb\|EFO20157.1\| hypothetical protein LOAG_08332 [*Loa loa*] |
| CAG11187.1 | unnamed protein product [*Tetraodon nigroviridis*] |
| XP_001111254.2 | PREDICTED: DNA polymerase theta isoform 2 [*Macaca mulatta*] |
| XP_003414242.1 | PREDICTED: helicase POLQ [*Loxodonta africana*] |
| XP 002681870.1 | predicted protein [*Naegleria gruberi*] >gb\|EFC49126.1\| predicted protein [*Naegleria gruberi*] |
| EAX05935.1 | DNA helicase HEL308, isoform CRA_b [*Homo sapiens*] |
| AAH59917.1 | Ascc3 protein [*Mus musculus*] |
| ZP_07082808.1 | DEAD (SEQ ID NO: 2)/DEAH (SEQ ID NO: 3) box helicase domain protein [*Sphingobacterium spiritivorum* ATCC 33861] >gb\|EFK55937.1\| DEAD (SEQ ID NO: 2)/DEAH (SEQ ID NO: 3) box helicase domain protein [*Sphingobacterium spiritivorum* ATCC 33861] |
| XP_001494572.3 | PREDICTED: LOW QUALITY PROTEIN: helicase POLQ-like [*Equus caballus*] |
| XP_002714920.1 | PREDICTED: activating signal cointegrator 1 complex subunit 3 [*Oryctolagus cuniculus*] |
| XP_002598278.1 | hypothetical protein BRAFLDRAFT_204526 [*Branchiostoma floridae*] >gb\|EEN54290.1\| hypothetical protein BRAFLDRAFT_204526 [*Branchiostoma floridae*] |

TABLE 1-continued

Exemplary Hel308 helicases

| Accession | Description |
|---|---|
| XP_001943294.1 | PREDICTED: helicase POLQ-like isoform 1 [*Acyrthosiphon pisum*] >ref|XP_003240510.1| PREDICTED: helicase POLQ-like isoform 2 [*Acyrthosiphon pisum*] |
| XP_002803889.1 | PREDICTED: activating signal cointegrator 1 complex subunit 3-like [*Macaca mulatta*] |
| XP_001651546.1 | DNA polymerase theta [*Aedes aegypti*] >gb|EAT42599.1| DNA polymerase theta [*Aedes aegypti*] |
| CAA11679.1 | RNA helicase [*Homo sapiens*] |
| XP_002837795.1 | hypothetical protein [*Tuber melanosporum* Mel28] >emb|CAZ1986.1| unnamed protein product [*Tuber melanosporum*] |
| EGT47882.1 | hypothetical protein CAEBREN_02542 [*Caenorhabditis brenneri*] |
| EDL99655.1 | activating signal cointegrator 1 complex subunit 3 (predicted), isoform CRA_b [*Rattus norvegicus*] |
| NP_932124.2 | activating signal cointegrator 1 complex subunit 3 [*Mus musculus*] |
| EDL05054.1 | mCG119534 [*Mus musculus*] |
| gi|352115865 | DEAD (SEQ ID NO: 2)/DEAH (SEQ ID NO: 3) box helicase domain protein |
| ZP_08963952.1 | [*Natrinema pellirubrum* DSM 15624] |

More embodiments of Hel308 helicases, as well as Hel308 motifs, and extended Hel308 motifs are shown in Table 2 below.

TABLE 2

Exemplary Hel308 helicases, Hel308 motifs, and extended Hel308 motifs.

| GI NO. | Helicase Names | | % Identity Hel308 Pfu | % Identity Hel308 Mbu | Hel308 motif | Extended Hel308 motif |
|---|---|---|---|---|---|---|
| GI: 121689265 | Hel308 Mbu | *Methanococcoides burtonii* | 37% | | QMAGRAGR (SEQ ID NO: 4) | QMAGRAGRP (SEQ ID NO: 5) |
| GI: 18202135 | Hel308 Pfu | *Pyrococcus furiosus* DMS 3638 | | 37% | QMLGRAGR (SEQ ID NO: 6) | QMLGRAGRP (SEQ ID NO: 7) |
| GI: 490144641 | Hel308 Hvo | *Haloferax volcanii* | 34% | 41% | QMMGRAGR (SEQ ID NO: 8) | QMMGRAGRP (SEQ ID NO: 9) |
| GI: 506391664 | Hel308 Hla | *Halorubrum lacusprofundi* | 35% | 42% | QMCGRAGR (SEQ ID NO: 10) | QMGRAGRP (SEQ ID NO: 11) |
| GI: 118576895 | Hel308 Cys | *Cenarchaeum symbiosum* | 34% | 34% | QLCGRAGR (SEQ ID NO: 12) | QLCGRAGRP (SEQ ID NO: 13) |
| GI: 18202627 | Hel308 Sso | *Sulfolobus solfataricus* | 35% | 33% | QMSGRAGR (SEQ ID NO: 14) | QMSGRAGRP (SEQ ID NO: 15) |
| *** | Hel308 Mfr | *Methanogenium frigidum* | 37% | 44% | QMAGRAGR (SEQ ID NO: 16) | QMAGRAGRP (SEQ ID NO: 17) |
| GI: 503633371 | Hel308 Mok | *Methanothermococcus okinawensis* | 37% | 34% | QCIGRAGR (SEQ ID NO: 18) | QCIGRAGRP (SEQ ID NO: 19) |
| GI: 333911571 | Hel308 Mig | *Methanotorris igneus* Kol 5 | 40% | 35% | QCIGRAGR (SEQ ID NO: 20) | QCIGRAGRP (SEQ ID NO: 21) |
| GI: 240102927 | Hel308 Tga | *Thermococcus gammatolerans* EJ3 | 60% | 38% | QMMGRAGR (SEQ ID NO: 22) | QMMGRAGRP (SEQ ID NO: 23) |
| GI: 315231273 | Hel308 Tba | *Thermococcus barophilus* MP | 57% | 35% | QMIGRAGR (SEQ ID NO: 24) | QMIGRAGRP (SEQ ID NO: 25) |
| GI: 242398904 | Hel308 Tsi | *Thermococcus sibiricus* MM739 | 56% | 35% | QMMGRAGR (SEQ ID NO: 26) | QMMGRAGRP (SEQ ID NO:27) |
| GI: 121723325 | Hel308 Mba | *Methanosarcina barkeri* str. Fusaro | 39% | 60% | QMAGRAGR (SEQ ID NO: 28) | QMAGRAGRP (SEQ ID NO:29) |
| GI: 24418451 | Hel308 Mac | *Methanosarcina acetivorans* | 38% | 60% | QMAGRAGR (SEQ ID NO: 30) | QMAGRAGRP (SEQ ID NO: 31) |
| GI: 294495240 | Hel308 Mmah | *Methanohalophilus mahii* DSM 5219 | 38% | 60% | QMAGRAGR (SEQ ID NO: 32) | QMAGRAGRP (SEQ ID NO: 33) |

TABLE 2-continued

Exemplary Hel308 helicases, Hel308 motifs, and extended Hel308 motifs.

| GI NO. | Helicase | Names | % Identity | % Identity | Hel308 motif | Extended Hel308 motif |
|---|---|---|---|---|---|---|
| GI: 24418450 | Hel308 Mmaz | *Methanosarcina mazei* | 38% | 60% | QMAGRAGR (SEQ ID NO: 34) | QMAGRAGRP (SEQ ID NO: 35) |
| GI: 116665561 | Hel308 Mth | *Methanosaeta thermophila* PT | 39% | 46% | QMAGRAGR (SEQ ID NO: 36) | QMAGRAGRP (SEQ ID NO: 37) |
| GI: 336477283 | Hel308 Mzh | *Methanosalsum zhilinae* DSM 4017 | 39% | 57% | QMAGRAGR (SEQ ID NO: 38) | QMAGRAGRP (SEQ ID NO: 39) |
| GI: 298674154 | Hel308 Mev | *Methanohalobium evestigatum* Z-7303 | 38% | 61% | QMAGRAGR (SEQ ID NO: 40) | QMAGRAGRP (SEQ ID NO: 41) |
| GI: 500195255 | Hel308 Mma | *Methanococcus maripaludis* | 36% | 32% | QCIGRAGR (SEQ ID NO: 42) | QCIGRAGRP (SEQ ID NO: 43) |
| GI: 490388033 | Hel308 Nma | *Natrialba magadii* | 37% | 43% | QMMGRAGR (SEQ ID NO: 44) | QMMGRAGRP (SEQ ID NO: 45) |
| GI: 226740606 | Hel308 Mbo | *Methanoregula boonei* 6A8 | 38% | 45% | QMAGRAGR (SEQ ID NO: 46) | QMAGRAGRP (SEQ ID NO: 47) |
| GI: 497573451 | Hel308 Fac | *Ferroplasma acidarmanus* | 34% | 32% | QMIGRAGR (SEQ ID NO: 48) | QMIGRAGRP (SEQ ID NO: 49) |
| GI: 256810263 | Hel308 Mfe | *Methanocaldococcus fervens* AG86 | 40% | 35% | QCIGRAGR (SEQ ID NO: 50) | QCIGRAGRP (SEQ ID NO: 51) |
| GI: 18202572 | Hel308 Mja | *Methanocaldococcus jannaschii* | 24% | 22% | QCIGRAGR (SEQ ID NO: 52) | QCIGRAGRP (SEQ ID NO: 53) |
| GI: 502864579 | Hel308 Min | *Methanocaldococcus infernus* | 41% | 33% | QCIGRAGR (SEQ ID NO: 54) | QCIGRAGRP (SEQ ID NO: 55) |
| GI: 88603707 | Hel308 Mhu | *Methanospirillum hungatei* JF-1 | 36% | 40% | QMAGRAGR (SEQ ID NO: 56) | QMAGRAGRP (SEQ ID NO: 57) |
| GI: 635552454 | Hel308 Afu | *Archaeoglobus fulgidus* DSM 4304 | 40% | 40% | QMAGRAGR (SEQ ID NO: 58) | QMAGRAGRP (SEQ ID NO: 59) |
| GI: 502709689 | Hel308 Htu | *Haloterrigena turkmenica* | 35% | 43% | QMAGRAGR (SEQ ID NO: 60) | QMAGRAGRP (SEQ ID NO: 61) |
| GI: 495257384 | Hel308 Hpa | *Haladaptatus paucihalophilus* DX253 | 38% | 45% | QMFGRAGR (SEQ ID NO: 62) | QMFGRAGRP (SEQ ID NO: 63) |
| GI: 15791161 | Ski2-like helicase | *Halobacterium* sp. NRC-1 | 36.8% | 42.0% | QMFGRAGR (SEQ ID NO: 64) | QMFGRAGRP (SEQ ID NO: 65) |

**see International Publication No. WO 2013/057495 for further details regarding the sequence of this Hel308 helicase.

A variant or mutant of a Hel308 helicase, that retains the polynucleotide binding and helicase enzyme activities, can also be used in the present embodiments. Such variant or mutant can be obtained according to methods that are well-known in the art, including site-specific mutagenesis of the nucleic acid encoding a native Hel308 helicase (Zoller, M. J., *Curr. Opin. Biotechnol.*, 3:348-354, (1992)).

Additionally, as noted above and as is known in the art, Hel308 helicases are in the SF2 family and are 3' to 5' helicases (which also can be referred to as type A helicases). The core domains of various helicases can include common motifs as one another, such as RecA binding folds containing the Walker A motif (which also can be referred to as motif I) and the Walker B motif (which also can be referred to as motif II) involved in nucleotide binding and hydrolysis, and motif VI. For further details, see Flechsig et al., "In Silico Investigation of Conformational Motions in Superfamily 2 Helicase Proteins," PLoS One: 6(7): e 21809 (2011). Additionally, helicases of family SF2 can share nine conserved motifs, which can be referred to as Q, I, Ia, Ib, II, III, IV, V, and VI. Because of the sequence of motif II (DEAD (SEQ ID NO: 2) or DEAH (SEQ ID NO: 3) or DEXH), the SF2 helicase family also can be referred to as DEAD-box (SEQ ID NO: 2) proteins or DEAH-box (SEQ ID NO: 3) helicases. Helicases included in the SF2 family include the RecQ-like family and the Snf2-like enzymes. Many SF2 helicases are type A, with a few exceptions such as the XPD family. X-ray crystallography studies of the SF2 family suggest that the conserved helicase motifs are closely associated in the tertiary structure of the protein, and that they may form a large functional domain. For further details, see Tuteja et al., "Unraveling DNA Helicases: Motif, structure, mechanism and function," European Journal of Biochemistry 271(10): 1849-1863 (2004), and Hall et al., "Helicase motifs: the engine that powers DNA unwinding," Molecular Microbiology 34: 867-877 (1999). FIG. 16, which is adapted from Tuteja, schematically illustrates various motifs that have been identified in the SF2 family, e.g., the DEAD-box (SEQ ID NO: 2) helicases, of which Hel308 is a member. As described in Tuteja, open boxes represent conserved motifs. The consensus sequence of each helicase motif is represented by single-letter codes, e.g., "C" in FIG. 16 can be D, E, H, K, or R; "O" in FIG. 16 can be S or T; and "X" in FIG. 16 can be any amino acid. The names assigned to the motifs, e.g., Q, I, Ia, Ib, II, III, IV, V, and VI, also are shown in FIG. 16. As noted further above, motif I can be referred to as the Walker A motif, and is referred to in Tuteja as ATPaseA Walker I, and motif II can be referred to as the Walker B motif, and is referred to in Tuteja as ATPaseB Walker II. The numbers between the motifs, to which the arrows point, are typical ranges of amino acid residues interposed between the motifs.

Additionally, as described in WO 2013/057495, a Hel308 helicase can include amino acid motif(s) Q-X1-X2-G-R-A-G-R (SEQ ID NO: 66), in which X1 can be C, M, or L; X1 can be C; X2 can be any residue, including a hydrophobic or neutral residue, such as A, F, M, C, V, L, I, S, T, P, or R. Optionally, the terminal R in the above motif(s) can be coupled to a P.

Given the teachings and guidance provided herein, one skilled in the art could determine whether a reference helicase is a Hel308 helicase by determining the sequence identity or alignment with one or more of the exemplified Hel308 helicases above.

Additionally, given the teachings and guidance provided herein, one skilled in the art could suitably mutate a Hel308 helicase so as to slow fractional translocation of a polynuclelotide through a pore, e.g., by slowing a hydrolysis step that the Hel308 helicase performs, by mutating a motif of the Hel308 analogously as a homologous motif of another protein in a manner that can slow hydrolysis. As one example, Tanaka et al., "ATPase/helicase motif mutants of *Escherichia coli* PriA protein essential for recombination-dependent DNA replication," Genes to Cells 8: 251-261 (2003), describes mutants of Pria protein (a DEXH-type helicase) carrying amino acid substitutions in its conserved ATPase/DNA helicase motifs, namely the Walker A, B, and QXXGRXGR motifs. According to Tanaka, certain mutants were highly compromised in hydrolyzing ATP in certain conditions, and all of the Walker A and Walker B mutant proteins showed highly attenuated DNA helicase activity in certain conditions. Accordingly, it can be expected that mutations to the Walker A and Walker B motifs of a Hel308 helicase that are analogous to those disclosed in Tanaka can be expected to attenuate DNA helicase activity or slow ATP hydrolysis, which can be expected to slow fractional translocation of a polynucleotide through a pore and thus to enhance characterization of that polynucleotide. As another example, Hishida et al., "Role of Walker Motif A of RuvB Protein in Promoting Branch Migration of Holliday Junctions: Walker motif A mutations affect ATP binding, ATP hydrolyzing, and DNA binding activities of RuvB," Journal of Biological Chemistry 274(36): 25335-25342 (1999), describes mutants of *Escherichia coli* RuvB protein, an ATP-dependent hexameric DNA helicase. According to Hishida, certain point mutations to the Walker motif A affected RuvB activities of ATP hydrolysis and ATP binding, as well as those of DNA binding, hexamer formation, and promotion of branch migration. Accordingly, it can be expected that mutations to the Walker A motifs of a Hel308 helicase that are analogous to those disclosed in Hishida can be expected to affect ATP hydrolysis and ATP binding, which can be expected to slow fractional translocation of a polynucleotide through a pore and thus can enhance characterization of that polynucleotide in certain embodiments.

Accordingly, the disclosure provides a method of characterizing a target polynucleotide. The method can include (a) applying a potential difference across a pore in contact with a Hel308 helicase and a target polynucleotide; (b) measuring one or more signals produced by one or more fractional translocation steps by said Hel308 helicase of said target polynucleotide through said pore; and (c) characterizing said target polynucleotide from said one or more signals produced by said fractional translocation steps.

The disclosure further provides a method of characterizing a target polynucleotide wherein the potential difference comprises an electric potential difference. Also provided is a method of characterizing a target polynucleotide wherein the signal includes an electrical signal or an optical signal. The electrical signal can be a measurement selected from current, voltage, tunneling, resistance, potential, voltage, conductance; and transverse electrical measurement. The electrical signal includes an electrical current passing through the pore.

In other aspects, the disclosure provides a method of characterizing a target polynucleotide wherein the fractional translocation step includes a first fractional translocation step of a full translocation cycle of the Hel308 helicase. The fractional translocation step also can include a second fractional translocation step of a full translocation cycle of the Hel308 helicase. Translocation of the target polynucleotide can be in a direction opposite of the applied force on the polynucleotide translocating through the pore or in a direction with the applied force on the polynucleotide translocating through the pore.

Additionally provided is a method of characterizing a target polynucleotide wherein one or more nucleotide residues in the target polynucleotide are characterized using electrical signals obtained from two fractional steps of a full translocation cycle with an accuracy greater than 50% compared to characterization of one or more nucleotides using a single electrical signal obtained from a full translocation cycle.

Further provided is a method of characterizing a target polynucleotide wherein the pore is a biological pore. The biological pore can be a polypeptide pore or a polynucleotide pore. In some aspects, the polypeptide pore has a constriction zone of five nucleotides or less. In other aspects, the polypeptide pore includes a *Mycobacterium smegmatis* porin A (MspA). The MspA can have an amino acid sequence of SEQ ID NO: 1 or having at least 15%, at least 20%, at least 25%, at least 30%, at least 35%, at least 40%, at least 45%, at least 50%, at least 55%, at least 60%, at least 65%, or at least 70% homology to SEQ ID NO: 1.

Also provided is a method of characterizing a target polynucleotide wherein the pore is a solid state pore or a biological and solid state hybrid pore. The biological and solid state hybrid pore includes a polypeptide-solid state hybrid pore or a polynucleotide-solid state hybrid pore.

The disclosure additionally provides a method of characterizing a target polynucleotide wherein the Hel308 helicase is a helicase shown in Tables 1 and 2 or a variant thereof. Further provided is a method of characterizing a target polynucleotide wherein the target polynucleotide is selected from the group consisting of a single stranded, a double stranded and a partially double stranded polynucleotide.

In some embodiments, characterizing the polynucleotide from said one or more signals produced by said fractional translocations steps comprises applying a modified Viterbi algorithm.

In some embodiments, the method further includes (d) after step (c), varying at least one parameter so as to vary a timing of one or more fractional translocation steps by said Hel308 helicase of said target polynucleotide through said pore; and (e) repeating steps (a)-(c) using the varied at least one parameter. The method further can include combining the signals produced by during steps (c) and (e) and characterizing said target polynucleotide based on the combined signals. In some embodiments, the varied at least one parameter is selected from the group consisting of temperature, salt concentration, cofactor concentration, concentration of ATP product (such as inorganic pyrophosphate), concentration of ADP, pH, and the particular Hel308 helicase used.

In some embodiments, said characterizing comprises detecting and identifying levels in the one or more signals and determining and outputting a sequence of the target polynucleotide based on the detected and identified levels.

Illustratively, said detecting and identifying the levels in the one or more signals includes outputting one or more of full levels, fractional levels, all levels, and level identifiers.

Said determining and outputting the sequence of the target polynucleotide based on the detected and identified levels can include taking as input the one or more of full levels, fractional levels, all levels, and level identifiers, calling a plurality of sequences based on said input, and selecting and outputting at least one of the called sequences based on confidence information about the called plurality of sequences.

Said determining and outputting the sequence of the target polynucleotide based on the detected and identified levels can include taking as input the one or more of full levels, fractional levels, all levels, and level identifiers, calling a plurality of sequences based on said input, and selecting and concatenating with one another portions of a plurality of the called sequences based on confidence information about the portions of the called plurality of sequences.

Said determining and outputting the sequence of the target polynucleotide based on the detected and identified levels can include taking as input the one or more of full levels, fractional levels, all levels, and level identifiers, calling a plurality of sequences based on said input, comparing the called sequences to model sequences, and selecting and outputting at least one of the called sequences based on confidence information about the comparison of the called sequence to the model sequence.

Said determining and outputting the sequence of the target polynucleotide based on the detected and identified levels can include taking as input the one or more of full levels, fractional levels, all levels, and level identifiers, calling a plurality of sequences based on said input, comparing the called sequences to model sequences, and selecting and concatenating with one another portions of a plurality of the called sequences based on confidence information about the comparison of portions of the called plurality of sequences to the model sequence.

The present disclosure also provides a method of modulating a fractional translocation step of a target polynucleotide through a pore. The method can include: (a) applying a potential difference across a pore in contact with a Hel308 helicase and a target polynucleotide; (b) contacting the Hel308 helicase with a concentration of a Hel308 helicase substrate that is different from a reference concentration of the substrate, the substrate concentration producing a change in duration of a fractional translocation step proportional to a difference in the substrate concentration compared to the reference concentration, and (c) measuring a signal produced by a fractional translocation step of the target polynucleotide through the pore. Step (b) can similarly include using a substrate analog or inhibitor to achieve a change in duration of a fractional translocation step. Accordingly, any of the substrate analogs or nucleotide inhibitors described herein or known in the art can be used in the method of the disclosure for modulating a fractional translocation step as either a Hel308 helicase substrate, a Hel308 substrate that is being used as a reference concentration or both a either a Hel308 helicase substrate and a Hel308 substrate that is being used as a reference concentration.

A Hel308 helicase substrate that is capable of modulating a fractional translocation step of a polynucleotide can be a nucleotide or nucleotide analogue that is capable of being hydrolyzed by helicase. The nucleotide substrate provides energy to unwind a double-stranded or partially double-stranded polynucleotide or translocate a single stranded polynucleotide through a pore. A common substrate for a Hel308 helicase includes, for example, ATP. Hel308 helicase substrates also include nucleotides and nucleotide analogues that are capable of being hydrolyzed by helicase.

As described herein, the dwell time for one or more fractional translocation steps that are related to nucleotide substrate binding can be inversely proportional to the concentration of the Hel308 helicase substrate. For example, under some conditions tested the dwell time for only one of two fractional translocation steps observed per nucleotide translocation is inversely proportional to the concentration of the Hel308 helicase substrate. Thus, one translocation step can be sensitive to substrate concentration while another translocation step is not.

Modulation of a fractional translocation step to obtain a different length of fractional translocation steps can be accomplished by changing the concentration of the Hel308 helicase substrate. The degree or magnitude of modulation can be determined so that one skilled in the art can select a particular length of fractional translocation steps suitable for a desired target polynucleotide characterization. The degree of modulation can be determined by placing a Hel308 helicase in a concentration of a Hel308 helicase substrate that is different from a reference concentration of the substrate. The change in substrate concentration compared to the reference concentration results in a different dwell time of a fractional translocation step that is proportional to the difference in the substrate concentration compared to the reference concentration.

Accordingly, the fractional translocation step of a target polynucleotide through a pore can be modulated by using a concentration of a Hel308 helicase substrate that is different from a reference concentration of the substrate. Other components within the helicase solution or the reaction conditions also can be used to alter the dwell time of a fractional translocation step and, therefore, the length of fractional translocation steps for a single translocation cycle. The differing fractional translocation steps can similarly be used to acquire additional signal information to increase accuracy of target polynucleotide characterization.

Components of the reaction and reaction conditions influencing, for example, the kinetics of substrate binding to a Hel308 helicase and substrate hydrolysis by the helicase can be used to alter the dwell time of a fractional translocation step. Such other factors include, for example, temperature, metal concentration, including divalent metal concentration, ion concentration, solvent viscosity of the reaction conditions. The hydrolysis step can be influenced by, for example, the above factors and conditions as well as by phosphate and/or pyrophosphate concentration. In addition, voltage across the pore can, for example, affect the substrate binding and/or helicase pause constituting the dwell time of a Hel308 helicase. Other factors include, for example, the pH, the type of cation or divalent cation concentration and type, helicase mutations, etc. all can affect dwell times. In this regard, for example, increasing pyrophosphate concentration can be used to slow the catalytic speed of a Hel308 helicase and therefore increase dwell time. Further, for example, sodium orthovanadate and adenosine 5'-(β,γ-imido)triphosphate lithium salt hydrate can also be used to slow helicase activity. The use of pyrophosphate and nucleotide analogs to modulate the helicase activity is exemplified below in Example V.

As current differences between sequential steps increase, the benefits of using fractional states for data analysis also increase. At first approximation, fractional translocation steps will take on values that are in between adjacent full translocation steps. Should a fractional translocation step be much less than ½ nucleotide, (0.3 Angstroms), the fractional value can be, in some cases, or even in many cases, difficult or even impossible to observe. Should the fractional translocation step be exactly the length of ½ nucleotide, then the resulting current can be, on average, maximally distinct from preceding and subsequent current values that correspond to full-nucleotide steps. The modification of the enzyme can allow the repositioning of polymer subunits by fractions of a nanometer. This can happen through enzyme modifications that increase or decrease the relative height of the enzyme's active hydrolysis site, to the limiting constriction of the nanopore. In some embodiments, this can be accomplished through adding or removing amino acids of the helicase, or substitution of amino acids with larger hydrodynamic radius. In other embodiments, this can be accomplished through the altering of amino-acid charge which can alter electrostatic repulsion or attraction to the rim of the nanopore. Without wishing to be bound by any theory, if the "grip-based" hypothesis is correct (such as described in greater detail with reference to FIG. 3), it can be possible that a particular mutation would affect the degree to which the helicase pushes upward the helicase-polynucleotide complex, which can translate to a change in z-axis translocation percentage of the nucleotide.

It is contemplated to tune the duration of the fractional translocation steps: it is reasonable to expect that certain mutations to the helicase ATPase domain would affect the rate at which the ATP is hydrolyzed. This would, in turn, be expected to affect dwell time for one of the fractional translocation steps. For example, if the hydrolysis rate were slowed, then the dwell time for one of the fractional translocation steps is expected to increase. Other mutations could affect the rate at which ATP binds to the helicase ($k_{on}$). In this case, as the time it takes for an ATP to bind increases, the dwell time for the corresponding fractional translocation step would increase.

A reference concentration of a Hel308 helicase can be, for example, the amount of substrate generally used in a target polynucleotide characterization or it can be different. For example, if the concentration of a Hel308 helicase substrate that is generally used is 1.0 mM, then 1 mM would correspond to the reference concentration. The reference concentration can be empirically derived or obtained from reports well known in the art. In this specific example, a concentration of substrate other than 1 mM would be the Hel308 helicase substrate that is different from the reference concentration. As described further below, various concentrations of a Hel308 helicase substrate and reference substrate can be employed to modulate or determine the amount of alteration of a fractional translocation step.

The concentration of the Hel308 helicase substrate concentration and the reference substrate concentration can vary so long as both concentrations are not saturating concentrations. Illustratively, a saturation concentration of a Hel308 helicase substrate is about 1 mM of nucleotide substrate. Accordingly, if a reference concentration is 1 mM then the Hel308 helicase substrate concentration to be varied can be any concentration less than 1 mM including, for example, 0.1 µM, 1.0 µM, 10 µM, 100 µM, 200 µM, 300 µM, 400 µM, 500 µM, 600 µM, 700 µM, 800 µM, 900 µM. Depending on the Hel308 helicase substrate concentration and/or the reference other exemplary concentrations can be, for example, 1.0 mM, 2.0 mM, 3.0 mM, 4.0 mM and 4.9 mM or less. Similarly, the concentration of both the Hel308 helicase substrate and the reference substrate concentration can be concentrations that are not saturating so long as they differ. Accordingly, Hel308 helicase substrate and reference concentrations can be any of the exemplary concentrations listed above as well as any concentration in between, for example, any concentration ranging from 0.01 µM to 5 mM and all concentrations in between this range.

The methods of the present disclosure for modulating a fractional translocation step can be performed as described previously with respect to methods of characterizing a target polynucleotide. Once a Hel308 helicase substrate concentration is determined that is suitable for a particular need that substrate concentration can be employed in the methods described herein for characterizing a target polynucleotide. In like fashion, similar determinations can be performed with components and conditions of the reaction that influence, for example, the kinetics of substrate binding and hydrolysis to determine a component concentration or reaction condition that is suitable for a particular need. That suitable concentration or condition can then be employed in a method of the present disclosure for characterizing a target polynucleotide. The new substrate concentration, reaction component concentration and/or reaction condition will result in a different dwell time that can provide addition signal information for enhancing the accuracy of the determination in a manner such as described below with reference to Example IX.

Accordingly, the disclosure provides a method of modulating a fractional translocation step of a target polynucleotide that further includes characterizing the target polynucleotide from the one or more signals of the one or more fractional translocation steps. The characterization can include identifying one or more of: (1) the sequence of the target polynucleotide; (2) the modification of the target polynucleotide; (3) the length of the target polynucleotide; (4) the identity of the target polynucleotide; (5) the source of the target polynucleotide, or (6) the secondary structure of the target polynucleotide.

The disclosure also provides a method of modulating a fractional translocation step of a target polynucleotide wherein the method employs a potential difference that includes an electric potential difference. Further provided is a method of modulating a fractional translocation step of a target polynucleotide wherein the signal produced by a fractional translocation step includes an electrical signal or an optical signal. Additionally provided is a method of modulating a fractional translocation step of a target polynucleotide the electrical signal is a measurement selected from current, voltage, tunneling, resistance, potential, voltage, conductance; and transverse electrical measurement. The electrical signal also can be an electrical current passing through the pore.

Still further provided is a method of modulating a fractional translocation step of a target polynucleotide wherein the substrate concentration is a subsaturating concentration of the Hel308 helicase substrate. In some embodiments, the reference concentration is a saturating concentration of the Hel308 helicase substrate. In other aspects, both of the substrate concentration and the reference concentration are subsaturating concentrations of the Hel308 helicase substrate. Further provided is a method of modulating a fractional translocation step of a target polynucleotide wherein the Hel308 helicase substrate is adenosine triphosphate (ATP).

Yet further provided is a method of modulating a fractional translocation step of a target polynucleotide wherein the fractional translocation step includes a first fractional translocation step of a full translocation cycle of the Hel308 helicase or a second fractional translocation step of a full translocation cycle of the Hel308 helicase. A translocation of the target polynucleotide can be in a direction opposite of the applied force on the polynucleotide translocating through the pore or in a direction with the applied force on the polynucleotide translocating through the pore.

Also further provided by the disclosure is a method of modulating a fractional translocation step of a target polynucleotide wherein one or more nucleotide residues in the target polynucleotide are characterized using electrical signals obtained from two fractional steps of a full translocation cycle with an accuracy greater than 50% compared to characterization of one or more nucleotides using a single electrical signal obtained from a full translocation cycle. In some aspects of the method of the disclosure, one or more nucleotide residues in the target polynucleotide are characterized with a greater accuracy at a lower substrate concentration compared to the reference concentration.

Additionally provided is a method of modulating a fractional translocation step of a target polynucleotide wherein the pore is a biological pore. The biological pore can be a polypeptide pore or a polynucleotide pore. In some aspects, the polypeptide pore has a constriction zone of five nucleotides or less. In other aspects, the polypeptide pore includes a *Mycobacterium smegmatis* porin A (MspA). The MspA can have an amino acid sequence of SEQ ID NO: 1 or having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% homology to SEQ ID NO: 1.

Still further provided is a method of modulating a fractional translocation step of a target polypeptide wherein the pore is a solid state pore or a biological and solid state hybrid pore. The biological and solid state hybrid pore can be a polypeptide-solid state hybrid pore or a polynucleotide-solid state hybrid pore.

Also provided is a method of modulating a fractional translocation step of a target polynucleotide wherein a Hel308 helicase in the method includes a helicase shown in Tables 1 and 2 or a variant thereof. The target polynucleotide is selected from the group consisting of a single stranded, a double stranded and a partially double stranded polynucleotide.

The present disclosure further provides a composition for characterizing a target polynucleotide. The composition includes a pore, a Hel308 helicase and a target polynucleotide contained in a solution of less than 1 mM ATP or a solution of a nucleotide analogue. In some aspects of the composition, the solution of less than 1 mM ATP is 0.1 µM, 1.0 µM, 10 µM, 100 µM, 0.5 mM, or 0.9 mM of ATP.

A composition of the present disclosure can include any of the components described above or below that are used in the methods of the present disclosure for characterizing a polynucleotide or for modulating a fractional translocation step of a target polynucleotide translocation. For example, a composition can include a pore as described previously. According to the teachings and guidance provided herein the pore can be, for example, a biological pore such as a polypeptide pore or polynucleotide pore. Alternatively, the pore can be a solid state pore or a hybrid pore as described previously.

In addition, the composition will include a target polynucleotide for characterization, a Hel308 helicase and a Hel308 helicase substrate. As with the pore, the target polynucleotide, Hel308 helicase and the Hel308 helicase substrate can be any of the exemplary polynucleotides, Hel308 helicases, substrates and variants and analogs described herein as well as those well known in the art.

Accordingly, the disclosure provides a composition for characterizing a target polynucleotide wherein the pore is a biological pore. The biological pore can be a polypeptide pore or a polynucleotide pore. The polypeptide pore can have a constriction zone of five nucleotides or less and can be a *Mycobacterium smegmatis* porin A (MspA). The MspA can have an amino acid sequence of SEQ ID NO: 1 or having at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% homology to SEQ ID NO: 1.

Also provided is a composition for characterizing a target polynucleotide wherein the pore is a solid state pore. Additionally provided is a composition for characterizing a target polynucleotide wherein the pore is a biological and solid state hybrid pore. The biological and solid state hybrid pore can be a polypeptide-solid state hybrid pore or a polynucleotide-solid state hybrid pore.

Further provided is a composition for characterizing a target polynucleotide wherein the Hel308 helicase is a helicase shown in Tables 1 and 2 or a variant thereof. Additionally provided is a composition for characterizing a target polynucleotide wherein the target polynucleotide is selected from the group consisting of a single stranded, a double stranded and a partially double stranded polynucleotide.

It is understood that modifications which do not substantially affect the activity of the various embodiments of this disclosure are also included within the definition of the disclosure provided herein. Accordingly, the following examples are intended to illustrate but not limit the present disclosure.

Example I

Fractional Translocation Step with a Hel308 Helicase

Example I describes the fractional translocation steps observed with an exemplary Hel308 helicase.

Lipid bilayers were formed from 1,2-diphytanoyl-sn-glycero-3-phosphocholine (Avanti Polar Lipids). The bilayer spanned a horizontal ~20 micron diameter aperture in Teflon. M2-NNN-MspA was added to the grounded side of the bilayer at a concentration of ~2.5 ng/ml. Once a single pore was inserted, the compartment was flushed with experimental buffer to avoid further insertions. An Axopatch-200B patch clamp amplifier (Axon Instruments) applied a voltage across the bilayer of 180 mV and measured the ionic currents. The analog signal was low-pass filtered at 50 kHz with a 4-pole Bessel filter and was then digitized at five times the low-pass filter frequency. Data acquisition was controlled with custom software written in LabWindows/CVI (National Instruments). The ~60 µl compartments on both sides of the bilayer contained experimental buffer of 0.3 M KCl, 1 mM EDTA, 1 mM DTT, 10 mM MgCl$_2$, and 10 mM HEPES/KOH buffered at pH 8.0. Either wild type Hel 308 Tga or wild type Phi29 polymerase was used as the motor. In the presence of Hel308 Tga, the buffer was supplemented with 1 mM ATP. In the presence of Phi29, the buffer was supplemented with 100 µM each of dCTP, dATP, dTTP and dGTP.

Figure 2A:
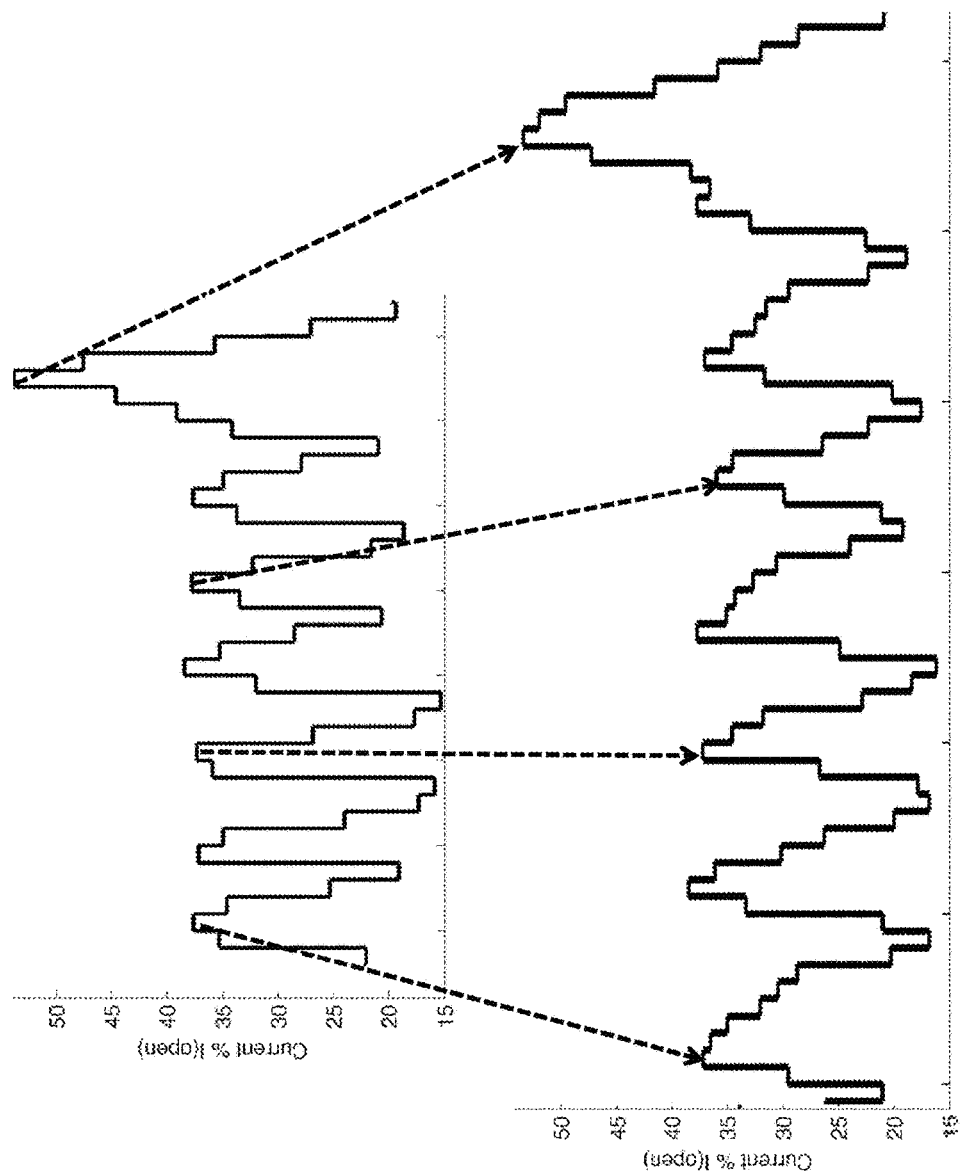
FIG. 2A shows a comparison of Phi29 polymerase and Hel308 Tga helicase translocation events, according to some embodiments. The fractional translocation steps observed with a Hel308 Tga helicase are shown in comparison to the observed translocation steps with a phi29 DNA polymerase.
Figure 2B:
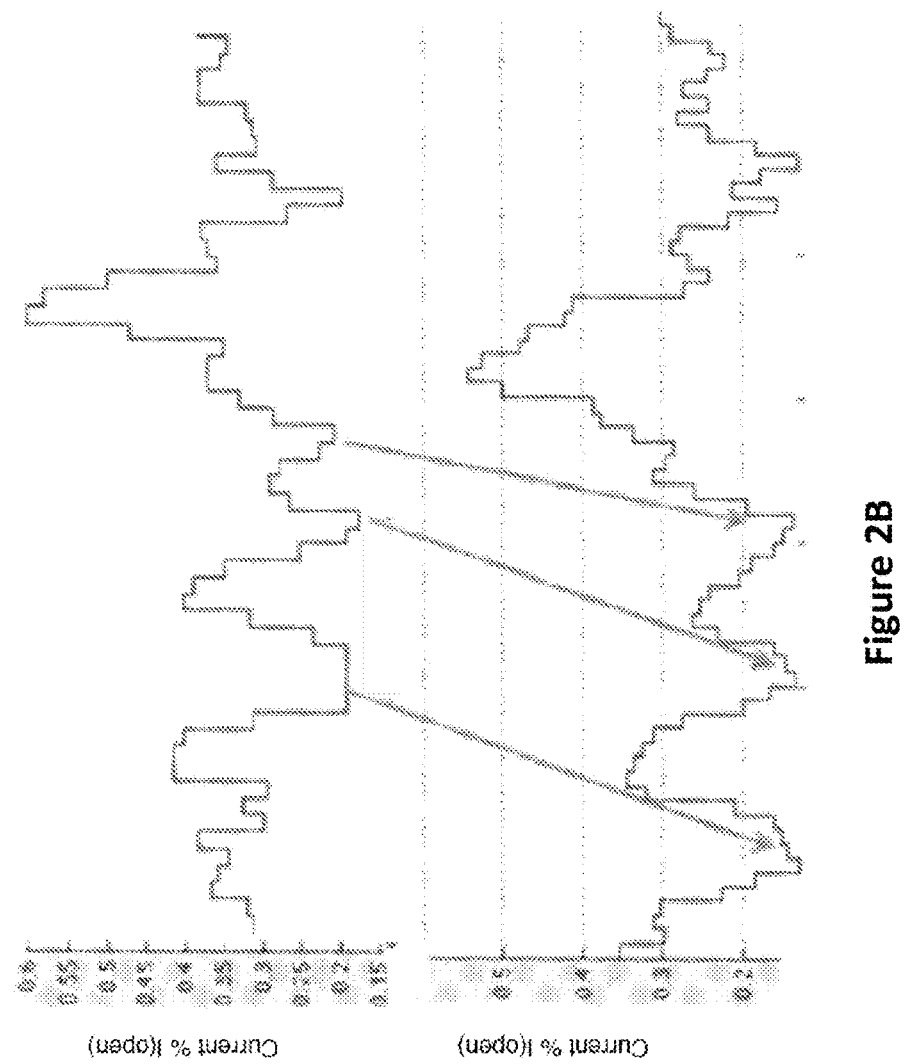
FIG. 2B shows a comparison of Phi29 polymerase and Hel308 Tga helicase translocation events, according to some embodiments. The fractional translocation steps observed with a Hel308 Tga helicase are shown in comparison to the predicted current levels generated by a single stranded polynucleotide template translocating through an MspA-M2 nanopore using a Phi29 polymerase as the molecular motor with those observed using a Hel308 Tga helicase as the molecular motor.
Figure 2C:
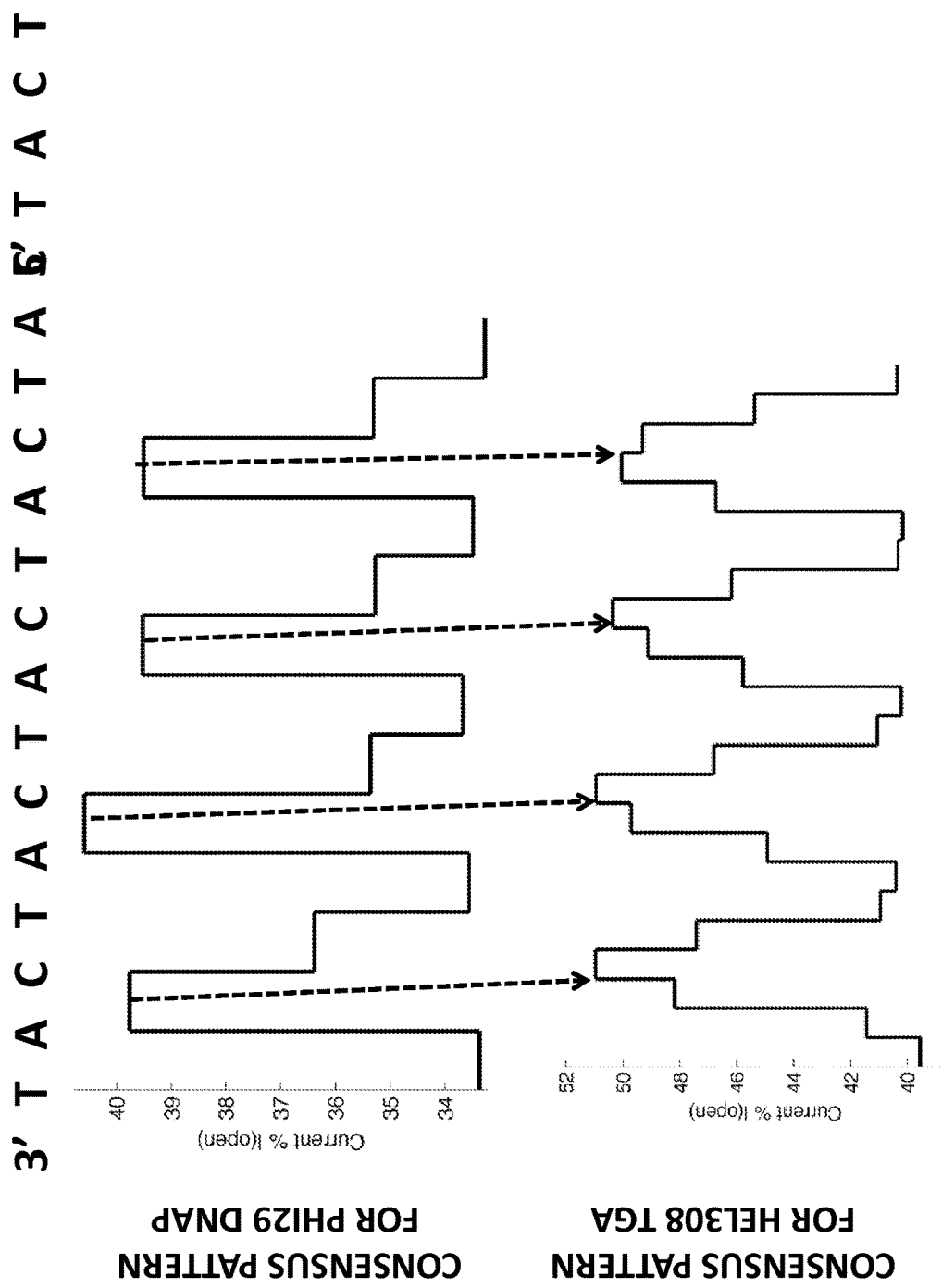
FIG. 2C shows a comparison of Phi29 polymerase and Hel308 Tga helicase translocation events, according to some embodiments. The fractional translocation steps observed with a Hel308 Tga helicase are shown in comparison to the observed translocation steps with a phi29 DNA polymerase for a simple repeated nucleotide sequence (SEQ ID NO: 74).

FIGS. 2A-2C show comparison of Phi29 polymerase and Hel308 Tga helicase translocation events, according to some embodiments. FIG. 2A shows the fractional translocation steps observed with a Hel308 Tga helicase in comparison to the observed translocation steps with a phi29 DNA polymerase (DNAP). The translocating polynucleotide (SEQ ID NO: 67: /5Phos/AAACCTTCCXCCCGTACCGTGCCG-TACCGTTCCGTTCCGTACCGTA TTTTTTTT TCTCAC-TATCGCATTCTCATGCAGGTCGTAGCC where X=abasic) was hybridized to a cholesterol-containing polynucleotide (SEQ ID NO: 68: CCTGCATGAGAATGCGA-TAGTGAGA TTTTTTTTTTTTTTTTTTTT-CholTEG). The MspA-M2 nanopore was used. The number of levels seen for the Hel308 Tga helicase polynucleotide translocation was nearly twice the number of levels observed for phi29 DNAP. Lines drawn between traces indicate corresponding levels. The phi29 trace (top) is a consensus, while the Hel308 helicase trace (bottom) is a measured single translocation event. A consensus can refer to combination of reliably-detected levels from multiple reads from the same sequence. Such a combination potentially can be more reliable than a single read, because it may not necessarily include errors such as may occur with single-molecule translocation, e.g., nucleotide "skipping" or nucleotide "toggling" such as are known in the art.

FIG. 2B shows the fractional translocation steps observed with a Hel308 Tga helicase in comparison with the predicted current levels generated by a single stranded polynucleotide template translocating through an MspA-M2 nanopore using a Phi29 polymerase as the molecular motor with those observed using a Hel308 Tga helicase as the molecular motor. The translocating polynucleotide (SEQ ID NO: 69: /5Phos/CTCACCTATCCTTCCACTXXC-CCCCTTTGGGTTTAAATTTTTTCAGATCTCACTATC TTTTTAAAGTTT TCTCACTATCGCATTCTCATGCAG-GTCGTAGCC where X=abasic) was hybridized to a cholesterol-containing polynucleotide (SEQ ID NO: 68: CCT-GCATGAGAATGCGATAGTGAGATTTTTTTTTTTTT TTTTTT-CholTEG). The phi29 trace (top) is predicted, while the Hel308 helicase trace (bottom) is a measured translocation event. A prediction, like a consensus, may not necessarily include errors such as may occur with single-molecule translocation, e.g., nucleotide "skipping" or nucleotide "toggling" such as are known in the art. A prediction can refer to simulated data based on a k-mer table, which had previously been collected. The Phi29 predicted pattern is based upon a full step per base, and illustrates a type of pattern that can be expected will a full step molecular motor. In comparison, it clearly can be seen that Hel308 Tga helicase has fractional steps.

FIG. 2C shows the fractional translocation steps observed with a Hel308 Tga helicase, in comparison to the observed translocation steps with a phi29 DNAP. The translocating polynucleotide sequence is: SEQ ID NO: 70: /5Phos/CAT-CATCATCATCATCATXXCCCCCTAAACAAGAATAC-CACGACTAGCATTTT TCAGATCTCACTATCGCAT-TCTCATGCAGGTCGTAGCC. The translocating polynucleotide was hybridized to cholesterol-containing polynucleotide (SEQ ID NO: 68: CCTGCATGAGAATGC-GATAGTGAGA TTTTTTTTTTTTTTTTTTTT-CholTEG) and passed through the MspA-M2 nanopore. The simple repeated sequence 5'-CAT-3' was used to show a repeated pattern. The number of levels seen for Hel308 Tga helicase polynucleotide translocation was twice the number of observed levels for phi29 DNAP. Both the phi29 and Hel308 helicase traces are consensus traces. The use of consensus traces can facilitate comparison of translocation step sizes between different molecular motors, and can reduce or remove artifacts such as skips and toggles that otherwise potentially can complicate interpretation.

Figure 3:
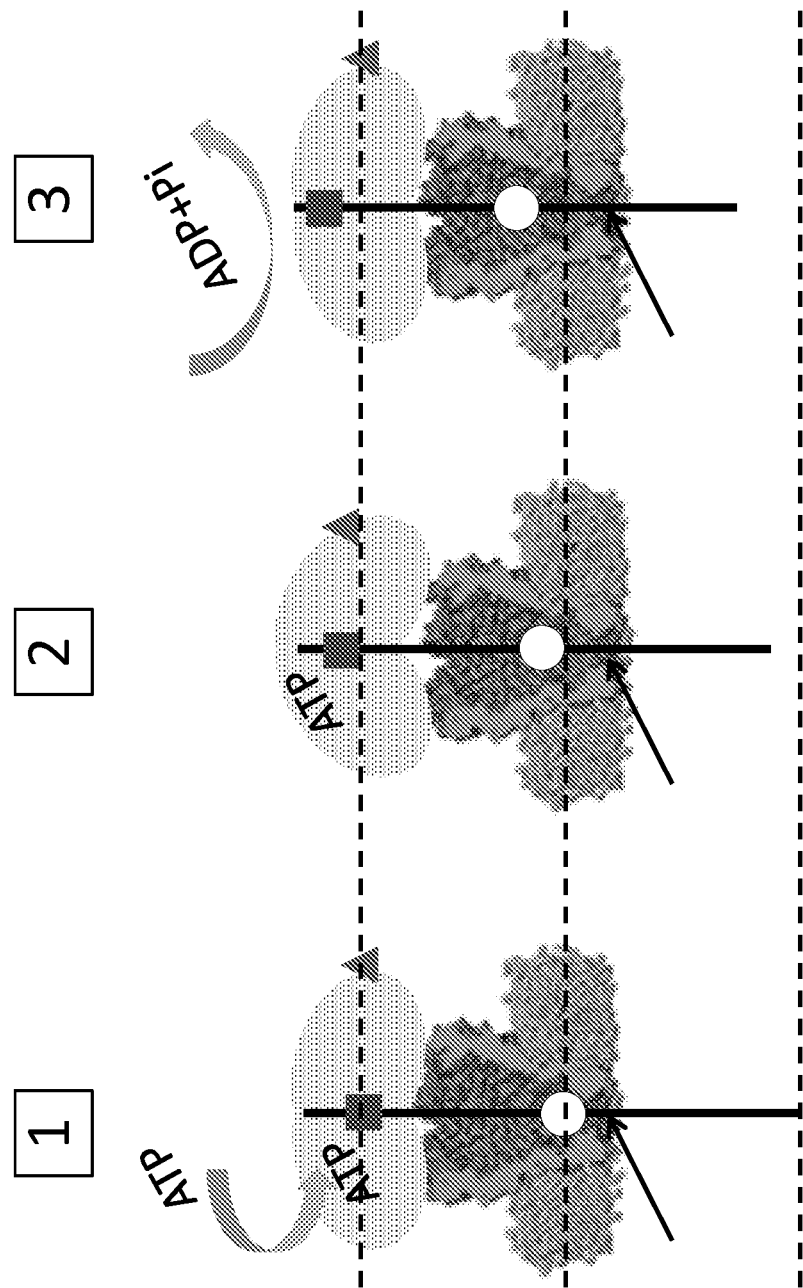
FIG. 3 shows a proposed "Grip-based" mechanism for a fractional translocation step, according to some embodiments.

Without wishing to be bound by any theory, in further explaining the fractional translocation steps, a "Grip-based" mechanism is proposed. FIG. 3 shows a proposed "Grip-based" mechanism for a fractional translocation step, according to some embodiments. The polynucleotide (black solid line) is bound by the helicase (shape with horizontal line fill). Upon ATP binding (Step 1), the helicase undergoes a conformational change (Step 2). Since the polynucleotide is gripped by the helicase, the location of the polynucleotide with respect to the helicase does not necessarily change. A reference point on the helicase (grey triangle) does not move with respect to the polynucleotide gripped by the helicase (see reference point on gripped polynucleotide, grey square). The helicase conformational change pushes the helicase-polynucleotide complex off the top of the nanopore, pulling the polynucleotide in the pore constriction (black line pointed to by black line with arrow head) along with it. A second polynucleotide reference point (white circle) shows the polynucleotide moving with respect to the pore constriction during the conformational change (Step 2), which results in the measured current change for the fractional step. Finally, the ATP is hydrolyzed and the helicase translocates along the polynucleotide (Step 3). This causes the polynucleotide to move a full nucleotide with respect to the helicase and pore. In summary, in the first fractional translocation step, the Hel308 helicase binds to ATP and undergoes a conformational change that pulls the polynucleotide gripped by the helicase and shifts the polynucleotide by a fractional of one nucleotide, which in turn produces a measurable current change. In the second fractional translocation step, ATP is hydrolyzed, and the Hel308 helicase completes the translocation of the one nucleotide through the nanopore. Other mechanisms suitably can be used to explain the present observations of fractional translocation steps.

Example II

The Relationship Between ATP Concentrations and Fractional Translocation Steps

Example II describes the effect of ATP concentration on dwell times of the fractional translocation steps.

To further elucidate the biochemical mechanism of the fractional translocation step, the dwell times of the fractional translocation steps were examined under varying concentrations of ATP. Cis and trans wells were first filled with a buffer solution consisting of 400 mM KCl, 10 mM HEPES, pH 8. A lipid bilayer consisting of DPhPC was formed by painting a mixture of hexadecane and lipid over a ~25 µm diameter Teflon pore and conductance measurements were performed to ensure a Gigaohm seal between the lipid bilayer and the Teflon pore. All electrical measurements were performed using an Axopatch 200B patch clamp amplifier connected to a pair of Ag/AgCl electrodes connected to the cis and trans wells. Following membrane formation, MspA nanopores were injected into the cis well where nanopore incorporation into the lipid bilayer was monitored via conductance measurements. Upon incorporation of a single nanopore into the bilayer, the cis chamber was perfused to prevent multi-pore insertion. Single-stranded polynucleotide was then injected into the cis chamber at a final concentration of 10 nM, voltage was applied across the membrane, and polynucleotide translocation through pores was detected via transient current responses. Upon polynucleotide translocation detection, the voltage was then set to 0 V, and 1 mM $MgCl_2$, 115 nM Hel308 helicase, and various concentrations of ATP (10 µM, 30 µM, 100 µM, and 1 mM) were injected into the cis well. The voltage was then set to a holding potential (140 mV for 0.01, 0.1, and 1 mM ATP; 180 mV for 0.03 mM ATP) and currents were recorded. The translocating polynucleotide (SEQ ID NO: 71: /5Phos/CATCATCATCATCATCATXXC-CCCCTAAACAAGAATACCACGACTAGCATTTT TCA-GATCTCACTATCGCATTCTCATGCAGGTCGTAGCC where X=abasic) was hybridized to a cholesterol-containing polynucleotide (SEQ ID NO: 68: CCTGCATGAGAATGC-GATAGTGAGA TTTTTTTTTTTTTTTTTTTT-CholTEG) prior to injection into the cis well as shown in FIGS. 14A-14D (described in greater detail elsewhere herein). In this manner, the 5' end of the polynucleotide translocated through the nanopore first, and then was pulled back through the nanopore via processing of the Hel308 helicase. The Axopatch amplifier recorded the current response of the system at a sampling rate of 50 kHz and with a low-pass filter of 10 kHz. Step transitions due to Hel308 helicase processing of the polynucleotide through the nanopore, including fractional translocation steps, were clearly identifiable within this frequency range. Following experimentation, computer algorithms were used to identify polynucleotide translocation events. Statistically significant current levels were identified within these translocation events by using a Student's t-test, which is commonly known in the art for determining statistical significance between neighboring values (for further details, see Carter et al., cited elsewhere herein, or John E. Freund, Mathematical Statistics, $5^{th}$ Edition, Prentice Hall). For the observed currents from this particular sequence, there nearly were twice as many statistically-significant current levels identified as there were nucleotides processed, with the topology (peaks and troughs of current levels) having nearly twice as many levels between each peak and between each trough, as measured by direct observation, than for a single-step molecular motor.

To reduce experimental error, data analyses of durations of polynucleotide translocation through nanopores were conducted in regions of large resolution of nucleotide translocation. In strand sequencing, and in particular, nanopore sequencing of polynucleotides, an abasic region can yield a relatively high signal-to-noise ratio due to the significant difference in ion flow being blocked when compared with that of neighboring polynucleotide sequences. For this reason, statistically significant levels within the vicinity of an abasic region potentially can be more likely due to nucleotide processing through the nanopore than due to some ulterior, "noisy" effect. For this reason, the durations of 27 current levels surrounding and including an abasic current peak for current level duration-based data analysis were selected.

Figure 4A:
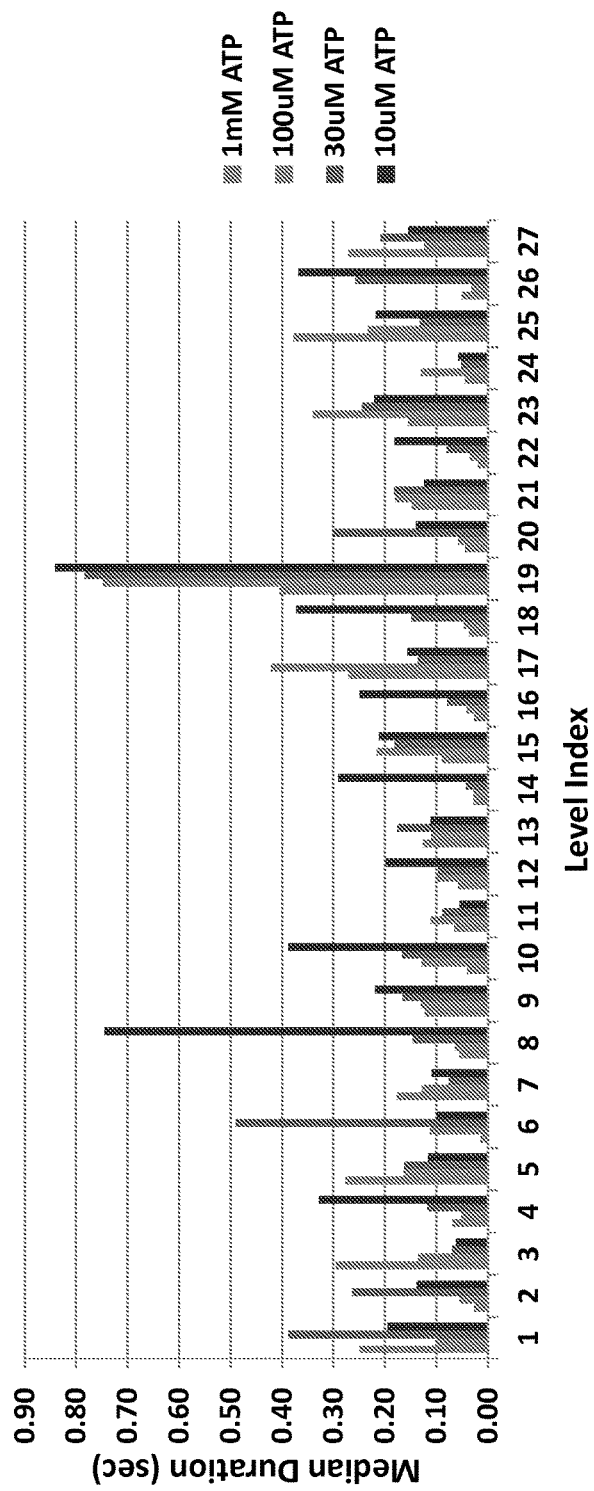
FIGS. 4A and 4B show the exemplary effect of ATP concentration on the dwell time of the fractional translocation steps, according to some embodiments.
Figure 4B:
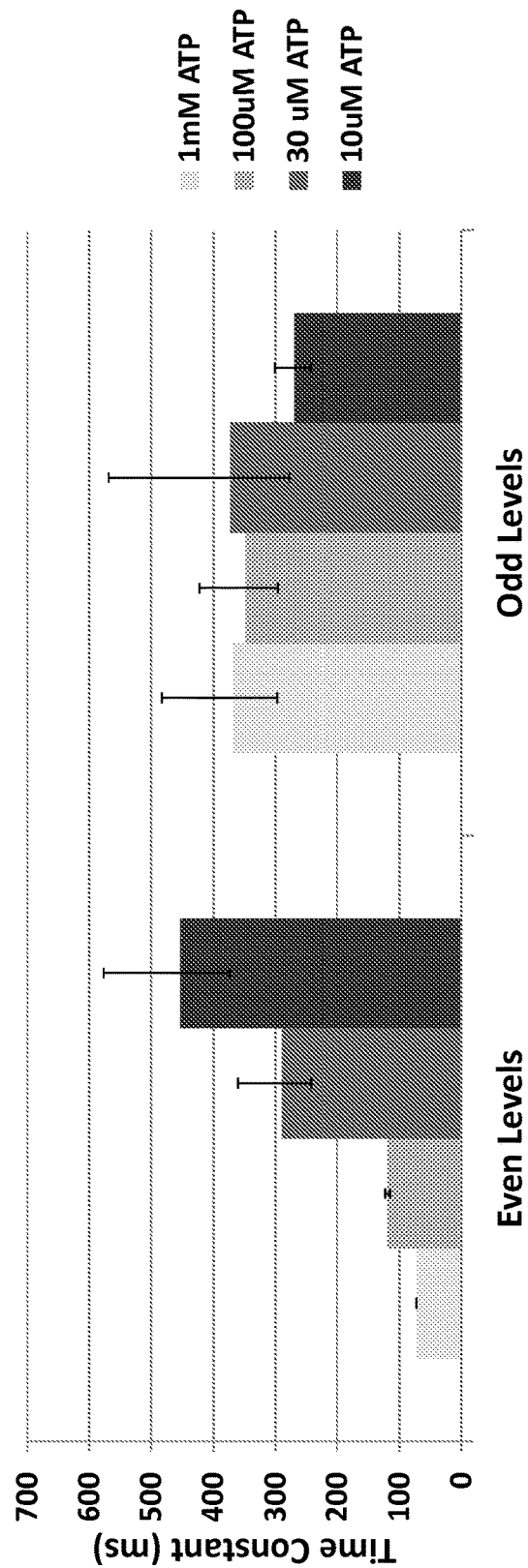

FIGS. 4A and 4B show the exemplary effect of ATP concentration on the dwell time of the fractional translocation steps, according to some embodiments. In FIG. 4A, the current levels surrounding that of an abasic current peak from a polynucleotide sequence translocating through a nanopore with fractional translocation step inclusion were sequentially labeled as 1 to 27, and the median durations were plotted.

Current levels were detected by an algorithm that uses a Student's t-test to determine statistical significance between neighboring current values (see Carter et al., cited elsewhere herein). Other techniques are capable of this, including velocity thresholding and chi-squared minimization, and these are all known in the art for nucleotide processing-related current changes, as well as for step detection in image processing. There was a duration associated with each of these levels, and in comparing the same level over multiple polynucleotides of the same sequence traversing the pore, the median duration for each level was calculated. These median durations were thus representative of the typical duration associated with each level. However, due to the exponential distribution of dwell times, the time constants of these dwell times are more indicative of their ATP dependence. For this reason, in FIG. 4B, duration histograms of even and odd levels (where "even" and "odd" are associated with the Level Indexes in FIG. 4A) were fit to exponential decay curves ($a*e^{-t/\tau}$), and time constants for each were plotted. Histograms of the levels' durations were constructed by incorporating the duration of each level in every polynucleotide-translocation event into equivalently-sized bins. These histograms were then fit using a commercially-available curve-fitting algorithm (the Matlab Curve Fitting Toolbox), which uses the method of least squares to fit the data to the exponential decay model. This method minimizes the sum of squared residuals, where a residual is defined as the difference between a datapoint and the fitted response to that point. This is a standard technique for fitting data to a parametric model. Error bars in FIG. 4B correspond to the 95% confidence bounds of each fit.

As FIG. 4B shows, the dwell time for the even levels increased with decreasing ATP concentration whereas the dwell time for the odd levels remained constant. Accordingly, the dwell time for the even levels, which corresponded with the first fractional translocation steps, were ostensibly associated with ATP binding and inversely proportional to ATP concentration with an exponential distribution, whereas the dwell time for the odd levels, which corresponded with the second fractional translocation steps, were ostensibly associated with ATP hydrolysis and ATP dependent.

Example III

Utility of Fractional Translocation Steps in Polynucleotide Sequencing

Example III describes the increased sequencing accuracy by using electrical signals obtained from two fractional translocation steps of a full translocation cycle compared with using a single electrical signal obtained from a full translocation cycle.

Because the MspA "read head" is sensitive to a stretch of 4 nucleotides (4-mer) within the constriction zone, current traces were generated from a quadromer map measuring currents corresponding to all 4-mer combinations seen in the MspA nanopore. For further details on measuring currents corresponding to 4-mer combinations, see Laszlo et al., "Decoding long nanopore sequencing reads of natural DNA," Nature Biotechnology 32: 829-833 (2014). However, it should be appreciated that different pores can be sensitive to different numbers of nucleotides within constriction zones. In the present example, sequencing accuracy was determined by comparing the Hidden Markov Model (HMM) results with the original de Bruijn sequence as described below. For typical experimental noise levels such as illustrated in FIG. 5 (i.e. ~0.5-2 pA, or approximately 0.5 to 1.5 pA), the reconstruction accuracy using full steps (Diamonds) was reduced compared to fractional steps (squares).

Briefly, pores were established with previously described methods (see Butler et al, *Proc. Natl. Acad. Sci. USA*, 105:20647-20652 (2008); Manrao et al., *PLoS ONE*, 6:e25723 (2011)). Briefly, lipid bilayers were formed across a horizontal ~20 micron diameter aperture in Teflon from 1,2-diphytanoyl-sn-glycerol-3-phosphocholine (Avanti Polar Lipids). Compartments on both sides of the bilayer contained experimental buffer of 10 mM Hepes, pH 8.0, 400 mM KCl, 1 mM DTT, and 10 mM $MgCl_2$. An Axopatch-200 B (Axon Instruments) was used to apply a voltage across the bilayer (140 mV or 180 mV) and measure the ionic current. MspA was added to the grounded cis compartment at a concentration of ~2.5 ng/ml. Once a single MspA protein was inserted into the Teflon aperture, the cis compartment was flushed with experimental buffer in order to inhibit or avoid further insertions. All experiments were performed at 23° C. The analog ion current signal was low-pass filtered at 20 kHz with a 4-pole Bessel filter and digitized at 100 kHz using a National Instruments 6363 digitizer. Data acquisition was controlled with custom software written in LabWindows/CVI (National Instruments). Data was analyzed with custom software written in Matlab (The Mathworks). ATP was typically used at 1 mM, except for the ATP titration experiments, in which case ATP concentrations ranged from 10 uM to 1 mM. Translocating polynucleotide hybridized to a cholesterol-containing polynucleotide was used at 10 nM. Hel308 Tga helicase was used at a final concentration of 115 nM. Polynucleotide and ATP were added to the cis chamber, followed lastly by Hel308 Tga helicase. Alternatively, an ATP regeneration systems well known in the art can be employed. One exemplary system includes 2 mM ATP, 10 mM creatine phosphate disodium salt, 3.5 U/mL creatine kinase and 0.6 U/mL inorganic pyrophosphatase.

Figure 5:
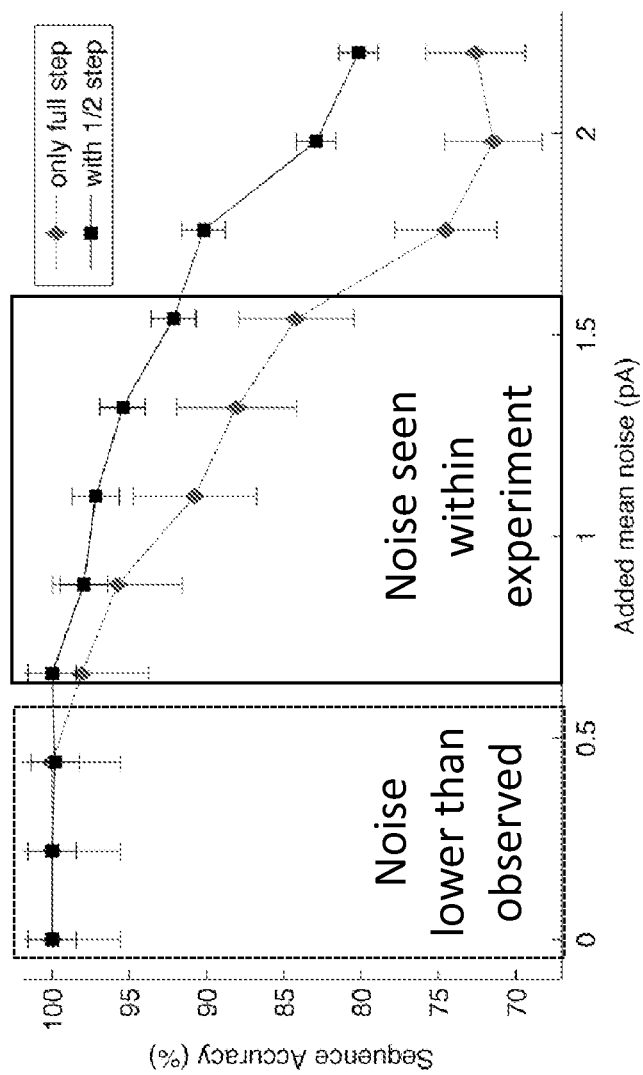
FIG. 5 plots the sequencing reconstruction accuracy (Hidden Markov Model (HMM)) for full step (diamonds) and ½ step (squares) in silico generated current traces (described below) with various levels of added noise, according to some embodiments.

FIG. 5 plots the sequencing reconstruction accuracy (Hidden Markov Model (HMM)) for full step (diamonds) and ½ step (squares) in silico generated current traces (described below) with various levels of added noise, according to some embodiments. FIG. 5 shows the sequence reconstruction accuracy derived from a HMM/Viterbi algorithm analysis of model current blockade traces for a de Bruijn sequence (256-mer). The general HMM algorithm is in some respects similar to what is described in Timp et al., Biophys J. 2012 May 16; 102(10):L37-9. doi: 10.1016/j.bpj.2012.04.009. This algorithm can recover the underlying set of M 'states' from a series of observed measurements. The basic form of this algorithm relies on two experimentally determined sets of probabilities: a state-state 'transition' probability, and state-observation 'emission' probability. Measurements given in steps i=1, 2, 3 . . . N for N measurements. One probability set is the transition matrix that describes the probability that for a given time i, and a state $S_i$ (where S is an state in the set of M states), the subsequent state $S_{i+1}$ (where $S_{i+1}$ is not necessarily $S_i$). For the nanopore system, with a nanopore that is sensitive to 4 nt, and is examining the 4 canonical nucleotides (A, C, G, T), results in $4^4$=256 states, corresponding to each combination of 4 nt. Each of these states can only transition to one of 4 adjacent states.

FIG. 6A depicts state transitions with non-zero probability needed for a HMM to decode sequence in a nanopore where the polynucleotide is moved by motor enzyme, according to some embodiments. The motor is phi29 DNAP or a similar enzyme moving polynucleotide in 1 nucleotide steps. FIG. 6B depicts state transitions with non-zero probability needed for a HMM to decode sequence in a nanopore where the polynucleotide is moved by motor enzyme, according to some embodiments. The motor is Hel308 helicase or similar enzyme that enables fractional motion of the polymer.

The non-zero transition probabilities for the transition matrix of this system is pictured in FIG. 6A for an enzyme that moves in single nucleotide steps. Using this type of enzyme each polynucleotide state or nmer must go to one of 4 adjacent n-mer states. For an enzyme that takes one fractional translocation step, there will be more states. In this regard, a given full-step state must go into a half-step (or fractional-step) state before another full-step state can be observed. Thus, there are more states available with more discernible paths, thus aiding the accuracy of polynucleotide characterization.

The number of states is given by $q*4^{n+1}$, where n is the read size of the nanopore, and q is the number of steps needed to complete a full translocation cycle. For q=2 and n=4, as is seen with Hel308 helicase and M2-NNN MspA, there are 2048 states. The transition probability matrix is pictorially described in FIG. 6B for an enzyme that moves in fractional nucleotide steps. Each state corresponding to a full state, can transition to only one of 1024 'half states' or 'fractional states', while each of the half (or fractional) states can transition to 4 different states, corresponding to a new within the read head of the nanopore. For the HMM decoding algorithm, another probability set is used: the probability that a current measurement at time t, $C_t$, belongs to the state $S_i$. This set of probabilities is determined experimentally, or estimated from previous experimental observations. Such estimation can be accomplished by iterative application of alignment algorithms such as disclosed in Laszlo et al. 2014 (cited elsewhere herein) or with expectation maximization of a HMM. To evaluate the utility of the fractional translocation steps, the sequencing accuracy for an enzyme with fractional nucleotide steps was compared to that of an enzyme with single nucleotide steps. HMM Viterbi decoding algorithms were implemented with custom software implemented in MATLAB, and 10 Monte-Carlo simulations in silico experiments were generated for each condition. Sequencing means and standard deviations were obtained from the average and standard deviations of these 100 Monte-Carlo simulations. Current levels were generated based on results from Manrao 2012 (cited elsewhere herein). Gaussian noise was added, with Gaussian widths given by values shown on the X-axis of FIG. 5, to shift the in silico observed current values that were used in sequence reconstruction, and a typical nanopore sequencing experiment has about 1 $pA_{rms}$ fluctuation in the average levels. For an added Gaussian shift with width of 0.5 pA, both the fractional and full step reconstruction yielded sequencing accuracy commensurate with 100%. Above added Gaussian shifts with widths above 0.5 pA, the sequencing accuracy for fractional translocation steps was larger than the sequencing accuracy for non-fractional translocation steps. Hence, the extra information of the fractional translocation steps provided or conferred enhanced sequence reconstruction accuracy when more than 0.5 pA Gaussian noise was added to the average current levels.

In addition to noise fluctuations, skipped levels caused by the stochastic motion of the enzymes will, or can be expected to, reduce sequencing accuracy. This reduction in accuracy is, or can be, partly offset by the rereading of nucleotide patterns in adjacent quadromers. With the added fractional translocation step there is an additional reread of the nucleotide patterns. For example, information about a given k-mer are included in the neighboring fractional steps, so the k-mer is 're-read' during those neighboring fractional steps. For example, assume that a polynucleotide having sequence ATCGTC is being fractionally translocated through a nanopore with a 4-nucleotide-sensitive readhead. Without wishing to be bound by any theory, for a full-stepping motor, the 4-mer TCGT is only read when the region between C and G is centered in the readhead (that is, the preceding 'step' would have 'TC' centered in the readhead, and only ATCG would be read; the following step would have 'GT' centered in the readhead and only read CGTC). Therefore, if the TCGT read step is skipped by the motor, no information associated with that particular 4-mer is ever measured. However, without wishing to be bound by any theory, with a fractional-stepping motor such as a Hel308 helicase, during full steps the region between two neighboring nucleotides can be centered in the readhead, while during fractional steps single nucleotides can be centered in the readhead. So when 'CG' of the above-mentioned polynucleotide is centered in the readhead, TCGT is read, as it was in the full-stepping case. The preceding fractional step can have only C centered in the readhead, and information about ATCGT can be read; the following fractional step has only G centered in the readhead and information about TCGTC is read. Because information regarding 'TCGT' can be read 3 times in the fractional stepping case and only once in the full-stepping case, this additional 're-reading' of the 4-mer can allow information to be obtained about TCGT even if the motor skips a step associated with it—which likely is not true in the full-stepping case. For all fractions of removed levels, there is an improvement in sequencing accuracy of 2-8%. This was shown with additional in silico Monte Carlo simulations performing the random removal of current levels. In conclusion, there was a robust increase in sequencing accuracy for error modes seen in nanopore sequencing experiments. FIGS. 10, 11 and 12 depict schemes by which the additional fractional translocation step information can be used to improve sequence accuracy. These schemes are further exemplified below in Example VI. The described schemes are exemplary uses, and are not intended to be limiting.

Example IV

Utility of Fractional Translocation Steps in Pattern Matching

Example IV describes the exemplary use of fractional translocation steps to identify levels using known algorithms. Using a dynamic programming algorithm, such as Needleman-Wunsch alignment, the additional levels provided assistance in accurately finding patterns within many levels. For further details on Needleman Wunsche alignment algorithms, see Durbin et al., *Biological Sequence Analysis*, ed. 11 (Cambridge University Press, Cambridge, UK 2006). In addition to, or as an alternative to, the level currents average, using the level durations, the level current standard deviations, or level distributions, can further enhance pattern matching accuracy. In this example, a Needleman Wunsch alignment algorithm was used to identify levels corresponding to a 15-base sequence embedded within levels corresponding to a 1000 base sequence. Use of the following were compared: (1) levels corresponding to full nucleotide motions, (2) levels corresponding to 2 half (or fractional) step motions, (3) levels and durations corresponding to 2 half-step (or fractional-step) motions. Observations were generated in silico with 10 Monte Carlo simulations with levels shifted by values given by random values generated from a Gaussian distribution of varying widths. The results are shown in FIG. 7, which depicts the expected accuracy of finding current patterns as a function of the Gaussian shift, according to some embodiments. Mean and standard deviation of alignment accuracy was generated from the mean and standard deviation of the 10 Monte Carlo simulations. In FIG. 7, diamonds depict a motor having a full nucleotide step, and circles depict a motor having a fractional translocation step, and squares depict a motor having a fractional translocational step combined with duration values. Briefly, level patterns corresponding to 15-nucleotide were embedded within level patterns corresponding to a random 1000-nucleotide sequence. Levels corresponded either to a motor with full nucleotide steps (diamonds) such as phi29 DNAP (only full translocation step), or to a motor with a fractional translocation step (circles), such as Hel308 helicase. Duration was used in addition to current values to further improve matches (squares). From the results in FIG. 7, it can be understood that for increasing noise, the matching quality was considerably greater for the algorithms that use the fractional translocation step motion. The matching quality was further improved if the duration values were also used. To match levels with the Needleman Wunsch algorithm, an input level similarity measure, or score, was used to compare levels. In the tests a Student's t-test was employed to compare current levels. To compare (score) the similarity of two durations, the difference of the natural logarithm of the durations was determined, and added to the score given by the Student's t-test. The term "score" can be defined in the nomenclature of the Needleman Wunsch algorithm. These scoring functions represent non-limiting examples of methods that can be used to compare signal levels (e.g., current values) and durations.

Example V

Modulating Helicase Fractional Steps

Example V exemplifies the use of varying reaction components to vary Hel308 helicase dwell time.

FIG. 8 shows the exemplary modulation of Hel308 helicase activity with varying concentrations of pyrophosphate, according to some embodiments. FIG. 9 shows the exemplary modulation of Hel308 helicase activity with the nucleotide inhibitor sodium orthovanadate and with the nucleotide analog adenosine 5'-(β,γ-imido)triphosphate lithium salt hydrate, according to some embodiments.

Hel308 helicase activity was modulated by increasing pyrophosphate concentration. Briefly, reaction conditions were those described in Example III with the inclusion of various concentrations of pyrophosphate ranging from 0 to 50 mM, e.g., 0 mM (control), 5 mM, 10 mM, 20 mM, 30 mM, 40 mM, and 50 mM. The results are shown in FIG. 8 and indicate the percent helicase activity compared to helicase activity in the absence of pyrophosphate (control). Concentrations of 5 and 10 mM pyrophosphate resulted in lowering helicase activity to more than 75% of control. Pyrophosphate concentrations greater than 10 mM resulted in further decreases in helicase activity and, therefore, helicase dwell time. A fluorescence assay was used to monitor the ability of a helicase to unwind duplex DNA. A 49-nt FRET polynucleotide (50 nM final concentration) included a 5' fluorescein group (/FAM/). A 40-nt quencher-containing polynucleotide (50 nM final) included a fluorescent quencher, Black Hole Quencher (/BHQ1/). These two polynucleotides were hybridized together by heating them past their melting temperatures to 75° C. and slowly cooling to room temperature using methods well-known in the art. The duplex included a 9-base 3' overhang that the 3' to 5' helicase can bind to. A complementary FRET 40-nt polynucleotide that was 100% complementary to the 40-nt quencher-containing polynucleotide was present at a minimum of 10-fold molar excess. Because the quencher and fluorophore were initially in close proximity, fluorescence was quenched. Based upon the helicase unwinding the duplex DNA, the 40-nt quencher-containing polynucleotide became more likely to bind to the complementary FRET 40-nt polynucleotide than to re-bind to 49-nt FRET polynucleotide. The newly single-stranded 49-nt FRET polynucleotide thus fluoresced in the presence of a suitable exciting light source. The assay buffer included 10 mM HEPES, pH 8.0, 400 mM KCl, 1 mM $MgCl_2$, 1 mM DTT, 1 mM ATP. The reaction was permitted to proceed for 20 minutes at room temperature before reading fluorescence.

Hel308 helicase activity and, thus, dwell time also was shown to be reduced in the presence of either of the nucleotide inhibitors or analogs sodium orthovanadate and adenosine 5'-(β,γ-imido)triphosphate lithium salt hydrate, respectively. Briefly, reaction conditions were those described in Example III with the inclusion of either sodium orthovanadate ("NaOthovanadate" in FIG. 9) or adenosine 5'-(β,γ-imido)triphosphate lithium salt hydrate ("AMP-PNP" in FIG. 9) at a concentration of 5 mM inhibitor or analog. The results are shown in FIG. 9 and indicate the percent helicase activity compared to helicase activity in the absence of the nucleotide inhibitor or analog (control). Concentrations of 5 mM inhibitor or analog resulted in lowering helicase activity to more than 85% of control and, therefore, can be expected to increase helicase dwell time, or the time it takes the helicase to move along the DNA. For example, an increase in dwell time can lengthen the time of a fractional step, thus permitting more time to acquire a signal.

Example VI

Methods for Processing Fractional Step Information to Improve Sequencing Accuracy Example VI exemplifies three methods of processing the additional information obtained from fractional translocation steps to improve sequencing accuracy.

FIG. 10 illustrates an exemplary method of processing the additional information obtained from fractional translocation steps using current level and duration information. The method can be applied to two independent sequence reads. Using this scheme, the current trace is subjected to a step detection algorithm, wherein the current levels and duration of those levels are found. Based at least in part on the durations for the levels, a two-state HMM identifies levels as a full step (long) or as a half (or fractional) step (short), or as a potential skip within the observations. These identified long and short steps and skip information are then used by a HMM, Viterbi, or pattern matching algorithm, or suitable combination thereof, to reconstruct the polynucleotide sequence for the two types of states separately (long and short, respectively corresponding to full step and half (or fractional) step levels). The called sequences are then compared and used to improve the polynucleotide sequencing accuracy, e.g., by adjusting the HMM, Viterbi, or pattern matching algorithm. Alignment can be used to identify poorly matching locations of the two independent sequence reads.

FIG. 11 illustrates an exemplary method of processing the additional information obtained from fractional translocation steps using current level and duration information. The method can be applied to two concurrent sequence reads. In this method, the current trace is first subjected to a step detection algorithm so as to find the levels. The mean (or median) level current values and the duration of each level are then input, as a pair, into a two dimensional HMM, Viterbi, or pattern matching algorithm, or suitable combination thereof, that examines duration and current values and estimates or calls optimal sequence for half (or fractional) states and full states. In this technique, the HMM emission probability is two dimensional: $P_i(emission_t) = P_i(cur_t, dur_t) = P_i(cur_t) * P_i(dur_t)$ where i is a "state" that corresponds to a long step or a short (fractional) translocation step of the polynucleotide, and $cur_t$ and $dur_t$ are, respectively the level current and duration for level number t. The two dimensional HMM can take as input a consensus map and probability distribution for long levels (full states), and a consensus map and probability distribution for short levels (half (or fractional) states). The two dimensional HMM can provide as output a call of the nucleotide sequence.

FIG. 12 illustrates an exemplary method of processing the additional information obtained from fractional translocation steps using current traces directly. The method can be applied with or without the use of duration information. By reference to the use of duration information, in this method the current trace is directly analyzed with a duration-dependent HMM. In this version of a HMM, the duration of a level is determined at the same time as-most likely sequence and full or half (or fractional) step state. If the state has remained unchanged between two time iterations, the duration for the given state will increase. This duration is then used to improve the evaluation of whether that state is in a full or fractional state.

Example VII

Additional Methods for Processing Fractional Step Information to Improve Sequencing Accuracy Example VII describes additional exemplary methods for processing fractional step information to improve sequencing accuracy.

Hidden Markov Models (HMMs) and Viterbi algorithms previously have been used for base-calling based on signals from polynucleotides translocating through nanopores suing single-step molecular motors. For further details, see Timp et al., "DNA Base-Calling from a Nanopore Using a Viterbi Algorithm," Biophysical Journal 102: L37-L39 (May 2012). FIG. 19A schematically illustrates an aspect of an exemplary Hidden Markov Model (HMM) used to characterize a signal from single-step translocation of a polynucleotide through a pore, e.g., in which a given signal level corresponds to translocation of one nucleotide through a pore, e.g., by a polymerase or a helicase. As noted elsewhere herein, a signal level may not necessarily correspond to presence of a single nucleotide within the constriction of a pore, but instead can correspond to presence of a "word" that includes a plurality of nucleotides, e.g., two, three, four, five, six, seven, eight, nine, ten, or more than ten nucleotides. Such a "word" also can be referred to as a "k-mer." In the embodiment illustrated in FIG. 19A, the "words" or "k-mers" are four nucleotides long or are "quadromers" or "4-mers," corresponding to a signal level being based upon the presence of four nucleotides in the constriction of a pore.

In FIG. 19A, it can be seen that for a given position i of a polynucleotide translocating through a pore, a given quadromer in the constriction of the pore can include any possible combination of four nucleotides, e.g., AAAA, AAAC, AAAG, AAAT, . . . TTTT. It may not necessarily be possible based on the signal level corresponding to such quadromer to uniquely identify that quadromer. For example, two different quadromers, e.g., two different quadromers that are adjacent to one another in the expected sequence, potentially may have the same signal levels as one another. Timp discloses exemplary current values for DNA triplets (3-mers), based upon which it can be seen that certain triplets can have the same signal levels as one another, thus inhibiting nucleotide base calling of the bases in that triplet based solely on current level corresponding to that triplet. It should be understood that certain quadromers (and, more generally, certain k-mers) can have signal levels that are indistinguishable from one another, thus inhibiting nucleotide base calling of the bases in that quadromer or k-mer based solely on current level corresponding to that 4-mer or k-mer. Accordingly, using the terminology of HMMs, the bases in such quadromers or k-mers that are indistinguishable from one another based on observation of signal level can be modeled as a "hidden state."

Additional information based on observations of other single-step positions of the polynucleotide in the pore constriction can be used so as to increase the likelihood of accurately identifying the bases in that quadromer or k-mer, and thus of accurately identifying the "hidden state." For example, in FIG. 19A, it also can be seen that for the next position i+1 of a polynucleotide translocating through a pore, a given quadromer in the constriction of the pore can have only certain possible combinations of four nucleotides, because the last three nucleotides of position i correspond to the first three nucleotides of position i+1. As such, measurements of signals for the i and i+1 states can be used to increase the likelihood of correctly identifying the quadromers present at one or both of i and the i+1 positions (or, equivalently, the i−1 and i positions). For example, based upon the sequence AAAA corresponding to position i of the polynucleotide, only the four sequences AAAA, AAAC, AAAG, and AAAT are available for position i+1. The available four sequences at position i+1 readily can be identified for each possible sequence at position i. Analogously, based on the sequence at position i+1 of the polynucleotide, the available four sequences at position i+2 of the polynucleotide readily can be identified. A Viterbi algorithm for a single step motor—in which there is a one-to-one correspondence between signal levels and positions i, i+1, i+2, . . . i+n, where n is the number of nucleotides in a polynucleotide, can express the signal from the set of ordered levels $L=\{l_1, l_2, \ldots l_n\}$. Each level $l_i$ which corresponds to the position i of the polynucleotide can be expressed as one or more of the mean of that signal level ($mean_i$), the standard deviation of that signal level ($std_i$), or the duration of that signal level ($dur_i$). The set of possible quadromers can be expressed as prev(q)=$\{q_1, q_2, \ldots q_4\}$ that defines the possible values of the quadromer corresponding to the previous location of the polynucleotide (the i−1 position), when the quadromer corresponding to the present location of the polynucleotide (the i position) is q. For example, prev(AACC)={AAAC, CAAC, GAAC, TAAC}. Based on the observed signal level $O_{ji}$ corresponding to the jth observed level, the likelihood score for a given quadromer q being present at the position i can be expressed as:

$$\text{score(level, } i, q) = \max \begin{cases} \text{score(level, } i-1, q) + InsPen \\ \max_{p \in prev(q)} \text{score(level, } i-1, p) + s(l_i | q) \\ \max_{p \in prev(q)} \text{score(level, } i, p) + DelPen \end{cases} \quad (1)$$

where $s(l_i|q)$ corresponds to an award representing likelihood of observing level $l_i$, given quadromer q, InsPen is an insertion penalty (a penalty corresponding to a signal level that is observed but does not correspond to a quadromer in the polynucleotide), and DelPen is a deletion penalty (a penalty corresponding to a quadromer in the polynucleotide but does not have a corresponding signal level).

FIG. 19B schematically illustrates an aspect of an exemplary HMM used to characterize signals from fractional step translocation of a polynucleotide through a pore using a Hel308 helicase, according to some embodiments. In FIG. 19B, it again can be seen that for a given position i of a polynucleotide translocating through a pore, a given quadromer in the constriction of the pore can include any possible combination of four nucleotides, e.g., AAAA, AAAC, AAAG, AAAT, . . . TTTT. Additional information based on observations of fractional-step positions, as well as other single-step positions, of the polynucleotide in the pore constriction can be used so as to increase the likelihood of accurately identifying the bases in that quadromer or k-mer, and thus of accurately identifying the "hidden state," with improved accuracy relative to the use of only single-step positions alone.

For example, in FIG. 19B, it also can be seen that for a fractional step motor, the next position of the polynucleotide translocating through a pore is "i fractional," and in which a given quadromer in the constriction of the pore can have only certain possible combinations of four nucleotides, because the last three nucleotides of position i correspond to the first three nucleotides of position "i fractional." As such, measurements of signals for the i and i fractional states can be used to increase the likelihood of correctly identifying the quadromers present. For example, based upon the sequence AAAA corresponding to position i of the polynucleotide, only the four sequences AAAA, AAAC, AAAG, and AAAT are available for position i fractional. The available four sequences at position i fractional readily can be identified for each possible sequence at position i.

Additionally, in FIG. 19B, it also can be seen that for the next position i+1 full of a polynucleotide translocating through a pore, which position immediately follows i fractional, a given quadromer in the constriction of the pore can have only one possible sequence, because the four nucleotides of position i+1 full correspond to the same nucleotides as for position i fractional. As such, measurements of signals corresponding to the i, i fractional and i+1 full positions can be used to increase the likelihood of correctly identifying the quadromers present at some or all of i, i fractional and i+1 full positions (or, equivalent, the i−1 and i positions). For example, based upon the sequence AAAA corresponding to position i of the polynucleotide, only the four sequences AAAA, AAAC, AAAG, and AAAT are available for position i fractional and for i+1 full. A modified Viterbi algorithm for a fractional step motor—in which there is a correspondence between signal levels and both fractional step and full step positions i, i fractional, i+1 full, i+1 fractional, i+2 full, i+2 fractional, . . . i+n fractional, i+n full, where n is the number of nucleotides in a polynucleotide, can express the signal levels l as the set of levels. Analogously as discussed above with reference to FIG. 19A, each signal level $l_i$ corresponding to the i full or i fractional position can be expressed as one or more of the mean of that signal level ($mean_i$), the standard deviation of that signal level ($std_i$), or the duration of that signal level ($dur_i$). Given the quadromer q at the current fractional translocation step, the set of possible quadromers corresponding to the previous full translocational step can be defined as prev(q)={$q_1$, $q_2$, . . . $q_4$}. For example, prev(AACC)={AAAC, CAAC, GAAC, TAAC}.

Based on the observed signal level $l_i$ corresponding to position i, the likelihood score $score_f$ for a given quadromer q being present at the position i for a location corresponding to a full translocation state, and the likelihood score $score_h$ for a given quadromer q being present at the position i for a location corresponding to a half (or fractional) translocation state, can be expressed as follows:

$$score_f(level_i, i, q) = \max \begin{Bmatrix} score_f(level, i-1, q) + InsPen \\ \max_{p \in prev(q)} score_h(level, i-1, p) + s_f(l_i \mid q) \\ \max_{p \in prev(q)} score_h(level, i, p) + DelPen \end{Bmatrix} \quad (2)$$

$$score_h(level_i, i, q) = \max \begin{Bmatrix} score_h(level, i-1, q) + InsPen \\ \max_{p \in prev(q)} score_f(level, i-1, p) + s_h(l_i \mid p, q) \\ \max_{p \in prev(q)} score_f(level, i, p) + DelPen \end{Bmatrix} \quad (3)$$

where $s_f(l_i|q)$ corresponds to an award representing likelihood of observing level $l_i$, given quadromer q at full translocational state, $s_h(l_i|p,q)$ corresponds to an award representing likelihood of observing level $l_i$, given quadromer q and previous quadromer p at fractional translocational state, InsPen is an insertion penalty (a penalty corresponding to a signal level that is observed but does not correspond to a quadromer in the polynucleotide), and DelPen is a deletion penalty (a penalty corresponding to a quadromer in the polynucleotide but does not have a corresponding signal level).

Additionally, dynamic programming can be used for pattern matching for a fractional step molecular motor (such as a Hel308 helicase). Dynamic pattern matching is described for a single-step molecular motor in Laszlo et al., "Decoding long nanopore sequencing reads of natural DNA," Nature Biotechnology 32: 829-833 (2014). For example, for a single-step molecular motor, the signal levels l can be expressed as the set of levels L={$l_1$, $l_2$, . . . $l_n$}, wherein each signal level $l_i$ corresponding to the full translocation step position of the polynucleotide can be expressed as one or more of the mean of that signal level ($mean_i$), the standard deviation of that signal level ($std_i$), or the duration of that signal level ($dur_i$). Based on the observed signal level $l_i$, the likelihood score for a given quadromer $q_j$ being measured can be expressed as:

$$score(i, j) = \max \begin{Bmatrix} score(i-1, j) + InsPen \\ score(i-1, j-1) + s(l_i \mid q_j) \\ score(i, j-1) + DelPen \end{Bmatrix} \quad (4)$$

where i stands for the position in the level sequence; j stands for the position in the DNA sequence, quadromer $q_j$'s last base would be the base at position j; score(i,j) represents how well is the match between levels $l_1$ . . . $l_i$ and quadromers $q_1$ . . . $q_j$; $s(l_i|q_j)$ corresponds to an award representing likelihood of observing level $l_i$, given quadromer $q_j$; InsPen is an insertion penalty (a penalty corresponding to a signal level that is observed but does not correspond to a quadromer in the polynucleotide); DelPen is a deletion penalty (a penalty corresponding to a quadromer in the polynucleotide but does not have a corresponding signal level).

For a fractional-step molecular motor such as Hel308, the signal levels l can be expressed as the set of levels L={$l_1$, $l_2$, . . . $l_n$}, wherein each signal level $l_i$ corresponding to the i full or i fractionall position of the polynucleotide can be expressed as one or more of the mean of that signal level ($mean_i$), the standard deviation of that signal level ($std_i$), or the duration of that signal level ($dur_i$). Based on the observed signal level $l_i$, the likelihood score $score_f$ for a given quadromer $q_j$ being measured corresponding to a full translocation state, and the likelihood score $score_h$ for a given quadromer $q_j$ being measured corresponding to a half (or fractional) translocation state, can be expressed as follows:

$$score_f(i, j) = \max \begin{Bmatrix} score_h(i-1, j) + InsPen \\ score_h(i-1, j-1) + s_f(l_i \mid q_j) \\ score_f(i, j-1) + DelPen \end{Bmatrix} \quad (5)$$

$$score_h(i, j) = \max \begin{Bmatrix} score_f(i, j) + InsPen \\ score_f(i, j-1) + s_h(l_i \mid q_{j-1}q_j) \\ score_h(i, j-1) + DelPen \end{Bmatrix} \quad (6)$$

where i stands for the position in the level sequence; j stands for the position in the DNA sequence, quadromer $q_j$'s last base would be the base at position j; $score_f(i,j)$ and $score_h(i,j)$ represent how well is the match between levels $l_1$ . . . $l_i$ and quadromers $q_1$ . . . $q_j$, respectively assuming a full or fractional state; $s_f(l_i|q_j)$ and $s_h(l_i|q_j)$ correspond to awards representing likelihood of observing level $l_i$, given quadromer $q_j$ in full and fractional states, respectively; InsPen is an insertion penalty (a penalty corresponding to a signal level that is observed but does not correspond to a quadromer in the polynucleotide); DelPen is a deletion penalty (a penalty corresponding to a quadromer in the polynucleotide but does not have a corresponding signal level).

Some exemplary de novo sequencing results using fractional steps now will be described with reference to FIG. 20A. A library of 75 500-mer polynucleotides was generated based on human DNA, and nanopore data was collected analogously as described elsewhere herein with reference to Examples II and III. Nucleotide base-calling based on the data was analyzed using the modified Viterbi algorithm described using Equations (2) and (3) above. The base-called sequence then was aligned to a set of 150 500-mers, 75 of which were the true 500-mers and 75 of which were "decoy" or "dummy" 500-mer sequences. In FIG. 20A, which illustrates the read length as a function of accuracy of the alignment (using a LASTAL aligner such as described in Kielbasa et al., "Adaptive seeds tame genomic sequence comparison," Genome Research 21: 487-493 (2011)), the open diamonds correspond to results in which the base-called sequence was aligned to the correct ("target") sequences, and the closed diamonds correspond to results in which the base-called sequence was aligned to a "decoy" or "dummy" sequence. It can be understood from FIG. 20A that for read lengths greater than about 200 base pairs, accuracies of greater than about 60% can be obtained. The accuracy further potentially can be increased using known techniques such as reading both strands of the DNA.

Some exemplary pattern matching results using fractional steps now will be described with reference to FIGS. 20B-20C. The same library of 75 500-mer polynucleotides and same experimental protocol was used as described above with reference to FIG. 20A. Nucleotide base-calling based on the data was analyzed using the dynamic programming for pattern matching described using Equations (5) and (6) above. The base-called sequence then was aligned to a set of 150 500-mers, 75 of which were the true 500-mers and 75 of which were "decoy" or "dummy" 500-mer sequences. In FIG. 20B, which illustrates the alignment size as a function of alignment score, the open diamonds correspond to results in which the base-called sequence was aligned to the correct ("target") sequences, and the closed diamonds correspond to results in which the base-called sequence was aligned to a "decoy" or "dummy" sequence. It can be understood from FIG. 20B that alignment scores of greater than about 40 can be obtained for alignment sizes of greater than about 200 base pairs. In FIG. 20C, which also illustrates the alignment size as a function of alignment score, the open diamonds correspond to results in which the base-called sequence was aligned to the correct ("target") sequences, and the closed diamonds correspond to results in which the base-called sequence was aligned to a "decoy" or "dummy" sequence. It can be understood from FIG. 20C that alignment scores of greater than about 20 can be obtained for alignment sizes of greater than about 50 base pairs. It can be observed that the fractional step model can accurately identify more events than can the single step model.

Additionally, it was observed that for a translocation event with 1332 levels, pattern matching (Equations 5 and 6) against a data set of 80 kb took about 145 seconds on a single thread, whereas for the same event with 1332 levels, de novo sequencing (Equations 2 and 3) against that data set took about 69 seconds on a single thread. It was observed that pattern matching complexity grows linearly with nucleotide dataset, while complexity of de novo sequencing was independent of the data set. Pattern matching was observed to accurately identify shorter events, which de novo sequencing failed to identify. Additionally, it was observed that the fractional step model for pattern matching produces more true positives than a single-step model, indicating that the fractional step model can be a better model to explain helicase data.

Example VIII

Fractional Translocation Step with Additional Hel308 Helicases

Example VIII describes the fractional translocation steps observed with exemplary Hel308 helicases used as molecular motors.

Experiments for Example VIII were conducted analogously as described above with reference to Example I, using a single 2NNN MspA nanopore in a DphPC lipid bilayer, and using the parameters listed below in Table 3, where "Hel308 Mbu (A)" refers to a set of parameters used for a first experiment using Hel308 Mbu and "Hel308 Mbu (B) refers to a set of parameters used for a second experiment using Hel308 Mbu. Lipid bilayers were formed from 1,2-diphytanoyl-sn-glycero-3-phosphocholine (Avanti Polar Lipids) The bilayer spanned a horizontal ~20 micron diameter aperture in Teflon. M2-NNN-MspA was added to the grounded side of the bilayer at a concentration of ~2.5 ng/ml. Once a single pore was inserted, the compartment was flushed with experimental buffer to avoid further insertions. An Axopatch-200B patch clamp amplifier (Axon Instruments) applied a voltage across the bilayer of 180 mV and measured the ionic currents. The analog signal was low-pass filtered at 50 kHz with a 4-pole Bessel filter and was then digitized at five times the low-pass filter frequency. Data acquisition was controlled with custom software written in LabWindows/CVI (National Instruments). The ~60 µl compartments on both sides of the bilayer contained experimental buffer of the appropriate concentration of KCl, 1 mM EDTA, 1 mM DTT, 1 mM ATP, 5 mM MgCl$_2$, and 10 mM HEPES/KOH buffered at pH 8.0. Wild type Mbu Hel 308 helicase was used at the indicated concentration as the molecular motor.

In both Hel308 Mbu experiments and the Hel308 Tga experiment, DNA was read in the 3' to 5' direction, while in the phi29 polymerase experiment, DNA was read in the 5' to 3' direction.

TABLE 3

| Parameter | Hel308 Mbu (A) | Hel308 Mbu (B) | Hel308 Tga | phi29 |
|---|---|---|---|---|
| [KCl] | 300 mM | 600 mM | 400 mM | 300 Mm |
| pH | 8.0 | 8.0 | 8.0 | 8.0 |
| [MgCl$_2$] | 5 mM | 5 mM | 5 mM | 5 mM |
| [ATP] | 1 mM | 1 mM | 1 mM | — |
| [DTT] | 1 mM | 1 mM | 1 mM | 1 mM |
| [EDTA] | 1 mM | 1 mM | 1 mM | 1 mM |
| [DNA] | 10 nM | 10 nM | 10 nM | 10 nM |
| [molecular motor] | 150 nM | 150 nM | 150 nM | 1.5 µM |
| Voltage | 180 mV | 180 mV | 180 mV | 180 mV |

Figure 17A:
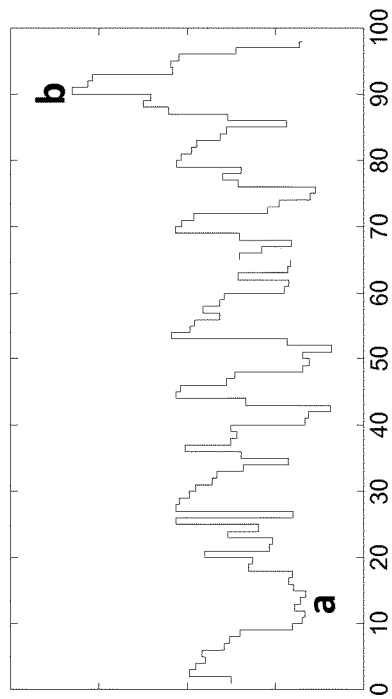
Figure 17B:
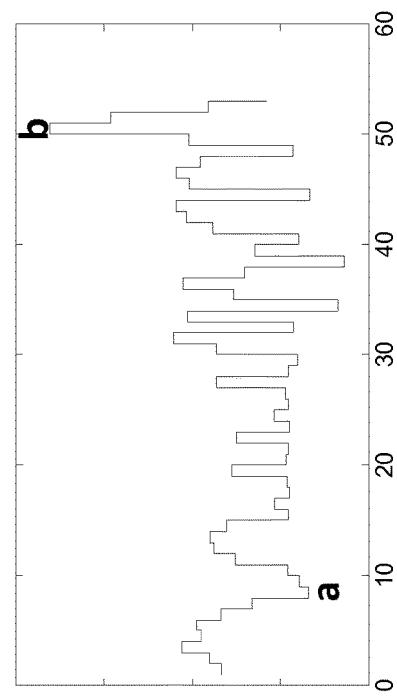
Figure 17C:
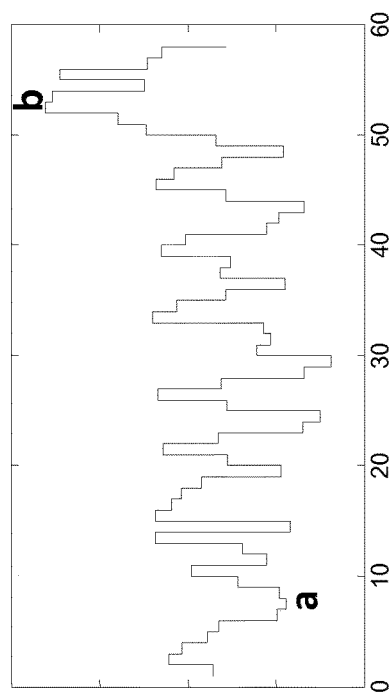
Figure 17D:
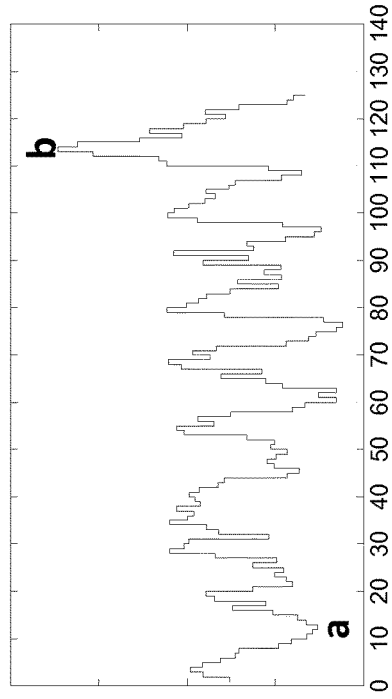

FIGS. 17A-17D show comparison Hel308 Mbu helicase, Hel308 Tga helicase, and phi29 polymerase translocation events using certain parameters, according to some embodiments. FIG. 17A shows the translocation steps observed with Hel308 Mbu helicase using the "Hel308 Mbu (A)" parameters shown in Table 3. The translocating polynucleotide (SEQ ID NO: 72: /5Phos/AAACCTTCCXCCCG-TACCGTGCCGTACCGTTCCGTTCCGTACCGT-ATTTTTTTT TCTCACTATCGCATTCTCATGCAGGTCGTAGCC, where X=abasic) was hybridized to a cholesterol-containing polynucleotide (SEQ ID NO: 73: AAAAAAAATACGG-TACGGAACGGAACGGTACGGCACGGTACGGG TTTTTTTTTTTTTTTT/3CholTEG). FIG. 17B shows the translocation steps observed with Hel308 Mbu helicase using the "Hel308 Mbu (B)" parameters shown in Table 3 and using the same polynucleotide sequences as in FIG. 17A. FIG. 17C shows the translocation steps observed with a Hel308 Tga helicase using the "Hel308 Tga" parameters shown in Table 3 and using the same polynucleotide sequences as in FIG. 17A. FIG. 17D shows the translocation steps observed with phi29 polymerase using the "phi29" parameters shown in Table 3 and using the same polynucleotide sequences as in FIG. 17A; the phi29 plot in FIG. 17D was reflected about the vertical axis in order to facilitate comparisons between FIGS. 17A, 17B, 17C, and 17D.

It can be seen in FIGS. 17A-17D that for sequencing with each helicase, the nanopore detected the features generally designated "a" (corresponding to a valley in the signal) and "b" (corresponding to a peak in the signal). It also can be seen that for sequencing with the Hel308 Tga helicase (FIG. 17C), approximately twice the number of levels was observed as for the phi29 helicase (FIG. 17D). It also can be seen that for sequencing with the Hel308 Mbu helicase under the "Hel308 Mbu (B)" conditions (FIG. 17B), a greater number of levels were observed as for the Hel308 Mbu helicase under the "Hel308 Mbu (A)" conditions (FIG. 17A). It also can be seen that for sequencing with the Hel308 Mbu helicase under the "Hel308 Mbu (B)" conditions (FIG. 17B), fewer levels were observed as for the Hel308 Tga helicase (FIG. 17C), but more levels were observed as for the phi29 helicase (FIG. 17D). FIGS. 17A-17D can be interpreted as signifying (1) that multiple variants of the Hel308 helicase (e.g., both Tga and Mbu) display a fractional step, whereas no fractional step was observed for the polymerase Phi29; and (2) that fractional steps can be elucidated by changing an environmental variable or parameter, e.g., KCl concentration. Additionally, other data indicates that the duration of levels increases with a decrease in ATP concentration when utilizing Mbu, e.g., that the durations and therefore physical mechanisms of fractional steps in Mbu also can be ATP-dependent.

Example IX

Use of Stressors, Optionally in Combination with Multi-Modality

As should be clear based on the disclosure provided herein, many environmental variables or parameters can affect how a nanopore system reads, or generates a signal based upon, a particular polynucleotide sequence. Exemplary variables or parameters that can provide such an effect can include temperature, salt concentration (e.g., Mg, Cl), cofactor (e.g., ATP) concentration, concentration of ATP products such as pyrophosphate, pH, the particular molecular motor used (e.g., the particular Hel308 helicase used), pressure, and the like.

For example, such as described above with reference to Example II and FIGS. 4A and 4B, the concentration of ATP can affect the dwell time of levels corresponding to certain translocation steps. For example, it was observed that the dwell times for first fractional translocation steps increased with decreasing ATP concentration, and ostensibly are associated with ATP binding and inversely proportional to ATP concentration. As another example, such as described above with reference to Example V and FIG. 8, the concentration of pyrophosphate can affect the activity of Hel308 helicase. For example, it was observed that the activity of Hel308 helicase decreased with increasing pyrophosphate concentration, thus increasing helicase dwell time. As another example, such as described above with reference to Example V and FIG. 9, the concentration of nucleotide inhibitor or analog can affect the activity of Hel308 helicase. For example, it was observed that the activity of Hel308 helicase decreased based on the presence of sodium orthovanadate or adenosine 5'-(β,γ-imido)triphosphate lithium salt hydrate (AMP-PNP) decreased helicase activity, thus increasing helicase dwell time. As yet another example, such as described above with reference to Example VIII and FIGS. 17A and 17B, the concentration of a salt can affect the number of levels observed. For example, it was observed that an increase in the concentration of salt (e.g., KCl) increased the number of levels observed during sequencing with Hel308 Mbu helicase. One skilled in the art readily would be able envision adjustments to any suitable parameters so as to adjust the manner in which signal is generated based on a polynucleotide sequence.

Additionally, it should be appreciated that different combinations of such parameters can affect the accuracy of the sequencing as well as the throughput of the sequencing. For example, increasing the dwell time of the helicase can increase accuracy, e.g., can increase the number of levels observed, but potentially can decrease throughput of the sequencing. For sequencing based on the observation of fractional steps, some steps potentially can be affected more by a particular variable than may another set of steps. The variable-independent steps can be used to set a baseline of accuracy, while other steps can be adjusted to meet the particular sequencing needs (e.g., increased accuracy with lower throughput, or increased throughput with decreased accuracy). In some embodiments, a multi-modal device can take advantage of this by tuning the accuracy and throughput based on the needs of the sequencer, e.g., by adjusting one or more parameters during sequencing. As one nonlimiting, illustrative example, and as noted above, it has been observed that a decrease in ATP concentration with Hel308 Tga can increase the durations of fractional states. An increase in fractional state duration can increase sequencing accuracy, e.g., by improving the signal-to-noise ratio (SNR) of the fractional state read or allowing for lower-frequency filters to be applied, but can reduce throughput. A multi-modal device can take advantage of this by beginning a sequencing run with high concentrations of ATP in order to relatively quickly determine a rough "scaffold" of the sequence, and then can reduce ATP concentration in order to "fill in the gaps" of the scaffold with higher quality, albeit slower, reads.

Additionally, note that any suitable number of different parameters can be used sequentially or in parallel with one another so as to increase resolution of one or more signals produced by translocation by a Hel308 helicase of a target polynucleotide through a pore. FIGS. 21A-21C schematically illustrate signals that can be generated as a function of time for different translocations of a polynucleotide through a pore, according to some embodiments. FIGS. 21A-21C each illustrate a dashed curve, which corresponds to an idealized signal generated under conditions in which a polynucleotide translocates through a pore under the applied force applied only a potential difference, rather than by a molecular motor, and with infinite signal resolution. Under such conditions, the signal is a continuously changing function of the positions and sequence of nucleotides as they pass through the pore.

FIG. 21A also illustrates an exemplary signal (heavy lines) generated using only full translocation steps that occur at times indicated by the vertical dotted lines. The signal can be an electronic or optical signal such as described elsewhere herein. Additionally, the signal can include any suitable characteristic of such an electronic or optical signal, such as the mean signal level, signal duration, or standard deviation (e.g., broadband noise or band limited noise). The signal can be seen in FIG. 21A to change from a relatively low level to a relatively high level via a single step, and then again to a relatively low level via a single step, corresponding to transitions occurring between the full translocation steps as the polynucleotide translocates through the pore. It also can be seen in FIG. 21A that the signal intersects the idealized signal at points (a), (b), and (c) at different times, and thus can be considered to "sample" the idealized signal at these points. However, because the effective sampling rate is relatively low, the signal samples the idealized signal relatively poorly. For example, the values at points (a) and (b) are the same as one another, corresponding to degenerate signal levels for different translocation steps. Because the signal does not adequately sample the portion of the idealized curve that lies between points (a) and (b), the physical translocation steps corresponding to points (a) and (b) can be indistinguishable from one another, resulting in the loss of information about the polynucleotide sequence. Additionally, because the signal does not adequately sample the portion of the idealized curve that lies between points (b) and (c), the physical translocation steps corresponding to the downward slope of the idealized curve between points (b) and (c) potentially can only partially characterize the portion of the polynucleotide translocated through the pore during such steps.

In addition to the idealized signal represented by the dashed curve as described above, FIG. 21B also illustrates an exemplary signal (heavy lines) generated using a combination of time-separated full translocation steps, or a combination of full and fractional translocation steps, that occur at times indicated by the vertical dotted lines. Time-separated full translocation steps can correspond to signals that are generated by two molecular motors that each translocate the polynucleotide, but at times that are shifted relative to one another, e.g., that are shifted relative to one another by approximately 50% of the time duration of a full translocation cycle. A combination of full and fractional translocation steps can correspond to signals that are generated by a single molecular motor (e.g., a Hel308 helicase) that fractionally translocates the polynucleotide through partial and full translocation steps, such as where the fractional translocation step occurs at approximately 50% of the time duration of a full translocation cycle. The signal can be as described above with reference to FIG. 21A. The signal can be seen in FIG. 21B to change from a relatively low level to a relatively high level via a sequence of steps, and then again to a relatively low level via another sequence of steps, corresponding to transitions occurring between the time-separated full translocation steps or by the combination of full and fractional translocation steps, as the polynucleotide translocates through the pore. It also can be seen in FIG. 21B that the signal intersects the idealized signal at a significantly greater number of points (and times) than in FIG. 21A, and thus can be considered to "sample" the idealized signal at these points. Because the effective sampling rate is relatively higher than in FIG. 21A, the signal samples the idealized signal relatively better than in FIG. 21A. For example, the values at points (a) and (b) are the same as one another, corresponding to degenerate signal levels for different translocation steps. Because the signal in FIG. 21A also samples the portion of the idealized curve that lies between points (a) and (b), the physical translocation steps corresponding to points (a) and (b) can be distinguished from one another, resulting in additional information about the polynucleotide sequence. Additionally, because the signal in FIG. 21B more fully samples the portion of the idealized curve that lies between points (b) and (c), the physical translocation steps corresponding to the downward slope of the idealized curve between points (b) and (c) can better characterize the portion of the polynucleotide translocated through the pore during such steps than potentially can be achieved using the signal in FIG. 21A.

In addition to the idealized signal represented by the dashed curve as described above, FIG. 21C also illustrates another exemplary signal (heavy lines) generated using a combination of time-separated full translocation steps, or a combination of full and fractional translocation steps, that occur at times indicated by the vertical dotted lines. Time-separated full translocation steps can correspond to signals that are generated by multiple molecular motors that each translocate the polynucleotide, but at times that are shifted relative to one another, e.g., that are shifted relative to one another by approximately 25%, 50%, and 75% of the time duration of a full translocation cycle. A combination of full and fractional translocation steps can correspond to signals that are generated by a single molecular motor (e.g., a Hel308 helicase) that fractionally translocates the polynucleotide through partial and full translocation steps, such as where the fractional translocation step occurs at approximately 25%, 50%, and 75% of the time duration of a full translocation cycle. The signal can be as described above with reference to FIG. 21A. The signal can be seen in FIG. 21C to change from a relatively low level to a relatively high level via a sequence of a greater number of steps than in FIG. 21B, and then again to a relatively low level via another sequence of a greater number of steps than in FIG. 21B, corresponding to transitions occurring between the time-separated full translocation steps or by the combination of full and fractional translocation steps, as the polynucleotide translocates through the pore. It also can be seen in FIG. 21C that the signal intersects the idealized signal at a significantly greater number of points (and times) than in FIG. 21B, and thus can be considered to "sample" the idealized signal at these points. Because the effective sampling rate is relatively higher than in FIG. 21B, the signal samples the idealized signal relatively better than in FIG. 21B, and thus can better characterize the polynucleotide translocated through the pore during such steps than potentially can be achieved using the signal in FIG. 21A or 21B.

It should be appreciated that any suitable selection of parameters can be used so as to increase sampling of any selected portion of an idealized sample curve. For example, as mentioned above, a combination of time-shifted (phase-shifted) full translocation steps from different molecular motors can be used. In this regard, although FIG. 21B describes time-shifting the molecular motors by 50% of the time of a full translocation step from one another, and although FIG. 21B describes time-shifting the molecular motors by 25%, 50%, and 75% of the time of a full translocation step from one another, such values are purely illustrative, and the molecular motors instead can be time-shifted by any suitable amount of time from one another, e.g., can be shifted anywhere from 5% to 95% of the time of a full translocation step from one another, e.g., can be shifted anywhere from 10% to 90% of the time of a full translocation step from one another, e.g., can be shifted anywhere from 25% to 75% of the time of a full translocation step from one another, e.g., can be shifted anywhere from 40% to 60% of the time of a full translocation step from one another. As another example, a combination of full and fractional translocation steps can correspond to signals that are generated by a single molecular motor (e.g., a Hel308 helicase) that fractionally translocates the polynucleotide through partial and full translocation steps. Although FIG. 21B describes the fractional translocation steps as occurring at 50% of the time of a full translocation step from one another, and although FIG. 21C describes the fractional translocation steps as occurring at 25%, 50%, and 75% of the time of a full translocation step from one another, such values are purely illustrative, and the fractional translocation steps instead can occur at any suitable time relative to the full translocation steps, e.g., at 5% to 95% of the time of a full translocation step, e.g., at 10% to 90% of the time of a full translocation step, e.g., at 25% to 75% of the time of a full translocation step, e.g., 40% to 60% of the time of a full translocation step.

Additionally, it should be appreciated that the relative times at which the full or fractional steps occur, and thus the times at which the signal samples the idealized signal, suitably can be adjusted by varying any suitable parameter. For example, as noted above. Exemplary variables or parameters that can effect signal generation can include temperature, salt concentration (e.g., Mg, Cl), cofactor (e.g., ATP) concentration, concentration of ATP products such as pyrophosphate, pH, the particular molecular motor used, and the like. In some embodiments, a first signal can be generated based on a first set of parameters so as to sample the idealized signal at a first discrete set of times, and a second signal can be generated based on a second set of parameters (which differs from the first set of parameters in at least one respect) so as to sample the idealized signal at a second discrete set of times. The first and second signals can be combined so as to provide a signal curve that samples the idealized signal with greater resolution than either the first or second signal alone. It should be appreciated that any suitable number of signals can be combined in an analogous manner so as to provide a signal curve that samples the idealized signal with greater resolution than any individual one of those signals.

Example X

Additional Approaches for Sequence Identification

Some additional approaches for sequence identification are described with reference to Example X.

In some embodiments, certain types of information can be used alone, or in combination with one another, for obtaining sequence-specific information: (A) full step response information alone, (B) fractional step response information alone, (C) full step and fractional step response information together without identifiers, and (D) full step and fractional step response information together with identifiers.

By "response information" it is meant data obtained from the system's response to a given polynucleotide sequence (k-mer) that is unique to that k-mer or a subset of k-mers (inclusive of the k-mer of interest). Examples of response information include a mean level current, median level current, broad-band level current noise, band-limited level current noise, level duration, and the like.

By "identifiers" it is meant data obtained while the polynucleotide (k-mer) interacts with the nanopore environment that identifies where along the "idealized response" a particular level lies with respect to other levels. For example, systems utilizing Hel308 Tga helicase as a molecular motor in the presence of relatively high or relatively low levels of ATP concentration can display relatively short or relatively long durations, respectively, for every other level, where every other level is approximately 50% along the idealized response from neighboring levels. In this example, level duration can be used as an identifier, because it can be used to identify sequence location along the idealized response (with respect to neighboring levels).

By "idealized response" it is meant response of the system for a particular polynucleotide translocating through the nanopore with sufficiently high resolution such that sufficiently small movements of the polynucleotide can be resolved. For example, an idealized response is a continuous current trace of infinitely-high resolution of DNA translocating through the nanopore.

Referring again to items (A)-(D) mentioned further above in this example, each of items (A)-(D) can be used independently, or in conjunction with one or more others of items (A)-(D), to identify a polynucleotide sequence. For example, one or more of items (A)-(D) can be calculated independently from any other of items (A)-(D), for example, owing to computational resource restrictions, time restrictions, a priori knowledge of an optimal approach, and the like. Based upon more than one of items (A)-(D) being calculated, the results of just one of items (A)-(D) can be used. The determination of which one of such calculations to use can be based on confidence in the results. For example, confidence in the results can be based on one or more of the following: (a) the response information itself (e.g., high levels of ATP can shorten fractional step sizes in Hel308 Tga, which can reduce the confidence in item (B) relative to item (A)); (b) the sequencing algorithm itself (e.g., a Viterbi algorithm can produce a likelihood score for the optimal sequence it proposes, which can be used to determine a level of confidence in that proposed sequence); (c) the sequence produced by the sequencing algorithm (e.g., confidence can be assigned based on a comparison between the sequence proposed by the algorithm and either a look-up table of sequences and/or any a priori knowledge of the polynucleotide being sequenced); or (d) any suitable combination of items (a)-(c).

Note that in some circumstances, it can be beneficial to determine the actual sequence by utilizing the proposed sequences from more than one of items (A)-(D). For example, one could determine a consensus sequence based on some or all of such proposed sequences. The consensus sequence can be determined based all or some of the proposed sequences. The consensus sequence can be applied globally to the entire polynucleotide sequence or locally to a portion of the sequence. The consensus sequence can be determined based on confidence values from some or all of items (A)-(D). Confidence values can be those described further above in this example. Confidence values can be applied locally, to a portion of a sequence, or globally, to the entire sequence. A final consensus sequence can be determined by multiple rounds of the above-mentioned approaches, where the resultant consensus of each round can be used as a proposed sequence, and confidence-determining methods for each round can differ between rounds.

As one example, a Viterbi algorithm can be used to determine two different proposed sequences by sequencing only full steps and only fractional steps of DNA translocating through a nanopore (items (A) and (B) set forth above in this example). The likelihood scores of this algorithm for each piece of DNA are used to determine the confidence for each region of the proposed sequence, and an aggregation of confidences for each region can result in a first-round proposed consensus sequence. This consensus sequence can then be compared to the two initially proposed sequences with regard to a look-up table of known sequences. The similarity between the look-up table and each of these three proposed sequences can result in confidence values for each region of each of the three proposed sequences. This second-round of confidence-based comparisons between the three proposed sequences can result in a final proposed consensus sequence.

Figure 22C:
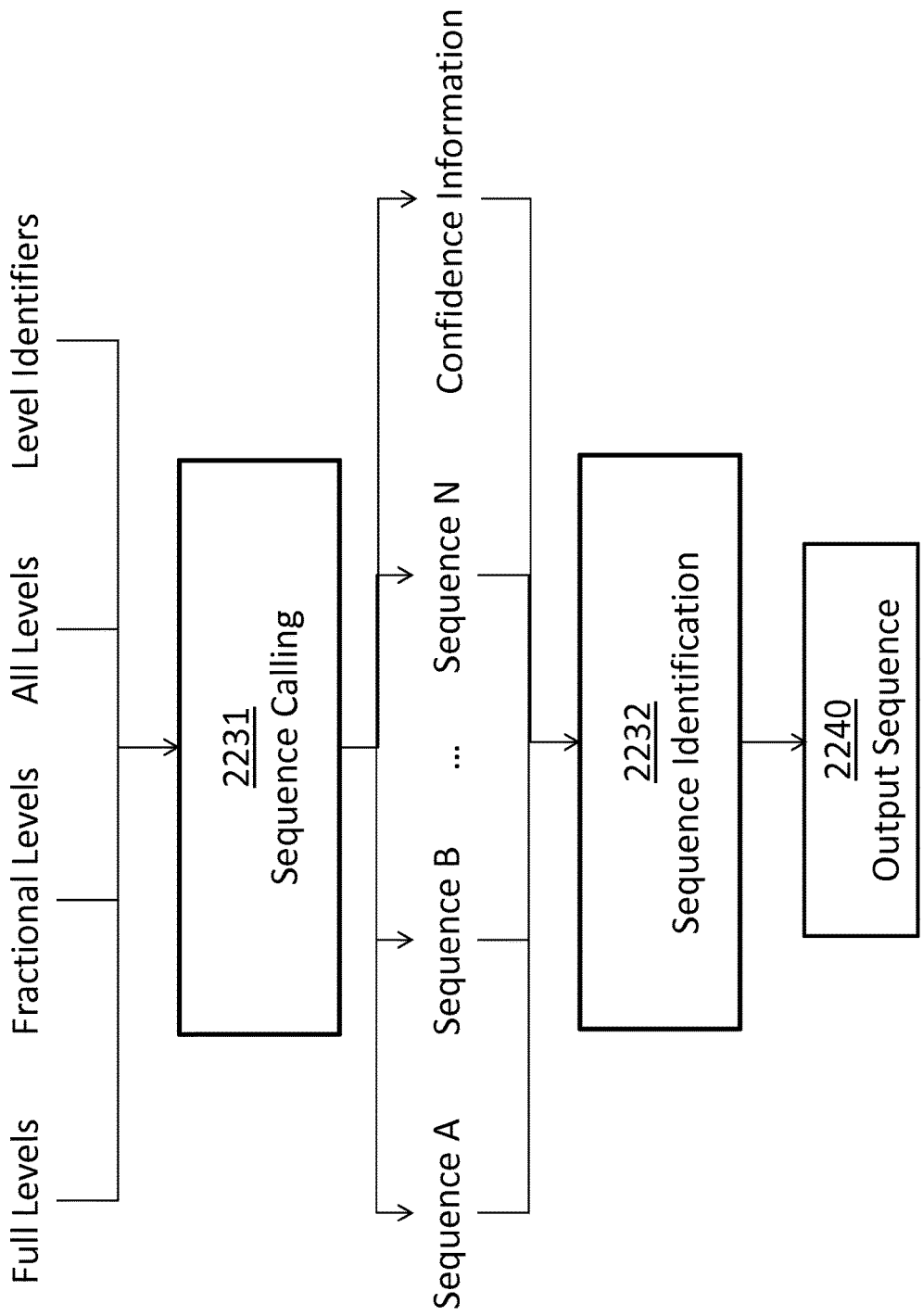

In some embodiments, FIGS. 22A-22D illustrate steps in illustrative methods for using information provided by fractional translocation of a polynucleotide through a pore, according to some embodiments. FIG. 22A illustrates a high level overview of a method for using information provided by fractional translocation of a polynucleotide through a pore, according to some embodiments. The method illustrated in FIG. 22A includes obtaining a signal (step 2210), such as one or more signals produced by one or more fractional translocation steps by a Hel308 helicase of a target polynucleotide through a pore such as described in greater detail elsewhere herein. The method illustrated in FIG. 22A also includes level detection and identification (step 2220), e.g., detecting and identifying different signal levels in the signal, e.g., detecting and identifying levels that correspond to fractional translocation steps of the polynucleotide through the pore, and also detecting and identifying levels that correspond to full translocation steps of the polynucleotide through the pore. The method illustrated in FIG. 22A also includes sequence determination (step 2230), e.g., characterizing the sequence of the polynucleotide based upon the detected and identified different signal levels in the signal. The method illustrated in FIG. 22A also includes outputting a sequence (step 2240), e.g., outputting a likely sequence of nucleotides of the actual nucleotide based on the results of the sequence calling.

Figure 22D:
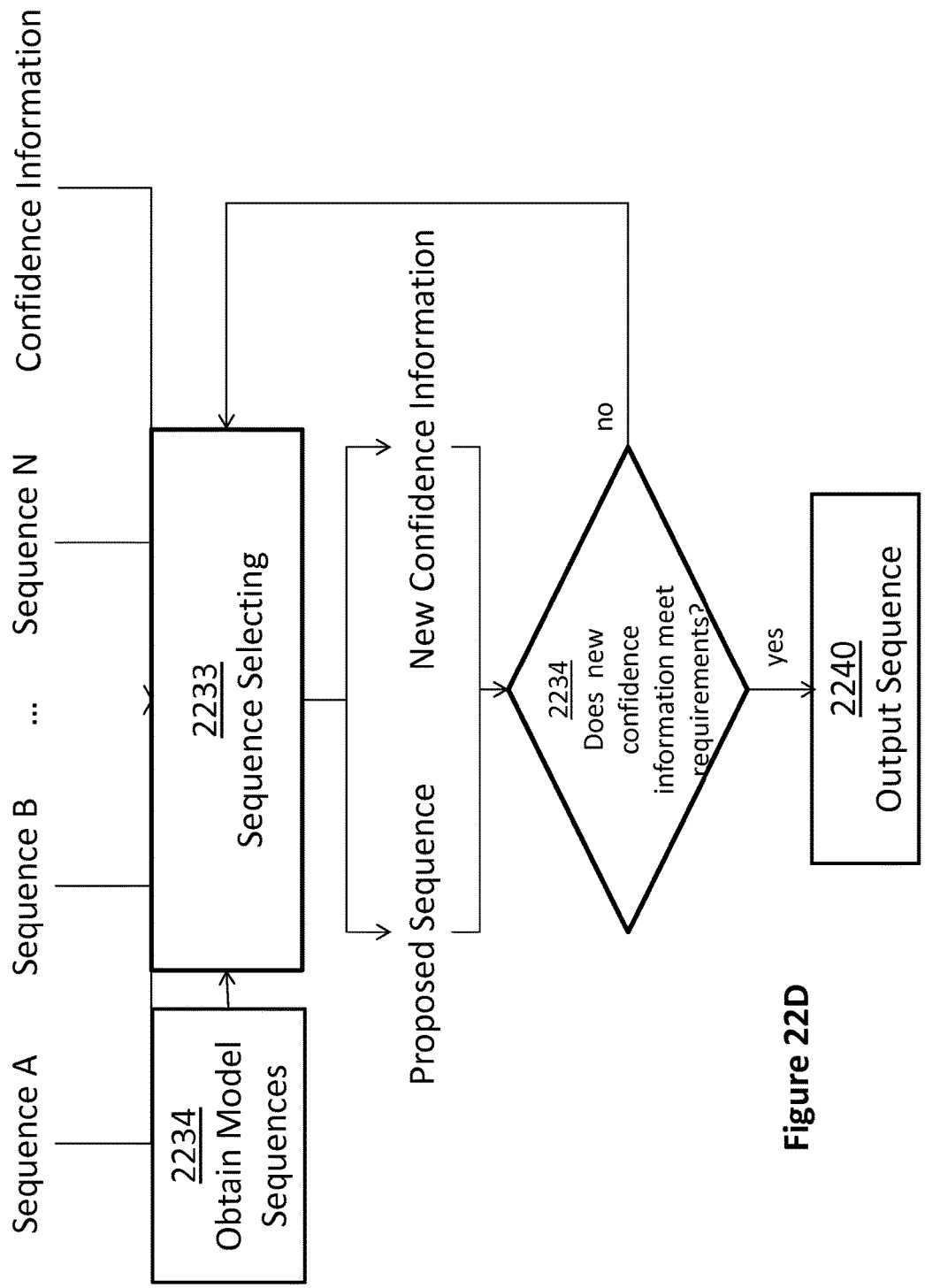

FIGS. 22B-22D illustrate optional substeps of one or more of the steps illustrated in FIG. 22A. For example, FIG. 22B illustrates additional detail of one potential implementation of steps 2210 and 2220 illustrated in FIG. 22A. The method illustrated in FIG. 22B again includes obtaining a signal (step 2210), such as one or more signals produced by one or more fractional translocation steps by a Hel308 helicase of a target polynucleotide through a pore such as described in greater detail elsewhere herein. The method illustrated in FIG. 22B also optionally can include obtaining input parameters (2211). Such input parameters can include, but are not limited to, parameters defining what characteristic signal features should be detected and determined to correspond to a signal. For example, the input parameters can define a threshold magnitude change in signal value, above which a magnitude change in signal can be detected as corresponding to a level. Or, for example, the input parameters can define that only signal levels corresponding to full translocation steps, or only signal levels corresponding to fractional translocation steps, or signal levels corresponding to both full and fractional translocation steps, should be detected. Input parameters can also contain information associated with error modes (e.g., nucleotide skipping or nucleotide toggling), possibly including the propensity and/or degree of certain error modes, which can be taken into account when determining levels. Input parameters also can include information associated with the particular environment between which the nanopore, molecular motor and polynucleotide are interacting (e.g., the temperature, salinity, pH, co-factor concentration, etc.), which can be used to determine levels for a given signal. The method illustrated in FIG. 22B also includes level detection, e.g., detecting different signal levels in the signal that correspond to fractional translocation steps of the polynucleotide through the pore (step 2221). For example, based on upon the signal obtained at step 2210 and the input parameters obtained at step 2211, such level detection can detect regions of the signal that are sufficiently statistically significantly different from other regions of the signal as to correspond to the level. Exemplary methods of level detection (which also can be referred to as edge detection or step detection) are known in the art, and include Student's t-test and chi-squared maximization. For some examples of step-detection algorithms that suitably can be adapted for use in detecting levels at step 2221, see Carter et al., "A Comparison of Step-Detection Methods: How Well Can You Do?," Biophysical Journal 94: 306-308 (January 2008).

The method illustrated in FIG. 22B also includes outputting level information (step 2222) based upon the level detection of step 2221. Level information can include the average, median, mode, distribution, duration, maximum, and/or minimum current detected for a given level, or any combination of these values, or these values pertaining to a subset of current values for a given level (e.g., one can utilize the average current after first removing current information associated with error modes). Level information can also include the standard deviation of the current, or a frequency band-limited subset of current (e.g., the current obtained after applying a low-pass, high-pass, band-pass, or band-stop filter, or any combintaiton of these filters). Level information can also include information associated with the durations of the levels, as well as error mode information associated with the levels. The method illustrated in FIG. 22B also includes level identification (step 2223), e.g., determining which of the levels detected at step 2221 for which level information is output at step 2222 correspond to full or fractional translocation steps of the target polynucleotide. For example, step 2223 can include analyzing the durations of the different levels detected at step 2221 for which level information is output at step 2222, and based on such durations, identifying certain levels as corresponding to full translocation steps, and identifying other certain levels as corresponding to fractional translocation steps. As one example, signal levels having a duration shorter than a first threshold can be assumed to correspond to noise and thus discarded, while signal levels having a duration longer than a first threshold and shorter than a second threshold can be assumed to correspond to a fractional translocation step and thus identified as such, while signal levels having a duration longer than the second threshold and shorter than a third threshold can be assumed to correspond to a full translocation step and thus identified as such, while signal levels having a duration longer than the third threshold can be assumed to correspond to an error, or to an absence of polynucleotide, and thus discarded.

The method illustrated in FIG. 22B also includes outputting one or more of the following outputs: full levels, fractional levels, all levels, and level identifiers. For example, as noted above, the input parameters obtained at step 2211 can define that only signal levels corresponding to full translocation steps, or only signal levels corresponding to fractional translocation steps, or signal levels corresponding to both full and fractional translocation steps (e.g., "all levels"), should be detected. Note that in some embodiments, selecting "all levels" via the input parameters can correspond to bypassing the level identification step, such that the level detection step 2221 directly outputs all levels. Alternatively, based upon the results of level detection 2223 and the input parameters 2211, the identified levels of the desired signals can be output, e.g., for further processing such as described below with reference to FIGS. 22C and 22D. Level identifiers can include any suitable information that facilitates further analysis of the levels, e.g., indices that indicate the durations for full or fractional steps that were used during step 2223 to denote the type of transition to which an identified level corresponds.

Referring again to FIG. 22A, one or more of full levels, fractional levels, all levels, and level identifiers, which can be generated using the method illustrated in FIG. 22B or using another suitable method, can be used as input to perform sequence determination (step 2230 in FIG. 22A). For example, FIG. 22C illustrates a first exemplary method for performing sequence determination based on one or more of such full levels, fractional levels, all levels, and level identifiers, e.g., that takes as input one or more of full levels, fractional levels, all levels, and level identifiers. The method illustrated in FIG. 22C includes a step of sequence calling based on the input of one or more of full levels, fractional levels, all levels, and level identifiers (step 2231). Sequence calling can include any suitable method based upon which nucleotide bases of the target polynucleotide can be called based on the input signal levels. Exemplary methods for sequence calling include, but are not limited to, Viterbi algorithms such as described in Example VII with reference to FIG. 19A, modified Viterbi algorithms such as described in Example VII with reference to FIG. 19B, or pattern matching analogous to that described in Example XI. Other methods for sequence calling suitably can be used. The output of the sequence calling (step 2231) can include a plurality of called sequences, e.g., Sequence A, Sequence B, . . . Sequence N, as well as confidence information for each such called sequence. The different called sequences can be based on a different inputs to step 2231 than one another. For example, a first called sequence (e.g., Sequence A) can be based upon an input to step 2231 in which only full translocation levels are identified based on a given signal obtained at step 2210, a second called sequence (e.g., Sequence B) can be based upon an input to step 2231 in which only fractional translocation levels are identified, and a third called sequence (e.g., Sequence N) can be based upon an input to step 2231 in which all translocation levels (e.g., both full and fractional translocation levels) are identified. Alternatively, or additionally, other called sequences can be based on other levels that were identified based on alternative input parameters obtained at step 2211, such as different values of parameters defining what characteristic signal features should be detected and determined to correspond to a signal, such as different threshold magnitude changes in signal value, above which a magnitude change in signal can be detected as corresponding to a level. Each different called sequence can have associated confidence information, e.g., a value representing the likelihood that the called sequence corresponds to the actual sequence of the target nucleotide.

In the embodiment illustrated in FIG. 22C, a step of sequence selection (step 2232) can select one or more of the called sequences and provide the selected sequence as output (step 2240). As one example, the step of sequence selection (step 2232) can include comparing the confidence information for the various called sequences, and can select and output at step 2240 the called sequence having highest confidence, e.g., the highest likelihood of corresponding to the actual sequence. As another example, the confidence information for a given called sequence can include a plurality of confidence values respectively representing the likelihood that corresponding portions of the called sequence correspond to the actual sequence of the target polynucleotide for that portion. For different portions of the called sequences (e.g., portions that are 10 base pairs long, or 50 base pairs long, or 100 base pairs long, or 10-100 base pairs long, or 10-50 base pairs long, or 50-100 base pairs long), the step of sequence selection (step 2232) can include comparing the confidence value for different called sequences at that portion, and selecting the portion of the called sequence that has the highest value for that portion. That selected portion can be concatenated with, or can be aligned with, the selected portions of other called sequences that have the highest value for such portions.

FIG. 22D illustrates an alternative method that can be used for sequence determination (2230). The method illustrated in FIG. 22D can include obtaining as input a plurality of called sequences, e.g., Sequence A, Sequence B, . . . Sequence N, as well as confidence information for each such called sequence, which can be analogous to those described above with reference to FIG. 22C. In this regard, although not specifically illustrated, the method illustrated in FIG. 22D can include step 2231 of sequence calling that receives inputs analogous to those described above with reference to FIG. 22C, provides outputs analogous to those described above with reference to FIG. 22C, and operates analogously as step 2231. Alternatively, the method illustrated in FIG. 22D can obtain the plurality of called sequences from any other suitable source.

The method illustrated in FIG. 22D also can include obtaining model sequences (step 2234). For example, such sequences can include a priori known sequences for one or more different species, such as one or more different pathogens. Illustratively, the model sequences can be stored in a lookup table, database, or other suitable data structure stored in a non-transitory computer-readable medium. The method illustrated in FIG. 22D also can include a step of sequence selecting (step 2233). In the embodiment illustrated in FIG. 22D, the step of sequence selecting can select one or more of the called sequences received as input, based on one or more of the model sequences obtained at step 2234, and provide as output a proposed sequence and new confidence information. As one example, the step of sequence selecting (step 2233 in FIG. 22D) can include comparing one or more of the various called sequences to one or more of the model sequences obtained at step 2234, and can select and output a proposed sequence, which can correspond to the called sequence having the highest new confidence information, e.g., the highest likelihood of corresponding to the model sequence. Input confidence information can be weighed with the likelihood of a sequence (or regions within that sequence) to match a model sequence (or regions within the model sequence) to determine the most likely sequence, which can be output as the proposed sequence. For example, for input sequence A best aligning to model sequence Z and input sequence B best aligning to model sequence Y, a proposed sequence can be model sequence Z based on better alignment between A and Z than between B and Y. However, in cases where B and Y have a better alignment, cases where A has a higher confidence value than B can allow Z to be the proposed sequence. Also, in another scenario, regions of sequences can be compared, allowing for the output proposed sequence to include sequence information from A, B, Z, and Y. Alternatively, a given called sequence can include new confidence information, e.g., a plurality of new confidence values respectively representing the likelihood that corresponding portions of the called sequence correspond to portions of one or more the model sequences for that portion. For different portions of the called sequences (e.g., portions that are 10 base pairs long, or 50 base pairs long, or 100 base pairs long, or 10-100 base pairs long, or 10-50 base pairs long, or 50-100 base pairs long), the step of sequence selecting (step 2233) can include comparing the new confidence value for different called sequences at that portion for the model sequence(s), and selecting the portion of the called sequence that has the highest new confidence value for that portion. That selected portion can be concatenated with, or can be aligned with, the selected portions of other called sequences that have the highest new confidence value for such portions.

The method illustrated in FIG. 22D further can include determining, based on the new confidence information output by step 2233, whether the new confidence information for the proposed sequence, also output by step 2233, meets requirements (step 2235). As one example, step 2235 can compare the new confidence information, which can be a new confidence value, to a threshold confidence value at or above which the proposed sequence can be determined to sufficiently match the model, and below which the proposed sequence can be determined to insufficiently match the model. New confidence information can include the result of input confindence information, the relationship between the proposed sequence and the input sequences, the relationship between the proposed sequence and the model sequences, and/or the relationship between the input sequences and the mdoel sequences. For example, in a case where the proposed sequence is simply one of the input sequences, the new confidence information can be a weighted mean between the input sequence's input confidence value and its alignment score to the best-aligning model sequence. In other cases, such as when the proposed sequence is a combination of regions of input sequences, the new confidence information can include a weighted mean of weighted means of input confidence values and alignment scores (to the model sequences) among the regions in the proposed sequence. Based on determining at step 2235 that the new confidence information meets the requirements ("yes"), step 2235 provides the proposed sequence as output (step 2240). Based on determining at step 2235 that the new confidence information does not meet the requirements, step 2235 returns to step 2233 at which sequence selecting continues, e.g., by performing further comparisons of the called sequences to model sequences. The sequence selection algorithm or the set of model sequences can be dependent upon parameters, which can include one or more of the proposed sequence, new confidence information, the number of times the sequence selection algorithm has been run, and the model sequences already utlized. For example, an initial pass through the sequence selection algorithm can utilize relatively few model sequences (e.g., for the sake of throughput). However, if the alignment between the input sequences and the model sequences is relatively poor, then the new confidence information may not meet requirements, and thus comparison to a new or more refined set of model sequences can be performed upon return to step 2233.

Example XI

Pattern Recognition, Optionally for SNP Identification

In some embodiments, the methods and compositions disclosed herein can be used in combination with methods for multiplex nucleic acid detection, genotyping and amplification. Methods for multiplex nucleic acid detection, genotyping and amplification are well known in the art and can be readily selected and applied by a person of ordinary skill. For example, in one embodiment, the methods and compositions disclosed herein can be used in combination with the methods of multiplex nucleic acid detection, genotyping and amplification described in U.S. Pat. Nos. 6,890,741, 6,913,884, 7,955,794, 7,582,420, and 8,288,103, and U.S. Publication 2013-0244882, which are herein incorporated by reference.

In some embodiments, the methods for multiplex nucleic acid detection, genotyping and amplification that can be combined with the methods and compositions disclosed herein include methods performed on or in combination with a solid support such as an array (both random and ordered) or beads. For example, in some aspects, the target polynucleotides to be assayed, such as genomic DNA, can be immobilized to a solid support. Such immobilized target polynucleotides can be subject to the multiplex nucleic acid detention and genotyping methods that are well known in the art. The resulting target polynucleotide can be characterized using the methods disclosed herein.

In some embodiments, the methods for characterizing a target polynucleotide can further include the steps necessary for generating the target polynucleotide to be assayed. Accordingly, in some embodiments, the method can include the steps of: (a) providing a plurality of target nucleic acid sequences each comprising from 3' to 5' a first, second and third target domain, the first target domain comprising a detection position, the second target domain being at least one nucleotide; (b) contacting the target nucleic acid sequences with sets of probes for each target sequence to form a set of first hybridization complexes, each set of probes comprising: a first probe comprising from 5' to 3', a universal priming sequence, and a sequence substantially complementary to the first target domain of a target sequence, and an interrogation position suitable for basepairing with the detection position (e.g., within the 3' four terminal bases), and a second probe comprising from 5' to 3', a sequence substantially complementary to the third target domain of a target sequence and universal priming sequence, wherein optionally at least one probe contains a locus identifying sequence (e.g., tag or barcode); (c) contacting the hybridization complexes with an extension enzyme and dNTPs, under conditions whereby if the base at the interrogation positions are perfectly complementary with the bases at the detection positions, extension of the first probes occurs through the second target domains to form second hybridization complexes; and (d) ligating the extended first probes to second probes to form amplification templates. In some aspects of this method, the first or second probe of the sets of probes can include an allele identifying sequence (e.g. tag or barcode).

In some embodiments, the methods for characterizing a target polynucleotide can further include the steps of: (a) providing a plurality of target nucleic acid sequences each comprising from 3' to 5' a first, second and third target domain, the first target domain comprising a detection position, the second target domain being at least one nucleotide; (b) contacting the target nucleic acid sequences with probes each comprising from 5' to 3', a universal priming sequence, and a sequence substantially complementary to the first target domain of a target sequence, and an interrogation position suitable for basepairing with the detection position (e.g., within the 3' four terminal bases), wherein optionally the probes contain a locus identifying sequence (e.g., tag or barcode); (c) contacting the hybridization complexes with an extension enzyme and dNTPs, under conditions whereby if the base at the interrogation positions are perfectly complementary with the bases at the detection positions, extension of the probes occurs through the second and third target domains to form extended probes that can act as amplification templates.

The method for generating the target polynucleotide for assaying in the methods described herein can further include amplifying the amplification templates to produce amplicons. In some aspects, the primers comprising the universal priming sequence for the first or second probe also include an allele identifying sequence or a locus identifying sequence (e.g. tag or barcode), depending upon what identifying sequence has already been incorporated in to the amplification template. These amplicons, which can include both a locus identifying sequence and an allele identifying sequence, can be characterized using the methods disclosed herein. The characterization of the target sequence can indicate the genotype of the sample based on the presence of the locus and allele identifying sequences.

In some embodiments, the primers used to produce amplicons include one or more modified residues that does not allow the extension enzyme used during amplification to traverse the residues. For example, in some aspects one primer includes an abasic site (apurinic/apyrimidinic site), a C3 spacer phosphoramidite (Int C3 Spacer), a triethylene glycol spacer (Int Spacer 9) or a an 18-atom hexa-ethyleneglycol spacer (Int Spacer 18) so as to prevent the extension enzyme from continuing the primer extension. It is understood that a person of ordinary skill in the art can select other modified residues that can perform this same function. The one or more modified residues can be located within the allele identifying sequence or to either side of the allele identifying sequence so long as a sufficient length 5' overhang is generated for characterizing the target polynucleotide using the methods disclosed herein. For example, the 5' overhang is of a sufficient length to allow immobilization of the amplicon.

In some embodiments, the amplicons generated by the above methods are further contacted with a nicking endonuclease so as to generate a 3' overhang in or near the second probe sequence. Such nicking enzymes can be sequence specific such that only one strand of a double-stranded product is cleaved. A variety of nicking endonucleases are well known in the art and it is recognized that a person of ordinary skill can readily select an appropriate endonuclease based on the probe and priming sequence. In order to generate the 3' overhang following cleavage by the nicking endonuclease, several methods known in the art can be used including, for example, partially denaturing the amplicons such that the smaller portion of the nicked strand is released from the amplicon, whereas the remainder of the amplicon remains hybridized together. In order to facility the smaller portion of the amplicon being removed, a reverse complement of the smaller portion can be added in order to hybridize to the undesired strand.

In some embodiments, a 3' overhang can be generated by including one or more uracil residues in the second probe sequence described in the methods above and contacting the amplicon with a uracil-specific enzyme that specifically generates a single nucleotide gap at the location of the the uraci. A non-limiting example of such a uracil-specific enzyme is the Uracil-Specific Excision Reagent (USER™) Enzyme (New England Biolabs). Accordingly, the smaller interspersed fragments generated by the enzyme can be readily denatured way from the amplicon using well known methods.

In certain aspects, the 3' overhang that is generated is of a sufficient length so as to facilitate binding of a helicase described herein. Accordingly, in some aspects, the 3' overhang includes at least 4 nucleotides in length. In other aspects the 3' overhang includes between 4-20 nucleotides in length, or in certain aspects between 8-16, or in other aspects between 10 and 16 nucleotides in length.

The phrase "locus identifying sequence" refers to a sequence of nucleic acid residues (e.g., a tag or barcode) that has been assigned to or is known to be connected to a particular location on a target polynucleotide. The location of a target polynucleotide can be, for example, a gene, a portion of a gene (e.g., exon or intron) or a non-coding region (e.g., promoter or enhancer) on a genome that is in proximity to the allele being assayed. The locus identifying sequence can be a naturally occurring sequence that is specific for the location of the target sequence of interest and/or a synthetic sequence that is not native to the target sequence of interest. The locus identifying sequence can be assigned by a signal pattern expected from the tag or barcode.

The phrase "allele identifying sequence" refers to a sequence of nucleic acid residues (e.g., a tag or barcode) that has been assigned to specific nucleic acid residue that is in a detection position of a target polynucleotide. The allele identifying sequence can indicate the presence of a nucleic acid residue (e.g., A, T, C, or G) in a detection position. The allele identifying sequence can also be assigned by a signal pattern expected from the tag or barcode.

In another embodiment, the methods for characterizing a target polynucleotide can further include the steps described in FIG. 18. Such a method can include the steps of: (a) providing a sample having different target nucleic acid sequences of interest, wherein the different target nucleic acid sequences are optionally immobilized on a solid support; (b) contacting the sample with a set of probes for each of the different target nucleic acid sequences of interest to form hybridization complexes, each set comprising: a first probe comprising from 5' to 3': a first universal priming sequence and a sequence that is substantially complementary to the first target domain and that has an interrogation position suitable for basepairing with the detection position; and a second probe comprising 5' to 3': a sequence substantially complementary to the third target domain, and a second universal priming sequence, wherein at least one probe contains a locus identifying sequence (e.g., tag or barcode) that is not native to the target sequence of interest; (c) contacting the hybridization complexes with an extension enzyme and dNTPs, wherein for each hybridization complex, if the base at the interrogation position is perfectly complementary to the base at the detection position, then the first probe is extended along the second target domain; (d) ligating the extended first probes to second probes to form amplification templates; (e) amplifying the amplification templates with first and second universal primers to produce amplicons, wherein at least one primer includes an allele identifying sequence (e.g. tag or barcode), wherein the allele identifying sequence comprises an abasic site; (f) contacting the amplicons with a nicking endonuclease so as to generate a 3' overhang in the second primer sequence; and (g) detecting the presence of both the locus identifying sequence and allele identifying sequence of different amplicons using the methods for target polynucleotide characterizations described herein, thereby indicating of the presence of the different target sequences of interest in the sample.

As used herein, the phrase "multiplex" or grammatical equivalents refers to the detection, analysis or amplification of more than one target sequence of interest. In one embodiment multiplex refers to at least 100 or 200 different target sequences while at least 500 different target sequences is preferred. More preferred is at least 1000, with more than 5000 or 10,000 particularly preferred and more than 50,000 or 100,000 most preferred. Detection can be performed on a variety of platforms as described herein.

In some aspects, the disclosure herein provides methods for the detection of nucleic acid target sequences in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples, such as purified genomic DNA, RNA, proteins, etc.; raw samples (bacteria, virus, genomic DNA, etc.). As will be appreciated by those in the art, virtually any experimental manipulation may have been done on the sample.

If required, the target polynucleotide is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, antimicrobial agents, etc., may be used, depending on the sample preparation methods and purity of the target.

In addition, in most embodiments, double stranded target polynucleotides are denatured to render them single stranded so as to permit hybridization of the primers and other probes described herein. One embodiment utilizes a thermal step, generally by raising the temperature of the reaction to about 95° C., although pH changes and other techniques may also be used.

As is outlined herein, the target polynucleotide can be a product of a reaction such as a detection sequence from a reaction, a ligated probe, an extended probe from a PCR reaction, or PCR amplification product, ("amplicon") etc.

In some embodiments, the target polynucleotide comprises a position for which sequence information is desired, generally referred to herein as the "detection position." In a certain embodiment, the detection position is a single nucleotide, although in some embodiments, it may comprise a plurality of nucleotides, either contiguous with each other or separated by one or more nucleotides. By "plurality" as used herein is meant at least two. As used herein, the base which basepairs with a detection position base in a hybrid is termed a "readout position" or an "interrogation position;" thus many of the first or second step probes of the invention comprise an interrogation position.

The methods disclosed herein can take on a wide variety of configurations, as are shown in the figures and described in more detail herein. Generally, these components include a complexity reduction component, a specificity component and an amplification component. The components can be configured in a variety of ways as disclosed below. That is, in one embodiment a complexity reduction step is first performed. This is followed by either the amplification or specificity step. Alternatively, the specificity step is performed first. This can be followed by the complexity reduction or amplification step. Alternatively, amplification is first performed. This is followed by the complexity and specificity steps.

While the above indicates that each of the three components can be performed in any order. One of skill in the art will appreciate that when amplification is performed first, there will likely be some degree of complexity reduction or specificity involved. In addition, when specificity components are performed first, there will be a degree of complexity reduction. In addition, in some embodiments when amplification is first performed, there will be some degree of specificity and complexity reduction. However, as described below, the method generally includes three components.

Probes and Primers

As one of skill in the art appreciates, there are several probes or primers that can be used in the methods disclosed herein. These probes/primers can take on a variety of configurations and may have a variety of structural components described in more detail below. The first step probe may be either an allele specific probe or locus specific probe. By "allele specific" probe or primer is meant a probe or primer that either hybridizes to a target sequence and discriminates between alleles or hybridizes to a target sequence and is modified in an allele specific manner. By "locus specific" probe or primer is meant a probe or primer that hybridizes to a target sequence in a locus specific manner, but does not necessarily discriminate between alleles. A locus specific primer also may be modified, i.e. extended as described below, such that it includes information about a particular allele, but the locus specific primer does not discriminate between alleles.

In many embodiments, the probes or primers comprise one or more universal priming site(s) and/or identifying sequences. For example, in one configuration, each of the four allele bases is associated with a different sequence, i.e. allele identifying sequence (e.g., tag or barcode), each sequence having similar amplification efficiencies. In another configuration, one of the probes includes a locus identifying sequence (e.g, tag or barcode).

The size of the primer and probe nucleic acid can vary, as will be appreciated by those in the art with each portion of the probe and the total length of the probe in general varying from 5 to 500 nucleotides in length. Each portion can be between 10 and 300, between 15 and 250, or between 10 to 35 nucleotides in length, depending on the use and amplification technique. Thus, for example, the universal priming site(s) of the probes can be between 15-20 nucleotides in length, with 18 being used in certain embodiments. The locus and/or allele identifying sequences of the probes can be between 10-300 nucleotides in length, with 20-100 being used in certain embodiments. The target specific portion of the probe can be from 15-50 nucleotides in length. In addition, the primer can include an additional amplification priming site.

In one embodiment, the allele or locus specific probe or probes comprises a target domain substantially complementary to a first domain of the target sequence. In general, probes can be designed to be complementary to a target sequence (either the target sequence of the sample or to other probe sequences, as is described herein), such that hybridization of the target and the probes described herein occurs. This complementarity need not be perfect; there can be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

Also, the probes used in the methods described herein can be constructed so as to contain the necessary priming site or sites for the subsequent amplification scheme. In certain embodiments, the priming sites are universal priming sites. By "universal priming site" or "universal priming sequences" herein is meant a sequence of the probe that will bind a primer for amplification.

As will be appreciated by those in the art, in general, highly multiplexed reactions can be performed, with all of the universal priming sites being the same for all reactions. Alternatively, "sets" of universal priming sites and corresponding probes can be used, either simultaneously or sequentially. The universal priming sites are used to amplify the modified probes to form a plurality of amplicons that are then detected in a variety of ways, as outlined herein.

Accordingly, the methods described herein provide first target probe sets. By "probe set" herein is meant a plurality of target probes that are used in a particular multiplexed assay. In this context, plurality means at least two, with more than 10 being preferred, depending on the assay, sample and purpose of the test. In one embodiment the probe set includes more than 100, with more than 500 probes being preferred and more than 1000 being particularly preferred. In a particularly preferred embodiment each probe contains at least 5000, with more than 10,000 probes being most preferred.

Complexity Reduction Component

Complexity reduction can be a component of the multiplex scheme set forth herein. Generally, complexity reduction is a method for enriching for a particular target or locus. That is, complexity reduction is considered a method that results in removal of non-target nucleic acids from the sample or removal of probes/primers that have not hybridized correctly or at all to a target nucleic acid. In addition, complexity reduction includes removal of probes that have not been modified during a enzymatic step. That is, complexity reduction includes removing non-target nucleic acids, i.e. enriching for target nucleic acids or removing non-hybridized probes or primers prior to an enzymatic step, i.e. either an amplification or specificity step, or both.

There are a variety of methods that include a complexity reduction step. These include, but are not limited to, selective immobilization of target nucleic acids or probes/primers that are modified in a target specific manner, selective removal of non-target nucleic acids, and selective destruction of non-target nucleic acids. Such destruction includes but is not limited to denaturation, degradation or cleavage of non-target nucleic acids. In addition, complexity reduction can include components such as target selective amplification, although this also includes amplification and components.

In certain embodiments, complexity reduction is accomplished by selectively immobilizing a primer that has been modified in a target specific manner. That is, either locus specific or allele specific primers are hybridized with a target. The target can be immobilized or in solution. Following hybridization, the primer is extended in a primer extension reaction. In some aspects, either the primer or NTPs include a purification tag that allows for removal or purification of the extended product from the reaction mixture. Once extended, generally the modified primer can be immobilized on a solid support. Following immobilization of the modified primer, the support can be washed to remove both non-target nucleic acids and primers that were not modified, i.e. extended. The immobilized primers, thus, include information about the target locus including particular allelic information. This results in enrichment of target nucleic acids or removal of non-target nucleic acids.

In another embodiment, the complexity reduction component includes selective immobilization of target polynucleotide. That is, target polynucleotides are preferentially immobilized on a solid support rather than non-target nucleic acids.

In one embodiment, the target polynucleotide, probe or primer, including a modified primer, is attached to a solid support. By "solid support" or other grammatical equivalents herein is meant any material that is appropriate for or can be modified to be appropriate for the attachment of the target sequences. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Magnetic beads and high throughput microtier plates are particularly preferred.

The composition and geometry of the solid support vary with its use. In certain embodiments, supports comprising microspheres or beads can be used for the solid support. By "microspheres" or "beads" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. Preferably, in this embodiment, when complexity reduction is performed, the microspheres are magnetic microspheres or beads.

Once attached to the solid support, the target sequence, probe or primers are amenable to analysis as described herein.

A variety of hybridization or washing conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10 C lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g. 10 to 50 nucleotides) and at least about 60 C for long probes (e.g. greater than 50 nucleotides). Stringent conditions may also be achieved with the addition of helix destabilizing agents such as formamide.

By "extension enzyme" herein is meant to be an enzyme that will extend a sequence by the addition of NTPs. As is well known in the art, there are a wide variety of suitable extension enzymes, of which polymerases (both RNA and DNA, depending on the composition of the target sequence and precircle probe) are preferred. Preferred polymerases are those that lack strand displacement activity, such that they will be capable of adding only the necessary bases at the end of the probe, without further extending the probe to include nucleotides that are complementary to a targeting domain and thus preventing circularization. Suitable polymerases include, but are not limited to, both DNA and RNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., or Q beta replicase from bacteriophage, also SP6, T3, T4 and T7 RNA polymerases can be used, among others.

Polymerases can also include those that are essentially devoid of a 5' to 3' exonuclease activity, so as to assure that the probe will not be extended past the 5' end of the probe. Exemplary enzymes lacking 5' to 3' exonuclease activity include the Klenow fragment of the DNA Polymerase and the Stoffel fragment of DNAPTaq Polymerase. For example, the Stoffel fragment of Taq DNA polymerase lacks 5' to 3' exonuclease activity due to genetic manipulations, which result in the production of a truncated protein lacking the N-terminal 289 amino acids. (See e.g., Lawyer et al., J. Biol. Chem., 264:6427-6437 (1989); and Lawyer et al., PCR Meth. Appl., 2:275-287 (1993)). Analogous mutant polymerases have been generated for polymerases derived from *T. maritima*, Tsps17, TZ05, Tth and Taf.

Additional polymerases are those that lack a 3' to 5' exonuclease activity, which is commonly referred to as a proof-reading activity, and which removes bases which are mismatched at the 3' end of a primer-template duplex. Although the presence of 3' to 5' exonuclease activity provides increased fidelity in the starnd synthesized, the 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of an oligonucleotide primer used in a primer extension process is critical as it is from this terminus that extension of the nascent strand begins. Degradation of the 3' end leads to a shortened oligonucleotide which in turn results in a loss of specificity in the priming reaction (i.e., the shorter the primer the more likely it becomes that spurious or non-specific priming will occur).

Yet additional polymerases are thermostable polymerases. A heat resistant enzyme can include any enzyme that retains most of its activity after one hour at 40° C. under optimal conditions. Examples of thermostable polymerase which lack both 5' to 3' exonuclease and 3' to 5' exonuclease include Stoffel fragment of Taq DNA polymerase. This polymerase lacks the 5' to 3' exonuclease activity due to genetic manipulation and no 3' to 5' activity is present as Taq polymerase is naturally lacking in 3' to 5' exonuclease activity. Tth DNA polymerase is derived form *Thermus thermophilus*, and is available form Epicentre Technologies, Molecular Biology Resource Inc., or Perkin-Elmer Corp. Other useful DNA polymerases which lack 3' exonuclease activity include a Vent[R](exo–), available from New England Biolabs, Inc., (purified from strains of *E. coli* that carry a DNA polymerase gene from the archaebacterium *Thermococcus litoralis*), and Hot Tub DNA polymerase derived from *Thermus flavus* and available from Amersham Corporation. Other preferred enzymes which are thermostable and deprived of 5' to 3' exonuclease activity and of 3' to 5' exonuclease activity include AmpliTaq Gold. Other DNA polymerases, which are at least substantially equivalent may be used like other N-terminally truncated *Thermus aquaticus* (Taq) DNA polymerase I. the polymerase named KlenTaq I and KlenTaq LA are quite suitable for that purpose. Of course, any other polymerase having these characteristics can also be used according to the invention.

The conditions for performing the addition of one or more nucleotides at the 3' end of the probe will depend on the particular enzyme used, and will generally follow the conditions recommended by the manufacturer of the enzymes used.

Specificity Component

Generally following a complexity reduction step, a specificity step is included in the method described herein. By "specificity component" is meant a step that discriminates between target nucleic acids, preferably at the level of the allele. That is, the specificity component is an allele specific step (e.g. genotyping or SNP analysis). While some level of specificity can be accomplished by simply hybridizing allele specific probes to the template (i.e. the product of the complexity reduction step above), in a preferred embodiment the specificity step includes an enzymatic step. That is, the fidelity of an enzymatic step improves specificity for allele discrimination. Preferred enzymes include DNA polymerases, RNA polymerases and ligases as described in more detail herein.

The polymerases as described above can also be suitable for the specificity steps.

Many ligases are known and are suitable for use in the methods described herein. Exemplary ligases are described in Lehman, Science, 186: 790-797 (1974); Engler et al, DNA Ligases, pages 3-30 in Boyer, editor, The Enzymes, Vol. 15B (Academic Press, New York, 1982); and the like. Preferred ligases include T4 DNA ligase, T7 DNA ligase, *E. coli* DNA ligase, Taq ligase, Pfu ligase, and Tth ligase. Protocols for their use are well known, e.g. Sambrook et al (cited above); Barany, PCR Methods an Applications, 1: 5-16 (1991); Marsh et al, Strategies, 5: 73-76 (1992); and the like. Generally, ligases require that a 5' phosphate group be present for ligation to the 3' hydroxyl of an abutting strand. Preferred ligases include thermostable or (thermophilic) ligases, such as pfu ligase, Tth ligase, Taq ligase and Ampligase™ DNA ligase (Epicentre Technologies, Madison, Wis.). Ampligase has a low blunt end ligation activity.

The certain embodiments, the ligase is one which has the least mismatch ligation. The specificity of ligase can be increased by substituting the more specific NAD+-dependant ligases such as *E. coli* ligase and (thermostable) Taq ligase for the less specific T4 DNA ligase. The use of NAD analogues in the ligation reaction further increases specificity of the ligation reaction. See, U.S. Pat. No. 5,508,179 to Wallace et al.

In one embodiment the specificity component is performed with immobilized targets. That is, the products of the complexity reduction step are immobilized on a solid support as outlined herein. As discussed herein the target of specificity reaction is referred to as a "specificity target". That is, the product of the complexity reduction step is the specificity target.

In one embodiment the support is the same support as in the initial complexity reduction step. In this embodiment the target nucleic acid is removed from the solid support prior to the specificity assay. The target nucleic acid can be removed by any method that denatures the hybridization complex resulting in release of the target nucleic acid. As one of skill in the art appreciates, in this embodiment the target nucleic acid is not covalently bound to the solid support. That is, it is the target probe that is stably attached to the support. That is, while the attachment of the probe is not necessarily covalent, it is stable enough to withstand denaturation of the hybridization complex and removal of the nonattached target nucleic acid.

In an alternative embodiment the specificity target is in solution. That is, following a complexity reduction step, the hybridization complex between the immobilized target nucleic acid and target probe is denatured and the modified target probe is eluted from the hybridization complex. In a certain embodiment the specificity target is analyzed in solution. In an alternative embodiment the solution phase specificity target is immobilized on a subsequent solid support.

These specificity assays, i.e. genotyping techniques, fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods. See generally U.S. Pat. Nos. 6,890,741, 6,913,884, 7,955,794, 7582,420, and 8,288,103, and U.S. Publication 2013-0244882, which are herein incorporated by reference.

In certain embodiments, extension genotyping is done. In this embodiment, any number of techniques can be used to add a nucleotide to the readout position of a probe hybridized to the target sequence adjacent to the detection position. By relying on enzymatic specificity, preferentially a perfectly complementary base is added. Some of the methods described herein rely on the enzymatic incorporation of nucleotides at the detection position. This may be done using any number of well known methods in the art such as single base extension or multi-base extension. In certain embodiments genotyping is accomplished by primer extension that does not use chain terminating nucleotides. As such, this genotyping is considered multi-base extension. The method includes providing an interrogator oligonucleotide designed to detect one allele of a given SNP. The number of oligonucleotides is determined by the number of distinct SNP alleles being probed. For instance, if one were probing 1000 SNPs, each with two alleles, 2000 oligonucleotides would be necessary. The interrogators are complementary to a stretch of DNA containing the SNP, with the terminal base of each interrogator corresponding to the SNP position, or with the SNP-specific position within the last 1, 2 3 or 4 nucleotides of the interrogator. In some embodiments the interrogator is not the terminal position of the primer, but rather resides at a position 1, 2, 3, 4, 5 or 6 nucleotides from the 3' terminus of the primer. For example, when a SNP has an A and C allele, interrogators ending in T and G are provided and in some embodiments may be immobilized on separate elements (beads) to detect the two. Although both the match and the mismatch will hybridize to a given allele, only the match can act as a primer for a DNA polymerase extension reaction. Accordingly, following hybridization of the probes with the target DNA, a polymerase reaction is performed. This results in the extension of the hybrids with a DNA polymerase in the presence of dNTPs.

In certain embodiments, it is desirable to remove the unextended or unreacted probes or primers from the assay mixture, and particularly from a solid support, as unextended probes or primers can compete with the extended primers in binding to capture probes. The concentration of the unextended primers relative to the extended primer may be relatively high, since a large excess of primer is usually required to generate efficient primer annealing. Accordingly, a number of different techniques may be used to facilitate the removal of unextended probes or primers. These generally include methods based on removal of unreacted primers by binding to a solid support, protecting the reacted primers and degrading the unextended ones, and separating the unreacted and reacted primers.

Amplification Component

In this embodiment, provided herein are methods that include amplification of a polynucleotide and products of nucleic acid amplification reactions, i.e. amplicons, can be used in the methods for characterizing a polynucleotide. Suitable amplification methods include both target amplification and signal amplification. Target amplification involves the amplification (i.e. replication) of the target sequence to be detected, resulting in a significant increase in the number of target molecules. Target amplification strategies include but are not limited to the polymerase chain reaction (PCR), strand displacement amplification (SDA), nucleic acid sequence based amplification (NASBA), and rolling-circle amplification (RCA). Such amplification strategies are well known to a person of skill in the art and can be readily selected for use in the described methods.

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), invasive cleavage techniques such as Invader™ technology, Q-Beta replicase (Q R) technology, and the use of "amplification probes" such as "branched DNA" that result in multiple label probes binding to a single target sequence.

All of these methods can include a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed.

In general, the modified primer serves as a target sequence for a secondary reaction, which then produces a number of amplified strands, which can be detected as outlined herein. As required, the unreacted primers are removed, in a variety of ways, as will be appreciated by those in the art and outlined herein. Accordingly, the reaction starts with the addition of a primer nucleic acid to the target sequence which forms a hybridization complex. Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identity of the enzyme will depend on the amplification technique used. Similarly, the modification will depend on the amplification technique.

In certain embodiments, the target amplification technique is polymerase chain reaction (PCR). PCR is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others. It is understood that a person of ordinary skill in the art could readily select the appropriate variation of PCR that could be used in the methods described herein.

In certain embodiments, the amplification reaction is a multiplex amplification reaction as described herein. In one embodiment the amplification reaction uses a plurality of PCR primers to amplify a plurality of target sequences. In this embodiment plurality of target sequences are simultaneously amplified with the plurality of amplification primer pairs.

An alternative embodiment the multiplex PCR reaction uses universal primers as described herein. That is, universal PCR primers hybridized to universal priming sites on the target sequence and thereby amplify a plurality of target sequences. This embodiment is potentially preferred because it requires only a limited number of PCR primers. That is, as few as one primer pairs can amplify a plurality of target sequences.

Golden Gate amplicons were generated using human DNA as a template as previously described (Cold Spring Harb Symp Quant Biol. 2003; 68:69-78. Highly parallel SNP genotyping. Fan J B et al.). The resulting amplicons had one of two primers, designated P1 and P2, depending upon the allele. Furthermore, universal reverse primer ("Reverse P3") was present on all amplicons.

```
                                   (SEQ ID NO: 82)
    P1:           TCTCGTCGCTCATCAACT (SEQ ID NO: 83)
    P2:           GAGTCGAGGTCATATCGT
```

```
                                   (SEQ ID NO: 84)
    Reverse P3:   GTCTGCCTATAGTGAGTC
```

A second round of PCR employing 16 cycles was used to add allele barcoding primers, termed "P1_barcode_A" and "P1_barcode_B". An extended universal reverse primer ("Universal dU Reverse") containing multiple deoxyuracil residues was used.

```
P1_barcode_A:
                                          (SEQ ID NO: 85)
/5phos/TTTTTTTTTTTTTTTCCTTCCXXTTTTCTTCTTCTTCAAGAAG
AAGATCTCGTCGCTCATCAACT P2_barcode_B:
                                          (SEQ ID NO: 86)
/5phos/TTTTTTTTTTTTTTTCCTTCCXXTTTTTTAATTAATTTTGTTG
TTGTGAGTCGAGGTCATATCGT Universal dU Reverse:
                                          (SEQ ID NO: 87)
ATACGGCG/dU/CCACCGACC/dU/CAGCGTC/dU/GCCTATAG/dU/GA
GTC
```

Where/5phos/ denotes a 5' phosphate, /dU/ is a deoxyuracil base, and X is an abasic moiety.

After PCR, the sample was incubated with USER enzyme (New England Biolabs, Ipswich, Mass.) for 2.5 hours at 37° C. to create single-stranded gaps wherever a dU residue was located. The sample was heated to 65° C. for 10 min. to remove the fragmented DNA and create a 3' overhang. The sample was purified using a PCR Cleanup Kit (Qiagen).

Samples were annealed to cholesterol-containing oligo "P3_Chol" at a 1:1 molar ratio by heating to 65° C. and slowly cooling.

```
P3_Chol:
                                          (SEQ ID NO: 88)
ACCGACACTGCGTCTGCCTATAGTGAGTC/iSp9//3CholTEG/
```

Where/iSp9/ denotes a 9-atom triethylene glycol spacer, and /3CholTEG/denotes a 3' cholesterol TEG (triethylene glycol) moiety.

Lipid bilayers were formed from 1,2-diphytanoyl-sn-glycero-3-phosphocholine (Avanti Polar Lipids) The bilayer spanned a horizontal ~20 micron diameter aperture in Teflon. M2-NNN-MspA was added to the grounded side of the bilayer at a concentration of ~2.5 ng/ml. Once a single pore inserted, the compartment was flushed with experimental buffer to avoid further insertions. An Axopatch-200B patch clamp amplifier (Axon Instruments) applied a voltage across the bilayer of 180 mV and measured the ionic currents. The analog signal was low-pass filtered at 50 kHz with a 4-pole Bessel filter and was then digitized at five times the low-pass filter frequency. Data acquisition was controlled with custom software written in LabWindows/CVI (National Instruments).

The ~60 μl compartments on both sides of the bilayer contained experimental buffer of 0.4 M KCl, 1 mM EDTA, 1 mM DTT, 1 mM ATP, 10 mM MgCl2, and 10 mM HEPES/KOH buffered at pH 8.0. Hel308 wild type Tga was used as the motor at 150 nM.

FIG. 23 illustrates exemplary simulated signals that can be generated as a function of time for a first illustrative polynucleotide sequence (SEQ ID NO: 89) and a second illustrative polynucleotide sequence (SEQ ID NO: 90) suitable for use as respective barcodes, according to some embodiments. It can be seen in FIG. 24 that the simulated signal (1) corresponding to fractional translocation of the first illustrative polynucleotide sequence through a pore by a Hel308 helicase has a charactersistic pattern over time that includes two "peaks" at a relatively high signal level, followed by a drop, followed by two more "peaks" at a relatively low signal level, whereas the simulated signal (2) corresponding to fractional translocation of the second illustrative polynucleotide sequence through a pore by a Hel308 helicase includes two "peaks" at a relatively low signal level, followed by an increase, followed by two more "peaks" at a relatively high signal level. Accordingly, it can be expected that actual signals that include distinctive features such as in simulated signals (1) and (2) readily can be distinguished from one another, e.g., using pattern matching, and thus can facilitate distinguishing assay results from one another. For example, FIGS. 24A-24D illustrate exemplary simulated signals that can be generated as a function of time for first and second illustrative polynucleotide sequences suitable for use as respective barcodes, according to some embodiments. It can be seen that the sections of the simulated signals generally designated "barcode" in FIGS. 24A and 24B include two "peaks" at a relatively high signal level, followed by a drop, followed by two more "peaks" at a relatively low signal level, and thus can be understood to correspond to the first illustrative polynucleotide sequence. It also can be seen that the sections of the simulated signals generally designated "barcode" in FIGS. 24C and 24D include two "peaks" at a relatively low signal level, followed by an increase, followed by two more "peaks" at a relatively high signal level, and thus can be understood to correspond to the second illustrative polynucleotide sequence.

In another example, a 2NNN MspA pore was inserted into a DPhPC lipid bilayer in a manner analogous to that described above in the present example. The buffer included 400 mM KCl, 10 mM HEPES pH 8, 5 mM $MgCl_2$, and 1 mM EDTA. The reagents included 1 mM DTT and 1 mM ATP. The enzyme included approximately 150 mM Hel308 Tga. The DNA was approximately 10 nM, and the single strands that were sequenced (denoted RS1801131 SNP1 and SNP2) were hybridized to a cholesterol-containing polynucleotide. The signals obtained during sequencing of such strands were deciphered using post-processing, which included level-finding and alignment to anticipated sequences using algorithms such as described elsewhere herein.

FIGS. 25A and 25B respectively illustrate exemplary simulated signals that can be generated as a function of time for first and second illustrative polynucleotide sequences suitable for use as respective barcodes, according to some embodiments. The sections of the simulated signals within the dotted boxes in FIGS. 25A and 25B respectively include distinctive patterns for the sequences respectively designated rs1801131 SNP1 and rs1801131 SNP2, and thus can be used as respective barcodes. The sequences used as the barcodes were the same as illustrated in FIG. 23.

FIGS. 26A-26D respectively illustrate exemplary measured signals that were generated as a function of time for first and second illustrative polynucleotide sequences suitable for use as respective barcodes, according to some embodiments. The sections of the measured signals within the dotted boxes in FIGS. 26A and 26B respectively include distinctive patterns that can be seen to correspond to the barcode of the sequence designated rs1801131 SNP1, while the sections of the measured signals within the dotted boxes in FIGS. 26C and 26D respectively include distinctive patterns that can be seen to correspond to the barcode of the sequence designated rs1801131 SNP2, and also are readily distinguishable from the barcode of the sequence designated rs1801131 SNP1.

INCORPORATION BY REFERENCE

Throughout this application various publications have been referenced within or without parentheses. The disclosures of these publications in their entireties are hereby incorporated by reference in this application for all purposes, including but not limited in order to more fully describe the state of the art to which this disclosure pertains.

OTHER ALTERNATIVE EMBODIMENTS

It should be noted that the systems and methods provided herein can be implemented using various types of data processor environments (e.g., on one or more data processors) which execute instructions (e.g., software instructions) to perform operations disclosed herein. Non-limiting examples include implementation on a single general purpose computer or workstation, or on a networked system, or in a client-server configuration, or in an application service provider configuration. For example, the methods and systems described herein can be implemented on many different types of processing devices by program code comprising program instructions that are executable by the device processing subsystem. The software program instructions can include source code, object code, machine code, or any other stored data that is operable to cause a processing system to perform the methods and operations described herein. Other implementations can also be used, however, such as firmware or even appropriately designed hardware configured to carry out the methods and systems described herein.

It is further noted that the systems and methods can include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

The systems' and methods' data (e.g., associations, data input, data output, intermediate data results, final data results, etc.) can be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods further can be provided on many different types of computer-readable storage media including computer storage mechanisms (e.g., non-transitory media, such as CD-ROM, diskette, RAM, flash memory, computer's hard drive, etc.) that contain instructions (e.g., software) for use in execution by a processor to perform the methods' operations and implement the systems described herein.

Moreover, the computer components, software modules, functions, data stores and data structures provided herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claims.

What is claimed is:

1. A system for characterizing a target polynucleotide, comprising:
    a polypeptide pore inserted into a membrane having a cis and a trans surface;
    a Hel308 helicase contacting the pore on the cis surface of the membrane;
    a solution comprising a target polynucleotide and less than 1 mM ATP or analogue thereof contacting the cis surface of the membrane;
    an amplifier adapted to provide a potential difference across the membrane;
    a processor with instructions to characterize signals from fractional step translocations of the polynucleotide through the polypeptide pore; and
    a detector adapted to measure an ionic current flowing through the pore.

2. The system of claim 1, wherein the instructions are adapted to characterize at least two signals during a full translocation cycle of the Hel308 helicase.

3. The system of claim 1, wherein the instructions comprise a Hidden Markov model.

4. The system of claim 1, wherein the detector is adapted to measure at least two signals during a full translocation cycle of the Hel308 helicase.

5. The system of claim 1, wherein the detector measures a current response at a sampling rate of about 50 kHz.

6. The system of claim 1, wherein the polypeptide pore comprises a constriction zone with a length that can hold no more than five nucleotides.

7. The system of claim 1, wherein the polypeptide pore comprises a constriction zone with a length that can hold no more than two nucleotides.

8. The system of claim 1, wherein the solution comprises less than about 100 µM ATP or analogue thereof.

9. The system of claim 1, wherein the polypeptide pore comprises a *Mycobacterium smegmatis* porin A (MspA) pore.

10. The system of claim 1, wherein the polypeptide pore comprises a wild type MspA polypeptide comprising one or more mutations selected from the group consisting of D90N, D91N, D93N, D118R, D134R and E139K.

11. The system of claim 1, wherein the polypeptide pore comprises an amino acid sequence having at least about 90% homology to SEQ ID NO: 1.

12. The system of claim 1, wherein the polypeptide pore comprises an amino acid sequence of SEQ ID NO: 1.

13. The system of claim 1, wherein the Hel308 helicase comprises a motif having an amino acid sequences selected from the group consisting of SEQ ID NO:04-65.

14. The system of claim 1, wherein the membrane comprises a lipid bilayer.

15. The system of claim 14, wherein the lipid bilayer comprises 1,2-diphytanoyl-sn-glycero-3-phosphocholine.

16. A method of characterizing a target polynucleotide, the method comprising:
    (a) obtaining the system of claim 1;
    (b) applying a potential difference across a pore in contact with a Hel308 helicase and the target polynucleotide;
    (c) measuring at least two signals for a unit of one or more nucleotides of the target polynucleotide moving through the pore during a full translocation cycle of the Hel308 helicase; and (d) characterizing the target polynucleotide using the at least two signals measured in (c).

17. The method of claim 16, wherein the at least two signals comprise electrical signals.

18. The method of claim 16, further comprising repeating steps (b) (d).

19. The method of claim 16, wherein a full translocation cycle of the Hel308 helicase comprises nucleotide substrate binding and nucleotide substrate hydrolysis.

* * * * *

SEQUENCE LISTING

```
<160> NUMBER OF SEQ ID NOS: 90

<210> SEQ ID NO 1
<211> LENGTH: 184
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 2
<211> LENGTH: 4
<212> TYPE: PRT
<213> ORGANISM: Unknown
<220> FEATURE:
<221> NAME/KEY: source
<223> OTHER INFORMATION: /note="Description of Unknown: 'DEAD' box motif
      sequence"

<400> SEQUENCE: 2

Asp Glu Ala Asp
1
```

```
<210> SEQ ID NO 3
<211> LENGTH: 4
<212> TYPE: PRT
<213> ORGANISM: Unknown
<220> FEATURE:
<221> NAME/KEY: source
<223> OTHER INFORMATION: /note="Description of Unknown: 'DEAH' box motif
      sequence"

<400> SEQUENCE: 3

Asp Glu Ala His
1

<210> SEQ ID NO 4
<211> LENGTH: 8
<212> TYPE: PRT
<213> ORGANISM: Methanococcoides burtonii

<400> SEQUENCE: 4

Gln Met Ala Gly Arg Ala Gly Arg
1               5

<210> SEQ ID NO 5
<211> LENGTH: 9
<212> TYPE: PRT
<213> ORGANISM: Methanococcoides burtonii

<400> SEQUENCE: 5

Gln Met Ala Gly Arg Ala Gly Arg Pro
1               5

<210> SEQ ID NO 6
<211> LENGTH: 8
<212> TYPE: PRT
<213> ORGANISM: Pyrococcus furiosus

<400> SEQUENCE: 6

Gln Met Leu Gly Arg Ala Gly Arg
1               5

<210> SEQ ID NO 7
<211> LENGTH: 9
<212> TYPE: PRT
<213> ORGANISM: Pyrococcus furiosus

<400> SEQUENCE: 7

Gln Met Leu Gly Arg Ala Gly Arg Pro
1               5

<210> SEQ ID NO 8
<211> LENGTH: 8
<212> TYPE: PRT
<213> ORGANISM: Haloferax volcanii

<400> SEQUENCE: 8

Gln Met Met Gly Arg Ala Gly Arg
1               5

<210> SEQ ID NO 9
<211> LENGTH: 9
<212> TYPE: PRT
<213> ORGANISM: Haloferax volcanii

<400> SEQUENCE: 9

Gln Met Met Gly Arg Ala Gly Arg Pro
1               5
```

<210> SEQ ID NO 10
<211> LENGTH: 8
<212> TYPE: PRT
<213> ORGANISM: Halorubrum lacusprofundi

<400> SEQUENCE: 10

Gln Met Cys Gly Arg Ala Gly Arg
1               5

<210> SEQ ID NO 11
<211> LENGTH: 8
<212> TYPE: PRT
<213> ORGANISM: Halorubrum lacusprofundi

<400> SEQUENCE: 11

Gln Met Gly Arg Ala Gly Arg Pro
1               5

<210> SEQ ID NO 12
<211> LENGTH: 8
<212> TYPE: PRT
<213> ORGANISM: Cenarchaeum symbiosum

<400> SEQUENCE: 12

Gln Leu Cys Gly Arg Ala Gly Arg
1               5

<210> SEQ ID NO 13
<211> LENGTH: 9
<212> TYPE: PRT
<213> ORGANISM: Cenarchaeum symbiosum

<400> SEQUENCE: 13

Gln Leu Cys Gly Arg Ala Gly Arg Pro
1               5

<210> SEQ ID NO 14
<211> LENGTH: 8
<212> TYPE: PRT
<213> ORGANISM: Sulfolobus solfataricus

<400> SEQUENCE: 14

Gln Met Ser Gly Arg Ala Gly Arg
1               5

<210> SEQ ID NO 15
<211> LENGTH: 9
<212> TYPE: PRT
<213> ORGANISM: Sulfolobus solfataricus

<400> SEQUENCE: 15

Gln Met Ser Gly Arg Ala Gly Arg Pro
1               5

<210> SEQ ID NO 16
<211> LENGTH: 8
<212> TYPE: PRT
<213> ORGANISM: Methanogenium frigidum

<400> SEQUENCE: 16

Gln Met Ala Gly Arg Ala Gly Arg
1               5

```
<210> SEQ ID NO 17
<211> LENGTH: 9
<212> TYPE: PRT
<213> ORGANISM: Methanogenium frigidum

<400> SEQUENCE: 17

Gln Met Ala Gly Arg Ala Gly Arg Pro
1               5

<210> SEQ ID NO 18
<211> LENGTH: 8
<212> TYPE: PRT
<213> ORGANISM: Methanothermococcus okinawensis

<400> SEQUENCE: 18

Gln Cys Ile Gly Arg Ala Gly Arg
1               5

<210> SEQ ID NO 19
<211> LENGTH: 9
<212> TYPE: PRT
<213> ORGANISM: Methanothermococcus okinawensis

<400> SEQUENCE: 19

Gln Cys Ile Gly Arg Ala Gly Arg Pro
1               5

<210> SEQ ID NO 20
<211> LENGTH: 8
<212> TYPE: PRT
<213> ORGANISM: Methanotorris igneus

<400> SEQUENCE: 20

Gln Cys Ile Gly Arg Ala Gly Arg
1               5

<210> SEQ ID NO 21
<211> LENGTH: 9
<212> TYPE: PRT
<213> ORGANISM: Methanotorris igneus

<400> SEQUENCE: 21

Gln Cys Ile Gly Arg Ala Gly Arg Pro
1               5

<210> SEQ ID NO 22
<211> LENGTH: 8
<212> TYPE: PRT
<213> ORGANISM: Thermococcus gammatolerans

<400> SEQUENCE: 22

Gln Met Met Gly Arg Ala Gly Arg
1               5

<210> SEQ ID NO 23
<211> LENGTH: 9
<212> TYPE: PRT
<213> ORGANISM: Thermococcus gammatolerans

<400> SEQUENCE: 23

Gln Met Met Gly Arg Ala Gly Arg Pro
1               5

<210> SEQ ID NO 24
<211> LENGTH: 8
```

```
<212> TYPE: PRT
<213> ORGANISM: Thermococcus barophilus

<400> SEQUENCE: 24

Gln Met Ile Gly Arg Ala Gly Arg
1               5

<210> SEQ ID NO 25
<211> LENGTH: 9
<212> TYPE: PRT
<213> ORGANISM: Thermococcus barophilus

<400> SEQUENCE: 25

Gln Met Ile Gly Arg Ala Gly Arg Pro
1               5

<210> SEQ ID NO 26
<211> LENGTH: 8
<212> TYPE: PRT
<213> ORGANISM: Thermococcus sibiricus

<400> SEQUENCE: 26

Gln Met Met Gly Arg Ala Gly Arg
1               5

<210> SEQ ID NO 27
<211> LENGTH: 9
<212> TYPE: PRT
<213> ORGANISM: Thermococcus sibiricus

<400> SEQUENCE: 27

Gln Met Met Gly Arg Ala Gly Arg Pro
1               5

<210> SEQ ID NO 28
<211> LENGTH: 8
<212> TYPE: PRT
<213> ORGANISM: Methanosarcina barkeri

<400> SEQUENCE: 28

Gln Met Ala Gly Arg Ala Gly Arg
1               5

<210> SEQ ID NO 29
<211> LENGTH: 9
<212> TYPE: PRT
<213> ORGANISM: Methanosarcina barkeri

<400> SEQUENCE: 29

Gln Met Ala Gly Arg Ala Gly Arg Pro
1               5

<210> SEQ ID NO 30
<211> LENGTH: 8
<212> TYPE: PRT
<213> ORGANISM: Methanosarcina acetivorans

<400> SEQUENCE: 30

Gln Met Ala Gly Arg Ala Gly Arg
1               5

<210> SEQ ID NO 31
<211> LENGTH: 9
<212> TYPE: PRT
<213> ORGANISM: Methanosarcina acetivorans
```

<400> SEQUENCE: 31

Gln Met Ala Gly Arg Ala Gly Arg Pro
1               5

<210> SEQ ID NO 32
<211> LENGTH: 8
<212> TYPE: PRT
<213> ORGANISM: Methanohalophilus mahii

<400> SEQUENCE: 32

Gln Met Ala Gly Arg Ala Gly Arg
1               5

<210> SEQ ID NO 33
<211> LENGTH: 9
<212> TYPE: PRT
<213> ORGANISM: Methanohalophilus mahii

<400> SEQUENCE: 33

Gln Met Ala Gly Arg Ala Gly Arg Pro
1               5

<210> SEQ ID NO 34
<211> LENGTH: 8
<212> TYPE: PRT
<213> ORGANISM: Methanosarcina mazei

<400> SEQUENCE: 34

Gln Met Ala Gly Arg Ala Gly Arg
1               5

<210> SEQ ID NO 35
<211> LENGTH: 9
<212> TYPE: PRT
<213> ORGANISM: Methanosarcina mazei

<400> SEQUENCE: 35

Gln Met Ala Gly Arg Ala Gly Arg Pro
1               5

<210> SEQ ID NO 36
<211> LENGTH: 8
<212> TYPE: PRT
<213> ORGANISM: Methanosaeta thermophila

<400> SEQUENCE: 36

Gln Met Ala Gly Arg Ala Gly Arg
1               5

<210> SEQ ID NO 37
<211> LENGTH: 9
<212> TYPE: PRT
<213> ORGANISM: Methanosaeta thermophila

<400> SEQUENCE: 37

Gln Met Ala Gly Arg Ala Gly Arg Pro
1               5

<210> SEQ ID NO 38
<211> LENGTH: 8
<212> TYPE: PRT
<213> ORGANISM: Methanosalsum zhilinae

<400> SEQUENCE: 38

```
Gln Met Ala Gly Arg Ala Gly Arg
1               5

<210> SEQ ID NO 39
<211> LENGTH: 9
<212> TYPE: PRT
<213> ORGANISM: Methanosalsum zhilinae

<400> SEQUENCE: 39

Gln Met Ala Gly Arg Ala Gly Arg Pro
1               5

<210> SEQ ID NO 40
<211> LENGTH: 8
<212> TYPE: PRT
<213> ORGANISM: Methanohalobium evestigatum

<400> SEQUENCE: 40

Gln Met Ala Gly Arg Ala Gly Arg
1               5

<210> SEQ ID NO 41
<211> LENGTH: 9
<212> TYPE: PRT
<213> ORGANISM: Methanohalobium evestigatum

<400> SEQUENCE: 41

Gln Met Ala Gly Arg Ala Gly Arg Pro
1               5

<210> SEQ ID NO 42
<211> LENGTH: 8
<212> TYPE: PRT
<213> ORGANISM: Methanococcus maripaludis

<400> SEQUENCE: 42

Gln Cys Ile Gly Arg Ala Gly Arg
1               5

<210> SEQ ID NO 43
<211> LENGTH: 9
<212> TYPE: PRT
<213> ORGANISM: Methanococcus maripaludis

<400> SEQUENCE: 43

Gln Cys Ile Gly Arg Ala Gly Arg Pro
1               5

<210> SEQ ID NO 44
<211> LENGTH: 8
<212> TYPE: PRT
<213> ORGANISM: Natrialba magadii

<400> SEQUENCE: 44

Gln Met Met Gly Arg Ala Gly Arg
1               5

<210> SEQ ID NO 45
<211> LENGTH: 9
<212> TYPE: PRT
<213> ORGANISM: Natrialba magadii

<400> SEQUENCE: 45

Gln Met Met Gly Arg Ala Gly Arg Pro
```

```
<210> SEQ ID NO 46
<211> LENGTH: 8
<212> TYPE: PRT
<213> ORGANISM: Methanoregula boonei

<400> SEQUENCE: 46

Gln Met Ala Gly Arg Ala Gly Arg
1               5

<210> SEQ ID NO 47
<211> LENGTH: 9
<212> TYPE: PRT
<213> ORGANISM: Methanoregula boonei

<400> SEQUENCE: 47

Gln Met Ala Gly Arg Ala Gly Arg Pro
1               5

<210> SEQ ID NO 48
<211> LENGTH: 8
<212> TYPE: PRT
<213> ORGANISM: Ferroplasma acidarmanus

<400> SEQUENCE: 48

Gln Met Ile Gly Arg Ala Gly Arg
1               5

<210> SEQ ID NO 49
<211> LENGTH: 9
<212> TYPE: PRT
<213> ORGANISM: Ferroplasma acidarmanus

<400> SEQUENCE: 49

Gln Met Ile Gly Arg Ala Gly Arg Pro
1               5

<210> SEQ ID NO 50
<211> LENGTH: 8
<212> TYPE: PRT
<213> ORGANISM: Methanocaldococcus fervens

<400> SEQUENCE: 50

Gln Cys Ile Gly Arg Ala Gly Arg
1               5

<210> SEQ ID NO 51
<211> LENGTH: 9
<212> TYPE: PRT
<213> ORGANISM: Methanocaldococcus fervens

<400> SEQUENCE: 51

Gln Cys Ile Gly Arg Ala Gly Arg Pro
1               5

<210> SEQ ID NO 52
<211> LENGTH: 8
<212> TYPE: PRT
<213> ORGANISM: Methanocaldococcus jannaschii

<400> SEQUENCE: 52

Gln Cys Ile Gly Arg Ala Gly Arg
1               5
```

<210> SEQ ID NO 53
<211> LENGTH: 9
<212> TYPE: PRT
<213> ORGANISM: Methanocaldococcus jannaschii

<400> SEQUENCE: 53

Gln Cys Ile Gly Arg Ala Gly Arg Pro
1               5

<210> SEQ ID NO 54
<211> LENGTH: 8
<212> TYPE: PRT
<213> ORGANISM: Methanocaldococcus infernus

<400> SEQUENCE: 54

Gln Cys Ile Gly Arg Ala Gly Arg
1               5

<210> SEQ ID NO 55
<211> LENGTH: 9
<212> TYPE: PRT
<213> ORGANISM: Methanocaldococcus infernus

<400> SEQUENCE: 55

Gln Cys Ile Gly Arg Ala Gly Arg Pro
1               5

<210> SEQ ID NO 56
<211> LENGTH: 8
<212> TYPE: PRT
<213> ORGANISM: Methanospirillum hungatei

<400> SEQUENCE: 56

Gln Met Ala Gly Arg Ala Gly Arg
1               5

<210> SEQ ID NO 57
<211> LENGTH: 9
<212> TYPE: PRT
<213> ORGANISM: Methanospirillum hungatei

<400> SEQUENCE: 57

Gln Met Ala Gly Arg Ala Gly Arg Pro
1               5

<210> SEQ ID NO 58
<211> LENGTH: 8
<212> TYPE: PRT
<213> ORGANISM: Archaeoglobus fulgidus

<400> SEQUENCE: 58

Gln Met Ala Gly Arg Ala Gly Arg
1               5

<210> SEQ ID NO 59
<211> LENGTH: 9
<212> TYPE: PRT
<213> ORGANISM: Archaeoglobus fulgidus

<400> SEQUENCE: 59

Gln Met Ala Gly Arg Ala Gly Arg Pro
1               5

<210> SEQ ID NO 60

```
<211> LENGTH: 8
<212> TYPE: PRT
<213> ORGANISM: Haloterrigena turkmenica

<400> SEQUENCE: 60

Gln Met Ala Gly Arg Ala Gly Arg
1               5

<210> SEQ ID NO 61
<211> LENGTH: 9
<212> TYPE: PRT
<213> ORGANISM: Haloterrigena turkmenica

<400> SEQUENCE: 61

Gln Met Ala Gly Arg Ala Gly Arg Pro
1               5

<210> SEQ ID NO 62
<211> LENGTH: 8
<212> TYPE: PRT
<213> ORGANISM: Haladaptatus paucihalophilus

<400> SEQUENCE: 62

Gln Met Phe Gly Arg Ala Gly Arg
1               5

<210> SEQ ID NO 63
<211> LENGTH: 9
<212> TYPE: PRT
<213> ORGANISM: Haladaptatus paucihalophilus

<400> SEQUENCE: 63

Gln Met Phe Gly Arg Ala Gly Arg Pro
1               5

<210> SEQ ID NO 64
<211> LENGTH: 8
<212> TYPE: PRT
<213> ORGANISM: Halobacterium sp.

<400> SEQUENCE: 64

Gln Met Phe Gly Arg Ala Gly Arg
1               5

<210> SEQ ID NO 65
<211> LENGTH: 9
<212> TYPE: PRT
<213> ORGANISM: Halobacterium sp.

<400> SEQUENCE: 65

Gln Met Phe Gly Arg Ala Gly Arg Pro
1               5

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Met" or "Leu"
<220> FEATURE:
<221> NAME/KEY: MOD_RES
```

<222> LOCATION: (3)..(3)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"
<220> FEATURE:
<221> NAME/KEY: misc_feature
<222> LOCATION: (1)..(8)
<223> OTHER INFORMATION: /note="Variant residues given in the sequence
      have no preference with respect to those in the annotations
      for variant positions"

<400> SEQUENCE: 66

Gln Cys Xaa Gly Arg Ala Gly Arg
1               5

<210> SEQ ID NO 67
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(10)
<223> OTHER INFORMATION: abasic nucleotide

<400> SEQUENCE: 67
aaaccttccn cccgtaccgt gccgtaccgt tccgttccgt accgtatttt tttttctcac      60
tatcgcattc tcatgcaggt cgtagcc                                         87

<210> SEQ ID NO 68
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
cctgcatgag aatgcgatag tgagattttt tttttttttt ttttt                     45

<210> SEQ ID NO 69
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (19)..(20)
<223> OTHER INFORMATION: abasic nucleotide

<400> SEQUENCE: 69
ctcacctatc cttccactnn cccccttttgg gtttaaattt tttcagatct cactatcttt     60
ttaaagtttt ctcactatcg cattctcatg caggtcgtag cc                       102

<210> SEQ ID NO 70
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(20)
<223> OTHER INFORMATION: abasic nucleotide

<400> SEQUENCE: 70
catcatcatc atcatcatnn ccccctaaac aagaatacca cgactagcat ttttcagatc    60
tcactatcgc attctcatgc aggtcgtagc c                                   91

<210> SEQ ID NO 71
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(20)
<223> OTHER INFORMATION: abasic nucleotide

<400> SEQUENCE: 71
catcatcatc atcatcatnn ccccctaaac aagaatacca cgactagcat ttttcagatc    60
tcactatcgc attctcatgc aggtcgtagc c                                   91

<210> SEQ ID NO 72
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(10)
<223> OTHER INFORMATION: abasic nucleotide

<400> SEQUENCE: 72
aaaccttccn cccgtaccgt gccgtaccgt tccgttccgt accgtatttt ttttttctcac   60 tatcgcattc tcatgcaggt cgtagcc                                        87

<210> SEQ ID NO 73
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
aaaaaaaata cggtacggaa cggaacggta cggcacggta cgggtttttt tttttttttt    60

<210> SEQ ID NO 74
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
atcatcatca tcat                                    14

<210> SEQ ID NO 75
<211> LENGTH: 9
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"

<400> SEQUENCE: 75

Gly Phe Cys Cys Pro Gln Ser Ile Gln
1               5

<210> SEQ ID NO 76
<211> LENGTH: 8
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 76

Ala Xaa Xaa Gly Xaa Gly Lys Thr
1               5

<210> SEQ ID NO 77
<211> LENGTH: 6
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"

<400> SEQUENCE: 77

Pro Thr Arg Glu Leu Ala
1               5

<210> SEQ ID NO 78
<211> LENGTH: 4
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"

<400> SEQUENCE: 78

Thr Pro Gly Arg
1

<210> SEQ ID NO 79
<211> LENGTH: 6
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"

<400> SEQUENCE: 79

Val Leu Asp Glu Ala Asp
1               5

<210> SEQ ID NO 80
<211> LENGTH: 4
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"

<400> SEQUENCE: 80

Phe Val Asn Thr
1

<210> SEQ ID NO 81
<211> LENGTH: 8
<212> TYPE: PRT
<213> ORGANISM: Unknown
<220> FEATURE:
<221> NAME/KEY: source
<223> OTHER INFORMATION: /note="Description of Unknown: 'SF2' family
      motif sequence"
<220> FEATURE:
<221> NAME/KEY: MOD_RES
<222> LOCATION: (6)..(7)
<223> OTHER INFORMATION: Any amino acid

<400> SEQUENCE: 81

His Arg Ile Gly Arg Xaa Xaa Arg
1               5

<210> SEQ ID NO 82
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
tctcgtcgct catcaact                                                 18

<210> SEQ ID NO 83
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gagtcgaggt catatcgt                                                 18

<210> SEQ ID NO 84
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
gtctgcctat agtgagtc                                              18

<210> SEQ ID NO 85
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(23)
<223> OTHER INFORMATION: abasic nucleotide

<400> SEQUENCE: 85 ttttttttt ttttccttc cnnttttctt cttcttcaag aagaagatct cgtcgctcat    60
caact                                                              65

<210> SEQ ID NO 86
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(23)
<223> OTHER INFORMATION: abasic nucleotide

<400> SEQUENCE: 86 ttttttttt ttttccttc cnnttttta attaattttg ttgttgtgag tcgaggtcat     60
atcgt                                                              65

<210> SEQ ID NO 87
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (9)..(9)
<223> OTHER INFORMATION: deoxyuracil
<220> FEATURE:
<221> NAME/KEY: modified_base
<222> LOCATION: (19)..(19)
<223> OTHER INFORMATION: deoxyuracil
<220> FEATURE:
<221> NAME/KEY: modified_base
<222> LOCATION: (27)..(27)
<223> OTHER INFORMATION: deoxyuracil
<220> FEATURE:
<221> NAME/KEY: modified_base
<222> LOCATION: (36)..(36)
<223> OTHER INFORMATION: deoxyuracil

<400> SEQUENCE: 87
atacggcgnc caccgaccnc agcgtcngcc tatagngagt c                     41

<210> SEQ ID NO 88

```
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
accgacactg cgtctgccta tagtgagtc                                           29

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ttaattaatt ttgttgttgt                                                     20

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
cttcttcttc aagaagaaga                                                     20
```